(12) United States Patent
Shen et al.

(10) Patent No.: US 11,530,260 B2
(45) Date of Patent: *Dec. 20, 2022

(54) COMPOSITIONS AND METHODS OF USE FOR TREATING METABOLIC DISORDERS

(71) Applicant: NGM Biopharmaceuticals, Inc., South San Francisco, CA (US)

(72) Inventors: Wenyan Shen, Redwood City, CA (US); Darrin Anthony Lindhout, Mountain View, CA (US); Raj Haldankar, Redwood City, CA (US); Hugo Matern, San Mateo, CA (US)

(73) Assignee: NGM Biopharmaceuticals, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/743,712

(22) Filed: Jan. 15, 2020

(65) Prior Publication Data

US 2020/0140536 A1    May 7, 2020

Related U.S. Application Data

(63) Continuation of application No. 15/885,438, filed on Jan. 31, 2018, now Pat. No. 10,562,965, which is a continuation of application No. 14/927,153, filed on Oct. 29, 2015, now Pat. No. 9,920,118.

(60) Provisional application No. 62/244,604, filed on Oct. 21, 2015, provisional application No. 62/073,737, filed on Oct. 31, 2014.

(51) Int. Cl.
| | |
|---|---|
| *C07K 14/495* | (2006.01) |
| *C07K 16/46* | (2006.01) |
| *A61K 38/18* | (2006.01) |
| *A61K 38/00* | (2006.01) |
| *C07K 16/22* | (2006.01) |

(52) U.S. Cl.
CPC ............ *C07K 16/22* (2013.01); *C07K 14/495* (2013.01); *C07K 2317/52* (2013.01); *C07K 2317/526* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 5,194,596 A | 3/1993 | Tischer | |
| 5,288,931 A * | 2/1994 | Chang | C07K 1/1133 435/69.1 |
| 5,350,836 A | 9/1994 | Kopchick | |
| 5,731,168 A | 3/1998 | Caner et al. | |
| 5,876,969 A | 3/1999 | Fleer et al. | |
| 5,994,102 A | 11/1999 | Hudson et al. | |
| 6,051,424 A | 4/2000 | Kato et al. | |
| 6,107,476 A | 8/2000 | Erlander et al. | |
| 6,165,470 A | 12/2000 | Becquart et al. | |
| 6,180,602 B1 | 1/2001 | Kato et al. | |
| 6,420,543 B1 | 7/2002 | Lee et al. | |
| 6,465,181 B2 | 10/2002 | Biling-Medel et al. | |
| 6,500,638 B2 | 12/2002 | Hudson et al. | |
| 6,521,227 B1 | 2/2003 | Hudson et al. | |
| 6,524,802 B1 | 2/2003 | Lee et al. | |
| 6,686,179 B2 | 2/2004 | Fleer et al. | |
| 6,737,056 B1 | 5/2004 | Presta | |
| 6,905,688 B2 | 6/2005 | Rosen et al. | |
| 6,972,322 B2 | 12/2005 | Fleer et al. | |
| 6,989,365 B2 | 1/2006 | Fleer et al. | |
| 7,056,701 B2 | 6/2006 | Fleer et al. | |
| 7,081,354 B2 | 7/2006 | Fleer et al. | |
| 7,094,577 B2 | 8/2006 | Fleer et al. | |
| 7,112,660 B1 * | 9/2006 | Domingues | C07K 14/5406 530/351 |
| 7,141,661 B2 | 11/2006 | Eling et al. | |
| 7,157,235 B2 | 1/2007 | Breit et al. | |
| 7,244,833 B2 | 7/2007 | Yu et al. | |
| 7,276,593 B2 | 10/2007 | Vernet et al. | |
| 7,282,351 B2 | 10/2007 | Hudson et al. | |
| 7,348,004 B2 | 3/2008 | Peters et al. | |
| 7,410,779 B2 | 8/2008 | Fleer et al. | |
| 7,435,410 B2 | 10/2008 | Fleer et al. | |
| 7,442,371 B2 | 10/2008 | Yu et al. | |
| 7,514,221 B2 | 4/2009 | Breit et al. | |
| 7,754,689 B2 | 7/2010 | Lu et al. | |
| 7,833,521 B2 | 11/2010 | Fleer et al. | |
| 7,863,239 B2 | 1/2011 | Timmerman et al. | |
| 7,919,084 B2 | 4/2011 | Breit et al. | |
| 7,968,303 B2 | 6/2011 | Breit et al. | |
| 8,021,880 B2 | 9/2011 | Peters et al. | |
| 8,067,548 B2 | 11/2011 | Wang et al. | |

(Continued)

FOREIGN PATENT DOCUMENTS

| | | |
|---|---|---|
| CL | 2017000201 | 1/2017 |
| CN | 102046207 | 5/2011 |
| CN | 203123206 | 8/2013 |
| CN | 103533951 | 1/2014 |
| EP | 1179067 | 12/2006 |
| EP | 1279039 | 1/2008 |
| EP | 1914554 | 4/2008 |
| EP | 0833912 | 2/2009 |
| EP | 2383571 | 11/2011 |
| EP | 2439535 | 4/2012 |
| EP | 2441466 | 4/2012 |
| EP | 2774620 | 9/2014 |
| EP | 2929891 | 10/2015 |
| EP | 3174894 | 6/2017 |
| JP | 07258293 | 10/1995 |
| JP | 1995250688 | 10/1995 |

(Continued)

OTHER PUBLICATIONS

Bauskin et al., 2000, EMBO J. 19(10):2212-2220.*

(Continued)

*Primary Examiner* — Elizabeth C. Kemmerer
(74) *Attorney, Agent, or Firm* — Fish & Richardson P.C.

(57) ABSTRACT

A complex comprising a GDF15 polypeptide is described. Methods of treating individuals with a metabolism disorder, such as, glucose metabolism disorder and/or a body weight disorder, and compositions associated therewith, are provided.

44 Claims, 10 Drawing Sheets

Specification includes a Sequence Listing.

(56) References Cited

U.S. PATENT DOCUMENTS

| | | |
|---|---|---|
| 8,084,021 B2 | 12/2011 | Yu et al. |
| 8,192,735 B2 | 6/2012 | Breit et al. |
| 8,222,384 B2 | 7/2012 | Wolfman et al. |
| 8,252,739 B2 | 8/2012 | Rosen et al. |
| 8,592,532 B2 | 11/2013 | Kannan et al. |
| 8,592,562 B2 | 11/2013 | Kannan et al. |
| 8,946,146 B2 | 2/2015 | Breit et al. |
| 8,986,698 B2 | 3/2015 | Amason et al. |
| 9,161,966 B2 | 10/2015 | Matern et al. |
| 9,550,819 B2 | 1/2017 | Lindhout et al. |
| 9,714,276 B2 | 7/2017 | Xiong et al. |
| 9,827,291 B2 | 11/2017 | Matern et al. |
| 9,828,415 B2 | 11/2017 | Matern et al. |
| 9,834,586 B2 | 12/2017 | Lindhout et al. |
| 9,862,752 B2 | 1/2018 | Xiong et al. |
| 9,920,118 B2 * | 3/2018 | Shen .................... A61P 3/04 |
| 10,195,250 B2 | 2/2019 | Lindhout et al. |
| 10,323,075 B2 | 6/2019 | Matern et al. |
| 10,336,798 B2 | 7/2019 | Xiong et al. |
| 10,562,965 B2 | 2/2020 | Shen et al. |
| 10,610,568 B2 | 4/2020 | Matern et al. |
| 10,869,909 B2 | 12/2020 | Lindhout et al. |
| 11,358,995 B2 | 6/2022 | Lindhout et al. |
| 2001/0011077 A1 | 8/2001 | Albone et al. |
| 2003/0023073 A1 | 1/2003 | Hsiao et al. |
| 2003/0045474 A1 * | 3/2003 | Sailer ................ A61P 19/00 |
| | | 514/8.8 |
| 2003/0053431 A1 | 3/2003 | Madour et al. |
| 2003/0232347 A1 | 12/2003 | Anderson et al. |
| 2003/0232385 A1 | 12/2003 | Breit et al. |
| 2004/0029770 A1 | 2/2004 | Baek et al. |
| 2004/0053325 A1 | 3/2004 | Breit et al. |
| 2004/0253207 A1 | 12/2004 | Hruska et al. |
| 2006/0148709 A1 | 7/2006 | Unsicker et al. |
| 2006/0253913 A1 | 11/2006 | Huang et al. |
| 2007/0077598 A1 | 4/2007 | Breit et al. |
| 2007/0166310 A1 | 7/2007 | Hudson et al. |
| 2009/0004181 A1 | 1/2009 | Breit et al. |
| 2009/0042780 A1 | 2/2009 | Knopf et al. |
| 2009/0291889 A1 | 11/2009 | Breit et al. |
| 2010/0112692 A1 | 5/2010 | Rezania et al. |
| 2010/0184217 A1 | 7/2010 | Cegilski et al. |
| 2010/0221777 A1 | 9/2010 | Choe et al. |
| 2010/0261284 A1 | 10/2010 | Spanuth |
| 2010/0266707 A1 | 10/2010 | Breit et al. |
| 2010/0278843 A1 | 11/2010 | Breit et al. |
| 2010/0286067 A1 | 11/2010 | De Frees |
| 2011/0033886 A1 | 2/2011 | Hess et al. |
| 2011/0039284 A1 | 2/2011 | Breit et al. |
| 2011/0065204 A1 | 3/2011 | Wollert et al. |
| 2011/0107821 A1 | 5/2011 | Hess et al. |
| 2011/0123454 A1 | 5/2011 | Breit et al. |
| 2011/0257022 A1 | 10/2011 | Hess et al. |
| 2011/0262444 A1 | 10/2011 | Kim et al. |
| 2011/0263443 A1 | 10/2011 | Hess et al. |
| 2011/0300562 A1 | 12/2011 | Lambrecht et al. |
| 2012/0107420 A1 | 5/2012 | Breit et al. |
| 2012/0128624 A1 | 5/2012 | Yu et al. |
| 2012/0309697 A1 | 12/2012 | Breit et al. |
| 2013/0004484 A1 | 1/2013 | Demeule et al. |
| 2013/0071935 A1 | 3/2013 | Bergman et al. |
| 2013/0323835 A1 | 12/2013 | McDonald et al. |
| 2014/0044674 A1 | 2/2014 | Duerner et al. |
| 2014/0086314 A1 | 3/2014 | Breit et al. |
| 2014/0113370 A1 | 4/2014 | Camphausen et al. |
| 2014/0154743 A1 * | 6/2014 | Levy .................... C07K 16/00 |
| | | 435/69.6 |
| 2014/0193427 A1 | 7/2014 | Lerner et al. |
| 2014/0199294 A1 | 7/2014 | Mimoto et al. |
| 2014/0213511 A1 | 7/2014 | Matern et al. |
| 2014/0314711 A1 | 10/2014 | Scheer et al. |
| 2014/0378665 A1 | 12/2014 | Xiong et al. |
| 2015/0023960 A1 | 1/2015 | Lindhout et al. |
| 2015/0307575 A1 | 10/2015 | Xiong et al. |
| 2015/0322081 A1 | 11/2015 | Hoehn |
| 2016/0031960 A1 | 2/2016 | Lindhout et al. |
| 2016/0120999 A1 | 5/2016 | Shen et al. |
| 2016/0129082 A1 | 5/2016 | Matern et al. |
| 2016/0168213 A1 | 6/2016 | Xiong et al. |
| 2016/0193295 A1 * | 7/2016 | Kannan .................. C07K 16/00 |
| | | 530/387.3 |
| 2016/0200787 A1 | 7/2016 | Matern et al. |
| 2017/0246249 A1 | 8/2017 | Lindhout et al. |
| 2017/0291929 A1 | 10/2017 | Xiong et al. |
| 2018/0079790 A1 | 3/2018 | Xiong et al. |
| 2018/0099025 A1 | 4/2018 | Matern et al. |
| 2018/0100003 A1 | 4/2018 | Matern et al. |
| 2018/0134761 A1 | 5/2018 | Lindhout et al. |
| 2018/0237514 A1 | 8/2018 | Shen et al. |
| 2019/0000923 A1 | 1/2019 | Chutkow et al. |
| 2019/0183974 A1 | 6/2019 | Lindhout et al. |
| 2020/0087366 A1 | 3/2020 | Matern et al. |
| 2020/0140536 A1 | 5/2020 | Shen et al. |
| 2020/0165314 A1 | 5/2020 | Lindhout et al. |
| 2021/0388047 A1 | 12/2021 | Matern et al. |

FOREIGN PATENT DOCUMENTS

| | | |
|---|---|---|
| JP | 2003532079 | 10/2003 |
| JP | 2006505617 | 2/2006 |
| JP | 2009539767 | 11/2009 |
| JP | 2014-511863 | 5/2014 |
| JP | 2015506373 | 3/2015 |
| WO | WO 1994/03599 | 2/1994 |
| WO | WO 1996/18730 | 6/1996 |
| WO | WO 1997/00958 | 1/1997 |
| WO | WO 1997/36926 | 10/1997 |
| WO | WO 1998/11224 | 3/1998 |
| WO | WO 1999/06445 | 2/1999 |
| WO | WO 2001/070968 | 9/2001 |
| WO | WO 2001/81928 | 11/2001 |
| WO | WO 2002/092620 | 11/2002 |
| WO | WO 2004/043385 | 5/2004 |
| WO | WO 2005/099746 | 10/2005 |
| WO | WO 2005/113585 | 12/2005 |
| WO | WO 2006/000448 | 1/2006 |
| WO | WO 2006/051288 | 5/2006 |
| WO | WO 2007143161 | 12/2007 |
| WO | WO 2008/013454 | 1/2008 |
| WO | WO 2009/016043 | 2/2009 |
| WO | WO 2009/021293 | 2/2009 |
| WO | WO 2009/046495 | 4/2009 |
| WO | WO 2009/058285 | 5/2009 |
| WO | WO 2009/089004 | 7/2009 |
| WO | WO 2009/141357 | 11/2009 |
| WO | WO 2010/019263 | 2/2010 |
| WO | WO 2010/048670 | 5/2010 |
| WO | WO 2010/093925 | 8/2010 |
| WO | WO 2010/099219 | 9/2010 |
| WO | WO 2010/129503 | 11/2010 |
| WO | WO 2011/005621 | 1/2011 |
| WO | WO 2011/050407 | 5/2011 |
| WO | WO 2011/057120 | 5/2011 |
| WO | WO 2011/064758 | 6/2011 |
| WO | WO 2011/066501 | 6/2011 |
| WO | WO 2011/127458 | 10/2011 |
| WO | WO 2012/025355 | 3/2012 |
| WO | WO 2012/138919 | 10/2012 |
| WO | WO 2013/113008 | 8/2013 |
| WO | WO 2013/148117 | 10/2013 |
| WO | WO 2014/000042 | 1/2014 |
| WO | WO 2014/100689 | 6/2014 |
| WO | WO 2014/120619 | 8/2014 |
| WO | WO 2015/017710 | 2/2015 |
| WO | WO 2016/018931 | 2/2016 |

OTHER PUBLICATIONS

Ulloa-Aguirre et al. (2004, Traffic 5:821-837).*
Bernier et al. (2004, Curr. Opin. Pharmacol. 4:528-533).*
U.S. Appl. No. 14/811,578, 2016/0031960, U.S. Pat. No. 9,834,586, filed Jul. 28, 2015, Darrin Anthony Lindhout.

(56) References Cited

OTHER PUBLICATIONS

U.S. Appl. No. 15/801,198, 2018/0134761, filed Nov. 1, 2017, Darrin Anthony Lindhout.
U.S. Appl. No. 16/784,877, 2020/0165314, filed Feb. 7, 2020, Darrin Anthony Lindhout.
U.S. Appl. No. 14/927,153, 2016/0120999, U.S. Pat. No. 9,920,118, filed Oct. 29, 2015, Wenyan Shen.
U.S. Appl. No. 15/885,438, 2018/0237514, U.S. Pat. No. 10,562,965, filed Jan. 31, 2018, Wenyan Shen.
U.S. Appl. No. 14/373,617, 2015/0023960, U.S. Pat. No. 9,550,819, filed Jul. 21, 2014, Darrin Anthony Lindhout.
U.S. Appl. No. 15/377,679, 2017/0246249, U.S. Pat. No. 10,195,250, filed Dec. 13, 2016, Darrin Anthony Lindhout.
U.S. Appl. No. 16/221,139, 2019/0183974, U.S. Pat. No. 10,869,909, filed Dec. 14, 2018, Darrin Anthony Lindhout.
U.S. Appl. No. 14/763,262, 2016/0200787, U.S. Pat. No. 9,828,415, filed Jul. 24, 2015, Hugo Matern.
U.S. Appl. No. 14/165,391, 2014/0213511, U.S. Pat. No. 9,161,966, filed Jan. 27, 2014, Hugo Matern.
U.S. Appl. No. 14/846,194, 2016/0129082, U.S. Pat. No. 9,827,291, filed Sep. 4, 2015, Hugo Matern.
U.S. Appl. No. 15/789,753, 2018/0099025, U.S. Pat. No. 10,610,568, filed Oct. 20, 2017, Hugo Matern.
U.S. Appl. No. 15/789,679, 2018/0100003, U.S. Pat. No. 10,323,075, filed Oct. 20, 2017, Hugo Matern.
U.S. Appl. No. 16/397,578, 2020/0087366, filed Apr. 29, 2019, Hugo Matern.
Bernier et al., "Pharmacological chaperone action on G-protein-coupled receptors," Curr. Opin. Pharmacol., Oct. 2004, 4(5):528-533.
Ulloa-Aguirre et al., "Pharmacologic rescue of conformationally-defective proteins: implications for the treatment of human disease," Traffic, Nov. 2004, 5(11):821-837.
U.S. Appl. No. 14/373,617, 2015/0023960, U.S. Pat. No. 9,550,819, Jul. 21, 2014, Lindhout.
U.S. Appl. No. 14/763,262, 2016/0200787, filed 9,828,415, filed Jul. 24, 2015, Matern.
U.S. Appl. No. 14/165,391, filed Jan. 27, 2014, Matern et al.
U.S. Appl. No. 14/373,617, filed Mar. 8, 2013, Matern et al.
U.S. Appl. No. 16/397,578, filed Apr. 29, 2019, Matern et al.
Bauskin et al., "The Propeptide Mediates Formation of Stromal Stores of PROMIC-1:" Role in Determining Prostate Cancer Outcome, Cancer Research, 2005, 65(6):2330-2336.
Bauskin et al., "The Propeptide of Macrophage Inhibitory Cytokine (MIC-1 ), a TGF-b Superfamily Member, Acts as a Quality Control Determinant for Correctly Folded MIC-1" EMBO J., 2000, 19:2212-2220.
Bauskin et al., "The TGF-13 superfamily cytokine MIC-1/GDF15: secretory mechanisms facilitate creation of latent stromal stores," Journal of Interferon & Cytokine Research, 2010, 30(6)389-397.
Benjamin et al., "A plasticity window for blood vessel remodel Ing is defined bv pericyte coverage of the preformed endothelial network and is regulated by PDGF-B and VEGF," Development, 1998, 125(9):1591-1598.
Bootcov et al., "MIC-1, a novel macrophage inhibitory cytokine, is a divergent member of the TGF-beta superfamily" Proc. Natl. Acad. Sci. USA, 1997, 94:11514-11519.
Bottner et al., "Characterization of the rat, mouse, and human genes of growth/differentiation factor-15/macrophage inhibiting cytokine-1 (G DF-15/MIC-1)," Gene, 1999, 237:105-111.
Breit et al., "The TGF-beta superfamily cytokine, MIC-1/GDF15: a pleotrophic cytokine with roles in inflammation, cancer and metabolism" Growth Factors, 2011, 29(5):187-95.
Chen et al., "Substitution of asparagine residues in Aspergillus awamori glucoamylase by site-directed mutagenesis to eliminate N-glycosylation and inactivation by deamidation" Biochem J., 1994, 301:275-81.
Clee et al., "The Genetic Landscape of Type 2 Diabetes in Mice", Endocrine Reviews, 2007, 28(1):48-83.

CTDbase.org [online], "Glucose Metabolism Disorders," Aug. 1, 2019, [retrieved on Aug. 23, 2019], retrieved from: URL: <http://ctdbase.org/detail.go?type=disease&acc=MESH%3AD044882>, 1 page.
Dostalova et al., "Increased serum concentrations of macrophage inhibitory cytokine-1 in patients with obesity and type 2 diabetes mellitus: the influence of very low calorie diet", Eur. J. Endocrinol., 2009, 161:397-404.
Ehses et al., "Increased Number of Islet-Associated Macrophages in Type 2 Diabetes", Diabetes, 2007, 56:2356-2370.
Fairlie et al., "Epitope Mapping of the Transforming Growth Factor-b Superfamily Protein, Macrophage Inhibitory Cytokine-1 (MIC-1): Identification of at Least Five Distinct Epitope Specificities" Biochem, 2001, 40:65-73.
Fairlie et al., "Expression of a TGF-13 superfamily protein, macrophage inhibitory cytokine-1, in the yeast *Pichia pastoris*" Gene, 2000, 254:67-76.
Fairlie et al., "The Propeptide of the Transforming Growth Factor-[beta] Superfamily Member, Macrophage Inhibitory Cytokine-1 (MIC-1), Is a Multifunctional Domain That Can Facilitate Protein Folding and Secretion", Priority Journal of Biological Chemistry May 18, 2001 American Society for Biochemistry and Molecular Biology Inc., 2001, 276(20):16911-16918.
Friedman et al., "Degradation of growth hormone releasing factor analogs in neutral aqueous solution is related to deamidation of asparagine residues" Int. J. Peptide Protein Res., 1991, 37:14-20.
Hamann et al., "Regulation of energy balance by leptin" Exp Endocrinol Diabetes, 1996, 104:293-200.
Hromas et al., "PLAB, a novel placental bone morphogenetic protein" Biochim, Biophys. Acta. 1997, 1354:40-4.
Johnen et al., "Tumor-induced anorexia and weight loss are mediated by the TGF-b superfamily cytokine MIC-1", Nature Medicine, 2007, 13(11):1333-1340.
JP Office Action in Japanese Appln. No. 2016-576027, dated Apr. 23, 2020, 2 pages (English translation).
Lajer et al., "Plasma growth differentiation factor-15 independently predicts allcause and cardiovascular mortality as well as deterioration of kidney function in type 1 diabetic patients with nephropathy", Diabetes Care, 2010, 33(7):1567-1572.
Lind et al., "Growth-differentiation factor-15 is an independent marker of cardiovascular dysfunction and disease in the elderly: results from the Prospective Investigation of the Vasculature in Uppsala Seniors (PIVUS) Study", European Heart Journal, 2009, 30(19),2346-2353.
Lingvay et al., "Effect of Insulin Glargine Up-titration vs Insulin Degludec/Liraglutide on Glycated Hemoglobin Levels in Patients with Uncontrolled Type 2 Diabetes", JAMA, 2016, 315(9):898-907.
Liu et al., "Enhancing the Secretion of Recombinant Proteins by Engineering N-Glycosylation Sites", Biotechnol. Prag., 2009, 25(5):1468-1475.
Macia et al., "Macrophage Inhibitory Cytokine 1 (MIC-1/GDF15) Decreases Food Intake, Body Weight and Improves Glucose Tolerance in Mice on Normal & Obesogenic Diets", PLoS ONE, 2012, 7(4):1-8.
Massague, "The TGF-beta Family of Growth and Differentiation Factors", Cell, 1987, 49:437-8.
Neto et al., "Interleukin-22 Forms Dimers that are Recognized by Two Interleukin-22R1 Receptor Chains" Biophysical Journal, 2008, 94:1754-1765.
Ngo et al., "Computational Complexity Protein Structure Prediction, and Levinthal Paradox", The Protein Folding Problem and Tertiary Structure Prediction, Birkhauser, Boston, 1994, 492-495.
Paralkar et al., "Cloning and characterization of a novel member of the transforming growth factor[beta]/bone morphogenetic protein family" J. Biol. Chem. 1998, 273:13760-13767.
PCT International Preliminary Report on Patentability in International Appln. No. PCT/US2013/029955, dated Oct. 1, 2014, 8 pages.
PCT International Preliminary Report on Patentability in International Appln. No. PCT/US2014/013232, dated Aug. 4, 2015, 8 pages.

(56) References Cited

OTHER PUBLICATIONS

PCT International Preliminary Report on Patentability in International Appln. No. PCT/US2015/058111, dated May 2, 2017, 9 pages.
PCT International Preliminary Report on Patentability in International Appln. No. PCT/US2015/42510, dated Jan. 31, 2017, 8 pages.
PCT International Search Report and Written Opinion in International Appln. No. PCT/US2013/029955, dated May 31, 2013, 11 pages.
PCT International Search Report and Written Opinion in International Appln. No. PCT/US2014/013232, dated Jul. 9, 2014, 13 pages.
PCT International Search Report and Written Opinion in International Appln. No. PCT/US2015/058111, dated Jan. 11, 2016, 12 pages.
PCT International Search Report and Written Opinion in International Appln. No. PCT/US2015/42510, dated Jan. 4, 2016, 12 pages.
Ridgway et al., "'Knobs-into-holes' Engineering of Antibody CH3 Domains for Heavy Chain Heterodimerization." Protein Engineering, Oxford University Press, Jan. 1996, 9(7):617-621.
Robinson et al., "Prediction of primary structure deamidation rates of asparaginyl and glutaminyl peptides through steric and catalytic effects" J. Pepide Res., 2004, 63:437-448.
SG Office Action in Singapore Appln. No. 11201702580P, dated Jan. 9, 2020, 3 pages.
Shen et al., "Bone morphogenetic proteins regulate ionotropic glutamate receptors in human retina" Eur. J. Neurosci., 2004, 20:2031-2037.
Sinobiological.com [online] "GDF15 Protein, Human, Recombinant (Fc Tag)," May 1, 2010, retrieved on Oct. 14, 2019, retrieved from URL http://www.sinobiological.com/GDF-15-Protein-g-570.html, 4 pages.
Soler et al., "New Experimental Models of Diabetic Nephropathy in Mice Models of Type2 Diabetes: Efforts to Replicate Human Nephropathy" Experimental Diabetes Research,, 2012, 2012:1-9.
Tokuriki et al., "Stability effects of mutations and protein evolvability," Curr. Opin. Struc. Biol., 2009, 19:596-604.
Vila et al., "The Relationship between Insulin Resistance and the Cardiovascular Bio marker Growth Differentiation Factor-15 in Obese Patients", Clinical Chemistry, 2011, 57(2):309-316.
Vukicevic et al., "Induction of nephrogenic mesenchyme by osteogenic protein 1 (bone morphogenetic protein 7)" PNAS, 1996, 93:9021-9026.
Wells, "Additivity of Mutational Effects in Proteins", Biochemistry, 1990, 29(37):8509-8517.
Welsh et al., "Large-scale delineation of secreted protein biomarkers overexpressed in cancer tissue and serum," PNAS, 2003, 100(6):3410-3415.
Yokoyama-Kobayashi et al., "Human cDNA encoding a novel TGF-beta superfamily protein highly expressed in placenta" J. Biochem, 1997, 122:622-626.
Griner et al., "Growth Differentiation Factor 15 Stimulates Rapamycin-Sensitive Ovarian Cancer Cell Growth and Invasion," Biochemical Pharmacology, 2013, 85(1):46-58.
Guoqiang et al., "Correlation between serum GDF-15 expression level and coronary heart disease," Modern Preventive Medicine, 2012, 39(20):5380-3.
Li Minjun et al., "Construction and Identification of iGG Fc-Segment Fusion Gene Vaccine in Intracellular Regions Associated with Islet Cell Tumors," Chinese Journal of Clinical Rehabilitation, 2006, pp. 80-83.
U.S. Appl. No. 15/377,679, 2017/0946249, U.S. Pat. No. 10,195,250, filed Dec. 13, 2016, Lindhout.
U.S. Appl. No. 16/221,139, 2019/0183974, filed Dec. 14, 2018, Lindhout.
U.S. Appl. No. 16/397,578, 2020/0087366, filed Apr. 29, 2019, Matern.
GenBank Accession No. AAC39537.1, "prepro placental TGF-beta [*Homo sapiens*]," Jun. 12, 2006, 1 page.
U.S. Appl. No. 14/811,578, 2016/0031960, U.S. Pat. No. 9,834,586, filed Jul. 28, 2015, Lindhout.
U.S. Appl. No. 15/801,198, 2018/0134761, filed Nov. 1, 2017, Lindhout.
U.S. Appl. No. 16/784,877, 2020/0165314, filed Feb. 7, 2020, Lindhout.
U.S. Appl. No. 14/927,153, 2016/0120999, U.S. Pat. No. 9,920,118, filed Oct. 29, 2015, Shen.
U.S. Appl. No. 15/885,438, 2018/0237514, U.S. Pat. No. 10,562,965, filed Jan. 31, 2018, Shen.
U.S. Appl. No. 14/373,617, 2015/0023960, U.S. Pat. No. 9,550,819, filed Jul. 21, 2014, Lindhout.
U.S. Appl. No. 15/377,679, 2017/0246249, U.S. Pat. No. 10,195,250, filed Dec. 13, 2016, Lindhout.
U.S. Appl. No. 16/221,139, 2019/0183974, U.S. Pat. No. 10,869,909, filed Dec. 14, 2018, Lindhout.
U.S. Appl. No. 14/763,262, 2016/0200787, U.S. Pat. No. 9,828,415, filed Jul. 24, 2015, Matern.
U.S. Appl. No. 14/165,391, 2014/0213511, U.S. Pat. No. 9,161,966, filed Jan. 27, 2014, Matern.
U.S. Appl. No. 14/846,194, 2016/0129082, U.S. Pat. No. 9,827,291, filed Sep. 4, 2015, Matern.
U.S. Appl. No. 15/789,753, 2018/0099025, U.S. pat. No. 10,610,568, filed Oct. 20, 2017, Matern.
U.S. Appl. No. 15/789,679, 2018/0100003, U.S. Pat. No. 10,323,075, filed Oct. 20, 2017, Matern.
U.S. Appl. No. 16/397,578, 2018/0087366, filed Apr. 29, 2019, Matern.
U.S. Appl. No. 17/330,984, 2021/0388047, filed May 26, 2021, Matern.

\* cited by examiner

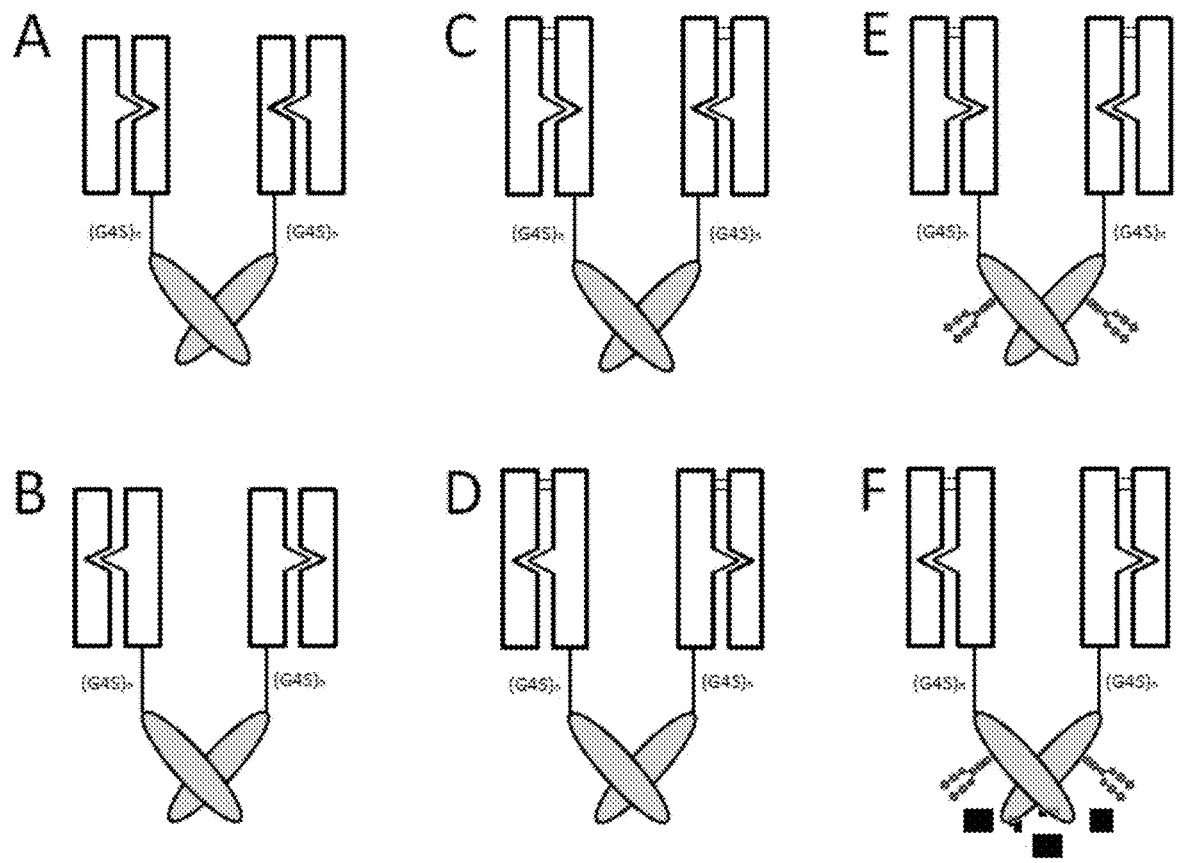
Figure 1 – Designs of knob-in-hole (Fc/Fc)-GDF15 molecules

Figure 2A – Recoveries of engineered knob-in-hole (Fc/Fc)-GDF15 molecules

| Fc-GDF15 chain A | Fc heterodimer (knob/hole) partner chain B | Variant number | GDF15 mutein (glycosylated) | Recovery (mg/L) |
|---|---|---|---|---|
| hIgG1-Fc(AA)(T366Y)-(G4S)5-ΔN3-GDF15 (G4-I112) | hIgG1-Fc(AA)(Y407T) | B1a/B1b | NO | <25 |
| hIgG1-Fc(AA)(Y407T)-(G4S)5-ΔN3-GDF15 (G4-I112) | hIgG1-Fc(AA)(T366Y) | B2a/B2b | NO | 25-49.9 |
| hIgG1-Fc(Δhinge, AA)(T366Y)-(G4S)5-ΔN3-GDF15 (G4-I112) | hIgG1-Fc(Δhinge, AA)(Y407T) | B3a/B3b | NO | 50-74.9 |
| hIgG1-Fc(Δhinge, AA)(Y407T)-(G4S)5-ΔN3-GDF15 (G4-I112) | hIgG1-Fc(Δhinge, AA)(T366Y) | B4a/B4b | NO | <25 |
| hIgG1-Fc(AA)(T366W)-(G4S)5-ΔN3-GDF15 (G4-I112) | hIgG1-Fc(AA)(T366S,L368A,Y407V) | B5a/B5b | NO | <25 |
| hIgG1-Fc(AA)(T366S,L368A,Y407V)-(G4S)5-ΔN6-GDF15 (C7-I112) | hIgG1-Fc(AA)(T366W) | B6a/B6b | NO | <25 |
| hIgG1-Fc(Δhinge, AA)(T366S,L368A,Y407V)-(G4S)5-ΔN3-GDF15 (G4-I112) | hIgG1-Fc(Δhinge, AA)(T366W) | B7a/B7b | NO | 25-49.9 |
| hIgG1-Fc(Δhinge, AA)(T366S,L368A,Y407V)-(G4S)5-ΔN6-GDF15(C7-I112) | hIgG1-Fc(Δhinge, AA)(T366W) | B8a/B8b | NO | N/A |
| hIgG1-Fc(AA)(T366W)-(G4S)3-GDF15 (A1-I112) | hIgG1-Fc(AA)(T366S,L368A,Y407V) | B9a/B9b | YES | >100 |
| hIgG1-Fc(AA)(T366W)-(G4S)4-GDF15 (A1-I112) (D5T) | hIgG1-Fc(AA)(T366S,L368A,Y407V) | B10a/B10b | YES | >100 |
| hIgG1-Fc(AA)(T366W)-(G4S)5-GDF15 (A1-I112) (D5T) | hIgG1-Fc(AA)(T366S,L368A,Y407V) | B11a/B11b | YES | >100 |
| hIgG1-Fc(AA)(T366W)-(G4S)2-ΔN2-GDF15 (N3-I112) (D5T) | hIgG1-Fc(AA)(T366S,L368A,Y407V) | B12a/B12b | YES | 75-99 |
| hIgG1-Fc(AA)(T366W)-(G4S)5-ΔN2-GDF15 (N3-I112) (D5T) | hIgG1-Fc(AA)(T366S,L368A,Y407V) | B13a/B13b | YES | >100 |
| hIgG1-Fc(AA)(T366W)-(G4S)5-ΔN3-GDF15 (G4-I112)(R21N) | hIgG1-Fc(AA)(T366S,L368A,Y407V) | B14a/B14b | YES | 75-99 |
| hIgG1-Fc(AA)(T366W)-(G4S)5-ΔN3-GDF15 (G4-I112)(S23N/E25T) | hIgG1-Fc(AA)(T366S,L368A,Y407V) | B15a/B15b | YES | 75-99 |
| hIgG1-Fc(AA)(T366W)-(G4S)5-ΔN3-GDF15 (G4-I112)(F52N/A54T) | hIgG1-Fc(AA)(T366S,L368A,Y407V) | B16a/B16b | YES | >100 |
| hIgG1-Fc(AA)(T366W)-(G4S)5-ΔN3-GDF15 (G4-I112)(R53N/A55T) | hIgG1-Fc(AA)(T366S,L368A,Y407V) | B17a/B17b | YES | 75-99 |
| hIgG1-Fc(AA)(T366W)-(G4S)5-ΔN3-GDF15 (G4-I112)(K91N/D93T) | hIgG1-Fc(AA)(T366S,L368A,Y407V) | B18a/B18b | YES | 75-99 |
| hIgG1-Fc(AA)(T366W)-(G4S)5-ΔN3-GDF15 (G4-I112)(D93N/G95T) | hIgG1-Fc(AA)(T366S,L368A,Y407V) | B19a/B19b | YES | 50-74.9 |

Figure 2B – Recoveries of GDF15 glycomuteins

| Glycovariant | Recovery (mg/L) |
|---|---|
| hGDF15 wild-type | < 0.99 |
| R21N | < 0.99 |
| R53N/A55T | 4 - 7.99 |
| S64N/H66T | 16 - 31.99 |
| P70N | 2 - 3.99 |
| Q90N | 4 - 7.99 |
| K91N/D93T | 16 - 31.99 |
| D93N/G95T | 8 - 15.99 |
| G95N | 8 - 15.99 |
| S97N/Q99T | 8 - 15.99 |
| L98N | 4 - 7.99 |

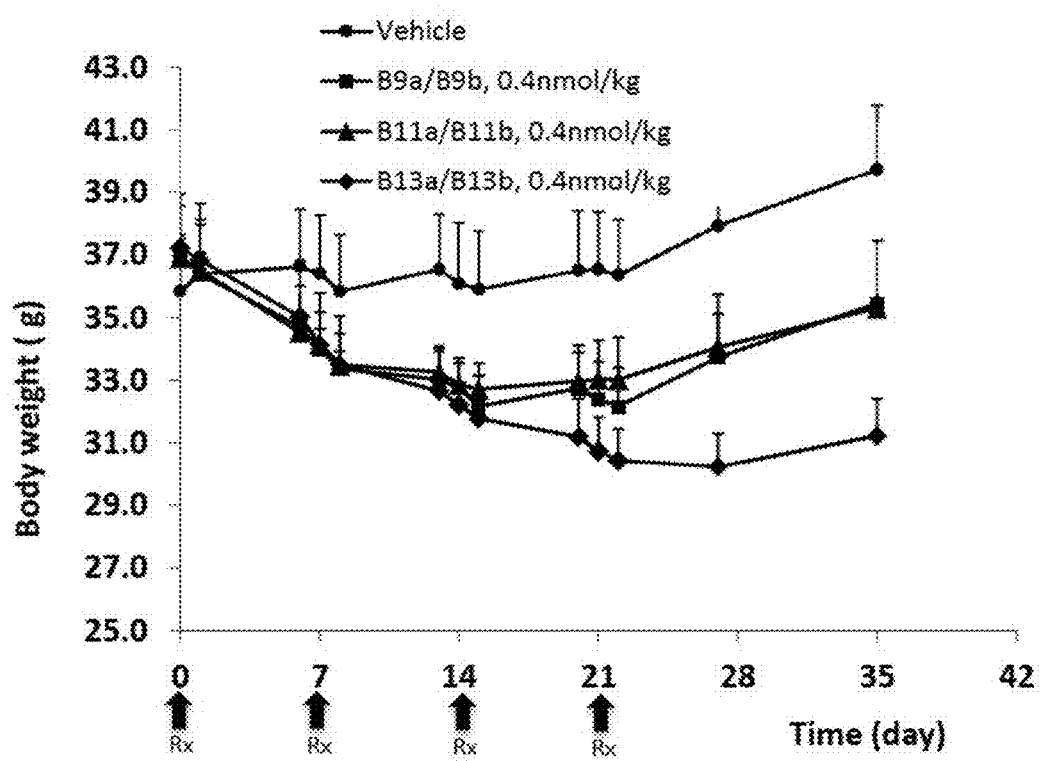
Figure 3 – Reduction of body weight in DIO mouse model upon delivery of 0.4nmol/kg of (Fc/Fc)-GDF15 molecules

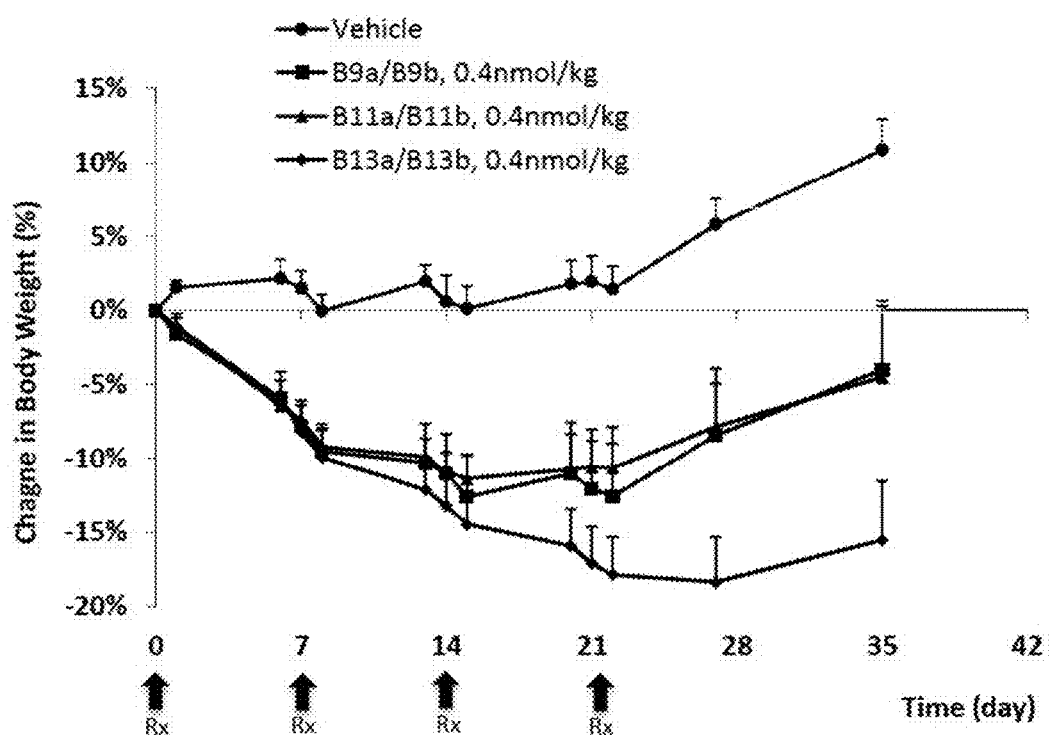
Figure 4 – Percent body weight Reduction in DIO mouse model upon delivery of 0.4nmol/kg of (Fc/Fc)-GDF15 molecules

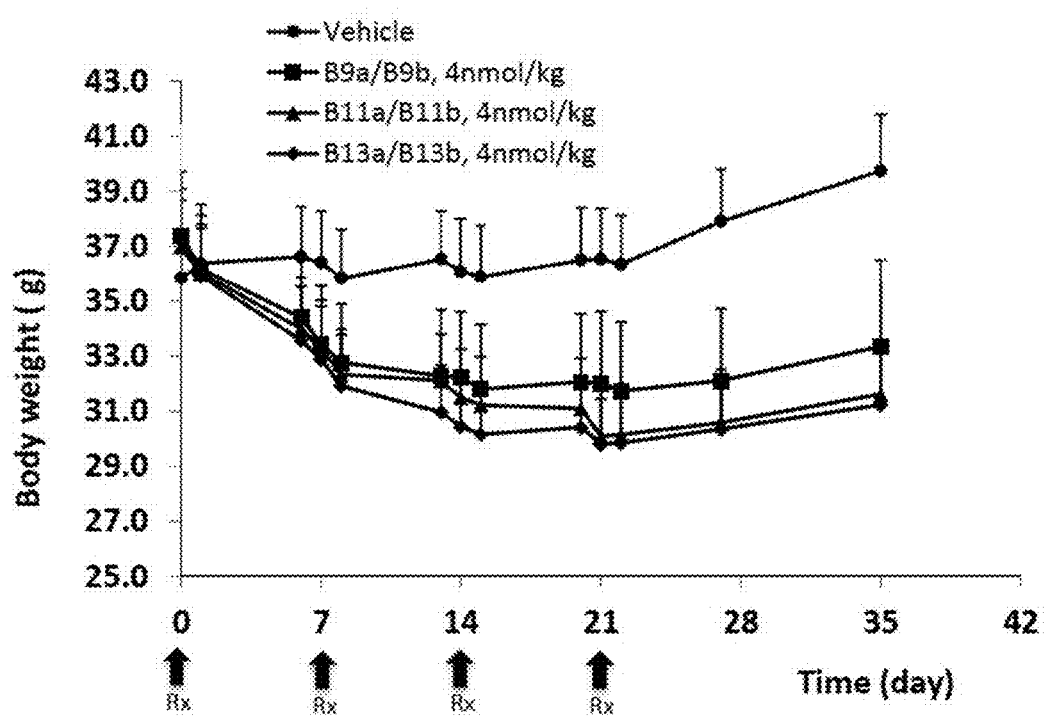
Figure 5 - Reduction of body weight in DIO mouse model upon delivery of 4.0nmol/kg of (Fc/Fc)-GDF15 molecules

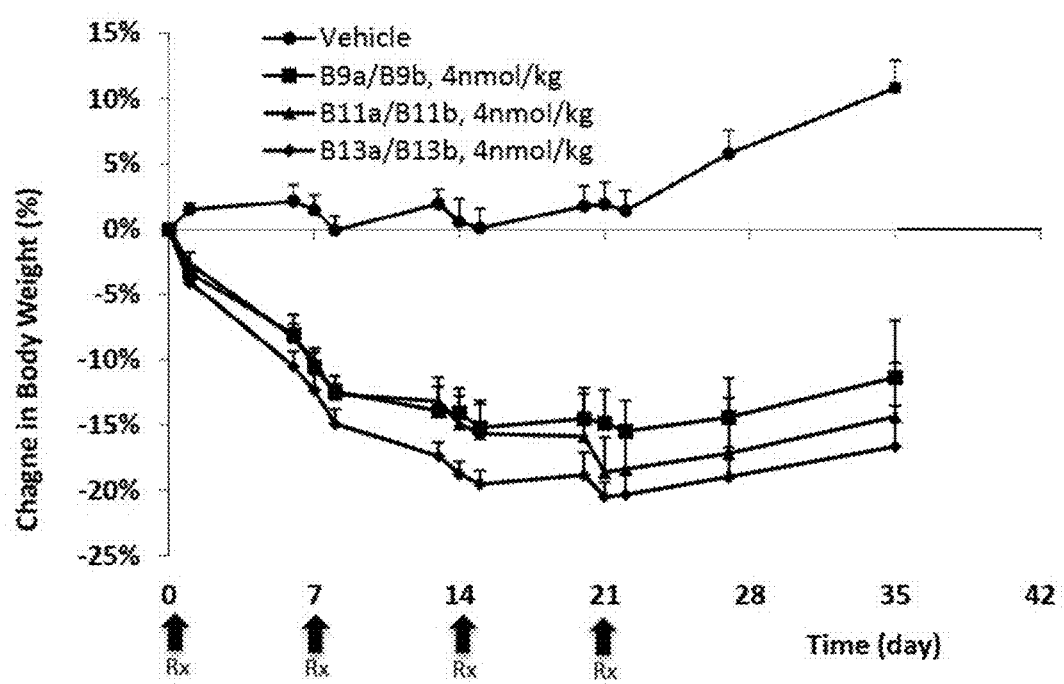
Figure 6 – Percent body weight Reduction in DIO mouse model upon delivery of 4.0nmol/kg of (Fc/Fc)-GDF15 molecules Figure 7 – Body weight (g) in DIO mouse for each time point for 0.4nmol/kg and 4.0nmol/kg of (Fc/Fc)-GDF15 molecules

|  | D 0 | D1 | D6 | D7 | D8 | D13 | D14 | D15 | D20 | D21 | D22 | D27 | D35 |
|---|---|---|---|---|---|---|---|---|---|---|---|---|---|
| Vehicle | 35.9 | 36.4 | 36.6 | 36.4 | 35.9 | 36.6 | 36.1 | 35.9 | 36.5 | 36.6 | 36.4 | 37.9 | 39.8 |
| B9a/B9b 0.4nmol/kg | 37.0 | 36.4 | 34.7 | 34.0 | 33.4 | 33.0 | 32.8 | 32.2 | 32.7 | 32.4 | 32.2 | 33.7 | 35.5 |
| B9a/B9b 4nmol/kg | 37.4 | 36.2 | 34.4 | 33.5 | 32.8 | 32.3 | 32.2 | 31.8 | 32.1 | 32.0 | 31.7 | 32.1 | 33.4 |
| B11a/B11b 0.4nmol/kg | 36.9 | 36.5 | 34.5 | 34.2 | 33.5 | 33.3 | 32.9 | 32.7 | 33.0 | 33.0 | 33.0 | 34.1 | 35.3 |
| B11a/B11b 4nmol/kg | 37.0 | 36.0 | 34.0 | 33.3 | 32.3 | 32.1 | 31.5 | 31.2 | 31.1 | 30.1 | 30.2 | 30.6 | 31.6 |
| B13a/B13b 0.4nmol/kg | 37.2 | 36.8 | 35.0 | 34.2 | 33.5 | 32.7 | 32.2 | 31.8 | 31.2 | 30.7 | 30.4 | 30.2 | 31.2 |
| B13a/B13b 4nmol/kg | 37.4 | 35.9 | 33.6 | 32.9 | 31.9 | 31.0 | 30.5 | 30.2 | 30.4 | 29.8 | 29.9 | 30.4 | 31.2 |

| sem | D 0 | D1 | D6 | D7 | D8 | D13 | D14 | D15 | D20 | D21 | D22 | D27 | D35 |
|---|---|---|---|---|---|---|---|---|---|---|---|---|---|
| Vehicle | 1.77 | 1.72 | 1.81 | 1.87 | 1.78 | 1.74 | 1.92 | 1.84 | 1.89 | 1.82 | 1.76 | 1.87 | 2.04 |
| B9a/B9b 0.4nmol/kg | 1.58 | 1.58 | 1.30 | 1.17 | 1.13 | 0.91 | 0.93 | 0.99 | 1.16 | 1.21 | 1.23 | 1.39 | 2.01 |
| B9a/B9b 4nmol/kg | 2.32 | 2.35 | 2.27 | 2.12 | 2.14 | 2.39 | 2.37 | 2.35 | 2.47 | 2.63 | 2.51 | 2.61 | 3.15 |
| B11a/B11b 0.4nmol/kg | 0.59 | 0.58 | 0.52 | 0.47 | 0.45 | 0.77 | 0.69 | 0.82 | 1.15 | 1.23 | 1.35 | 1.69 | 2.15 |
| B11a/B11b 4nmol/kg | 1.70 | 1.78 | 1.89 | 1.76 | 1.65 | 1.69 | 1.76 | 1.76 | 1.81 | 1.72 | 1.68 | 1.93 | 1.87 |
| B13a/B13b 0.4nmol/kg | 1.69 | 1.80 | 1.81 | 1.64 | 1.55 | 1.44 | 1.33 | 1.36 | 1.21 | 1.09 | 1.02 | 1.07 | 1.17 |
| B13a/B13b 4nmol/kg | 1.70 | 1.75 | 1.96 | 1.94 | 1.87 | 1.70 | 1.66 | 1.69 | 1.71 | 1.64 | 1.63 | 1.71 | 1.97 |

Figure 8- Total body weight change (g) in DIO mouse model for each time point for 0.4nmol/kg and 4.0nmol/kg of (Fc/Fc)-GDF15 molecules

|  | D 0 | D1 | D6 | D7 | D8 | D13 | D14 | D15 | D20 | D21 | D22 | D27 | D35 |
|---|---|---|---|---|---|---|---|---|---|---|---|---|---|
| Vehicle | 0.0 | 0.5 | 0.8 | 0.5 | 0.0 | 0.7 | 0.2 | 0.0 | 0.6 | 0.7 | 0.5 | 2.1 | 3.9 |
| B9a/B9b 0.4nmol/kg | 0.0 | -0.6 | -2.3 | -3.0 | -3.6 | -4.0 | -4.2 | -4.8 | -4.3 | -4.6 | -4.8 | -3.3 | -1.5 |
| B9a/B9b 4nmol/kg | 0.0 | -1.2 | -3.0 | -4.0 | -4.6 | -5.1 | -5.2 | -5.6 | -5.3 | -5.4 | -5.7 | -5.3 | -4.1 |
| B11a/B11b 0.4nmol/kg | 0.0 | -0.4 | -2.4 | -2.8 | -3.4 | -3.7 | -4.1 | -4.2 | -4.0 | -3.9 | -3.9 | -2.9 | -1.6 |
| B11a/B11b 4nmol/kg | 0.0 | -1.0 | -3.0 | -3.7 | -4.7 | -4.9 | -5.5 | -5.8 | -5.9 | -6.9 | -6.8 | -6.4 | -5.4 |
| B13a/B13b 0.4nmol/kg | 0.0 | -0.4 | -2.2 | -3.1 | -3.7 | -4.6 | -5.0 | -5.5 | -6.0 | -6.5 | -6.8 | -7.0 | -6.0 |
| B13a/B13b 4nmol/kg | 0.0 | -1.5 | -3.9 | -4.5 | -5.5 | -6.5 | -7.0 | -7.3 | -7.0 | -7.6 | -7.6 | -7.1 | -6.2 |

| sem | D 0 | D1 | D6 | D7 | D8 | D13 | D14 | D15 | D20 | D21 | D22 | D27 | D35 |
|---|---|---|---|---|---|---|---|---|---|---|---|---|---|
| Vehicle | 0.00 | 0.16 | 0.43 | 0.38 | 0.37 | 0.38 | 0.60 | 0.50 | 0.53 | 0.59 | 0.53 | 0.61 | 0.77 |
| B9a/B9b 0.4nmol/kg | 0.00 | 0.21 | 0.48 | 0.59 | 0.75 | 1.06 | 1.08 | 1.14 | 1.38 | 1.30 | 1.44 | 1.31 | 1.54 |
| B9a/B9b 4nmol/kg | 0.00 | 0.17 | 0.53 | 0.47 | 0.46 | 0.58 | 0.58 | 0.68 | 0.79 | 0.80 | 0.76 | 1.02 | 1.51 |
| B11a/B11b 0.4nmol/kg | 0.00 | 0.22 | 0.35 | 0.52 | 0.47 | 0.45 | 0.50 | 0.60 | 0.86 | 0.91 | 0.99 | 1.43 | 1.88 |
| B11a/B11b 4nmol/kg | 0.00 | 0.30 | 0.31 | 0.34 | 0.26 | 0.69 | 0.77 | 0.82 | 1.22 | 1.03 | 1.22 | 1.60 | 1.58 |
| B13a/B13b 0.4nmol/kg | 0.00 | 0.34 | 0.65 | 0.84 | 0.80 | 0.92 | 1.01 | 0.91 | 1.07 | 1.12 | 1.16 | 1.31 | 1.62 |
| B13a/B13b 4nmol/kg | 0.00 | 0.13 | 0.34 | 0.37 | 0.29 | 0.31 | 0.29 | 0.31 | 0.62 | 0.36 | 0.57 | 0.83 | 1.13 |

| Unpaired t-test | D 0 | D1 | D6 | D7 | D8 | D13 | D14 | D15 | D20 | D21 | D22 | D27 | D35 |
|---|---|---|---|---|---|---|---|---|---|---|---|---|---|
| Vehicle | | | | | | | | | | | | | |
| B9a/B9b 0.4nmol/kg | | ** | *** | *** | ** | ** | ** | ** | ** | ** | ** | ** | * |
| B9a/B9b 4nmol/kg | | *** | *** | *** | *** | *** | *** | *** | *** | *** | *** | *** | *** |
| B11a/B11b 0.4nmol/kg | | ** | *** | *** | *** | *** | *** | *** | ** | ** | ** | ** | * |
| B11a/B11b 4nmol/kg | | ** | *** | *** | *** | *** | *** | *** | *** | *** | *** | *** | *** |
| B13a/B13b 0.4nmol/kg | | * | ** | ** | ** | *** | ** | *** | *** | *** | *** | *** | *** |
| B13a/B13b 4nmol/kg | | *** | *** | *** | *** | *** | *** | *** | *** | *** | *** | *** | *** |

Figure 9 - Percent Body weight reduction (%) in DIO mouse for each time point for 0.4nmol/kg and 4.0nmol/kg of (Fc/Fc)-GDF15 molecules

|  | D0 | D1 | D6 | D7 | D8 | D13 | D14 | D15 | D20 | D21 | D22 | D27 | D35 |
|---|---|---|---|---|---|---|---|---|---|---|---|---|---|
| Vehicle | 0.0% | 1.5% | 2.2% | 1.5% | 0.0% | 2.0% | 0.6% | 0.1% | 1.8% | 1.9% | 1.4% | 5.8% | 10.8% |
| B9a/B9b 0.4nmol/kg | 0.0% | -1.6% | -6.0% | -7.9% | -9.5% | -10.3% | -11.0% | -12.6% | -11.0% | -12.1% | -12.6% | -8.4% | -4.0% |
| B9a/B9b 4nmol/kg | 0.0% | -3.3% | -8.1% | -10.6% | -12.4% | -13.9% | -14.1% | -15.2% | -14.5% | -14.8% | -15.5% | -14.4% | -11.4% |
| B11a/B11b 0.4nmol/kg | 0.0% | -1.1% | -6.4% | -7.4% | -9.2% | -9.9% | -11.0% | -11.4% | -10.8% | -10.6% | -10.7% | -7.9% | -4.5% |
| B11a/B11b 4nmol/kg | 0.0% | -2.6% | -8.3% | -10.2% | -12.6% | -13.2% | -14.9% | -15.6% | -15.9% | -18.6% | -18.4% | -17.2% | -14.4% |
| B13a/B13b 0.4nmol/kg | 0.0% | -1.1% | -6.0% | -8.2% | -9.9% | -12.2% | -13.2% | -14.5% | -15.9% | -17.1% | -17.9% | -18.4% | -15.5% |
| B13a/B13b 4nmol/kg | 0.0% | -4.1% | -10.5% | -12.3% | -14.9% | -17.4% | -18.8% | -19.5% | -18.8% | -20.5% | -20.3% | -19.0% | -16.7% |

| sem | D0 | D1 | D6 | D7 | D8 | D13 | D14 | D15 | D20 | D21 | D22 | D27 | D35 |
|---|---|---|---|---|---|---|---|---|---|---|---|---|---|
| Vehicle | 0.00% | 0.48% | 1.27% | 1.14% | 1.10% | 1.10% | 1.77% | 1.48% | 1.56% | 1.69% | 1.52% | 1.77% | 2.09% |
| B9a/B9b 0.4nmol/kg | 0.00% | 0.60% | 1.25% | 1.45% | 1.86% | 2.65% | 2.63% | 2.77% | 3.46% | 3.24% | 3.58% | 3.49% | 4.29% |
| B9a/B9b 4nmol/kg | 0.00% | 0.58% | 1.53% | 1.13% | 1.19% | 1.85% | 1.86% | 2.09% | 2.36% | 2.52% | 2.35% | 3.01% | 4.37% |
| B11a/B11b 0.4nmol/kg | 0.00% | 0.59% | 0.89% | 1.29% | 1.16% | 1.23% | 1.32% | 1.63% | 2.38% | 2.54% | 2.77% | 3.94% | 5.16% |
| B11a/B11b 4nmol/kg | 0.00% | 0.86% | 1.00% | 1.00% | 0.76% | 1.83% | 2.09% | 2.25% | 3.23% | 2.68% | 3.13% | 4.24% | 4.09% |
| B13a/B13b 0.4nmol/kg | 0.00% | 0.92% | 1.82% | 2.12% | 1.98% | 2.22% | 2.35% | 2.14% | 2.46% | 2.46% | 2.55% | 3.04% | 3.97% |
| B13a/B13b 4nmol/kg | 0.00% | 0.44% | 1.15% | 1.22% | 1.11% | 1.03% | 0.96% | 1.04% | 1.72% | 1.13% | 1.57% | 2.24% | 3.15% |

Unpaired t-test

|  | D0 | D1 | D6 | D7 | D8 | D13 | D14 | D15 | D20 | D21 | D22 | D27 | D35 |
|---|---|---|---|---|---|---|---|---|---|---|---|---|---|
| Vehicle |  |  |  |  |  |  |  |  |  |  |  |  |  |
| B9a/B9b 0.4nmol/kg |  | ** | *** | *** | ** | ** | ** | ** | ** | ** | ** | ** | * |
| B9a/B9b 4nmol/kg |  | *** | *** | *** | *** | *** | *** | *** | *** | *** | *** | *** | *** |
| B11a/B11b 0.4nmol/kg |  | ** | *** | *** | *** | *** | *** | *** | *** | *** | ** | * | * |
| B11a/B11b 4nmol/kg |  | ** | *** | *** | *** | *** | *** | *** | *** | *** | *** | *** | *** |
| B13a/B13b 0.4nmol/kg |  | * | ** | ** | ** | *** | *** | *** | *** | *** | *** | *** | *** |
| B13a/B13b 4nmol/kg |  | *** | *** | *** | *** | *** | *** | *** | *** | *** | *** | *** | *** |

COMPOSITIONS AND METHODS OF USE FOR TREATING METABOLIC DISORDERS

CROSS-REFERENCE TO RELATED APPLICATIONS

This application is a continuation of U.S. patent application Ser. No. 15/885,438, filed Jan. 31, 2018, now issued as U.S. Pat. No. 10,562,965, which is a continuation of U.S. patent application Ser. No. 14/927,153, filed Oct. 29, 2015, now issued as U.S. Pat. No. 9,920,118, which claims priority benefit of U.S. provisional application No. 62/073,737, filed on Oct. 31, 2014 and U.S. provisional application No. 62/244,604 filed on Oct. 21, 2015, which applications are incorporated herein by reference in their entirety.

INCORPORATION BY REFERENCE OF SEQUENCE LISTING

A Sequence Listing is provided herewith as a text file, "NGMB-142_SeqList.txt" created on Oct. 28, 2015 and having a size of 192,512 bytes. The contents of the text file are incorporated by reference herein in their entirety.

FIELD OF THE INVENTION

The present invention relates to, among other things, polypeptide complex and compositions thereof which are useful in treating metabolism related conditions.

INTRODUCTION

Obesity is most commonly caused by excessive food intake coupled with limited energy expenditure and/or lack of physical exercise. Obesity increases the likelihood of development of various diseases, such as diabetes mellitus, hypertension, atherosclerosis, coronary artery disease, sleep apnea, gout, rheumatism and arthritis. Moreover, mortality risk directly correlates with obesity, such that, for example, a body-mass index in excess of 40 results in an average decreased life expectancy of more than 10 years.

Current pharmacological treatment modalities include appetite suppressors targeting receptor classes (e.g., CB1, 5-$HT_{2C}$, and NPY); regulators of the appetite circuits in the hypothalamus and the molecular actions of ghrelin; and nutrient-absorption inhibitors targeting lipases. Unfortunately, none of the current modalities has been shown to effectively treat obesity without causing adverse effects, some of which can be very severe.

High blood glucose levels stimulate the secretion of insulin by pancreatic beta-cells. Insulin in turn stimulates the entry of glucose into muscles and adipose cells, leading to the storage of glycogen and triglycerides and to the synthesis of proteins. Activation of insulin receptors on various cell types diminishes circulating glucose levels by increasing glucose uptake and utilization, and by reducing hepatic glucose output. Disruptions within this regulatory network can result in diabetes and associated pathologic syndromes that affect a large and growing percentage of the human population.

Patients who have a glucose metabolism disorder can suffer from hyperglycemia, hyperinsulinemia, and/or glucose intolerance. An example of a disorder that is often associated with the aberrant levels of glucose and/or insulin is insulin resistance, in which liver, fat, and muscle cells lose their ability to respond to normal blood insulin levels.

In view of the prevalence and severity of obesity, diabetes and associated metabolic and non-metabolic disorders, treatment modalities that modulate, for example, appetite, glucose and/or insulin levels and enhance the biological response to fluctuating glucose levels in a patient remain of interest.

Wild type GDF15, also known as MIC-1 (macrophage inhibitory cytokine-1) has been linked to regulation of body weight (Tsai V W, et al., PLoS One 2013; 8 (2): e55174; U.S. Pat. No. 8,192,735).

SUMMARY

Modified GDF15 polypeptides for treatment of metabolic disorders are provided. The modified GDF15 polypeptides may be present in a complex. A complex of the present disclosure may include two GDF15 polypeptides.

In certain cases, a complex of the present invention comprises a first polypeptide comprising an IgG Fc sequence, the IgG Fc sequence comprising a CH3 sequence comprising at least one engineered protuberance; and a second polypeptide comprising an IgG Fc sequence, the IgG Fc sequence comprising a CH3 sequence comprising at least one engineered cavity, wherein the first polypeptide dimerizes with the second polypeptide via positioning of the protuberance of the first polypeptide into the cavity of the second polypeptide, and wherein either the C-terminus of the first polypeptide or the C-terminus of the second polypeptide is conjugated to the N-terminus of a GDF15 mutein comprising at least one N-linked glycosylation consensus site.

In certain cases, a complex of the present invention comprises a first heterodimer and a second heterodimer, each of the first heterodimer and second heterodimer comprising a first polypeptide and a second polypeptide, the first polypeptide comprising an IgG Fc sequence, the IgG Fc sequence comprising a CH3 sequence comprising at least one engineered protuberance; and the second polypeptide comprising an IgG Fc sequence, the IgG Fc sequence comprising a CH3 sequence comprising at least one engineered cavity; wherein the first polypeptide dimerizes with the second polypeptide via positioning of the protuberance of the first polypeptide into the cavity of the second polypeptide, wherein either the C-terminus the first polypeptide or the C-terminus the second polypeptide is conjugated to the N-terminus of a GDF15 mutein comprising at least one N-linked glycosylation consensus site, and wherein the GDF15 mutein in the first heterodimer dimerizes with the GDF15 mutein in the second heterodimer thereby forming the complex comprising the first heterodimer and second heterodimer.

In exemplary embodiments, the C-terminus of the first polypeptide maybe conjugated to the N-terminus of the GDF15 mutein. In other cases, the C-terminus of the second polypeptide may be conjugated to the N-terminus of the GDF15 mutein.

Also contemplated herein is a first polypeptide comprising an IgG Fc sequence, the IgG Fc sequence comprising a CH3 sequence comprising at least one engineered protuberance, wherein the first polypeptide dimerizes with a second polypeptide comprising an IgG Fc sequence, the IgG Fc sequence comprising a CH3 sequence comprising at least one engineered cavity; and a GDF15 mutein comprising at least one N-linked glycosylation consensus site, wherein the C-terminus the first polypeptide is conjugated to the N-terminus of the GDF15 mutein. The first polypeptide may be present in a complex that may also include the second polypeptide.

Also disclosed herein is a first polypeptide comprising an IgG Fc sequence, the IgG Fc sequence comprising a CH3 sequence comprising at least one engineered cavity, wherein the first polypeptide dimerizes with a second polypeptide comprising an IgG Fc sequence, the IgG Fc sequence comprising a CH3 sequence comprising at least one engineered protuberance; and a GDF15 mutein comprising at least one N-linked glycosylation consensus site, wherein the C-terminus the first polypeptide is conjugated to the N-terminus of the GDF15 mutein. The first polypeptide may be present in a complex that may also include the second polypeptide.

In certain cases, the GDF15 mutein in the complex may comprise a contiguous amino acid sequence that is at least 90% identical to the amino acid sequence of wild type GDF15 (SEQ ID NO: 1). For example, the GDF15 mutein may include at least one substitution of the corresponding amino acid in SEQ ID NO: 1 that creates the N-linked glycosylation consensus site, e.g., the substitution may be D5T or D5S. In other cases, the substitution may be R21N.

In exemplary cases, the GDF15 mutein may include at least one of the following pairs of substitutions of the corresponding amino acids in SEQ ID NO: 1 that create the N-linked glycosylation consensus site: R16N and H18T/S; S23N and E25T/S; L24N and D26T/S; S50N and F52T/S; F52N and A54T/S; Q51N and R53T/S; R53N and A55T/S; S64N and H66T/S; L65N and R67T/S; S82N and N84T/S; K91N and D93T/S; D93N and G95T/S; T94N and V96T/S; V96N and L98T/S; S97N and Q99T/S; and A106N and D108T/S.

In exemplary cases, the GDF15 mutein may include at least one of the following pairs of substitutions of the corresponding amino acids in SEQ ID NO: 1 that create the N-linked glycosylation consensus site: R16N and H18T; S23N and E25T; L24N and D26T; S50N and F52T; F52N and A54T; Q51N and R53T; R53N and A55T; S64N and H66T; L65N and R67T; S82N and N84T; K91N and D93T; D93N and G95T; T94N and V96T; V96N and L98T; S97N and Q99T; and A106N and D108T.

In some cases, the GDF15 mutein may include at least one of the following pairs of substitutions of the corresponding amino acids in SEQ ID NO: 1 that create the N-linked glycosylation consensus site: R16N and H18S; S23N and E25S; L24N and D26S; S50N and F52S; F52N and A54S; Q51N and R53S; R53N and A55S; S64N and H66S; L65N and R67S; S82N and N84S; K91N and D93S; D93N and G95S; T94N and V96S; V96N and L98S; S97N and Q99S; and A106N and D108S.

In certain embodiments, the GDF15 mutein may include at least one of the following pairs of substitutions of the corresponding amino acids in SEQ ID NO: 1: S23N and E25T/S; R53N and A55T/S; S64N and H66T/S; K91N and D93T/S; D93N and G95T/S; S97N and Q99T/S; and A106N and D108T/S.

In certain embodiments, the GDF15 mutein may include at least one of the following pairs of substitutions of the corresponding amino acids in SEQ ID NO: 1: S23N and E25T; R53N and A55T; S64N and H66T; K91N and D93T; D93N and G95T; S97N and Q99T; and A106N and D108S.

In certain embodiments, the GDF15 mutein may include at least one of the following pairs of substitutions of the corresponding amino acids in SEQ ID NO: 1: S23N and E25S; R53N and A55S; S64N and H66S; K91N and D93S; D93N and G95S; S97N and Q99S; and A106N and D108S.

In certain embodiments, the GDF15 mutein may include at least one of the following pairs of substitutions of the corresponding amino acids in SEQ ID NO: 1: S64N and H66T/S; K91N and D93T/S; D93N and G95T/S; and S97N and Q99T/S. For example, the GDF15 mutein may include at least one of the following pairs of substitutions of the corresponding amino acids in SEQ ID NO: 1: S64N and H66T; K91N and D93T; D93N and G95T; and S97N and Q99T; or S64N and H66S; K91N and D93S; D93N and G95S; and S97N and Q99S.

In other embodiments, the GDF15 mutein may include at least one of the following pairs of substitutions of the corresponding amino acids in SEQ ID NO: 1: K91N and D93T or D93S; and D93N and G95T or G95S.

In other embodiments, the GDF15 mutein in the complex may comprise a contiguous amino acid sequence that may be at least 98 amino acids long and may be at least 90% identical to the amino acid sequence of SEQ ID NO: 1, where the C-terminal amino acid of the GDF15 mutein corresponds to Isoleucine at position 112 in SEQ ID NO: 1.

In other embodiments, the contiguous amino acid sequence may be at least 98 amino acids long and may be at least 95% identical to the amino acid sequence of SEQ ID NO: 1, where the C-terminal amino acid of the GDF15 mutein corresponds to Isoleucine at position 112 in SEQ ID NO: 1.

Exemplary GDF15 mutein present in the complex disclosed herein include a contiguous amino acid sequence that is at least 98 amino acids long, at least 90% identical to the amino acid sequence of SEQ ID NO: 1, and have deletions of amino acids relative to SEQ ID NO: 1. For example, the polypeptides may have an N-terminal truncation relative to SEQ ID NO: 1. The N-terminal truncation may be of 1, 2, 3, 4, 5, 6, 7, 8, 9, 10, 11, 12, 13, 14 or more amino acids relative to SEQ ID NO: 1, e.g., 1-14 amino acids, 2-14 amino acids, 3-14 amino acids, 2-3 amino acids, 3-5 amino acids, or 4-6 amino acids.

Exemplary complexes disclosed herein include the GDF15 mutein that includes a contiguous amino acid sequence at least 98 amino acids long and at least 95% identical to the amino acid sequence of SEQ ID NO: 1, wherein the C-terminal amino acid of the polypeptide corresponds to Isoleucine at position 112 in SEQ ID NO: 1.

In certain cases, the contiguous amino acid sequence in the GDF15 mutein is at least 98 amino acids long and does not include the first amino acid that corresponds to the first amino acid present at the N-terminus of SEQ ID NO: 1, wherein the C-terminal amino acid corresponds to Isoleucine at position 112 in SEQ ID NO: 1.

In certain cases, the contiguous amino acid sequence in the GDF15 mutein is at least 98 amino acids long and does not include the first two amino acids that correspond to the first two amino acids present at the N-terminus of SEQ ID NO: 1, wherein the C-terminal amino acid corresponds to Isoleucine at position 112 in SEQ ID NO: 1.

In certain cases, the contiguous amino acid sequence is at least 98 amino acids long and does not include the first three amino acids that correspond to the first three amino acids present at the N-terminus of SEQ ID NO: 1, wherein the C-terminal amino acid corresponds to Isoleucine at position 112 in SEQ ID NO: 1.

In certain cases, the contiguous amino acid sequence is at least 98 amino acids long and does not include the first six amino acids that correspond to the first six amino acids present at the N-terminus of SEQ ID NO: 1, wherein the C-terminal amino acid corresponds to Isoleucine at position 112 in SEQ ID NO: 1.

In certain cases, the contiguous amino acid sequence is at least 98 amino acids long and does not include the first fourteen amino acids that correspond to the first fourteen amino acids present at the N-terminus of SEQ ID NO: 1.

In certain cases, the C-terminus of either the first polypeptide (for example, Fc-knob) or the second polypeptide (for example, Fc-hole) is conjugated to the N-terminus of the GDF15 mutein via a linker. Exemplary linkers include the sequence $(G_4S)_n$, wherein n=1-10, e.g., 1-5 or 2-5, for examples 2, 3, 4, or 5.

In certain cases, the IgG Fc comprises a contiguous amino acid sequence at least 90% identical to the amino acid sequence in SEQ ID NO: 2 (human IgG1 Fc sequence). The engineered protuberance may include at least one substitution of the corresponding amino acid in a human IgG1 Fc sequence, wherein the substitution is at a position selected from the group consisting of amino acid residues 347, 366 and 394, according to EU numbering. For example, the at least one substitution is selected from the group consisting of Q347W/Y, T366W/Y, and T394W/Y, according to EU numbering.

In certain cases, the engineered cavity comprises at least one substitution of the corresponding amino acid in a human IgG1 Fc sequence, wherein the substitution is at a position selected from the group consisting of amino acid residues 366, 368, 394, 405, and 407, according to EU numbering. For example, the least one substitution is selected from the group consisting of T366S, L368A, T394S, F405T/V/A, and Y407T/V/A, according to EU numbering.

In certain cases, the protuberance may include the substitution T366W/Y and the cavity may include the substitutions T366S, L368A, and Y407T/V/A, according to EU numbering.

For example, the protuberance may include the substitution T366W/Y and the cavity may include the substitution Y407T/V/A, according to EU numbering. In other cases, the protuberance may include the substitution T366Y and the cavity may include the substitution Y407T, according to EU numbering. In other examples, the protuberance may include the substitution T366W and the cavity may include the substitution Y407A, according to EU numbering. In further examples, the protuberance may include the substitution T394Y and the cavity may include the substitution Y407T, according to EU numbering.

In certain embodiments, the IgG Fc sequences of the first and second polypeptides may each include a hinge region that forms at least one disulphide bond between the first and second polypeptides. In certain embodiments, the IgG Fc sequences of the first and second polypeptides may each include a hinge region, a CH2 region, and a CH3 region, where the hinge regions form at least one disulphide bond between the first and second polypeptides.

Also provided herein is a nucleic acid molecule encoding the above described first and second polypeptides. The nucleic acid molecule may be operably linked to an expression control element that confers expression of the nucleic acid molecule encoding the polypeptides in vitro or in vivo. A vector that includes the nucleic acid molecule is also contemplated. The vector may be a viral vector. In certain cases, a first nucleic acid encoding the first polypeptide and a second nucleic acid encoding the second polypeptide are provided. Each of the nucleic acids is operably linked to an expression control element that confers expression of the first and second polypeptides from the first and second nucleic acids, respectively. A first vector comprising the first nucleic and a second vector comprising the second nucleic acid is also disclosed. As noted here, the vector may be a viral vector.

Some embodiments include transformed host cells that express one or more of the aforementioned polypeptides. For example, a host cell that includes the first and second nucleic acids is provided. The host cell expresses the first polypeptide and the second polypeptide.

In particular embodiments of the present disclosure, one or more of the aforementioned complexes is formulated to yield a pharmaceutical composition, wherein the composition also includes one or more pharmaceutically acceptable diluents, carriers or excipients. In certain embodiments, a pharmaceutical composition also includes at least one additional prophylactic or therapeutic agent.

Also provided is a composition (for example, pharmaceutical composition) of one or more of the aforementioned complexes for treating or preventing a body weight disorder in a subject; for treating or preventing a glucose metabolism disorder in a subject. The composition may include an amount of the complex that is effective for treating or preventing a body weight disorder in a subject. The composition may include an amount of the complex that is effective for treating or preventing a glucose metabolism disorder in a subject.

Still further embodiments of the present disclosure comprise an antibody that binds specifically to one of the aforementioned first or second polypeptides.

Furthermore, the present disclosure contemplates pharmaceutical compositions comprising an antibody as described above formulated with at least one pharmaceutically acceptable excipient, carrier or diluent. Such pharmaceutical compositions may also contain at least one additional prophylactic or therapeutic agent.

Certain embodiments of the present disclosure contemplate a sterile container that contains one of the above-mentioned pharmaceutical compositions and optionally one or more additional components. By way of example, but not limitation, the sterile container may be a syringe. In still further embodiments, the sterile container is one component of a kit; the kit may also contain, for example, a second sterile container that contains at least one prophylactic or therapeutic agent.

Also disclosed herein is a method of making the aforementioned polypeptides and complexes. The method may include culturing a host cell expressing the polypeptides; and isolating the complex that includes the expressed polypeptides.

The present disclosure also contemplates a method of treating or preventing a glucose metabolism disorder in a subject (e.g., a human) by administering to the subject a therapeutically effective amount of the aforementioned complex. In some methods, the treating or preventing results in a reduction in plasma glucose in the subject, a reduction in plasma insulin in the subject, a reduction in body weight and/or food intake, or an increase in glucose tolerance in the subject. In particular embodiments, the glucose metabolism disorder is diabetes mellitus.

A method of treating or preventing a body weight disorder in a subject is also disclosed. The method may include administering to the subject the complex of the present disclosure, wherein the complex is administered in an amount effective in treating or preventing the body weight disorder in the subject. In some methods, the treating or preventing results in a reduction in body weight and/or food intake in the subject.

In some embodiments, the subject is obese and/or has a body weight disorder.

Though not limited to any particular route of administration or dosing regimen, in some embodiments the administering is by parenteral (e.g., subcutaneous) injection.

BRIEF DESCRIPTION OF THE DRAWINGS

FIG. 1 depicts a cartoon schematic of homodimeric complex of heterodimers of (Fc/Fc)-GDF15 molecules where the Fc/Fc polypeptides are knob-in-hole Fc pairs (A-F) and the incorporation of N-linked glycans on the GDF15 molecule (E, F) to enhance expression and assembly of the homodimeric complex of the heterodimers.

FIG. 2A depicts the recoveries from Expi 293F transient expression of engineered (Fc/Fc)-GDF15 complexes. Recoveries are as follows: (0=aggregates/no expression, <25 mg/L, 25 mg/L-49.9 mg/L, 50 mg/L-74.9 mg/L, 75 mg/L-99.0 mg/L, >100 mg/L). The addition of a N-linked glycan on the GDF15 sequence in the (Fc/Fc)-GDF15 provides a significant increase to overall recoveries following purification. FIG. 2B provides the recoveries from Expi 293F transient expression of wild-type GDF15 and GDF15-glycosylation mutants (glycomuteins) that were not conjugated to Fc.

FIG. 3 depicts the reduction in body weight in diet-induced obese (DIO) mouse model upon subcutaneous delivery of 0.4 nmol/kg of (Fc/Fc)-GDF15 complexes, once a week for 4 weeks, followed by a 14 day recovery period. B13a/B13b variant has significantly improved efficacy compared to B9a/B9b and B11a/B11b variants.

FIG. 4 depicts the percent reduction in body weight in DIO mouse model upon subcutaneous delivery of 0.4 nmol/kg of (Fc/Fc)-GDF15 complex, once a week for 4 weeks, followed by a 14 day recovery period. B13a/B13b variant has a vehicle subtracted % change in body weight of greater than 20% after 14 days of recovery following dosing.

FIG. 5 depicts the reduction in body weight in DIO mouse model upon subcutaneous delivery of 4.0 nmol/kg of (Fc/Fc)-GDF15 complexes, once a week for 4 weeks, followed by a 14 day recovery period.

FIG. 6 depicts the percent reduction in body weight in DIO mouse model upon subcutaneous delivery of 4.0 nmol/kg of (Fc/Fc)-GDF15 complexes, once a week for 4 weeks, followed by a 14 day recovery period.

FIGS. 7 and 8 summarize the observed body weight decreases (including SEM and p-values) for each group of DIO mice (n=6) for 0.4 nmol/kg and 4.0 nmol/kg dose groups depicted in FIGS. 3 and 5. For all groups. (*=$p<0.05$, =$p<0.01$ and *=$p<0.001$) via unpaired t-test.

FIG. 9 summarizes the percent body weight decreases (including SEM and p-values) for each group of DIO mice (n=6) for 0.4 nmol/kg and 4.0 nmol/kg dose groups depicted in FIGS. 4 and 6. For all groups, (*=$p<0.05$, =$p<0.01$ and *=$p<0.001$) via unpaired t-test.

DETAILED DESCRIPTION

Before the methods and compositions of the present disclosure are further described, it is to be understood that the disclosure is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

It must be noted that as used herein and in the appended claims, the singular forms "a," "an," and "the" include plural referents unless the context clearly dictates otherwise. Thus, for example, reference to "the complex" includes reference to one or more complexes, and so forth. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence, fusion proteins with heterologous and homologous leader sequences, with or without N-terminus methionine residues; immunologically tagged proteins; and the like. In specific embodiments, the terms refer to a polymeric form of amino acids of any length which include genetically coded amino acids. In particular embodiments, the terms refer to a polymeric form of amino acids of any length which include genetically coded amino acids fused to a heterologous amino acid sequence. In particular embodiments, the terms refer to an amino acid of 98-112 amino acids in length, optionally fused to a heterologous sequence. In specific embodiments, as appropriate, when referring to proteins and molecules disclosed and described herein, the terms "polypeptide," "peptide," and "protein" refer to Polypeptides as defined herein.

The term "complex" as used herein refers to a protein complex that comprises at least two polypeptides, each of which polypeptides comprise an N-terminus and a C-terminus. The at least two polypeptides may be associated with each other via one or both of a covalent and a non-covalent interaction (e.g., electrostatic, n-effects, van der Waals forces, and hydrophobic effects). The at least two polypeptides may be the same, i.e., have identical amino acid sequence or may be different, i.e., not have identical amino acid sequences. A complex having two polypeptides, where both the polypeptides are identical, is referred to as a homodimer. A complex having two polypeptides, where the polypeptides are different, is referred to as a heterodimer. A complex having three polypeptides, where the three polypeptides are identical, is referred to as a homotrimer. A complex having three polypeptides, where at least one of the three polypeptides is different from the other polypeptide(s), is referred to as a heterotrimer. A complex having four polypeptides, where the four polypeptides are identical, is referred to as a homotetramer. A complex having four polypeptides, where at least one of the four polypeptides is different from the other polypeptide(s), is referred to as a heterotetramer. An exemplary complex of four polypeptides—two molecules of a first polypeptide and two molecules of a second polypeptide, where the first polypeptide dimerizes with the second polypeptide to form a heterodimer and where two such heterodimers dimerize to form the complex may be referred to as a homodimeric complex of the two heterodimers.

The present disclosure contemplates complexes as defined above, including but not limited to a heterodimer having a first polypeptide associated with a second polypeptide, where the first polypeptide is a 'knob' Fc and the second polypeptide is a 'hole' Fc, and where either the first polypeptide or the second polypeptide is fused to a GDF15 (or GDF15 mutein, such as, a GDF15 mutein described herein) amino acid sequence. The first and second polypeptides may be physically associated with each other via a non-covalent interaction (e.g., hydrophobic effects, such as, hydrophobic interaction between the knob and hole regions of the Fc), a covalent bond (e.g., a disulfide bond, such as, one or two or more disulphide bonds between hinge regions of the Fc in the first and second polypeptides), or both.

The present disclosure also contemplates a complex that includes two heterodimers associated with each other, each heterodimer having a first polypeptide and a second polypeptide, where the first polypeptide is a 'knob' Fc and the second polypeptide is a 'hole' Fc, and where either the first polypeptide or the second polypeptide is fused to a GDF15 (or GDF15 mutein) amino acid sequence. Within the complex, the two heterodimers may be physically associated by a non-covalent interaction (e.g., hydrophobic effects), a covalent bond (e.g., a disulfide bond), or both. The first and second polypeptides in each of the heterodimers in the complex may be physically associated with each other by a non-covalent interaction (e.g., hydrophobic effects), a covalent bond (e.g., a disulfide bond), or both.

The present disclosure also contemplates a complex that includes two heterodimers associated with each other, each heterodimer having a first polypeptide and a second polypeptide, where the first polypeptide is a 'knob' Fc and the second polypeptide is a 'hole' Fc, and where either the first polypeptide or the second polypeptide is fused to a GDF15 (or GDF15 mutein) amino acid sequence. Within the complex, the two heterodimers may be physically associated by a non-covalent interaction (e.g., hydrophobic effects) or a covalent interaction (e.g., disulfide bond(s)) between the GDF15 polypeptides and the first and second polypeptides in each of the heterodimers may be physically associated with each other by a non-covalent interaction (e.g., knob into hole), a covalent bond (e.g., a disulfide bond), or both.

The terms "patient" or "subject" are used interchangeably to refer to a human or a non-human animal (e.g., a mammal).

The terms "treat", "treating", treatment" and the like refer to a course of action (such as administering a an agent, e.g., a polypeptide, a complex, or a pharmaceutical composition comprising a polypeptide, a complex) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (i.e., arresting the development or further development of the disease, disorder or condition or clinical symptoms association therewith) an active disease (e.g., so as to decrease the level of insulin and/or glucose in the bloodstream, to increase glucose tolerance so as to minimize fluctuation of glucose levels, and/or so as to protect against diseases caused by disruption of glucose homeostasis, decrease body weight, arrest increase in body weight).

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering an agent, e.g., a polypeptide, a complex, or a pharmaceutical composition comprising a polypeptide, a complex) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as a part of a pharmaceutical composition and either in a single dose or as part of a series of doses, in an amount that is capable of having any detectable, positive effect on any symptom, aspect, or characteristics of a disease, disorder or condition when administered to a patient. The therapeutically effective amount can be ascertained by measuring relevant physiological effects. For example, in the case of a hyperglycemic condition, a lowering or reduction of blood glucose or an improvement in glucose tolerance test can be used to determine whether the amount of an agent is effective to treat the hyperglycemic condition. For example, a therapeutically effective amount is an amount sufficient to reduce or decrease any level (e.g., a baseline level) of fasting plasma glucose (FPG), wherein, for example, the amount is sufficient to reduce a FPG level greater than 200 mg/dl to less than 200 mg/dl, wherein the amount is sufficient to reduce a FPG level between 175 mg/dl and 200 mg/dl to less than the starting level, wherein the amount is sufficient to reduce a FPG level between 150 mg/dl and 175 mg/dl to less than the starting level, wherein the amount is sufficient to reduce a FPG level between 125 mg/dl and 150 mg/dl to less than the starting level, and so on (e.g., reducing FPG levels to less than 125 mg/dl, to less than 120 mg/dl, to less than 115 mg/dl, to less than 110 mg/dl, etc.). In the case of HbA1c levels, the effective amount is an amount sufficient to reduce or decrease levels by more than about 10% to 9%, by more than about 9% to 8%, by more than about 8% to 7%, by more than about 7% to 6%, by more than about 6% to 5%, and so on. More particularly, a reduction or decrease of HbA1c levels by about 0.1%, 0.25%, 0.4%, 0.5%, 0.6%, 0.7%, 0.8%, 0.9%, 1%, 1.5%, 2%, 3%, 4%, 5%, 10%, 20%, 30%, 33%, 35%, 40%, 45%, 50%, or more is contemplated by the present disclosure. The therapeutically effective amount can be adjusted in connection with the dosing regimen and diagnostic analysis of the subject's condition and the like.

The phrase "in a sufficient amount to effect a change" means that there is a detectable difference between a level of an indicator measured before (e.g., a baseline level) and after administration of a particular therapy. Indicators include any objective parameter (e.g., level of glucose or insulin or food intake or body weight) or subjective parameter (e.g., a subject's feeling of well-being or appetite).

The phrase "glucose tolerance", as used herein, refers to the ability of a subject to control the level of plasma glucose and/or plasma insulin when glucose intake fluctuates. For example, glucose tolerance encompasses the subject's ability to reduce, within about 120 minutes, the level of plasma glucose back to a level determined before the intake of glucose.

The terms "diabetes" and "diabetic" refer to a progressive disease of carbohydrate metabolism involving inadequate production or utilization of insulin, frequently characterized by hyperglycemia and glycosuria. The terms "pre-diabetes" and "pre-diabetic" refer to a state wherein a subject does not have the characteristics, symptoms and the like typically observed in diabetes, but does have characteristics, symptoms and the like that, if left untreated, may progress to diabetes. The presence of these conditions may be determined using, for example, either the fasting plasma glucose (FPG) test or the oral glucose tolerance test (OGTT). Both usually require a subject to fast for at least 8 hours prior to initiating the test. In the FPG test, a subject's blood glucose is measured after the conclusion of the fasting; generally, the subject fasts overnight and the blood glucose is measured in the morning before the subject eats. A healthy subject would generally have a FPG concentration between about 90 and about 100 mg/dl, a subject with "pre-diabetes" would generally have a FPG concentration between about 100 and about 125 mg/dl, and a subject with "diabetes" would generally have a FPG level above about 126 mg/dl. In the OGTT, a subject's blood glucose is measured after fasting and again two hours after drinking a glucose-rich beverage. Two hours after consumption of the glucose-rich beverage, a healthy subject generally has a blood glucose concentration below about 140 mg/dl, a pre-diabetic subject generally has a blood glucose concentration about 140 to about 199 mg/dl, and a diabetic subject generally has a blood glucose concentration about 200 mg/dl or above. While the aforementioned glycemic values pertain to human subjects, normoglycemia, moderate hyperglycemia and overt hyperglycemia are scaled differently in murine subjects. A healthy murine subject after a four-hour fast would generally have a FPG concentration between about 100 and about 150 mg/dl, a murine subject with "pre-diabetes" would generally have a FPG concentration between about 175 and about 250 mg/dl and a murine subject with "diabetes" would generally have a FPG concentration above about 250 mg/dl.

The term "insulin resistance" as used herein refers to a condition where a normal amount of insulin is unable to produce a normal physiological or molecular response. In some cases, a hyper-physiological amount of insulin, either endogenously produced or exogenously administered, is able to overcome the insulin resistance, in whole or in part, and produce a biologic response.

The term "metabolic syndrome" refers to an associated cluster of traits that includes, but is not limited to, hyperinsulinemia, abnormal glucose tolerance, obesity, redistribution of fat to the abdominal or upper body compartment, hypertension, dysfibrinolysis, and dyslipidemia characterized by high triglycerides, low high density lipoprotein (HDL)-cholesterol, and high small dense low density lipoprotein (LDL) particles. Subjects having metabolic syndrome are at risk for development of Type 2 diabetes and/or other disorders (e.g., atherosclerosis).

The phrase "glucose metabolism disorder" encompasses any disorder characterized by a clinical symptom or a combination of clinical symptoms that is associated with an elevated level of glucose and/or an elevated level of insulin in a subject relative to a healthy individual. Elevated levels of glucose and/or insulin may be manifested in the following diseases, disorders and conditions: hyperglycemia, type II diabetes, gestational diabetes, type I diabetes, insulin resistance, impaired glucose tolerance, hyperinsulinemia, impaired glucose metabolism, pre-diabetes, other metabolic disorders (such as metabolic syndrome, which is also referred to as syndrome X), and obesity, among others. The complexes of the present disclosure, and compositions thereof, can be used, for example, to achieve and/or maintain glucose homeostasis, e.g., to reduce glucose level in the bloodstream and/or to reduce insulin level to a range found in a healthy subject.

The term "hyperglycemia", as used herein, refers to a condition in which an elevated amount of glucose circulates in the blood plasma of a subject relative to a healthy individual. Hyperglycemia can be diagnosed using methods known in the art, including measurement of fasting blood glucose levels as described herein.

The term "hyperinsulinemia", as used herein, refers to a condition in which there are elevated levels of circulating insulin when, concomitantly, blood glucose levels are either elevated or normal. Hyperinsulinemia can be caused by insulin resistance which is associated with dyslipidemia, such as high triglycerides, high cholesterol, high low-density lipoprotein (LDL) and low high-density lipoprotein (HDL); high uric acids levels; polycystic ovary syndrome; type II diabetes and obesity. Hyperinsulinemia can be diagnosed as having a plasma insulin level higher than about 2 µU/mL.

As used herein, the phrase "body weight disorder" refers to conditions associated with excessive body weight and/or enhanced appetite. Various parameters are used to determine whether a subject is overweight compared to a reference healthy individual, including the subject's age, height, sex and health status. For example, a subject may be considered overweight or obese by assessment of the subject's Body Mass Index (BMI), which is calculated by dividing a subject's weight in kilograms by the subject's height in meters squared. An adult having a BMI in the range of ~18.5 to ~24.9 kg/m$^2$ is considered to have a normal weight; an adult having a BMI between ~25 and ~29.9 kg/m$^2$ may be considered overweight (pre-obese); and an adult having a BMI of ~30 kg/m$^2$ or higher may be considered obese. Enhanced appetite frequently contributes to excessive body weight. There are several conditions associated with enhanced appetite, including, for example, night eating syndrome, which is characterized by morning anorexia and evening polyphagia often associated with insomnia, but which may be related to injury to the hypothalamus.

The term "Activators" refers to agents that, for example, stimulate, increase, activate, facilitate, enhance activation, sensitize or up-regulate the function or activity of one or more agents, e.g., polypeptides or complex used to treat or prevent a metabolic disorder. In addition, Activators include agents that operate through the same mechanism of action as the polypeptides of the present invention (i.e., agents that modulate the same signaling pathway as the polypeptides in a manner analogous to that of the polypeptides) and are capable of eliciting a biological response comparable to (or greater than) that of the polypeptides. Examples of Activators include agonists such as small molecule compounds.

The term "Modulators" collectively refers to the polypeptides of the present invention and the Activators.

The terms "modulate", "modulation" and the like refer to the ability of an agent (e.g., an Activator) to increase the function or activity of one or more polypeptides (or the nucleic acid molecules encoding them), either directly or indirectly; or to the ability of an agent to produce an effect comparable to that of one or more polypeptides.

It will be appreciated that throughout this disclosure reference is made to amino acids according to the single letter or three letter codes. For the reader's convenience, the single and three letter amino acid codes are provided below:

| G | Glycine | Gly | P | Proline | Pro |
|---|---|---|---|---|---|
| A | Alanine | Ala | V | Valine | Val |
| L | Leucine | Leu | I | Isoleucine | Ile |
| M | Methionine | Met | C | Cysteine | Cys |
| F | Phenylalanine | Phe | Y | Tyrosine | Tyr |
| W | Tryptophan | Trp | H | Histidine | His |
| K | Lysine | Lys | R | Arginine | Arg |
| Q | Glutamine | Gln | N | Asparagine | Asn |
| E | Glutamic Acid | Glu | D | Aspartic Acid | Asp |
| S | Serine | Ser | T | Threonine | Thr |

As used herein, the term "variant" encompasses naturally-occurring variants (e.g., homologs and allelic variants) and non-naturally-occurring variants (e.g., recombinantly modified). Naturally-occurring variants include homologs, i.e., nucleic acids and polypeptides that differ in nucleotide or amino acid sequence, respectively, from one species to another. Naturally-occurring variants include allelic variants, i.e., nucleic acids and polypeptides that differ in nucleotide or amino acid sequence, respectively, from one individual to another within a species. Non-naturally-occurring variants include nucleic acids and polypeptides that comprise a change in nucleotide or amino acid sequence, respectively, where the change in sequence is artificially introduced, e.g., the change is generated in the laboratory or other facility by human intervention ("hand of man").

The term "native" or "wild type", in reference to GDF15, refers to biologically active, naturally-occurring GDF15, including biologically active, naturally-occurring GDF15 variants. The term includes the 112 amino acid human GDF15 mature sequence (SEQ ID NO: 1).

The term "muteins" as used herein refers broadly to recombinant proteins, i.e., a polypeptide comprising an artificially introduced change in amino acid sequence, e.g., a change in amino acid sequence generated in the laboratory or other facility by human intervention ("hand of man"). These polypeptides usually carry single or multiple amino acid substitutions or deletions and are frequently derived from cloned genes that have been subjected to site-directed or random mutagenesis, or from completely synthetic genes. "GDF15 Muteins" of the present disclosure thus encompass, for example, amino acid substitutions and/or amino acid deletions (e.g., N-terminal truncations of 1, 2, 3, 4, 5, 6, 7, 8, 9, 10, 11, 12, 13, or 14 or more amino acids) relative to a reference polypeptide. e.g., relative to native/wild type mature human GDF15 (SEQ ID NO: 1).

As used herein in reference to native human GDF15 or a GDF15 mutein, the terms "modified", "modification" and the like refer to one or more changes that modify a property of a human GDF15, a naturally-occurring GDF15 variant, or a GDF15 mutein, where the change does not alter the primary amino acid sequence of the GDF15 polypeptide (native or mutein) itself. Such a property includes, for example, solubility, circulation half-life, stability, clearance, immunogenicity or allergenicity, and manufacturability (e.g., cost and efficiency). "Modification" includes a covalent chemical modification that does not alter the primary amino acid sequence of the GDF15 polypeptide (native or mutein) itself. Changes to human GDF15, a naturally-occurring GDF15 variant, or a GDF15 mutein that may be carried out include, but are not limited to, one or more of pegylation (covalent attachment of one or more molecules of polyethylene glycol (PEG), or derivatives thereof); glycosylation (e.g., N-glycosylation), polysialylation and hesylation; maltose binding protein fusion; albumin fusion (e.g., HSA fusion); albumin binding through, for example, a conjugated fatty acid chain (acylation); Fc-fusion; and fusion with a PEG mimetic. Some particular embodiments entail modifications involving fusion to a Fc, and still other particular modifications entail modifications involving glycosylation, or a combination thereof.

The terms "DNA", "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

The term "probe" refers to a fragment of DNA or RNA corresponding to a gene or sequence of interest, wherein the fragment has been labeled radioactively (e.g., by incorporating $^{32}$P or $^{35}$S) or with some other detectable molecule, such as biotin, digoxygenin or fluorescein. As stretches of DNA or RNA with complementary sequences will hybridize, a probe can be used, for example, to label viral plaques, bacterial colonies or bands on a gel that contain the gene of interest. A probe can be cloned DNA or it can be a synthetic DNA strand; the latter can be used to obtain a cDNA or genomic clone from an isolated protein by, for example, microsequencing a portion of the protein, deducing the nucleic acid sequence encoding the protein, synthesizing an oligonucleotide carrying that sequence, radiolabeling the sequence and using it as a probe to screen a cDNA library or a genomic library.

The term "heterologous" refers to two components that are defined by structures derived from different sources. For example, in the context of a polypeptide, a "heterologous" polypeptide may include operably linked amino acid sequences that are derived from different polypeptides (e.g., a first component comprising a recombinant polypeptide and a second component derived from a native GDF15 polypeptide). Similarly, in the context of a polynucleotide encoding a chimeric polypeptide, a "heterologous" polynucleotide may include operably linked nucleic acid sequences that can be derived from different genes (e.g., a first component from a nucleic acid encoding a polypeptide according to an embodiment disclosed herein and a second component from a nucleic acid encoding a carrier polypeptide). Other exemplary "heterologous" nucleic acids include expression constructs in which a nucleic acid comprising a coding sequence is operably linked to a regulatory element (e.g., a promoter) that is from a genetic origin different from that of the coding sequence (e.g., to provide for expression in a host cell of interest, which may be of different genetic origin than the promoter, the coding sequence or both). For example, a T7 promoter operably linked to a polynucleotide encoding a GDF15 polypeptide or domain thereof is said to be a heterologous nucleic acid. In the context of recombinant cells, "heterologous" can refer to the presence of a nucleic acid (or gene product, such as a polypeptide) that is of a different genetic origin than the host cell in which it is present.

The term "operably linked" refers to linkage between molecules to provide a desired function. For example, "operably linked" in the context of nucleic acids refers to a functional linkage between nucleic acid sequences. By way of example, a nucleic acid expression control sequence (such as a promoter, signal sequence, or array of transcription factor binding sites) may be operably linked to a second polynucleotide, wherein the expression control sequence affects transcription and/or translation of the second polynucleotide. In the context of a polypeptide, "operably linked" refers to a functional linkage between amino acid sequences (e.g., different domains) to provide for a described activity of the polypeptide.

As used herein in the context of the structure of a polypeptide, "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. "Immediately N-terminal" or "immediately C-terminal" refers to a position of a first amino acid residue relative to a second amino acid residue where the first and second amino acid residues are covalently bound to provide a contiguous amino acid sequence.

"Derived from", in the context of an amino acid sequence or polynucleotide sequence (e.g., an amino acid sequence "derived from" a GDF15 polypeptide), is meant to indicate that the polypeptide or nucleic acid has a sequence that is based on that of a reference polypeptide or nucleic acid (e.g., a naturally occurring GDF15 polypeptide or a GDF15-encoding nucleic acid), and is not meant to be limiting as to the source or method in which the protein or nucleic acid is made. By way of example, the term "derived from" includes homologues or variants of reference amino acid or DNA sequences.

In the context of a polypeptide, the term "isolated" refers to a polypeptide of interest that, if naturally occurring, is in an environment different from that in which it may naturally occur. "Isolated" is meant to include polypeptides that are within samples that are substantially enriched for the polypeptide of interest and/or in which the polypeptide of interest is partially or substantially purified. Where the polypeptide is not naturally occurring, "isolated" indicates the polypeptide has been separated from an environment in which it was made by either synthetic or recombinant means.

"Enriched" means that a sample is non-naturally manipulated (e.g., in a laboratory, for example, by a scientist or a clinician) so that a polypeptide of interest is present in a) a greater concentration (e.g., at least 3-fold greater, at least 4-fold greater, at least 8-fold greater, at least 64-fold greater, or more) than the concentration of the polypeptide in the starting sample, such as a biological sample (e.g., a sample in which the polypeptide naturally occurs or in which it is present after administration), or b) a concentration greater than the environment in which the polypeptide was made (e.g., as in a bacterial cell).

"Substantially pure" indicates that a component (e.g., a polypeptide, a dimer, a tetramer, a complex) makes up greater than about 50% of the total content of the composition, and typically greater than about 60% of the total polypeptide content. More typically, "substantially pure" refers to compositions in which at least 75%, at least 85%, at least 90% or more of the total composition is the component of interest. In some cases, the component will make up greater than about 90%, or greater than about 95% of the total content of the composition.

The terms "antibodies" (Abs) and "immunoglobulins" (Igs) refer to glycoproteins having the same structural characteristics. While antibodies exhibit binding specificity to a specific antigen, immunoglobulins include both antibodies and other antibody-like molecules which lack antigen specificity. Antibodies are described in detail hereafter.

The term "monoclonal antibody" refers to an antibody obtained from a population of substantially homogeneous antibodies, that is, the individual antibodies comprising the population are identical except for possible naturally occurring mutations that may be present in minor amounts. Monoclonal antibodies are highly specific, being directed against a single antigenic site. In contrast to polyclonal antibody preparations, which can include different antibodies directed against different determinants (epitopes), each monoclonal antibody is directed against a single determinant on the antigen.

In the context of an antibody, the term "isolated" refers to an antibody that has been separated and/or recovered from contaminant components of its natural environment; such contaminant components include materials which might interfere with diagnostic or therapeutic uses for the antibody, and may include enzymes, hormones, and other proteinaceous or nonproteinaceous solutes.

The phrase "conservative amino acid substitution" refers to substitution of amino acid residues within the following groups: 1) L, I, M, V, F; 2) R, K; 3) F, Y, H, W, R; 4) G, A, T, S; 5) Q, N; and 6) D, E. Conservative amino acid substitutions may preserve the activity of the protein by replacing an amino acid(s) in the protein with an amino acid with a side chain of similar acidity, basicity, charge, polarity, or size of the side chain. Guidance for substitutions, insertions, or deletions may be based on alignments of amino acid sequences of different variant proteins or proteins from different species.

Growth Differentiation Factor 15 (GDF15)

GDF15, also known as MIC-1 (macrophage inhibitory cytokine-1), PDF (prostate differentiation factor), PLAB (placental bone morphogenetic protein), NAG-1 (non-steroidal anti-inflammatory drugs (NSAIDs) activated gene), TGF-PL, and PTGFB, is a member of the transforming growth factor β (TGF-β) super-family. GDF15, which is synthesized as a 62 kDa intracellular precursor protein that is subsequently cleaved by a furin-like protease, is secreted as a 25 kDa disulfide-linked protein. (See, e.g., Fairlie et al., J. Leukoc. Biol 65:2-5 (1999)). GDF15 mRNA is seen in several tissues, including liver, kidney, pancreas, colon and placenta, and GDF15 expression in liver can be significantly up-regulated during injury of organs such as the liver, kidneys, heart and lungs.

The GDF15 precursor is a 308 amino acid polypeptide (NCBI Ref. Seq. NP_004855.2) containing a 29 amino acid signal peptide, a 167 amino acid pro-domain, and a mature domain of 112 amino acids which is excised from the pro-domain by furin-like proteases. A 308-amino acid GDF15 polypeptide is referred to as a "full-length" GDF15 polypeptide; a 112-amino acid GDF15 polypeptide (amino acids 197-308 of "full-length" GDF15) is a "mature" GDF15 polypeptide (SEQ ID NO: 1). Unless otherwise indicated, the term "GDF15" refers to the 112 amino acid mature human sequence. In addition, numerical references to particular GDF15 residues refer to the 112 amino acid mature sequence (i.e., residue 1 is Ala (A), and residue 112 is Ile (I); see SEQ ID NO: 1). Of note, while the GDF15 precursor amino acid sequence predicts three excision sites, resulting in three putative forms of "mature" human GDF15 (i.e., 110, 112 and 115 amino acids), the 112 amino acid mature sequence is accepted as being correct.

The scope of the present disclosure includes GDF15 orthologs, and modified forms thereof, from other mammalian species, and their use, including mouse (NP_035949), chimpanzee (XP_524157), orangutan (XP_002828972), Rhesus monkey (EHH29815), giant panda (XP_002912774), gibbon (XP_003275874), guinea pig (XP_003465238), ferret (AER98997), cow (NP_001193227), pig (NP_001167527), dog (XP_541938) and platypus (*Ornithorhynchus anatinus*; AFV61279). The mature form of human GDF15 has approximately 67% amino acid identity to the mouse ortholog.

For the sake of convenience, the modified human GDF15 molecules, the GDF15 variants (e.g., muteins), and modified GDF15 muteins described henceforward are collectively referred to hereafter as the "Polypeptide(s)". It should be noted that any reference to "human" in connection with the Polypeptides and nucleic acid molecules of the present disclosure is not meant to be limiting with respect to the manner in which the Polypeptide or nucleic acid is obtained or the source, but rather is only with reference to the sequence as it may correspond to a sequence of a naturally occurring human Polypeptide or nucleic acid molecule. In particular embodiments, the modified human GDF15 molecules are N-glycosylated dimers. In addition to the human polypeptides and the nucleic acid molecules which encode them, the present disclosure contemplates GDF15-related polypeptides and corresponding nucleic acid molecules from other species.

A. Polypeptides Having Desired Physical Properties

The present disclosure contemplates, in part, Polypeptides that include a contiguous amino acid sequence that is at least 80%, 85%, 90%, 95%, 96%, 97%, 98%, 99%, or 100% identical to the amino acid sequence of SEQ ID NO: 1 (mature 112 amino acid long human GDF15). The Polypeptides may include one or more amino acid substitutions and/or deletions relative to the amino acid sequence of SEQ ID NO: 1. In certain embodiments, in addition to the amino acid substitutions, the Polypeptides of the present disclosure may also include amino acid deletions relative to the amino acid sequence of SEQ ID NO: 1. In some embodiments, the Polypeptides of the present disclosure may include amino acid deletions relative to the amino acid sequence of SEQ ID NO: 1.

For convenience and clarity, the amino acid sequence of SEQ ID NO: 1 is used as a reference sequence for the Polypeptides presented herein. Therefore, the amino acid residue positions are numbered herein with reference to SEQ ID NO: 1. The sequence of SEQ ID NO: 1 is presented below:

ARNGDHCPLGPGRCCRLHTVRASLEDLGWADWVLSPREVQVTMCIGAC
PSQFRAANMHAQIKTSLHRLKPDTVPAPCCVPASYNPMVLIQKTDTGV
SLQTYDDLLAKDCHCI

In some embodiments, the Polypeptides of the present disclosure may include one, two, three or more amino acid substitutions, additions, or deletions that introduce one or more N-linked glycosylation consensus site(s) at a location where such a site is not present in SEQ ID NO: 1. The N-linked glycosylation consensus site includes the sequence NXS/T, where N is Asn; X is an amino acid other than proline; followed by either Ser (S) or Thr (T).

Examples of Polypeptides of the present disclosure include polypeptides that have one, two, three, four, or more glycosylation consensus sites (e.g., N-linked Glycosylation consensus sites) at an amino acid location where such a site is not present in the amino acid sequence of SEQ ID NO: 1.

In certain embodiments, the polypeptide may include one amino acid substitution relative to SEQ ID NO: 1 that provides one N-linked Glycosylation consensus site at the position of the substitution (e.g., a NG<u>D</u> sequence in SEQ ID NO: 1 may be changed to NGT/S by one substitution; position of substitution underlined). In other cases, the polypeptide may include two amino acid substitutions relative to SEQ ID NO: 1 that provide one N-linked Glycosylation consensus site at the position of the substitutions (e.g., a <u>KTD</u> sequence in SEQ ID NO: 1 may be changed to NTT/S by two substitutions; positions of substitutions underlined). In some embodiments, the polypeptide may include three amino acid substitutions relative to SEQ ID NO: 1 that provide one N-linked glycosylation consensus site at the position of the substitution (e.g., a <u>GPG</u> sequence in SEQ ID NO: 1 may be changed to NTT/S by three substitutions; position of substitutions underlined).

In certain embodiments, the polypeptide may include one or more amino acid deletion relative to SEQ ID NO: 1 that provides an N-linked glycosylation consensus site at the position of the deletion. For example, a NG<u>DHCPLGPGRCCRLH</u>T (SEQ ID NO: 119)

sequence in SEQ ID NO: 1 may be changed by deletion of amino acids D through H (underlined)) thereby providing an N-linked glycosylation consensus site: NGT.

In certain embodiments, the polypeptide may include one or more amino acid additions relative to SEQ ID NO: 1 that provides an N-linked glycosylation consensus site at the position(s) of the addition(s). An example of introduction of an N-linked glycosylation consensus site by addition of one amino acid includes adding an N to a sequence LHT in SEQ ID NO: 1, thereby generating the sequence LNHT, where NHT is an N-linked glycosylation consensus site.

As noted above, the polypeptide may include one or more substitutions relative to SEQ ID NO: 1 and the substitutions may be numbered as the position of the corresponding amino acid in SEQ ID NO: 1.

In certain embodiments, the Polypeptide may include a contiguous amino acid sequence that is at least 80%, 85%, 90%, 95%, 96%, 97%, 98%, 99%, or 100% identical to the amino acid sequence of SEQ ID NO: 1, where the contiguous amino acid sequence has the substitution D5T/S or R21N.

In certain embodiments, the polypeptide may include a contiguous amino acid sequence that is at least 80%, 85%, 90%, 95%, 96%, 97%, 98%, 99%, or 100% identical to the amino acid sequence of SEQ ID NO: 1, where the contiguous amino acid sequence has at least one of the following pairs of substitutions relative to the corresponding amino acids in SEQ ID NO: 1:
  i. R16N and H18T or R16N and H18S;
  ii. S23N and E25T or S23N and E25S;
  iii. L24N and D26T or L24N and D26S;
  iv. S50N and F52T or S50N and F52S;
  v. F52N and A54T or F52N and A54S;
  vi. Q51N and R53T or Q51N and R53S;
  vii. R53N and A55T or R53N and A55S;
  viii. S64N and H66T or S64N and H66S;
  ix. L65N and R67T or L65N and R67S;
  x. S82N and N84T or S82N and N84S;
  xi. K91N and D93T or K91N and D93S;
  xii. D93N and G95T or D93N and G95S;
  xiii. T94N and V96T or T94N and V96S;
  xiv. V96N and L98T or V96N and L98S;
  xv. S97N and Q99T or S97N and Q99S; and
  xvi. A106N and D108T or A106N and D108S For example, the substitutions in i) above, denotes that the polypeptide has a threonine (T) or serine (S) at an amino acid position that corresponds to amino acid position 18 in SEQ ID NO: 1, wherein in SEQ ID NO: 1 a histidine (H) is present at the amino acid position 18. Similarly, a substitution of a D at position 5 with a T or S can be denoted by D5T/S. The position of the corresponding amino acid in a polypeptide relative to SEQ ID NO: 1 may be determined by aligning the amino acid sequences.

In certain embodiments, the polypeptide may include two amino acid substitutions (a pair of substitutions) that provide a single N-glycosylation consensus sequence at a position where a N-glycosylation consensus sequence is not present in SEQ ID NO: 1. Examples of such substitutions include R16N and H18T/S; K91N and D93T/S; T94N and V96T/S; and others listed above. R16N and H18T/S denotes that the polypeptide has a N at a position that corresponds to position 16 of SEQ ID NO: 1, where in SEQ ID NO: 1 an R is present and the polypeptide has a either T or S at a position that corresponds to position 18 in SEQ ID NO: 1, where H is present. Since the sequence RXH (at position 16-18) in SEQ ID NO: 1 does not include any residue for the N-linked glycosylation consensus sequence, the pair of substitutions leads to the introduction of the N-linked glycosylation consensus sequence.

In alternate embodiments, a single amino acid substitution may suffice to provide the N-linked glycosylation consensus sequence, for example, since the sequence NGD (at position 3-5) is present in SEQ ID NO: 1, a single substitution of D with T or S produces the sequence NGT or NGS, respectively, which are both N-glycosylation consensus sequences.

In certain cases, more than one N-glycosylation consensus sequence may be introduced into the wild type GDF15. For example, the wild type GDF15 amino acid sequence may be modified by substitutions and/or deletions to provide one, two, three, four or more N-glycosylation consensus sequences. In certain embodiments, the polypeptide may be include 112 contiguous amino acids that has a sequence identity of at least 90% to the 112 amino acids sequence of SEQ ID NO: 1, where the 112 contiguous amino acids include one, two, three, four or more N-glycosylation consensus sequences, such as, 1-12, 1-10, 1-8, 1-6, 1-4, 1-3, or 1-2 N-glycosylation consensus sequences.

In certain embodiments, the polypeptide may be include 112 contiguous amino acids that has a sequence identity of at least 90% to the 112 amino acids sequence of SEQ ID NO: 1, where the 112 contiguous amino acids include one, two, three, four or more of the pairs of substitutions set forth herein.

The present disclosure also contemplates polypeptides that are active fragments (e.g., subsequences) of the polypeptides described above. The length of active fragments or subsequences may be 40 amino acids to 111 amino acids, e.g., 40, 45, 50, 55, 60, 65, 70, 75, 80, 85, 90, 95, 98, 106, 109, or up to 111 amino acids.

The polypeptides have a defined sequence identity compared to a reference sequence over a defined length of contiguous amino acids (e.g., a "comparison window"). Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Madison, Wis.), or by manual alignment and visual inspection (see, e.g., Current Protocols in Molecular Biology (Ausubel et al., eds. 1995 supplement)).

As an example, a suitable Polypeptide can comprise an amino acid sequence having at least about 75%, at least about 80%, at least about 85%, at least about 90%, at least about 95%, at least about 98%, or at least about 99%, amino acid sequence identity to a contiguous stretch of 40, 45, 50, 55, 60, 65, 70, 75, 80, 85 or up to 112 amino acids in SEQ ID NO: 1.

Exemplary fragments of the polypeptides disclosed herein include polypeptides that have deletions of amino acids relative to SEQ ID NO: 1. For example, the polypeptides may have N-terminal truncations and/or C-terminal truncations relative to SEQ ID NO: 1. The truncations may be of 1, 2, 3, 4, 5, 6, 7, 8, 9, 10, 11, 12, 13, 14 or more amino acids relative to a reference polypeptide, e.g., SEQ ID NO: 1. In certain embodiments, a polypeptide of interest may include one or more substitutions that introduce an N-linked glycosylation consensus sequence, such as the one disclosed herein, and N-terminal truncations and/or C-terminal truncations relative to SEQ ID NO: 1.

In certain embodiments, the polypeptide may be at least 98 amino acids long and have an amino acid sequence identity of at least 90%, 92%, 95%, 96%, 97%, 98%, 99%, or 100% to a corresponding stretch of 98 amino acids in SEQ ID NO: 1. This polypeptide may be lacking the first two to first fourteen amino acids (e.g., 2, 3, 4, 5, 6, 7, 8, 9, 10, 11, 12, 13, or 14 amino acids) present at the N-terminus of SEQ ID NO: 1, while retaining the amino acids present at the C-terminus of SEQ ID NO:1. In other words, the deleted amino acid(s) correspond to the N-terminus amino acids of SEQ ID NO: 1.

In certain embodiments, the GDF15 mutein may be at least 106 amino acids long and have an amino acid sequence identity of at least 90%, 92%, 95%, 96%, 97%, 98%, 99%, or 100% to a corresponding stretch of 106 amino acids in SEQ ID NO: 1. The GDF15 mutein may be lacking the first six amino acids present at the N-terminus of SEQ ID NO: 1.

In certain embodiments, the polypeptide may be at least 109 amino acids long and have an amino acid sequence identity of at least 90%, 92%, 95%, 96%, 97%, 98%, 99%, or 100% to a corresponding stretch of 109 amino acids in SEQ ID NO: 1. The GDF15 mutein may be lacking the first three amino acids present at the N-terminus of SEQ ID NO: 1.

Exemplary polypeptides of the present disclosure may include a deletion of the two N-terminal amino acids (ΔN2) relative to the WT hGDF15 and may fused to a Fc sequence at the N-terminus. However, when referring to the position of the amino acid substitutions, the residue number indicated is the one that corresponds to the position in the WT mature hGDF15 (WT; SEQ ID NO: 1). Thus, the amino acid N at the N-terminus of a polypeptide missing the first two amino acids at the N-terminus may be referred to as residue 3 although it is the first amino acid in the GDF15 mutein polypeptide amino acid sequence and preceded by heterologous amino acid sequences (e.g., Fc).

As noted above, these polypeptide fragments may include one or more amino acid substitutions that introduce a N-glycosylation consensus sequence relative to the sequence of SEQ ID NO: 1, such as, one, two, or more of the amino acids substitutions disclosed herein.

As indicated above and as described in more detail below, the polypeptides of the present disclosure may be modified through, for example, pegylation (covalent attachment of one or more molecules of polyethylene glycol (PEG), or derivatives thereof); glycosylation (e.g., N-glycosylation); polysialylation; albumin fusion molecules comprising serum albumin (e.g., human serum albumin (HSA), cyno serum albumin, or bovine serum albumin (BSA)); albumin binding through, for example, a conjugated fatty acid chain (acylation); Fc-fusion; and fusion with a PEG mimetic. In certain embodiments, the modifications are introduced in a site-specific manner. In other embodiments, the modifications include a linker. The linker may conjugate the modifying moiety to the polypeptide.

In particular embodiments, the present disclosure contemplates modification of mature human GDF15 and GDF15 muteins (such as the polypeptides describe above) by conjugation with albumin. In other embodiments, the present disclosure contemplates modification of the polypeptides via N-glycosylation or O-glycosylation. The characteristics of albumins and polypeptide conjugates thereof (e.g., fusion proteins), and glycosylated polypeptides are described further hereafter.

Fc-GDF15 Fusion Polypeptides and Complexes Thereof

In exemplary embodiments, the GDF15 polypeptides disclosed herein may be present as a fusion polypeptide comprising an Fc polypeptide or fragment thereof fused to the amino acid sequence of one or more of the Polypeptides described herein (e.g., human GDF15 molecules, modified human GDF15 molecules, GDF15 muteins, and modified GDF15 muteins). As provided herein, the GDF15 polypeptide may be a wild type polypeptide or a mutein, e.g., a glycosylation mutein. As used herein, a "glycosylation mutein" or "glycomutein" or "glycosylation variant" or "glycovariant" in the context of a polypeptide, for example, a GDF15 polypeptide refers to a polypeptide that includes one or more glycosylation consensus site at a position in the amino acid sequence at which position the reference (wild type) polypeptide does not include the glycosylation consensus site. In certain cases, the fusion polypeptide may include an Fc-sequence fused to N-terminus of a GDF15 glycomutein disclosed herein.

Any Fc polypeptide sequence described herein or known in the art can be a component of the fusion proteins of the present disclosure. The components of the fusion proteins can be optionally covalently bonded through a linker, such as those linkers described herein. In some of the embodiments of the present disclosure, the fusion proteins comprise the Fc polypeptide sequence as an N-terminal moiety and the Polypeptides described herein as a C-terminal moiety.

In certain cases, the Fc partner of the Fc-GDF15 fusion polypeptides disclosed herein may be an Fc having the sequence of human IgG Fc (e.g., IgG1, IgG2, IgG3, or IgG4) or a variant thereof. Amino acid sequence of human IgG1 Fc is provided as SEQ ID NO: 2:

(SEQ ID NO: 2)
*EPKSCDKTHTCPPCP*APELLGGPSVFLFPPKPKDTLMISRTPEVTCVV

VDVSHEDPEVKFNWYVDGVEVHNAKTKPREEQYNSTYRVVSVLTVLHQ

DWLNGKEYKCKVSNKALPAPIEKTISKAKG̲Q̲P̲R̲E̲P̲Q̲V̲Y̲T̲L̲P̲P̲S̲R̲D̲E̲L̲T̲

K̲N̲Q̲V̲S̲L̲T̲C̲L̲V̲K̲G̲F̲Y̲P̲S̲D̲I̲A̲V̲E̲W̲E̲S̲N̲G̲Q̲P̲E̲N̲N̲Y̲K̲T̲T̲P̲P̲V̲L̲D̲S̲D̲G̲S̲F̲F̲L̲Y̲

S̲K̲L̲T̲V̲D̲K̲S̲R̲W̲Q̲Q̲G̲N̲V̲F̲S̲C̲S̲V̲M̲H̲E̲A̲L̲H̲N̲H̲Y̲T̲Q̲K̲S̲L̲S̲L̲S̲P̲G̲K̲

Hinge region is italicized, CH2 domain is underlined and CH3 domain is double underlined. The numbering of the position of the amino acid in the Fc sequence is according to the EU numbering (Edelman, G. M. et al., Proc. Natl. Acad. USA, 63, 78-85 (1969)). Thus, the glutamic acid residue "E" at position 1 in SEQ ID NO: 2 is numbered as 216; CH2 domain starts with alanine (A) which is numbered 231; CH3 domain starts at glycine (G) which is numbered 341, according to EU numbering.

Fc partner of the Fc-GDF15 fusion polypeptides disclosed herein may be an Fc having a contiguous amino acid sequence that is at least 90% identical to SEQ ID NO: 2, for example, at least 93%, at least 95%, at least 97%, at least 98%, or more identical to SEQ ID NO: 2. In certain embodiments, the Fc partner may be a fragment of Fc comprising a CH3 domain or a contiguous amino acid sequence that is at least 90%, 92%, 95%, 96%, 97%, 98%, 99%, or 100% identical to the CH3 domain in SEQ ID NO: 2. In certain embodiments, the Fc partner may be a fragment of Fc comprising a CH2 domain and a CH3 domain or a contiguous amino acid sequence that is at least 90%, 92%, 95%, 96%, 97%, 98%, 99%, or 100% identical to the CH2 and CH3 domains in SEQ ID NO: 2. In certain embodiments, the Fc partner may be a fragment of Fc comprising a partial hinge region, a CH2 domain, and a CH3 domain or a contiguous amino acid sequence that is at least 90%, 92%, 95%, 96%, 97%, 98%, 99%, or 100% identical to the hinge region, CH2 domain, and CH3 domain in SEQ ID NO: 2. In certain embodiments, the Fc partner may have an amino acid sequence at least 90%, 92%, 95%, 96%, 97%, 98%, 99%, or 100% identical to the amino acid sequence set forth in SEQ ID NO: 2.

In certain cases, the Fc partner of the Fc-GDF15 fusion polypeptides may include an engineered protuberance which protuberance can associate another Fc polypeptide that includes an engineered cavity. In other cases, the Fc partner of the Fc-GDF15 fusion polypeptides may include an engineered cavity which cavity can associate another Fc polypeptide that includes an engineered protuberance. Exemplary Fc sequences with engineered protuberance and/or cavity are described in U.S. Pat. No. 8,216,805. In certain cases, the protuberance and the cavity may be engineered into CH3 domain of the Fc polypeptide. In certain cases, the Fc partner that associates with the Fc-GDF15 fusion polypeptides of the present disclosure, is not conjugated to a GDF15 polypeptide. Accordingly, the Fc partner dimerizes with the Fc-GDF15 fusion polypeptide forming a heterodimer, with one GDF15 molecule per heterodimer.

"Protuberances" or "knobs" may be engineered by replacing small amino acid side chains in a CH3 domain of a first polypeptide with larger side chains (e.g. tyrosine or tryptophan). Compensatory "cavities" or "holes" of identical or similar size to the protuberances are optionally created in the CH3 domain of a second polypeptide by replacing large amino acid side chains with smaller ones (e.g. alanine or threonine).

The "first polypeptide" may any polypeptide which is to be associated with a second polypeptide. The first and second polypeptide meet at an "interface" (defined below). In addition to the interface, the first polypeptide may comprise one or more additional domains, such as a CH2 domain or a hinge region. In certain cases, the first polypeptide includes a CH3 domain which can form the interface of the first polypeptide.

The "second polypeptide" may be any polypeptide which is to be associated with the first polypeptide via an "interface". In addition to the interface, the second polypeptide may comprise one or more additional domains, such as a CH2 domain or a hinge region. In certain cases, the second polypeptide includes a CH3 domain which can form the interface of the second polypeptide.

The "interface" comprises those "contact" amino acid residues (or other non-amino acid groups such as carbohydrate groups, NADH, biotin, FAD or haem group) in the first polypeptide which interact with one or more "contact" amino acid residues (or other non-amino acid groups) in the interface of the second polypeptide. In certain cases, the interface may be a domain of an immunoglobulin such as a constant domain (or fragments thereof). In certain cases, the interface comprises the CH3 domain of an immunoglobulin which is derived from an IgG antibody, for example, an human IgG1, IgG2, IgG3, or IgG4 antibody.

A "protuberance" refers to at least one amino acid side chain which projects from the interface of the first polypeptide and is therefore positionable in a compensatory cavity in the adjacent interface (i.e. the interface of the second polypeptide) so as to stabilize the heterodimer, and thereby favor heterodimer formation over homodimer formation, for example. The cavity may exist in the original interface or may be introduced synthetically (e.g. by altering nucleic acid encoding the interface). The protuberance may be introduced synthetically (e.g. by altering nucleic acid encoding the interface) for example, by recombinant means.

A "cavity" refers to at least one amino acid side chain which is recessed from the interface of the second polypeptide and therefore accommodates a corresponding protuberance on the adjacent interface of the first polypeptide. The cavity may exist in the original interface or may be introduced synthetically (e.g. by altering nucleic acid encoding the interface). For example, nucleic acid encoding the interface of the second polypeptide is altered to encode the cavity.

A protuberance is also referred to as a 'knob' and a cavity is also referred to as a 'hole'. Exemplary protuberances and cavities are disclosed in U.S. Pat. No. 8,216,805 and include substitutions at the following amino acid positions: 347, 366, 368, 394, 405, and 407. The numbering of the position of the amino acid is according to the EU numbering. The engineered protuberance may include at least one substitution of the corresponding amino acid in a human IgG1 Fc sequence, wherein the substitution is at a position selected from the group consisting of amino acid residues 347, 366 and 394. For example, the at least one substitution is selected from the group consisting of Q347W/Y, T366W/Y, and T394W/Y. In certain cases, the engineered cavity comprises at least one substitution of the corresponding amino acid in a human IgG1 Fc sequence, wherein the substitution is at a position selected from the group consisting of amino acid residues 366, 368, 394, 405, and 407. For example, the least one substitution is selected from the group consisting of T366S, L368A, T394S, F405T/V/A, and Y407T/V/A.

In certain cases, the protuberance may include the substitution T366W/Y and the cavity may include the substitutions T366S, L368A, and Y407T/V/A.

For example, the protuberance may include the substitution T366W/Y and the cavity may include the substitution Y407T/V/A. In other cases, the protuberance may include the substitution T366Y and the cavity may include the substitution Y407T. In other examples, the protuberance may include the substitution T366W and the cavity may include the substitution Y407A. In further examples, the protuberance may include the substitution T394Y and the cavity may include the substitution Y407T.

In certain embodiments, the Fc partner of GDF15 polypeptide in the fusion polypeptide may include additional mutations that improve a property of the fusion polypeptide. As such, the Fc sequences in the first and the second polypeptides described herein, may include additional mutations. For example, the Fc partner sequence may include a mutation(s) that abrogates (e.g., decreases or eliminates) IgG effector function that otherwise may be a characteristic of the Fc partner. In certain cases, the Fc partner sequence may include mutation(s) that abrogate effector functions such as complement-dependent cytotoxicity (CDC), antibody-dependent cellular cytotoxicity (ADCC) and antibody-dependent cell phagocytosis (ADCP).

The four human IgG isotypes bind the activating Fcγ receptors (FcγRI, FcγRIIa, FcγRIIIa), the inhibitory FcγRIIb receptor, and the first component of complement (C1q) with different affinities, yielding very different effector functions. Thus, mutations within the binding regions may have a significant impact on effector function.

Binding of IgG to the FcγRs or C1q depends on residues located in the hinge region and the CH2 domain. Two regions of the CH2 domain are critical for FcγRs and C1q binding, and have unique sequences in IgG2 and IgG4. Substitutions into human IgG1 of IgG2 residues at positions 233-236 and IgG4 residues at positions 327, 330 and 331 were shown to greatly reduce ADCC and CDC activity (Armour K L. et al., 1999. Eur J Immunol. 29(8):2613-24; Shields R L et al., 2001, J Biol Chem. 276(9):6591-604). Furthermore, Idusogie et al. demonstrated that alanine substitution at different positions, including K322, significantly reduced complement activation (Idusogie E E. et al., 2000. J Immunol. 164(8):4178-84). Similarly, mutations in the CH2 domain of murine IgG2A were shown to reduce the binding to FcγRI, and C1q (Steurer W. et al., 1995. J Immunol. 155(3): 1165-74). In certain embodiments, the Fc polypeptide may include a mutation in the CH2 domain that abrogates IgG effector function(s). Exemplary mutations in the CH2 regions include: APELLGGP (SEQ ID NO: 96)→APALLGGP (SEQ ID NO: 98); APELLGGP (SEQ ID NO: 96)→APELAGGP (SEQ ID NO: 99); and APELLGGP (SEQ ID NO: 96)→APALAGGP (SEQ ID NO: 97).

In some embodiments, an Fc polypeptide conjugated to the GDF15 glycomuteins comprises part or all of a wild type hinge sequence (generally at its N terminus). In some embodiments, an Fc polypeptide does not comprise a functional or wild type hinge sequence. In certain cases, the Fc sequence may include one of the following hinge sequences: EPKSCDKTHTCPPCP (SEQ ID NO: 100); KSCDKTHTCPPCP (SEQ ID NO: 101); SCDKTHTCPPCP (SEQ ID NO: 102); CDKTHTCPPCP (SEQ ID NO: 103); DKTH-TCPPCP (SEQ ID NO: 104); KTHTCPPCP (SEQ ID NO: 105); THTCPPCP (SEQ ID NO: 106); or CPPCP (SEQ ID NO: 107); or a variant thereof having one or more substitutions (e.g., 1-6 substitutions, for example, 1-5, 1-4, 1, 2, 3, 4, 5, or 6 substitutions). In certain cases, the Fc sequence may include hinge region that forms a covalent bond (e.g., one or more disulphide bonds) with the hinge region of another Fc. Thus, in certain embodiments, the first and second polypeptides in the complexes disclosed herein may be associated via a covalent interaction between the hinge regions of the first and second polypeptides. The covalent interaction may include one or two intermolecular disulphide bonds.

In described in detail herein, a first polypeptide comprising an Fc knob or hole sequence conjugated to a GDF15 glycomutein is contemplated. Such a polypeptide may be in a complex with a second Fc polypeptide with which the first polypeptide can physically associate via the placement of the knob into the hole of the Fc sequence.

In certain cases, a complex of a first Fc polypeptide and a second Fc polypeptide is disclosed. One of the first or the second polypeptide may be a fusion polypeptide of Fc and GDF15. As noted herein, the GDF15 polypeptide may include a glycosylation mutation(s) leading to glycosylation of the GDF15 polypeptide. A glycosylated GDF15 polypeptide may also be referred to as GDF15-glycan or GDF15-glycomutein. The GDF15-glycan or GDF15-glycomutein may be as disclosed herein. In certain cases, the GDF15-glycan or GDF15-glycomutein fused to the Fc-knob or Fc-hole polypeptide provided herein may be a Polypeptide that includes a contiguous amino acid sequence that is at least 80%, 85%, 90%, 95%, 96%, 97%, 98%, 99%, or 100% identical to the amino acid sequence of SEQ ID NO: 1, where the contiguous amino acid sequence has the substitution D5T; D5S; or R21N relative to the amino acid sequence of SEQ ID NO: 1. In certain embodiments, the GDF15-glycan or GDF15-glycomutein fused to the Fc-knob or Fc-hole polypeptide may be a Polypeptide that has an amino acid sequence that is at least 80%, 85%, 90%, 95%, 96%, 97%, 98%, 99%, or 100% identical to the amino acid sequence of SEQ ID NO: 1, where the amino acid sequence includes one or more of the following pairs of substitutions relative to the amino acid sequence of SEQ ID NO: 1:

xvii. R16N and H18T or R16N and H18S;
xviii. S23N and E25T or S23N and E25S;
xix. S50N and F52T or S50N and F52S;
xx. F52N and A54T or F52N and A54S;
xxi. R53N and A55T or R53N and A55S;
xxii. S64N and H66T or S64N and H66S;
xxiii. K91N and D93T or K91N and D93S;
xxiv. D93N and G95T or D93N and G95S;
xxv. T94N and V96T or T94N and V96S;
xxvi. V96N and L98T or V96N and L98S;
xxvii. S97N and Q99T or S97N and Q99S; and
xxviii. A106N and D108T or A106N and D108S In certain cases, the complex may include a first and a second polypeptide. The first polypeptide may include an IgG Fc sequence, the IgG Fc sequence may include a CH3 sequence that includes at least one engineered protuberance; and a second polypeptide comprising an IgG Fc sequence, the IgG Fc sequence comprising a CH3 sequence comprising at least one engineered cavity, wherein the first polypeptide dimerizes with the second polypeptide via positioning of the protuberance of the first polypeptide into the cavity of the second polypeptide, and wherein either the C-terminus of the first polypeptide or the C-terminus of the second polypeptide is conjugated to the N-terminus of a GDF15 mutein comprising at least one N-linked glycosylation consensus site. Accordingly, the complex comprises a heterodimer of the first polypeptide and the second polypeptide. Since either the first or the second polypeptide is fused to the GDF15 muteins disclosed herein, one GDF15 molecule is present per heterodimer. In certain cases, the GDF15 mutein may be a GDF15 mutein described herein.

As discussed herein the first and second polypeptides may interact to form a heterodimer via covalent and/or non-covalent interactions, such as, hydrophobic interaction, disulfide bonds, or both.

In certain embodiments, a complex comprising a first heterodimer and a second heterodimer is disclosed. Each of the first heterodimer and second heterodimer may include a first polypeptide and a second polypeptide, wherein the first polypeptide may include an IgG Fc sequence, the IgG Fc sequence may include a CH3 sequence comprising at least one engineered protuberance; the second polypeptide may include an IgG Fc sequence, the IgG Fc sequence may include a CH3 sequence comprising at least one engineered cavity; wherein the first polypeptide dimerizes with the second polypeptide via positioning of the protuberance of the first polypeptide into the cavity of the second polypeptide, wherein either the C-terminus the first polypeptide or the C-terminus the second polypeptide is conjugated to the N-terminus of a GDF15 mutein comprising at least one N-linked glycosylation consensus site, wherein the GDF15 mutein in the first heterodimer dimerizes with the GDF15 mutein in the second heterodimer thereby forming the complex comprising the first heterodimer and second heterodimer. In a complex of the present disclosure which complex includes the first heterodimer physically associated with a second heterodimer, two molecules of GDF15 are present per heterodimer-heterodimer complex.

As noted herein, the first and second polypeptides may interact to form a heterodimer via covalent and/or non-covalent interactions, such as, hydrophobic interaction, disulfide bonds, or both and the first and second heterodimers dimers may interact to form a dimer-dimer complex by covalent and/or non-covalent interactions, such as, hydrophobic interaction, disulfide bonds, or both.

In certain cases, the GDF15 muteins present in each of the heterodimers described herein, for example, in a complex of two heterodimers, may be identical in sequence or different. In certain cases, the GDF15 mutein in a complex of two heterodimers, may be identical in sequence.

Exemplary, Fc sequences for fusion to GDF15 muteins and as binding partners to Fc-GDF15 fusion proteins are disclosed herein. In certain embodiments, Fc sequences present in the complexes of the present disclosure may be similar or identical in sequence other than the engineered 'knob' and 'hole' sequences.

In certain cases, the first and second polypeptides that may interact to form the complexes disclosed herein may be as set forth below as Pair I through VIII. In the sequences set out below, the human immunoglobinG1 (hIgG1) Fc sequence is followed by a linker sequence (underlined), followed by GDF15 mutein sequence (in bold).

PAIR I:
First Polypeptide: hIgG1-Fc(AA)(T366W)-(G4S)2-ΔN2-GDF15(N3-I112)(D5T)
(SEQ ID NO: 3)

DKTHTCPPCPAPALAGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLWCLVKGFYPSDIAVEWESNGQPE

NNYKTTPPVLDSDGSFFLYSKLTVDKSRWQQGNVFSCSVMHEALHNHYTQKSLSLSPG

<u>KGGGGSGGGGS</u>NGTHCPLGPGRCCRLHTVRASLEDLGWADWVLSPREVQVTMCI

GACPSQFRAANMHAQIKTSLHRLKPDTVPAPCCVPASYNPMVLIQKTDTGVSLQTY

DDLLAKDCHCI

Second Polypeptide: hIgG1-Fc(AA)(T366S)(L368A)(Y407V)
(SEQ ID NO: 4)

DKTHTCPPCPAPALAGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLSCAVKGFYPSDIAVEWESNGQPEN

NYKTTPPVLDSDGSFFLVSKLTVDKSRWQQGNVFSCSVMHEALHNHYTQKSLSLSPGK

PAIR II:
First Polypeptide: hIgG1-Fc(AA)(T366W)-(G4S)5-ΔN2-GDF15(N3-I112)(D5T)
(SEQ ID NO: 5)

DKTHTCPPCPAPALAGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLWCLVKGFYPSDIAVEWESNGQPE

NNYKTTPPVLDSDGSFFLYSKLTVDKSRWQQGNVFSCSVMHEALHNHYTQKSLSLSPG

<u>KGGGGSGGGGSGGGGSGGGGSGGGGS</u>NGTHCPLGPGRCCRLHTVRASLEDLGWAD

WVLSPREVQVTMCIGACPSQFRAANMHAQIKTSLHRLKPDTVPAPCCVPASYNPM

VLIQKTDTGVSLQTYDDLLAKDCHCI

Second Polypeptide: hIgG1-Fc(AA)(T366S)(L368A)(Y407V)
(SEQ ID NO: 6)

DKTHTCPPCPAPALAGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLSCAVKGFYPSDIAVEWESNGQPEN

NYKTTPPVLDSDGSFFLVSKLTVDKSRWQQGNVFSCSVMHEALHNHYTQKSLSLSPGK

PAIR III:
First Polypeptide: hIgG1-Fc(AA)(T366W)-(G4S)5-ΔN3-GDF15(G4-I112)(R21N)
(SEQ ID NO: 7)

DKTHTCPPCPAPALAGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLWCLVKGFYPSDIAVEWESNGQPE

NNYKTTPPVLDSDGSFFLYSKLTVDKSRWQQGNVFSCSVMHEALHNHYTQKSLSLSPG

<u>KGGGGSGGGGSGGGGSGGGGSGGGGS</u>GDHCPLGPGRCCRLHTVNASLEDLGWAD

WVLSPREVQVTMCIGACPSQFRAANMHAQIKTSLHRLKPDTVPAPCCVPASYNPM

VLIQKTDTGVSLQTYDDLLAKDCHCI

Second Polypeptide: hIgG1-Fc(AA)(T366S)(L368A)(Y407V)
(SEQ ID NO: 8)

DKTHTCPPCPAPALAGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLSCAVKGFYPSDIAVEWESNGQPEN

NYKTTPPVLDSDGSFFLVSKLTVDKSRWQQGNVFSCSVMHEALHNHYTQKSLSLSPGK

-continued

PAIR IV:
First Polypeptide: hIgG1-Fc(AA)(T366W)-(G4S)5-ΔN3-GDF15(G4-I112)(S23N/E25T)
(SEQ ID NO: 9)

DKTHTCPPCPAPALAGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLWCLVKGFYPSDIAVEWESNGQPE

NNYKTTPPVLDSDGSFFLYSKLTVDKSRWQQGNVFSCSVMHEALHNHYTQKSLSLSPG

KGGGGSGGGGSGGGGSGGGGSGGGGSGDHCPLGPGRCCRLHTVRANLTDLGWAD

WVLSPREVQVTMCIGACPSQFRAANMHAQIKTSLHRLKPDTVPAPCCVPASYNPM

VLIQKTDTGVSLQTYDDLLAKDCHCI

Second Polypeptide: hIgG1-Fc(AA)(T366S)(L368A)(Y407V)
(SEQ ID NO: 10)

DKTHTCPPCPAPALAGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLSCAVKGFYPSDIAVEWESNGQPEN

NYKTTPPVLDSDGSFFLVSKLTVDKSRWQQGNVFSCSVMHEALHNHYTQKSLSLSPGK

PAIR V:
First Polypeptide: hIgG1-Fc(AA)(T366W)-(G4S)5-ΔN3-GDF15(G4-I112)(F52N/A54T)
(SEQ ID NO: 11)

DKTHTCPPCPAPALAGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLWCLVKGFYPSDIAVEWESNGQPE

NNYKTTPPVLDSDGSFFLYSKLTVDKSRWQQGNVFSCSVMHEALHNHYTQKSLSLSPG

KGGGGSGGGGSGGGGSGGGGSGGGGSGDHCPLGPGRCCRLHTVRASLEDLGWAD

WVLSPREVQVTMCIGACPSQNRTANMHAQIKTSLHRLKPDTVPAPCCVPASYNPM

VLIQKTDTGVSLQTYDDLLAKDCHCI

Second Polypeptide: hIgG1-Fc(AA)(T366S)(L368A)(Y407V)
(SEQ ID NO: 12)

DKTHTCPPCPAPALAGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLSCAVKGFYPSDIAVEWESNGQPEN

NYKTTPPVLDSDGSFFLVSKLTVDKSRWQQGNVFSCSVMHEALHNHYTQKSLSLSPGK

PAIR VI:
First Polypeptide: hIgG1-Fc(AA)(T366W)-(G4S)5-ΔN3-GDF15(G4-I112)(R53N/A55T)
(SEQ ID NO: 13)

DKTHTCPPCPAPALAGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLWCLVKGFYPSDIAVEWESNGQPE

NNYKTTPPVLDSDGSFFLYSKLTVDKSRWQQGNVFSCSVMHEALHNHYTQKSLSLSPG

KGGGGSGGGGSGGGGSGGGGSGGGGSGDHCPLGPGRCCRLHTVRASLEDLGWAD

WVLSPREVQVTMCIGACPSQFNATNMHAQIKTSLHRLKPDTVPAPCCVPASYNPM

VLIQKTDTGVSLQTYDDLLAKDCHCI

Second Polypeptide: hIgG1-Fc(AA)(T366S)(L368A)(Y407V)
(SEQ ID NO: 14)

DKTHTCPPCPAPALAGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLSCAVKGFYPSDIAVEWESNGQPEN

NYKTTPPVLDSDGSFFLVSKLTVDKSRWQQGNVFSCSVMHEALHNHYTQKSLSLSPGK

```
PAIR VII:
First Polypeptide: hIgG1-Fc(AA)(T366W)-(G4S)5-ΔN3-GDF15(G4-I112)(K91N/D93T)
                                                                          (SEQ ID NO: 15)
DKTHTCPPCPAPALAGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLWCLVKGFYPSDIAVEWESNGQPE

NNYKTTPPVLDSDGSFFLYSKLTVDKSRWQQGNVFSCSVMHEALHNHYTQKSLSLSPG

KGGGGSGGGGSGGGGSGGGGSGGGGSGDHCPLGPGRCCRLHTVRASLEDLGWAD

WVLSPREVQVTMCIGACPSQFRAANMHAQIKTSLHRLKPDTVPAPCCVPASYNPM

VLIQNTTTGVSLQTYDDLLAKDCHCI

Second Polypeptide: hIgG1-Fc(AA)(T366S)(L368A)(Y407V)
                                                                          (SEQ ID NO: 16)
DKTHTCPPCPAPALAGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLSCAVKGFYPSDIAVEWESNGQPEN

NYKTTPPVLDSDGSFFLVSKLTVDKSRWQQGNVFSCSVMHEALHNHYTQKSLSLSPGK

PAIR VIII:
First Polypeptide: hIgG1-Fc(AA)(T366W)-(G4S)5-ΔN3-GDF15(G4-I112)(D93N/G95T)
                                                                          (SEQ ID NO: 17)
DKTHTCPPCPAPALAGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLWCLVKGFYPSDIAVEWESNGQPE

NNYKTTPPVLDSDGSFFLYSKLTVDKSRWQQGNVFSCSVMHEALHNHYTQKSLSLSPG

KGGGGSGGGGSGGGGSGGGGSGGGGSGDHCPLGPGRCCRLHTVRASLEDLGWAD

WVLSPREVQVTMCIGACPSQFRAANMHAQIKTSLHRLKPDTVPAPCCVPASYNPM

VLIQKTNTTVSLQTYDDLLAKDCHCI

Second Polypeptide: hIgG1-Fc(AA)(T366S)(L368A)(Y407V)
                                                                          (SEQ ID NO: 18)
DKTHTCPPCPAPALAGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLSCAVKGFYPSDIAVEWESNGQPEN

NYKTTPPVLDSDGSFFLVSKLTVDKSRWQQGNVFSCSVMHEALHNHYTQKSLSLSPGK
```

In certain cases, the first and second polypeptides that may interact to form the complexes disclosed herein may have an amino acid sequence at least 80% identical to the amino acid sequence of the first and second polypeptides, respectively, as disclosed above in Pairs I through VIII. For example, the sequence identity may be at least 85%, at least 90%, at least 95%, at least 97%, at least 99%, or more.

In certain embodiments, the complex may include a first polypeptide having an amino acid sequence at least 90%, 92%, 95%, 96%, 97%, 98%, 99%, or 100% identical to amino acid sequence of SEQ ID NO: 3; and a second polypeptide having an amino acid sequence at least 90%, 92%, 95%, 96%, 97%, 98%, 99%, or 100% identical to amino acid sequence of SEQ ID NO:4, where the first and second polypeptides are covalently linked via at least one intermolecular disulphide bond. Also provided herein is a complex comprising a first heterodimer and a second heterodimer, each of the first heterodimer and second heterodimer comprising a first polypeptide having an amino acid sequence at least 90%, 92%, 95%, 96%, 97%, 98%, 99%, or 100% identical to amino acid sequence of SEQ ID NO: 3; and a second polypeptide having an amino acid sequence at least 90%, 92%, 95%, 96%, 97%, 98%, 99%, or 100% identical to amino acid sequence of SEQ ID NO:4.

In certain embodiments, the complex may include a first polypeptide having an amino acid sequence at least 90%, 92%, 95%, 96%, 97%, 98%, 99%, or 100% identical to amino acid sequence of SEQ ID NO: 5; and a second polypeptide having an amino acid sequence at least 90%, 92%, 95%, 96%, 97%, 98%, 99%, or 100% identical to amino acid sequence of SEQ ID NO:6, where the first and second polypeptides are covalently linked via at least one intermolecular disulphide bond. Also provided herein is a complex comprising a first heterodimer and a second heterodimer, each of the first heterodimer and second heterodimer comprising a first polypeptide having an amino acid sequence at least 90%, 92%, 95%, 96%, 97%, 98%, 99%, or 100% identical to amino acid sequence of SEQ ID NO: 5; and a second polypeptide having an amino acid sequence at least 90%, 92%, 95%, 96%, 97%, 98%, 99%, or 100% identical to amino acid sequence of SEQ ID NO:6.

In certain embodiments, the complex may include a first polypeptide having an amino acid sequence at least 90%, 92%, 95%, 96%, 97%, 98%, 99%, or 100% identical to amino acid sequence of SEQ ID NO: 7; and a second polypeptide having an amino acid sequence at least 90%, 92%, 95%, 96%, 97%, 98%, 99%, or 100% identical to amino acid sequence of SEQ ID NO:8, where the first and second polypeptides are covalently linked via at least one intermolecular disulphide bond. Also provided herein is a complex comprising a first heterodimer and a second heterodimer, each of the first heterodimer and second heterodimer comprising a first polypeptide having an amino acid sequence at least 90%, 92%, 95%, 96%, 97%, 98%, 99%, or 100% identical to amino acid sequence of SEQ ID NO: 7; and a second polypeptide having an amino acid sequence at least 90%, 92%, 95%, 96%, 97%, 98%, 99%, or 100% identical to amino acid sequence of SEQ ID NO:8.

In particular embodiments, the complexes disclosed herein may include two heterodimers, each heterodimer comprising:

```
(a) a hIgG1-Fc polypeptide comprising a knob
(Fc-knob) and having the sequence:
                                 (SEQ ID NO: 127)
DKTHTCPPCPAPALAGGPSVFLFPPKPKDTLMISRTPEVTCVVVDVS

HEDPEVKFNWYVDGVEVHNAKTKPREEQYNSTYRVVSVLTVLHQDWL

NGKEYKCKVSNKALPAPIEKTISKAKGQPREPQVYTLPPSREEMTKN

QVSLWCLVKGFYPSDIAVEWESNGQPENNYKTTPPVLDSDGSFFLYS

KLTVDKSRWQQGNVFSCSVMHEALHNHYTQKSLSLSPGK;
and (b) a hIgG1-Fc polypeptide comprising a hole
(Fc-hole) and having the sequence:
                                 (SEQ ID NO: 4)
DKTHTCPPCPAPALAGGPSVFLFPPKPKDTLMISRTPEVTCVVVDVS

HEDPEVKFNWYVDGVEVHNAKTKPREEQYNSTYRVVSVLTVLHQDWL

NGKEYKCKVSNKALPAPIEKTISKAKGQPREPQVYTLPPSREEMTKN

QVSLSCAVKGFYPSDIAVEWESNGQPENNYKTTPPVLDSDGSFFLVS

KLTVDKSRWQQGNVFSCSVMHEALHNHYTQKSLSLSPGK,
``` where either the Fc-knob (a) or the Fc-hole (b) is fused at the C-terminus to the N-terminus of a GDF15 glycomutein. The sequence of the GDF15 glycomutein may be as follows:

```
GDF15 (A1-I112)D5T;
                                 (SEQ ID NO: 128)
ARNGTHCPLGPGRCCRLHTVRASLEDLGWADWVLSPREVQVTMCIGAC

PSQFRAANMHAQIKTSLHRLKPDTVPAPCCVPASYNPMVLIQKTDTGV

SLQTYDDLLAKDCHCI;
or

ΔN2-GDF15(N3-I112)D5T;
                                 (SEQ ID NO: 129)
NGTHCPLGPGRCCRLHTVRASLEDLGWADWVLSPREVQVTMCIGACPS

QFRAANMHAQIKTSLHRLKPDTVPAPCCVPASYNPMVLIQKTDTGVSL

QTYDDLLAKDCHCI;
or

ΔN3-GDF15(G4-I112)D5T;
                                 (SEQ ID NO: 130)
GTHCPLGPGRCCRLHTVRASLEDLGWADWVLSPREVQVTMCIGACPSQ

FRAANMHAQIKTSLHRLKPDTVPAPCCVPASYNPMVLIQKTDTGVSLQ

TYDDLLAKDCHCI;
or

ΔN3-GDF15(GR-I112)R21N;
                                 (SEQ ID NO: 131)
GDHCPLGPGRCCRLHTVNASLEDLGWADWVLSPREVQVTMCIGACPSQ

FRAANMHAQIKTSLHRLKPDTVPAPCCVPASYNPMVLIQKTDTGVSLQ

TYDDLLAKDCHCI;
or

ΔN3-GDF15(G4-I112)(S23N/E25T);
                                 (SEQ ID NO: 132)
GDHCPLGPGRCCRLHTVRANLTDLGWADWVLSPREVQVTMCIGACPSQ

FRAANMHAQIKTSLHRLKPDTVPAPCCVPASYNPMVLIQKTDTGVSLQ

TYDDLLAKDCHCI;
or

ΔN3-GDF15(G4-I112)(F52N/A54T);
                                 (SEQ ID NO: 133)
GDHCPLGPGRCCRLHTVRASLEDLGWADWVLSPREVQVTMCIGACPSQ

NRTANMHAQIKTSLHRLKPDTVPAPCCVPASYNPMVLIQKTDTGVSLQ

TYDDLLAKDCHCI;
or

ΔN3-GDF15(G4-I112)(R53N/A55T);
                                 (SEQ ID NO: 134)
GDHCPLGPGRCCRLHTVRASLEDLGWADWVLSPREVQVTMCIGACPSQ

FNATNMHAQIKTSLHRLKPDTVPAPCCVPASYNPMVLIQKTDTGVSLQ

TYDDLLAKDCHCI;
or

ΔN3-GDF14(G4-I112)(K91N/D93T);
                                 (SEQ ID NO: 135)
GDHCPLGPGRCCRLHTVRASLEDLGWADWVLSPREVQVTMCIGACPSQ

FRAANMHAQIKTSLHRLKPDTVPAPCCVPASYNPMVLIQNTTTGVSLQ

TYDDLLAKDCHCI;
or

ΔN3-GDF15(G4-I112)(D93N/G95T);
                                 (SEQ ID NO: 136)
GDHCPLGPGRCCRLHTVRASLEDLGWADWVLSPREVQVTMCIGACPSQ

FRAANMHAQIKTSLHRLKPDTVPAPCCVPASYNPMVLIQKTNTTVSLQ

TYDDLLAKDCHCI.
```

In certain examples, the amino acid sequence of the Fc-knob may be at least 85%, 90%, 92%, 95%, 96%, 97%, 98%, 99%, or more identical to amino acid sequence of SEQ ID NO: 127. In certain examples, the amino acid sequence of the Fc-hole may be at least 85%, 90%, 92%, 95%, 96%, 97%, 98%, 99%, or more identical to amino acid sequence of SEQ ID NO: 4. In certain examples, the amino acid sequence of the GDF15 mutein may be at least 85%, 90%, 92%, 95%, 96%, 97%, 98%, 99%, or more identical to amino acid sequence of any one of SEQ ID NOs: 128-136.

The Fc-knob or the Fc-hole may be joined with the GDF15 glycomutein via a linker sequence $(G_4S)_n$, wherein n=1-10, such as, 2, 3, 4, or 5.

In certain examples, the complexes of the present disclosure may have a recovery of at least 50 mg/L, for example at least more than 55 mg/L, 60 mg/L, 65 mg/L, 70 mg/L, 75 mg/L, 80 mg/L, 85 mg/L, 90 mg/L, 95 mg/L, 100 mg/L, 110 mg/L, 120 mg/L, 130 mg/L, 140 mg/L, 150 mg/L, 160 mg/L, 170 mg/L, 180 mg/L, 190 mg/L, 200 mg/L, or more. In certain cases, the complexes of the present disclosure may have a recovery of at least 50 mg/L-300 mg/L, such as 60 mg/L-300 mg/L, 75 mg/L-300 mg/L, 75 mg/L-250 mg/L, 75 mg/L-200 mg/L, 75 mg/L-175 mg/L, 75 mg/L-150 mg/L, 100 mg/L-300 mg/L, 100 mg/L-250 mg/L, 100 mg/L-200 mg/L, 100 mg/L-150 mg/L, 100 mg/L-125 mg/L, 110 mg/L-300 mg/L, or 150 mg/L-300 mg/L. Recovery of the complex refers to the amount of fully assembled dimer-dimer complex obtained from culture media in which a host cell expressing the first and second polypeptides that form the two dimers present in each fully assembled complex, is cultured.

The present disclosure also contemplates Fc polypeptide fusion partners, and fusion proteins comprising such, where the Fc polypeptide fusion partner is modified to be one partner of a charged Fc pair. A "partner of a charged Fc pair" refers to a (i) a "negatively charged" Fc sequence (optionally lacking the hinge region) and comprising a charged pair mutation or (ii) a "positively charged" Fc sequence (optionally lacking the hinge region) and comprising a charged pair mutation. "Positively charged" and "negatively charged" are used herein for ease of reference to describe the nature of the charge pair mutations in the Fc sequences, and not to indicate that the overall sequence or construct necessarily has a positive or negative charge. Charged Fc amino acid sequences suitable for use in Polypeptide constructs (e.g., GDF15 glycomutein, modified GDF15 glycomuteins) of the present disclosure are described in, for example WO 2013/113008.

Examples of a positively charged Fc ("Fc(+)") include an Fc comprising an aspartatic acid-to-lysine mutation (E356K) and a glutamic acid-to-lysine mutation (D399K) of an Fc sequence lacking the hinge region. Examples of a negatively charged Fc ("Fc(−)") include an Fc comprising two lysine-to-aspartate mutations (K392D, K409D) in an Fc sequence lacking the hinge region. The C-terminal lysine (K477) also may also be optionally deleted. When a Fc(+) Polypeptide fusion protein (e.g., Fc(+)GDF15 mutein fusion protein) and a Fc(−)Polypeptide fusion protein (e.g., Fc(−) GDF15 mutein fusion protein) are incubated together, the aspartate residues associate with the lysine residues through electrostatic force, facilitating formation of Fc heterodimers between the Fc(+) and the Fc(−) sequences of the GDF15 Polypeptide fusion proteins.

The present disclosure also contemplates constructs designated "hemi" or "hemiFc" constructs, which comprise two Fc sequences joined in tandem by a linker that connects the N-terminus of a first Fc sequence to the C-terminus of a second Fc sequence. In some embodiments, a monomer comprises a Polypeptide (e.g., a mature modified GDF15 or GDF15 glycomutein) sequence linked to the first Fc sequence by a first linker that connects the N-terminus of the GDF15 sequence to the C-terminus of the first Fc sequence, wherein the first Fc sequence is linked to the second Fc sequence by a second linker that connects the N-terminus of the first Fc sequence to the C-terminus of the second Fc sequence. The first and second Fc sequences also are associated by the Fc hinge regions. Two such monomers associate to form a dimer in which the monomers are linked via an interchain disulfide bond between the two Polypeptide sequences. For examples of hemiFc polypeptides suitable for use with the GDF15 muteins of the present disclosure see WO 2013/113008.

The present disclosure also contemplates fusion proteins having a multimer of Fc polypeptides, or fragments thereof, including a partner of a charged Fc pair (e.g., multimer of an Fc).

The complexes of the present disclosure have improved properties such as increased solubility, decreased aggregation, and/or increase serum half-life. In certain cases, the solubility of the complexes is generally improved relative to unconjugated recombinant human GDF15 and Fc (knob or hole) conjugated wild type GDF15. In certain embodiments, the complex has a solubility of at least 1 mg/mL in phosphate buffered saline (PBS) at pH 7.0. In other embodiments, the complex has a solubility of at least 2 mg/mL, at least 3 mg/mL, at least 4 mg/mL, or at least 5 mg/mL. In other embodiments, the complex has a solubility of at least 6 mg/mL in phosphate buffered saline (PBS) at pH 7.0, at least 7 mg/mL, at least 8 mg/mL, at least 9 mg/mL, or at least 10 mg/mL. In particular embodiments, the complex has a solubility of greater than 10 mg/mL.

Glycosylation:

For purposes of the present disclosure, "glycosylation" is meant to broadly refer to the enzymatic process that attaches glycans to proteins, lipids or other organic molecules. The use of the term "glycosylation" in conjunction with the present disclosure is generally intended to mean adding or deleting one or more carbohydrate moieties (either by removing the underlying glycosylation site or by deleting the glycosylation by chemical and/or enzymatic means), and/or adding one or more glycosylation sites that may or may not be present in the native sequence. In addition, the phrase includes qualitative changes in the glycosylation of the native proteins involving a change in the nature and proportions of the various carbohydrate moieties present.

Glycosylation can dramatically affect the physical properties of proteins and can also be important in protein stability, secretion, and subcellular localization. Indeed, glycosylation of the GDF15 mutein polypeptides described herein imparts beneficial improvements to their physical properties. By way of example, but not limitation, solubility of GDF15 muteins can be improved by glycosylation, and such improvement may be substantial (see Examples). The solubility improvement exhibited by such modified GDF15 muteins can, for example, enable the generation of formulations more suitable for pharmaceutical administration than non-glycosylated GDF15/GDF15 muteins. The glycosylated GDF15/GDF15 mutein polypeptides may also exhibit enhanced stability. Moreover, the polypeptides may improve one or more pharmacokinetic properties, such as half-life.

Addition of glycosylation sites can be accomplished by altering the amino acid sequence as described above. The alteration to the polypeptide may be made, for example, by the addition of, or substitution by, one or more serine or threonine residues (for O-linked glycosylation sites) or asparagine residues (for N-linked glycosylation sites). The structures of N-linked and O-linked oligosaccharides and the sugar residues found in each type may be different. One type of sugar that is commonly found on both is N-acetylneuraminic acid (hereafter referred to as sialic acid). Sialic acid is usually the terminal residue of both N-linked and O-linked oligosaccharides and, by virtue of its negative charge, may confer acidic properties to the glycoprotein. A particular embodiment of the present disclosure comprises the generation and use of N-glycosylation variants as described above.

Another means of increasing the number of carbohydrate moieties on the polypeptide is by chemical or enzymatic coupling of glycosides to the polypeptide.

Dihydrofolate reductase (DHFR)—deficient Chinese Hamster Ovary (CHO) cells are a commonly used host cell for the production of recombinant glycoproteins. These cells do not express the enzyme beta-galactoside alpha-2,6-sialyltransferase and therefore do not add sialic acid in the alpha-2,6 linkage to N-linked oligosaccharides of glycoproteins produced in these cells.

In particular embodiments, the GDF15 muteins comprising at least one N-linked glycosylation consensus site are glycosylated. Thus, in particular embodiments, the GDF15 muteins in the complexes disclosed herein may be glycosylated at the N-linked glycosylation consensus site introduced into the GDF15 mutein. In certain cases, while a complex disclosed herein may include glycosylated GDF15, such as, glycosylated GDF15 produced during expression from a cell line, the complex may be treated post-production to remove the carbohydrate moiety. The post-production removal of the carbohydrate moiety may result in removal of substantially all carbohydrate groups attached to the GDF15 mutein (and the Fc sequence) during expression in a eukaryotic host cell.

Thus, the present disclosure contemplates conjugation of one or more additional components or molecules at the N- and/or C-terminus of a polypeptide sequence, such as another protein (e.g., a protein having an amino acid sequence heterologous to the subject protein), or a carrier molecule. Thus, an exemplary polypeptide sequence can be provided as a conjugate with another component or molecule.

A Polypeptide may also be conjugated to large, slowly metabolized macromolecules such as proteins; polysaccharides, such as sepharose, agarose, cellulose, cellulose beads; polymeric amino acids such as polyglutamic acid, polylysine; amino acid copolymers; inactivated virus particles; inactivated bacterial toxins such as toxoid from diphtheria, tetanus, cholera, leukotoxin molecules; inactivated bacteria; and dendritic cells. Such conjugated forms, if desired, can be used to produce antibodies against a polypeptide of the present disclosure. In certain cases, the GDF15 in the complexes described herein may be polypeptide conjugated to a large, slowly metabolized macromolecule.

Additional candidate components and molecules for conjugation include those suitable for isolation or purification. Particular non-limiting examples include binding molecules, such as biotin (biotin-avidin specific binding pair), an antibody, a receptor, a ligand, a lectin, or molecules that comprise a solid support, including, for example, plastic or polystyrene beads, plates or beads, magnetic beads, test strips, and membranes.

Purification methods such as cation exchange chromatography may be used to separate conjugates by charge difference, which effectively separates conjugates into their various molecular weights. For example, the cation exchange column can be loaded and then washed with ~20 mM sodium acetate, pH ~4, and then eluted with a linear (0 M to 0.5 M) NaCl gradient buffered at a pH from about 3 to 5.5, e.g., at pH ~4.5. The content of the fractions obtained by cation exchange chromatography may be identified by molecular weight using conventional methods, for example, mass spectroscopy, SDS-PAGE, or other known methods for separating molecular entities by molecular weight.

Linkers:

Any of the foregoing components and molecules used to modify the polypeptide sequences of the present disclosure may optionally be conjugated via a linker. Suitable linkers include "flexible linkers" which are generally of sufficient length to permit some movement between the modified polypeptide sequences and the linked components and molecules. The linker molecules can be about 6-50 atoms long. The linker molecules may also be, for example, aryl acetylene, ethylene glycol oligomers containing 2-10 monomer units, diamines, diacids, amino acids, or combinations thereof. Suitable linkers can be readily selected and can be of any suitable length, such as 1, 2, 3, 4, 5, 6, 7, 8, 9, 10, 10-20, 20-30, 30-50 amino acids.

Exemplary flexible linkers include glycine polymers $(G)_n$, glycine-alanine polymers, alanine-serine polymers, glycine-serine polymers (for example, $(G_m S_o)_n$, $(GSGGS)_n$ (SEQ ID NO: 120), $(G_m S_o G_m)_n$, $(G_m S_o G_m S_o G_m)_n$ (SEQ ID NO: 121), $(GSGGS_m)_n$ (SEQ ID NO: 122), $(GSGS_m G)_n$ (SEQ ID NO: 123) and $(GGGS_m)_n$ (SEQ ID NO: 124), and combinations thereof, where m, n, and o are each independently selected from an integer of at least 1 to 20, e.g., 1-18, 2-16, 3-14, 4-12, 5-10, 1, 2, 3, 4, 5, 6, 7, 8, 9, or 10), and other flexible linkers. Glycine and glycine-serine polymers are relatively unstructured, and therefore may serve as a neutral tether between components. Exemplary flexible linkers include, but are not limited to GGSG (SEQ ID NO:21), GGSGG (SEQ ID NO:22), GSGSG (SEQ ID NO:23), GSGGG (SEQ ID NO:24), GGGSG (SEQ ID NO:25), and GSSSG (SEQ ID NO:26).

Additional flexible linkers include glycine polymers $(G)_n$ or glycine-serine polymers (e.g., $(GS)_n$, $(GSGGS)_n$ (SEQ ID NO: 120), $(GGGS)_n$ (SEQ ID NO: 125) and $(GGGGS)_n$ (SEQ ID NO: 126), where n=1 to 50, for example, 1, 2, 3, 4, 5, 6, 7, 8, 9, 10, 10-20, 20-30, 30-50). Exemplary flexible linkers include, but are not limited to GGGS (SEQ ID NO: 19), GGGGS (SEQ ID NO: 20), GGSG (SEQ ID NO: 21), GGSGG (SEQ ID NO: 22), GSGSG (SEQ ID NO: 23), GSGGG (SEQ ID NO: 24), GGGSG (SEQ ID NO: 25), and GSSSG (SEQ ID NO: 26). A multimer (e.g., 1, 2, 3, 4, 5, 6, 7, 8, 9, 10, 10-20, 20-30, or 30-50) of these linker sequences may be linked together to provide flexible linkers that may be used to conjugate a heterologous amino acid sequence to the Polypeptides disclosed herein. As described herein, the heterologous amino acid sequence may be a signal sequence and/or a fusion partner, such as, albumin, Fc sequence, and the like.

Examples of linkers include, e.g., $(GGGGS)_n$ (SEQ ID NO: 126), where n is an integer from 1 to about 10 (e.g., n=1, 2, 3, 4, 5, 6, 7, 8, 9, or 10); GGGSGGGSIEGR (SEQ ID NO: 48); GGGGG (SEQ ID NO: 27); EGGGS (SEQ ID NO: 28).

In some cases, the linker may be a cleavable linker, e.g., an enzymatically cleavable linker. In other cases, the linker may be a non-cleavable linker, e.g., a linker that is not cleaved enzymatically under normal physiological conditions in vivo.

For example, a proteolytically cleavable linker can include a matrix metalloproteinase (MMP) cleavage site, e.g., a cleavage site for a MMP selected from collagenase-1, -2, and -3 (MMP-1, -8, and -13), gelatinase A and B (MMP-2 and -9), stromelysin 1, 2, and 3 (MMP-3, -10, and -11), matrilysin (MMP-7), and membrane metalloproteinases (MT1-MMP and MT2-MMP). Cleavage sequence of MMP-9 is Pro-X-X-Hy (wherein, X represents an arbitrary residue; Hy, a hydrophobic residue) (SEQ ID NO: 29), e.g., Pro-X-X-Hy-(Ser/Thr) (SEQ ID NO: 30), e.g., Pro-Leu/Gln-Gly-Met-Thr-Ser (SEQ ID NO: 31) or Pro-Leu/Gln-Gly-Met-Thr (SEQ ID NO: 32). Another example of a protease cleavage site is a plasminogen activator cleavage site, e.g., a uPA or a tissue plasminogen activator (tPA) cleavage site. Specific examples of cleavage sequences of uPA and tPA include sequences comprising Val-Gly-Arg. Another example is a thrombin cleavage site, e.g., CGLVPAGSGP (SEQ ID NO: 33). Additional suitable linkers comprising protease cleavage sites include linkers comprising one or more of the following amino acid sequences: 1) SLLKSRMVPNFN (SEQ ID NO: 34) or SLLIARRMPNFN (SEQ ID NO: 35), cleaved by cathepsin B; SKLVQASASGVN (SEQ ID NO: 36) or SSYLKAS-DAPDN (SEQ ID NO: 37), cleaved by an Epstein-Barr virus protease; RPKPQQFFGLMN (SEQ ID NO: 38) cleaved by MMP-3 (stromelysin); SLRPLALWRSFN (SEQ ID NO: 39) cleaved by MMP-7 (matrilysin); SPQGIAGQRNFN (SEQ ID NO: 40) cleaved by MMP-9; DVDER-DVRGFASFL (SEQ ID NO: 41) cleaved by a thermolysin-like MMP; SLPLGLWAPNFN (SEQ ID NO: 42) cleaved by matrix metalloproteinase 2 (MMP-2); SLLIFRSWANFN (SEQ ID NO: 43) cleaved by cathespin L; SGVVIATVIVIT (SEQ ID NO: 44) cleaved by cathepsin D; SLGPQGIWGQFN (SEQ ID NO: 45) cleaved by matrix metalloproteinase 1 (MMP-1); KKSPGRVVGGSV (SEQ ID NO: 46) cleaved by urokinase-type plasminogen activator; PQGLLGAPGILG (SEQ ID NO: 47) cleaved by membrane type 1 matrixmetalloproteinase (MT-MMP); HGPEGLRVGFYESDVMGRGHARLVHVEEPHT (SEQ ID NO: 94) cleaved by stromelysin 3 (or MMP-11), thermolysin, fibroblast collagenase and stromelysin-1; GPQGLAGQRGIV (SEQ ID NO: 49) cleaved by matrix metalloproteinase 13 (collagenase-3); GGSGQRGRKALE (SEQ ID NO: 50) cleaved by tissue-type plasminogen activator (tPA); SLSALLSSDIFN (SEQ ID NO: 51) cleaved by human prostate-specific antigen; SLPRFKIIGGFN (SEQ ID NO: 52) cleaved by kallikrein (hK3); SLLGIAVPGNFN (SEQ ID NO: 53) cleaved by neutrophil elastase; and FFKNIVTPRTPP (SEQ ID NO: 54) cleaved by calpain (calcium activated neutral protease).

In addition to the specific amino acid sequences and nucleic acid sequences provided herein, the disclosure also contemplates polypeptides and nucleic acids having sequences that are at least 80%, at least 85%, at least 90%, or at least 95% identical in sequence to the amino acid and nucleic acids. The terms "identical" or percent "identity," in the context of two or more polynucleotide sequences, or two or more amino acid sequences, refers to two or more sequences or subsequences that are the same or have a specified percentage of amino acid residues or nucleotides that are the same (e.g., at least 80%, at least 85%, at least 90%, or at least 95% identical over a specified region), when compared and aligned for maximum correspondence over a designated region. The disclosure specifically contemplates first and second polypeptide present in a complex, the first polypeptide and the second polypeptide having an amino acid sequence that is at least 80%, at least 85%, at least 90%, at least 95%, at least 96%, at least 97%, at least 98%, or at least 99% identical in sequence to the amino acid sequence of the first and second polypeptide, respectively, of the first and second polypeptide pairs provided herein.

Methods of Production of Polypeptides

A polypeptide of the present disclosure can be produced by any suitable method, including recombinant and non-recombinant methods (e.g., chemical synthesis).

A. Chemical Synthesis

Where a polypeptide is chemically synthesized, the synthesis may proceed via liquid-phase or solid-phase. Solid-phase peptide synthesis (SPPS) allows the incorporation of unnatural amino acids and/or peptide/protein backbone modification. Various forms of SPPS, such as Fmoc and Boc, are available for synthesizing polypeptides of the present disclosure. Details of the chemical synthesis are known in the art (e.g., Ganesan A. 2006 Mini Rev. Med. Chem. 6:3-10; and Camarero J. A. et al., 2005 Protein Pept Lett. 12:723-8).

B. Recombinant Production

Where a polypeptide is produced using recombinant techniques, the polypeptide may be produced as an intracellular protein or as a secreted protein, using any suitable construct and any suitable host cell, which can be a prokaryotic or eukaryotic cell, such as a bacterial (e.g., E. coli) or a yeast host cell, respectively. Other examples of eukaryotic cells that may be used as host cells include insect cells, mammalian cells, and/or plant cells. Where mammalian host cells are used, they may include human cells (e.g., HeLa, 293, H9 and Jurkat cells); mouse cells (e.g., NIH3T3, L cells, and C127 cells); primate cells (e.g., Cos 1, Cos 7 and CV1) and hamster cells (e.g., Chinese hamster ovary (CHO) cells). In specific embodiments, the Polypeptide and complexes comprising the Polypeptide is produced in CHO cells. In other embodiments, the Polypeptide and complexes comprising the Polypeptide is produced in a yeast cell and in particular embodiments may be a yeast cell genetically engineered to produce glycoproteins with mammalian-like N-glycans.

A variety of host-vector systems suitable for the expression of a polypeptide may be employed according to standard procedures known in the art. See, e.g., Sambrook et al., 1989 Current Protocols in Molecular Biology Cold Spring Harbor Press, New York; and Ausubel et al. 1995 Current Protocols in Molecular Biology, Eds. Wiley and Sons. Methods for introduction of genetic material into host cells include, for example, transformation, electroporation, conjugation, calcium phosphate methods and the like. The method for transfer can be selected so as to provide for stable expression of the introduced polypeptide-encoding nucleic acid. The polypeptide-encoding nucleic acid can be provided as an inheritable episomal element (e.g., a plasmid) or can be genomically integrated. A variety of appropriate vectors for use in production of a polypeptide of interest are commercially available.

Vectors can provide for extrachromosomal maintenance in a host cell or can provide for integration into the host cell genome. The expression vector provides transcriptional and translational regulatory sequences, and may provide for inducible or constitutive expression where the coding region is operably-linked under the transcriptional control of the transcriptional initiation region, and a transcriptional and translational termination region. In general, the transcriptional and translational regulatory sequences may include, but are not limited to, promoter sequences, ribosomal binding sites, transcriptional start and stop sequences, translational start and stop sequences, and enhancer or activator sequences. Promoters can be either constitutive or inducible, and can be a strong constitutive promoter (e.g., T7).

Expression constructs generally have convenient restriction sites located near the promoter sequence to provide for the insertion of nucleic acid sequences encoding proteins of interest. A selectable marker operative in the expression host may be present to facilitate selection of cells containing the vector. Moreover, the expression construct may include additional elements. For example, the expression vector may have one or two replication systems, thus allowing it to be maintained in organisms, for example, in mammalian or insect cells for expression and in a prokaryotic host for cloning and amplification. In addition, the expression construct may contain a selectable marker gene to allow the selection of transformed host cells. Selectable genes are well known in the art and will vary with the host cell used.

Isolation and purification of a protein can be accomplished according to methods known in the art. For example, a protein can be isolated from a lysate of cells genetically modified to express the protein constitutively and/or upon induction; from culture medium in which the host cell is grown; or from a synthetic reaction mixture, by affinity purification, which may involve contacting the sample (cell lysate, culture medium, or reaction mixture) with an tag that specifically binds to the protein, washing to remove nonspecifically bound material, and eluting the specifically bound protein. The isolated protein can be further purified by dialysis and other methods normally employed in protein purification methods. In one embodiment, the protein may be isolated using metal chelate chromatography methods. Proteins may contain modifications to facilitate isolation. In certain embodiments, the complexes of the present disclosure may be separated based on size.

In certain embodiments, a complex comprising a first polypeptide and a second polypeptide, the first polypeptide comprising an IgG Fc sequence, the IgG Fc sequence comprising a CH3 sequence comprising at least one engineered protuberance: the second polypeptide comprising an IgG Fc sequence, the IgG Fc sequence comprising a CH3 sequence comprising at least one engineered cavity; where the first polypeptide dimerizes with the second polypeptide via positioning of the protuberance of the first polypeptide into the cavity of the second polypeptide, where either the C-terminus the first polypeptide or the C-terminus the second polypeptide is conjugated to the N-terminus of a GDF15 mutein comprising at least one N-linked glycosylation consensus site may be isolated from the medium in which a host cell expressing the first and second polypeptides is cultured.

In certain embodiments, a complex comprising a first heterodimer and a second heterodimer, each of the first heterodimer and second heterodimer comprising a first polypeptide and a second polypeptide, the first polypeptide comprising an IgG Fc sequence, the IgG Fc sequence comprising a CH3 sequence comprising at least one engineered protuberance; the second polypeptide comprising an IgG Fc sequence, the IgG Fc sequence comprising a CH3 sequence comprising at least one engineered cavity; where the first polypeptide dimerizes with the second polypeptide via positioning of the protuberance of the first polypeptide into the cavity of the second polypeptide, where either the C-terminus the first polypeptide or the C-terminus the second polypeptide is conjugated to the N-terminus of a GDF15 mutein comprising at least one N-linked glycosylation consensus site, where the GDF15 mutein in the first heterodimer dimerizes with the GDF15 mutein in the second heterodimer thereby forming the complex comprising the first heterodimer and second heterodimer may be isolated from the medium in which a host cell expressing the first and second polypeptides is cultured.

As noted herein, a first and a second nucleic acid may be present in a single vector or separate vectors in a single host cell or two different host cells. In certain cases, the first and second polypeptides of the present disclosure may be encoded by a first and second nucleic acid respectively that may be present expressed in the same cell. In embodiments where the first and second nucleic acids are present in different cells, the cells may be fused as some point during the production process.

The complexes may be prepared in substantially pure or isolated form (e.g., free from other polypeptides). The complexes can be present in a composition that is enriched for the complexes relative to other components that may be present (e.g., other polypeptides or other complexes (e.g. homodimers, homotetramers) or other host cell components). For example, purified complex (e.g., a heterodimer-heterodimer complex) may be provided such that the complex is present in a composition that is substantially free of other expressed proteins, e.g., less than 90%, less than 60%, less than 50%, less than 40%, less than 30%, less than 20%, less than 10%, less than 5%, or less than 1%, of the composition is made up of other expressed proteins.

Antibodies

The present disclosure provides antibodies, including isolated antibodies that specifically bind a polypeptide or fusion protein of the present disclosure. The term "antibody" encompasses intact monoclonal antibodies, polyclonal antibodies, multispecific antibodies (e.g., bispecific antibodies) formed from at least two intact antibodies, and antibody binding fragments including Fab and F(ab)′$_2$, provided that they exhibit the desired biological activity. The basic whole antibody structural unit comprises a tetramer, and each tetramer is composed of two identical pairs of polypeptide chains, each pair having one "light" chain (about 25 kDa) and one "heavy" chain (about 50-70 kDa). The amino-terminal portion of each chain includes a variable region of about 100 to 110 or more amino acids primarily responsible for antigen recognition. In contrast, the carboxy-terminal portion of each chain defines a constant region primarily responsible for effector function. Human light chains are classified as kappa and lambda, whereas human heavy chains are classified as mu, delta, gamma, alpha, or epsilon, and define the antibody's isotype as IgM, IgD, IgG, IgA, and IgE, respectively. Binding fragments are produced by recombinant DNA techniques, or by enzymatic or chemical cleavage of intact antibodies. Binding fragments include Fab. Fab′, F(ab′)$_2$, Fv, and single-chain antibodies.

Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Within light and heavy chains, the variable and constant regions are joined by a "J" region of about 12 or more amino acids, with the heavy chain also including a "D" region of about 10 more amino acids. The antibody chains all exhibit the same general structure of relatively conserved framework regions (FR) joined by three hyper-variable regions, also called "complementarity-determining regions" or "CDRs". The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4.

An intact antibody has two binding sites and, except in bifunctional or bispecific antibodies, the two binding sites are the same. A bispecific or bifunctional antibody is an artificial hybrid antibody having two different heavy/light chain pairs and two different binding sites. Bispecific antibodies can be produced by a variety of methods including fusion of hybridomas or linking of Fab′ fragments.

As set forth above, binding fragments may be produced by enzymatic or chemical cleavage of intact antibodies. Digestion of antibodies with the enzyme papain results in two identical antigen-binding fragments, also known as "Fab" fragments, and an "Fc" fragment which has no antigen-binding activity. Digestion of antibodies with the enzyme pepsin results in a F(ab′)$_2$ fragment in which the two arms of the antibody molecule remain linked and comprise two-antigen binding sites. The F(ab′)$_2$ fragment has the ability to crosslink antigen.

As used herein, the term "Fab" refers to a fragment of an antibody that comprises VH and VL regions as well as the constant domain of the light chain and the CH1 domain of the heavy chain.

When used herein, the term "Fv" refers to the minimum fragment of an antibody that retains both antigen-recognition and antigen-binding sites. In a two-chain Fv species, this region includes a dimer of one heavy-chain and one light-chain variable domain in non-covalent association. In a single-chain Fv species, one heavy-chain and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. While the six CDRs, collectively, confer antigen-binding specificity to the antibody, even a single variable domain (or half of an Fv comprising only three CDRs specific for an antigen) has the ability to recognize and bind antigen.

When used herein, the term "complementarity determining regions" or "CDRs" refers to parts of immunological receptors that make contact with a specific ligand and determine its specificity.

The term "hypervariable region" refers to the amino acid residues of an antibody which are responsible for antigen-binding. The hypervariable region generally comprises amino acid residues from a CDR and/or those residues from a "hypervariable loop".

As used herein, the term "epitope" refers to binding sites for antibodies on protein antigens. Epitopic determinants usually comprise chemically active surface groupings of molecules such as amino acids or sugar side chains, as well as specific three-dimensional structural and charge characteristics. An antibody is said to bind an antigen when the dissociation constant is ≤1 µM, ≤100 nM, or ≤10 nM. An increased equilibrium constant ("$K_D$") means that there is less affinity between the epitope and the antibody, whereas a decreased equilibrium constant means that there is more affinity between the epitope and the antibody. An antibody with a $K_D$ of "no more than" a certain amount means that the antibody will bind to the epitope with the given $K_D$ or more strongly. Whereas $K_D$ describes the binding characteristics of an epitope and an antibody, "potency" describes the effectiveness of the antibody itself for a function of the antibody. There is not necessarily a correlation between an equilibrium constant and potency; thus, for example, a relatively low $K_D$ does not automatically mean a high potency.

The term "selectively binds" in reference to an antibody does not mean that the antibody only binds to a single substance, but rather that the $K_D$ of the antibody to a first substance is less than the $K_D$ of the antibody to a second substance. An antibody that exclusively binds to an epitope only binds to that single epitope.

When administered to humans, antibodies that contain rodent (i.e., murine or rat) variable and/or constant regions are sometimes associated with, for example, rapid clearance from the body or the generation of an immune response by the body against the antibody. In order to avoid the utilization of rodent-derived antibodies, fully human antibodies can be generated through the introduction of human antibody function into a rodent so that the rodent produces fully human antibodies. Unless specifically identified herein, "human" and "fully human" antibodies can be used interchangeably. The term "fully human" can be useful when distinguishing antibodies that are only partially human from those that are completely, or fully, human. The skilled artisan is aware of various methods of generating fully human antibodies.

In order to address possible human anti-mouse antibody responses, chimeric or otherwise humanized antibodies can be utilized. Chimeric antibodies have a human constant region and a murine variable region, and, as such, human anti-chimeric antibody responses may be observed in some patients. Therefore, it is advantageous to provide fully human antibodies against multimeric enzymes in order to avoid possible human anti-mouse antibody or human anti-chimeric antibody responses.

Fully human monoclonal antibodies can be prepared, for example, by the generation of hybridoma cell lines by techniques known to the skilled artisan. Other preparation methods involve the use of sequences encoding particular antibodies for transformation of a suitable mammalian host cell, such as a CHO cell. Transformation can be by any known method for introducing polynucleotides into a host cell, including, for example, packaging the polynucleotide in a virus (or into a viral vector) and transducing a host cell with the virus (or vector) or by transfection procedures known in the art. Methods for introducing heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. Mammalian cell lines available as hosts for expression are well known in the art and include, but are not limited to, CHO cells, HeLa cells, and human hepatocellular carcinoma cells.

The antibodies can be used to detect a polypeptide of the present disclosure. For example, the antibodies can be used as a diagnostic by detecting the level of one or more polypeptides of the present disclosure in a subject, and either comparing the detected level to a standard control level or to a baseline level in a subject determined previously (e.g., prior to any illness).

Therapeutic and Prophylactic Uses

The present disclosure provides methods for treating or preventing metabolic and metabolic-associated diseases, such as, obesity and other body weight disorders, hyperglycemia, hyperinsulinemia, glucose intolerance, and glucose metabolism disorders, by the administration of the complex of the present disclosure, or compositions thereof, as described herein. Such methods may also have an advantageous effect on one or more symptoms associated with a disease, disorder or condition by, for example, decreasing the severity or the frequency of a symptom.

In order to determine whether a subject may be a candidate for the treatment or prevention of a body weight disorder (e.g., obesity) by the methods provided herein, parameters such as, but not limited to, the etiology and the extent of the subject's condition (e.g., how overweight the subject is compared to reference healthy individual) should be evaluated. For example, an adult having a BMI between ~25 and ~29.9 kg/m$^2$ may be considered overweight (pre-obese), while an adult having a BMI of ~30 kg/m$^2$ or higher may be considered obese. As discussed herein, a complex of the present invention can effect appetite suppression, for example, decrease appetite leading to a reduction in body weight.

In order to determine whether a subject may be a candidate for the treatment or prevention of hyperglycemia, hyperinsulinemia, glucose intolerance, and/or glucose disorders by the methods provided herein, various diagnostic methods known in the art may be utilized. Such methods include those described elsewhere herein (e.g., fasting plasma glucose (FPG) evaluation and the oral glucose tolerance test (oGTT)).

The complexes provided herein when administered to a subject for treating or preventing metabolic and metabolic-associated diseases, such as, obesity and other body weight disorders, hyperglycemia, hyperinsulinemia, glucose intolerance, glucose metabolism disorders may lead to a reduction in blood glucose level, a reduction in body weight, and/or a reduction in food intake.

In certain embodiments, the complexes contemplated herein may decrease blood glucose level, body weight, and/or food intake by at least 5% compared to that in the absence of administration of the complexes. For example, complexes contemplated herein may decrease blood glucose level, body weight, and/or food intake by at least 10%, 20%, 30%, 50%, 60%, 70%, 80%, or 90% as compared to that prior to the start of the treatment or prevention.

In certain embodiments, a complex of the present disclosure used to treat a metabolic disorder may be a complex that includes two heterodimer molecules per complex, where each heterodimer is the same, and includes a first polypeptide and a second polypeptide, where the first polypeptide includes an IgG Fc sequence, the IgG Fc sequence may include a CH3 sequence comprising at least one engineered protuberance; the second polypeptide comprising an IgG Fc sequence, the IgG Fc sequence comprising a CH3 sequence comprising at least one engineered cavity; wherein the first polypeptide dimerizes with the second polypeptide via positioning of the protuberance of the first polypeptide into the cavity of the second polypeptide to form a heterodimer, wherein either the C-terminus the first polypeptide or the C-terminus the second polypeptide in each heterodimer is conjugated to the N-terminus of a GDF15 mutein comprising at least one N-linked glycosylation consensus site, wherein the GDF15 mutein in the heterodimer dimerizes with the GDF15 mutein in another of the heterodimer thereby forming the complex comprising two heterodimers.

In yet other embodiments, a complex of the present disclosure used to treat a metabolic disorder may be a complex that includes two heterodimer molecules (heterodimer associated with heterodimer) per complex, where each heterodimer is the same, and each heterodimer includes a first polypeptide having an IgG Fc sequence, the IgG Fc sequence may include a CH3 sequence comprising at least one engineered protuberance, where the C-terminus of the first polypeptide is fused to N-terminus of the GDF15 glycomutein; and the second polypeptide comprising an IgG Fc sequence, the IgG Fc sequence comprising a CH3 sequence comprising at least one engineered cavity; wherein the first polypeptide dimerizes with the second polypeptide via positioning of the protuberance of the first polypeptide into the cavity of the second polypeptide to form the heterodimer, wherein the GDF15 mutein in the heterodimer dimerizes with the GDF15 mutein in another of the heterodimer thereby forming the complex comprising the two heterodimers.

Pharmaceutical Compositions

The complexes of the present disclosure may be in the form of compositions suitable for administration to a subject. In general, such compositions are "pharmaceutical compositions" comprising one or more complexes and one or more pharmaceutically acceptable or physiologically acceptable diluents, carriers or excipients. In certain embodiments, the complexes are present in a therapeutically effective amount in the pharmaceutical composition. The pharmaceutical compositions may be used in the methods of the present disclosure; thus, for example, the pharmaceutical compositions can be administered ex vivo or in vivo to a subject in order to practice the therapeutic and prophylactic methods and uses described herein. As noted herein, the complexes may or may not be glycosylated. For example, the complexes may be glycosylated as produced in a eukaryotic host cell and may be subject to a process for removal of the carbohydrate moiety prior to formulation into a pharmaceutical composition. The removal of carbohydrate moieties may result in significant reduction in glycosylation of the polypeptides in the complexes or complete absence of glycosylation of the polypeptides in the complexes.

In specific embodiments, the present disclosure provides methods for treating a glucose metabolism or body weight disorder by the administration of the complexes, N-glycosylated complexes, or compositions thereof. In particular embodiment, the present disclosure methods for reducing food intake or decreasing body weight by the administration of the complexes, N-glycosylated complexes, or compositions thereof. The present disclosure further provides a use of the foregoing sequences, complexes, N-glycosylated complexes, or compositions thereof in the manufacture of a medicament for use in treating a condition selected from metabolic and metabolic-associated diseases, such as, obesity and other body weight disorders, hyperglycemia, hyperinsulinemia, glucose intolerance, and glucose metabolism disorders. The present disclosure further provides a use of the foregoing sequences, complexes, N-glycosylated complexes, or compositions thereof in the manufacture of a medicament for use in treating a glucose metabolism or body weight disorder. The present disclosure further provides a use of the foregoing sequences, complexes, N-glycosylated complexes, or compositions thereof in the manufacture of a medicament for use in reducing food intake or body weight.

Also provided herein are compositions, for example, pharmaceutical compositions of the sequences, complexes, and N-glycosylated complexes disclosed herein for treating or preventing a condition selected from metabolic and metabolic-associated diseases, such as, obesity and other body weight disorders, hyperglycemia, hyperinsulinemia, glucose intolerance, and glucose metabolism disorders. The present disclosure further provides a composition (e.g., pharmaceutical composition) of the foregoing sequences, complexes, or N-glycosylated complexes for treating a glucose metabolism or body weight disorder. The present disclosure further provides a composition (e.g., pharmaceutical composition) of the foregoing sequences, complexes, or N-glycosylated complexes for reducing food intake or body weight.

The pharmaceutical compositions of the present disclosure can be formulated to be compatible with the intended method or route of administration; exemplary routes of administration are set forth herein. Furthermore, the pharmaceutical compositions may be used in combination with other therapeutically active agents or compounds (e.g., glucose lowering agents) as described herein in order to treat or prevent the diseases, disorders and conditions as contemplated by the present disclosure.

The pharmaceutical compositions typically comprise a therapeutically effective amount of at least one of the complexes contemplated by the present disclosure and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that could be used in the pharmaceutical compositions and dosage forms. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments. Any drug delivery apparatus may be used to deliver the complexes, including implants (e.g., implantable pumps) and catheter systems, both of which are well known to the skilled artisan. Depot injections, which are generally administered subcutaneously or intramuscularly, may also be utilized to release the complexes disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor EL™ (BASF, Parsippany, N.J.) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be employed including synthetic mono- or diglycerides. Moreover, fatty acids such as oleic acid find use in the preparation of injectables. Prolonged absorption of particular injectable formulations can be achieved by including an agent that delays absorption (e.g., aluminum monostearate or gelatin).

The pharmaceutical compositions containing the active ingredient (e.g., complexes of the present disclosure) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylenevinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods of preparing liposomes are described in, for example, U.S. Pat. Nos. 4,235,871, 4,501,728, and 4,837,028. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinylpyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present disclosure may also be in the form of oil-in-water emulsions. The oily phase may be a vegetable oil, for example olive oil or arachis oil, or a mineral oil, for example, liquid paraffin, or mixtures of these. Suitable emulsifying agents may be naturally-occurring gums, for example, gum acacia or gum tragacanth; naturally-occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

Formulations can also include carriers to protect the composition against rapid degradation or elimination from the body, such as a controlled release formulation, including implants, liposomes, hydrogels, prodrugs and microencapsulated delivery systems. For example, a time delay material such as glyceryl monostearate or glyceryl stearate alone, or in combination with a wax, may be employed.

The present disclosure contemplates the administration of the complexes in the form of suppositories for rectal administration of the drug. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The complexes contemplated by the present disclosure may be in the form of any other suitable pharmaceutical composition (e.g., sprays for nasal or inhalation use) currently known or developed in the future.

The concentration of a complex of polypeptides in a formulation can vary widely (e.g., from less than about 0.1%, usually at or at least about 2% to as much as 20% to 50% or more by weight) and will usually be selected primarily based on fluid volumes, viscosities, and subject-based factors in accordance with, for example, the particular mode of administration selected.

Contemplated herein is the use of Nano Precision Medical's depot delivery technology (Nano Precision Medical; Emeryville, Calif.). The technology utilizes a titania nanotube membrane that produces zero-order release rates of macromolecules, such as protein and peptide therapeutics. The biocompatible membrane is housed in a small, subcutaneous implant that provides long-term (e.g., up to one year), constant-rate delivery of therapeutic macromolecules. The technology is currently being evaluated for the delivery of GLP-1 agonists for the treatment of Type II diabetes. In certain embodiments, the complex(es) disclosed herein may be a formulation with a membrane. For example, the complex may be impregnated into the membrane or surrounded by the membrane. The membrane may be in shape of a disc, tube or sphere. In certain embodiments, the tube may be a nanotube or the sphere may be a nanosphere.

Routes of Administration

The present disclosure contemplates the administration of the disclosed complexes, and compositions thereof, in any appropriate manner. Suitable routes of administration include parenteral (e.g., intramuscular, intravenous, subcutaneous (e.g., injection or implant), intraperitoneal, intracisternal, intraarticular, intraperitoneal, intracerebral (intraparenchymal) and intracerebroventricular), oral, nasal, vaginal, sublingual, intraocular, rectal, topical (e.g., transdermal), sublingual and inhalation.

Depot injections, which are generally administered subcutaneously or intramuscularly, may also be utilized to release the complexes disclosed herein over a defined period of time. Depot injections are usually either solid- or oil-based and generally comprise at least one of the formulation components set forth herein. One of ordinary skill in the art is familiar with possible formulations and uses of depot injections.

Regarding antibodies, in an exemplary embodiment an antibody or antibody fragment of the present disclosure is stored at 10 mg/ml in sterile isotonic aqueous saline solution for injection at 4° C. and is diluted in either 100 ml or 200 ml 0.9% sodium chloride for injection prior to administration to the subject. The antibody is administered by intravenous infusion over the course of 1 hour at a dose of between 0.2 and 10 mg/kg. In other embodiments, the antibody is administered by intravenous infusion over a period of between 15 minutes and 2 hours. In still other embodiments, the administration procedure is via subcutaneous bolus injection.

The present disclosure contemplates methods wherein the complexes of the present disclosure is administered to a subject at least twice daily, at least once daily, at least once every 48 hours, at least once every 72 hours, at least once weekly, at least once every 2 weeks, or once monthly.

Combination Therapy

The present disclosure contemplates the use of a complex provided herein in combination with one or more active therapeutic agents or other prophylactic or therapeutic modalities. In such combination therapy, the various active agents frequently have different mechanisms of action. Such combination therapy may be especially advantageous by allowing a dose reduction of one or more of the agents, thereby reducing or eliminating the adverse effects associated with one or more of the agents; furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, a complex is administered or applied sequentially, e.g., where one agent is administered prior to one or more other agents. In other embodiments, the complex is administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present disclosure.

The complexes of the present disclosure can be used in combination with other agents useful in the treatment, prevention, suppression or amelioration of the diseases, disorders or conditions set forth herein, including those that are normally administered to subjects suffering from obesity, eating disorder, hyperglycemia, hyperinsulinemia, glucose intolerance, and other glucose metabolism disorders.

The present disclosure contemplates combination therapy with numerous agents (and classes thereof), including 1) insulin, insulin mimetics and agents that entail stimulation of insulin secretion, including sulfonylureas (e.g., chlorpropamide, tolazamide, acetohexamide, tolbutamide, glyburide, glimepiride, glipizide) and meglitinides (e.g., repaglinide (PRANDIN) and nateglinide (STARLIX)); 2) biguanides (e.g., metformin (GLUCOPHAGE)) and its pharmaceutically acceptable salts, in particular, metformin hydrochloride, and extended-release formulations thereof, such as Glumetzar™, Fortametr™, and GlucophageXR™) and other agents that act by promoting glucose utilization, reducing hepatic glucose production and/or diminishing intestinal glucose output; 3) alpha-glucosidase inhibitors (e.g., acarbose, voglibose and miglitol) and other agents that slow down carbohydrate digestion and consequently absorption from the gut and reduce postprandial hyperglycemia; 4) thiazolidinediones (e.g., rosiglitazone (AVANDIA), troglitazone (REZULIN), pioglitazone (ACTOS), glipizide, balaglitazone, rivoglitazone, netoglitazone, AMG 131, MBX2044, mitoglitazone, lobeglitazone, IDR-105, troglitazone, englitazone, ciglitazone, adaglitazone, darglitazone that enhance insulin action (e.g., by insulin sensitization) including insulin, and insulin mimetics (e.g., insulin degludec, insulin glargine, insulin lispro, insulin detemir, insulin glulisine and inhalable formulations of each), thus promoting glucose utilization in peripheral tissues; 5) glucagon-like-peptides including DPP-IV inhibitors (e.g., alogliptin, omarigliptin, linagliptin, vildagliptin (GALVUS) and sitagliptin (JANUVIA)) and Glucagon-Like Peptide-1 (GLP-1) and GLP-1 agonists and analogs (e.g., exenatide (BYETTA and ITCA 650 (an osmotic pump inserted subcutaneously that delivers an exenatide analog over a 12-month period; Intarcia, Boston, Mass.)) and GLP-1 receptor agonists (e.g., dulaglutide, semaglutide, albiglutide, exenatide, liraglutide, lixisenatide, taspoglutide, CJC-1131, and BIM-51077, including intranasal, transdermal, and once-weekly formulations thereof); 6) and DPP-IV-resistant analogues (incretin mimetics), PPAR gamma agonists, PPAR alpha agonists such as fenofibric acid derivatives (e.g., gemfibrozil, clofibrate, ciprofibrate, fenofibrate, bezafibrate), dual-acting PPAR agonists (e.g., ZYH2, ZYH1, GFT505, chiglitazar, muraglitazar, aleglitazar, sodelglitazar, and naveglitazar), pan-acting PPAR agonists, PTP1B inhibitors (e.g., ISIS-113715 and TTP814), SGLT inhibitors (e.g., ASP1941, SGLT-3, empagliflozin, dapagliflozin, canagliflozin, BI-10773, PF-04971729, remogloflozin, TS-071, tofogliflozin, ipragliflozin, and LX-4211), insulin secretagogues, angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), angiotensin II receptor antagonists (e.g., losartan i.e., COZAAR®, valsartan, candesartan, olmesartan, telmesartan and any of these drugs used in combination with hydrochlorothiazide such as HYZAAR®) or other anti-hypertensive drugs such as LCZ 696, RXR agonists, glycogen synthase kinase-3 inhibitors, immune modulators, sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine); beta-3 adrenergic receptor agonists, 11beta-HSD1 inhibitors, neutral endopeptidase inhibitors (e.g., thiorphan and phosphoramidon), aldosterone antagonists, aldosterone synthase inhibitors, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635), endothelin receptor antagonists, phosphodiesterase-5 inhibitors (e.g. sildenafil, tadalfil and vardenafil), vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), lipid lowering agents e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), cerivastatin, and fluvastatin (particularly the sodium salt sold in LESCOL®); a cholesterol absorption inhibitor such as ezetimibe (ZETIA®) and ezetimibe in combination with any other lipid lowering agents such as the HMG-CoA reductase inhibitors noted above and particularly with simvastatin (VYTORIN®) or with atorvastatin calcium; HDL-raising drugs, (e.g., niacin and nicotinic acid receptor agonists, and extended- or controlled-release versions thereof, and/or with an HMG-CoA reductase inhibitor; niacin receptor agonists such as acipimox and acifran, as well as niacin receptor partial agonists; glucagon receptor antagonists (e.g., MK-3577, MK-0893, LY-2409021 and KT6-971); bile acid sequestering agents (e.g., colestilan, colestimide, colesevalam hydrochloride, colestipol, cholestyramine, and dialkylaminoalkyl derivatives of a cross-linked dextran), acyl CoA:cholesterol acyltransferase inhibitors, (e.g., avasimibe); agents intended for use in inflammatory conditions, such as aspirin, non-steroidal anti-inflammatory drugs or NSAIDs, glucocorticoids, and selective cyclooxygenase-2 or COX-2 inhibitors; glucokinase activators (GKAs) (e.g., AZD6370); inhibitors of 11β-hydroxysteroid dehydrogenase type 1, (e.g., such as those disclosed in U.S. Pat. No. 6,730,690, and LY-2523199); CETP inhibitors (e.g., anacetrapib, evacetrapib, and torcetrapib); inhibitors of fructose 1,6-bisphosphatase, (e.g., such as those disclosed in U.S. Pat. Nos. 6,054,587; 6,110,903; 6,284,748; 6,399,782; and 6,489,476); inhibitors of acetyl CoA carboxylase-1 or 2 (ACC1 or ACC2); PCSK9 inhibitors; GPR-40 partial agonists; SCD modulators; inhibitors of fatty acid synthase; amylin and amylin analogues (e.g., pramlintide); including pharmaceutically acceptable salt forms of the above active agents where chemically possible.

Furthermore, the present disclosure contemplates combination therapy with agents and methods for promoting weight loss, such as agents that stimulate metabolism or decrease appetite, and modified diets and/or exercise regimens to promote weight loss.

The complexes of the present disclosure may be used in combination with one or more other agent in any manner appropriate under the circumstances. In one embodiment, treatment with the at least one active agent and at least one complex of the present disclosure is maintained over a period of time. In another embodiment, treatment with the at least one active agent is reduced or discontinued (e.g., when the subject is stable), while treatment with a complex of the present disclosure is maintained at a constant dosing regimen. In a further embodiment, treatment with the at least one active agent is reduced or discontinued (e.g., when the subject is stable), while treatment with the complex(es) of the present disclosure is reduced (e.g., lower dose, less frequent dosing or shorter treatment regimen). In yet another embodiment, treatment with the at least one active agent is reduced or discontinued (e.g., when the subject is stable), and treatment with the complex of the present disclosure is increased (e.g., higher dose, more frequent dosing or longer treatment regimen). In yet another embodiment, treatment with the at least one active agent is maintained and treatment with a complex of the present disclosure is reduced or discontinued (e.g., lower dose, less frequent dosing or shorter treatment regimen). In yet another embodiment, treatment with the at least one active agent and treatment with the complex(es) of the present disclosure are reduced or discontinued (e.g., lower dose, less frequent dosing or shorter treatment regimen).

Dosing

The complexes of the present disclosure may be administered to a subject in an amount that is dependent upon, for example, the goal of the administration (e.g., the degree of resolution desired); the age, weight, sex, and health and physical condition of the subject to be treated; the nature of the polypeptide, and/or formulation being administered; the route of administration; and the nature of the disease, disorder, condition or symptom thereof (e.g., the severity of the dysregulation of glucose/insulin and the stage of the disorder). The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (i.e., the maximum tolerated dose, "MTD") and not less than an amount required to produce a measurable effect on the subject. Such amounts are determined by, for example, the pharmacokinetic and pharmacodynamic parameters associated with absorption, distribution, metabolism, and excretion ("ADME"), taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount is more than the calculated ED50, in other situations the effective amount is less than the calculated ED50, and in still other situations the effective amount is the same as the calculated ED50.

In addition, an effective dose of the complex(es) of the present disclosure may be an amount that, when administered in one or more doses to a subject, produces a desired result relative to a healthy subject. For example, an effective dose may be one that, when administered to a subject having elevated plasma glucose and/or plasma insulin, achieves a desired reduction relative to that of a healthy subject by at least about 10%, at least about 20%, at least about 25%, at least about 30%, at least about 40%, at least about 50%, at least about 60%, at least about 70%, at least about 80%, or more than 80%.

An appropriate dosage level will generally be about 0.001 to 100 mg/kg of patient body weight per day, which can be administered in single or multiple doses. In some embodiments, the dosage level will be about 0.01 to about 25 mg/kg per day, and in other embodiments about 0.05 to about 10 mg/kg per day. A suitable dosage level may be about 0.01 to 25 mg/kg per day, about 0.05 to 10 mg/kg per day, or about 0.1 to 5 mg/kg per day. Within this range, the dosage may be 0.005 to 0.05, 0.05 to 0.5 or 0.5 to 5.0 mg/kg per day.

For administration of an oral agent, the compositions can be provided in the form of tablets, capsules and the like containing from 1.0 to 1000 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient. The complex may be administered on a regimen of, for example, 1 to 4 times per day, and often once or twice per day.

The dosage of the complex(es) of the present disclosure may be repeated at an appropriate frequency, which may be in the range of once per day to once every month, depending on the pharmacokinetics of the complex (e.g. half-life) and the pharmacodynamic response (e.g. the duration of the therapeutic effect of the complex). In some embodiments, dosing is frequently repeated between once per week, once every two weeks, once every month. In other embodiments, complex may be administered approximately once per month.

In certain embodiments, the dosage of the disclosed complex is contained in a "unit dosage form". The phrase "unit dosage form" refers to physically discrete units, each unit containing a predetermined amount of a complex of the present disclosure, either alone or in combination with one or more additional agents, sufficient to produce the desired effect. It will be appreciated that the parameters of a unit dosage form will depend on the particular agent and the effect to be achieved.

Kits

The present disclosure also contemplates kits comprising the disclosed complex(es), and pharmaceutical compositions thereof. The kits are generally in the form of a physical structure housing various components, as described below, and may be utilized, for example, in practicing the methods described above (e.g., administration of a complex to a subject in need of weight reduction).

A kit can include one or more of the complex(es) disclosed herein (provided in, e.g., a sterile container), which may be in the form of a pharmaceutical composition suitable for administration to a subject. The complex(es) can be provided in a form that is ready for use or in a form requiring, for example, reconstitution or dilution prior to administration. When the complex(es) are in a form that needs to be reconstituted by a user, the kit may also include buffers, pharmaceutically acceptable excipients, and the like, packaged with or separately from the complex(es). When combination therapy is contemplated, the kit may contain the several agents separately or they may already be combined in the kit. Each component of the kit can be enclosed within an individual container and all of the various containers can be within a single package. A kit of the present disclosure can be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampoule, tube or vial). Exemplary instructions include those for reducing or lowering blood glucose, treatment of hyperglycemia, treatment of diabetes, etc. with the disclosed Modulators, and pharmaceutical compositions thereof Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: bp=base pair(s); kb=kilobase(s); pl=picoliter(s); s or sec=second(s); min=minute(s); h or hr=hour(s); aa=amino acid(s); kb=kilobase(s); nt=nucleotide(s); ng=nanogram; µg=microgram; mg=milligram; g=gram; kg=kilogram; dl or dL=deciliter; µl or µL=microliter; ml or mL=milliliter; l or L=liter; µM=micromolar; mM=millimolar; M=molar; kDa=kilodalton; i.m.=intramuscular(ly); i.p.=intraperitoneal (ly); s.c.=subcutaneous(ly); bid=twice daily; HPLC=high performance liquid chromatography; BW=body weight; U=unit; ns=not statistically significant; PG=fasting plasma glucose; FPI=fasting plasma insulin; ITT=insulin tolerance test; PTT=pyruvate tolerance test; oGTT=oral glucose tolerance test; GSIS=glucose-stimulated insulin secretion; PBS=phosphate-buffered saline; PCR=polymerase chain reaction; NHS=N-Hydroxysuccinimide; DMEM=Dulbeco's Modification of Eagle's Medium; GC=genome copy; EDTA=ethylenediaminetetraacetic acid.

Materials and Methods

The following methods and materials were used in the Examples below:

Animals.

Diet-induced obese (DIO) male C57BL/6J mice (The Jackson Laboratory, Bar Harbor, Me.) were maintained on a high-fat diet (D12492, Research Diets, Inc, New Brunswick, N.J.) containing 60 kcal % fat, 20 kcal % protein and 20 kcal % carbohydrate for 12-20 weeks. All animal studies were approved by the NGM Institutional Animal Care and Use Committee. DIO C57BL/6J mice offer a human-like model of obesity, where the obesity is based upon excessive intake of calories. C57BL/6J mice are obesity-prone in which pronounced weight gain, as well as hyperinsulinemia and sometimes hyperglycemia, is observed. The strain is most-commonly used mouse strain for modeling diet-induced obesity. (Nilsson C., et al., Acta Pharmacologica Sinica (2012) 33: 173-181).

Nucleic Acid and Amino Acid Sequences.

GenBank Accession No. BC000529.2 sets forth the cDNA of ORF encoding human GDF15 variants, and GenBank Accession No. NP_004855.2 sets forth the amino acid sequence encoded by the cDNA. The cDNA for the Fc-fusion partner was purchased at InvivoGen (pFUSE-CHIg-hG1, GenBank: AY623427.1, protein ID=AAT49050) and modified as indicated. The amino acid sequence of the Fc-fusion partner encoded by the pFUSE-CHIg-hG1 vector is:

(SEQ ID NO: 55)
DKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNG

KEYKCKVSNKALPAPIEKTISKAKGQPREPQVYTLPPSREEMTKNQVS

LTCLVKGFYPSDIAVEWESNGQPENNYKTTPPVLDSDGSFFLYSKLTV

DKSRWQQGNVFSCSVMHEALHNHYTQKSLSLSPGK

Construction of Expression Constructs.

The mammalian expression vector pTT5 (National Research Council Canada) was modified by inserting a Kozak element and human IgK-Signal Peptide sequence: (CACCATGGACAT-GAGGGTCCCCGCTCAGCTCCTGGGGCTCCTGC-TACTCTGGCTCCGAGGTGCCAGATGT) (SEQ ID NO: 56) between the PmeI and EcoRI site. While both restriction sites were eliminated an AgeI site was created for further in-frame cloning of secreted factors. For single fragment insertion (e.g., Fc portion of human IgG1). In-Fusion technology (Clontech) was used. For the insertion of two or more PCR generated fragments (i.e. hIgG1-Fc+GDF15) we used Gibson Assembly Master Mix (NEB) according to manufactures protocols. All PCR fragments were amplified by Sapphire PCR mix and gel-purified using Qiagen Gel Extraction kit. TOP10 Electro-competent cells (Life Technologies) were transformed with cloning reactions, plated on LB-agar plates containing carbenicillin and incubated over night at 37° C. Single colonies were picked and analyzed by sequencing. DNA from positive colonies was amplified (DNA-Maxi-prep, Qiagen), fully sequence confirmed and used to transfect mammalian cells for recombinant protein expression.

To create specific muteins, site directed mutagenesis was performed with either QuikChange Lightning or QuikChange Lightning Multi Site-Directed Mutagenesis Kits (Agilent) and appropriate primers, following manufactures protocols.

(Fc/Fc)-GDF15 Fusion Molecule, Wild Type GDF15, and GDF15-Glycomutein Expression.

All molecules were recovered from transiently transfected in Expi 293F cells (Invitrogen Corporation, Carlsbad, Calif.). Cells were routinely subcultured in Expi expression medium (Invitrogen) and maintained as suspension cultures in shake flasks of varying sizes. Typically, cells were subcultured at a cell density of 5e5 viable cells/ml and grown for 3 days before subculturing. The flasks were maintained in a humidified $CO_2$ incubator (37° C., and 5% $CO_2$) on New Brunswick shaker platforms (New Brunswick Scientific Company, Edison, N.J.) at an agitation rate of 110 RPM.

Transfections were performed when the cell density of the culture reached 2.5e6 viable cells/mL at greater than 95% viability. Typically, for 50 mL transfection, 2.5e6 cells/mL× 50 mL cells were inoculated in a 250 mL shaker flask in 42.5 mL culture volume. Fifty micrograms (50 µg) plasmid DNA consisting of the expression vector containing the gene of interest was first diluted in 2.5 mL OPTI-MEM reduced-serum medium (Invitrogen). Simultaneously, Expifectamine transfection reagent (Invitrogen), 2.67 times the volume (of the amount of plasmid DNA) was also diluted in 2.5 mL OPTI-MEM reduced-serum medium. After a 5 min incubation at room temperature, the diluted transfection reagent was slowly added to the diluted plasmid DNA to form transfection competent complexes. After a further 20 min incubation period at room temperature, 5 mL of the transfection complex was added to the 42.5 mL cell culture. The transfected cells were then placed in the humidified $CO_2$ incubator on an orbital shaker maintained at 110 RPM. Twenty-four hours post-transfection, the transfected culture was fed with 250 µL enhancer 1 solution (Invitrogen) and 2.5 mL enhancer 2 solution (Invitrogen). The culture was then replaced in the humidified $CO_2$ incubator on an orbital shaker. Six-to-seven days post-transfection, cultures were harvested by centrifugation at 3000 RPM for 30 min before being filtered through a 0.2 µm filter (Nalgene). Samples were then analyzed on a commassie stain gel for expression.

Purification of Recombinant Protein.

(Fc/Fc)-GDF15 molecules expressed into conditioned media (CM) were assessed for recovery and activity following purification. CM was passed over mAb SelectSuRe column (GE) at a loading capacity of no greater than 20 mg/mL of resin. CM volumes ranged from 50 mL-1000 mL for assessment of recoveries. Following mAb SelectSuRe loading of CM, the column was washed with 5-10 column volumes of 1×PBS (Corning Cellgro) followed by step elution with low pH Glycine buffer (Polysciences Inc). Following elution, the (Fc/Fc)-GDF15 pools were pH neutralized with 1M Tris pH 8.0 (Teknova) and then injected onto a Superdex200 (GE) column pre-equilibrated in 1×PBS (Corning Cellgro). Fractions of (Fc/Fc)-GDF15 intact, fully assembled molecules were pooled and assessed for purity and quantitated via A280 methods using appropriate extinction coefficient and molecular weights to determine recovery based on starting CM volumes. The fully assembled molecules were dimer-dimer complex of two heterodimers. Each heterodimer having a Fc associated with Fc-GDF15 glycomutein via knob in hole interaction, and two heterodimers associated via GDF15-GDF15 interaction.

Purification of WT GDF15 and GDF15 Glycomuteins.

Wild type GDF15 and the GDF15 glycomuteins not conjugated to Fc were purified from cultured media using ion-exchange capture. WT GDF15 and GDF15 glycomuteins were eluted using a gradient of appropriate salt/pH conducive for optimal elution and separation from host cell protein impurities. All GDF15 molecules were then further purified using GE HiTrap Phenyl HP at pH 8.0 using a decreasing linear gradient of ammonium sulfate. Fractions were assessed and pooled based on purity and glycosylation properties via gel-shift on non-reduced SDS-PAGE gels. Similar to the (Fc/Fc)-GDF15 molecules, the wild type GDF15 and the GDF15 glycomuteins were expressed using the IgK signal peptide.

Example 1: Design of Heterodimeric Knob-In-Hole (Fc/Fc)-GDF15 Fusion Molecules

Fc-GDF15 designs are described in FIG. 1 and primary sequences are depicted below (Constructs B1a/b-B19a/b). To achieve productive assembly of Fc-GDF15 molecules, an efficient system was designed to allow for Fc/Fc dimerization whilst allowing for GDF15/GDF15 dimerization. To avoid mis-folding and aggregation potential of single-chain Fc-GDF15, a heterodimeric fusion partner was designed for the Fc/Fc interaction to allow for high fidelity GDF15/GDF15 homodimerization. Knob-in-hole Fc/Fc heterodimers were designed to address GDF15 assembly and secretion from Expi 293F transient systems. Fc/Fc heterodimeric knob-in-hole systems were assessed using a [T366Y (knob)// Y407T (hole)] or a [T366W (knob)//T366S-L368A-Y407V (hole)] system, coupled with a $(G_4S)_n$ linker (n=2, 3, 4, or 5) and GDF15. It is noted that the numbering of the amino acid position in the CH3 domain of Fc is based on the EU numbering system (Edelman, G. M. et al., Proc. Natl. Acad. USA, 63, 78-85 (1969)). In all cases, the Fc-fusion (knob/ hole) partner was coupled to the N-terminus of mature GDF15 comprising amino acid residues A1-I112, R2-I112, N3-I112, G4-I112, D5-I112, H6-I112, or C7-I112. Truncations of the N-terminus of GDF15 (Δ1=R2–I1, Δ112, Δ2=N3–I112, Δ3=G4–I112, Δ4=D5–I112, Δ5=H6–I112, or Δ6=C7–I112) were incorporated for stability enhancement as the sequence at the N-terminus (ARNGDH, SEQ ID NO: 95) has previously been demonstrated as a site of proteolytic susceptibility and N-terminal truncations provide superior stability vs. GDF15 that does not include these N-terminal truncations.

FIGS. 1A-1D describe the placement of the knob vs. hole on the Fc-GDF15 (chain A), coupled with the corresponding hole vs. knob on the heterodimeric Fc partner (chain B), coupled with either a wild-type IgG hinge containing two intermolecular disulfide bonds or without the hinge domain (Δhinge). For the Fc heterodimeric knob or hole A/B chains, an AA mutation (APELLGGP (SEQ ID NO: 96)→APAL AGGP (SEQ ID NO: 97)) was introduced for removal of IgG1 effector functionality. (Fc/Fc)-GDF15 heterodimeric knob-in-hole designs were expression profiled for assembly and are reported in FIG. 2A. In all cases, transient expression of knob-in-hole (Fc/Fc)-GDF15 resulted in recoveries, following purification, between 0 mg/L and 74.9 mg/L of correctly assembled product (0=aggregates/no expression, <25 mg/L, 25 mg/L-49.9 mg/L, 50 mg/L-74.9 mg/L, 75 mg/L-99.0 mg/L, >100 mg/L). In all cases, assembly and secretion of the knob-in-hole heterodimeric Fc/Fc-GDF15 molecules were accompanied with various contaminating levels of mis-folded homodimeric species such as Fc(hole):Fc(hole), Fc(knob):Fc(knob), Fc(knob)-GDF15:Fc(knob)-GDF15 and Fc(hole)-GDF15:Fc(hole)-GDF15. Based on expression profiling, the T366W (knob) placed on the Fc-GDF15 chain, coupled with the T366S-L368A-Y407V (hole) on the heterodimeric Fc partner chain (FIG. 1D) was found to produce a product with maximal stability and minimized mis-pairing of Fc/Fc-homodimeric products (FIG. 2A—variant B5a/B5b). This design was the focus of further expression engineering and optimization.

Variant B5a/B5b recovery from transiently expressed Expi 293F source provided recoveries in the range of 0.0 mg/L to 24.9 mg/L. To enhance expression, assembly & recoveries, N-glycosylation sites were introduced within the mature sequence of GDF15 (FIG. 1F). In the designed constructs, the presence of a single N-linked glycan consensus site on GDF15 significantly improved expression, assembly and recovery of the fully mature (Fc/Fc)-GDF15 knob-in-hole heterodimer B5a/B5b (FIG. 2A—variants B9a/B9b to B19a/B19b). The linker length was found to be optimal when n=5 for $(G_4S)_n$ for receptor binding & activity via an in vitro assay. The presence of a glycan on position D5T completely removes a primary deamidation site on position N3 of mature GDF15 and appears to further enhance stability of the molecule as is evidenced in Example 2.

The presence of N-linked glycans within the sequence of GDF15 is proposed to help expression and minimize misfolded products from accumulating due to increased residence time in the Endoplasmic Reticulum and Golgi Apparatus during the secretory process. This additional residence time is proposed to have a beneficial effect on folding kinetics and allows for significantly improved hetero-dimeric (Fc/Fc) knob-in-hole pairing and recoveries from mammalian tissue culture.

The sequences of the variants (B1a/b-B19a/b) are provided below. In the sequences depicted below, human IgK signal peptide is in lower case followed by Fc sequence. In the sequences that also include linker and GDF15 sequence, the Fc sequence is followed by linker sequence (underlined) which is followed by GDF15 sequence (in bold). The numbering of the position of amino acid substitutions in the Fc sequence is based on EU numbering, the substitutions with reference to the amino acid present at corresponding position in human IgG1Fc (SEQ ID NO: 2). The numbering of N-terminal deletion in GDF15 sequence and amino acid substitution(s) is with reference to wild type human mature GDF15 (SEQ ID NO: 1).

```
B1a: hIgK-hIgG1-Fc(AA)(T366Y)-(G4S)5-ΔN3-GDF15(G4-I112)
                                                        (SEQ ID NO: 57)
mdmrvpaqllglllllwlrgarcDKTHTCPPCPAPALAGGPSVFLFPPKPKDTLMISRTPEV

TCVVVDVSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSLYCLVKGFYP

SDIAVEWESNGQPENNYKTTPPVLDSDGSFFLYSKLTVDKSRWQQGNVFSCSVMHEAL

HNHYTQKSLSLSPGKGGGGSGGGGSGGGGSGGGGSGGGGSGDHCPLGPGRCCRLHT

VRASLEDLGWADWVLSPREVQVTMCIGACPSQFRAANMHAQIKTSLHRLKPDTVP

APCCVPASYNPMVLIQKTDTGVSLQTYDDLLAKDCHCI

B1b: hIgK-hIgG1-Fc(AA)(Y407T)
                                                        (SEQ ID NO: 58)
mdmrvpaqllglllllwlrgarcDKTHTCPPCPAPALAGGPSVFLFPPKPKDTLMISRTPEV

TCVVVDVSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSLTCLVKGFYPS

DIAVEWESNGQPENNYKTTPPVLDSDGSFFLTSKLTVDKSRWQQGNVFSCSVMHEALH

NHYTQKSLSLSPGK

B2a: hIgK-hIgG1-Fc(AA)(Y407T)-(G4S)5-ΔN3-GDF15(G4-I112)
                                                        (SEQ ID NO: 59)
mdmrvpaqllglllllwlrgarcDKTHTCPPCPAPALAGGPSVFLFPPKPKDTLMISRTPEV

TCVVVDVSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSLTCLVKGFYPS

DIAVEWESNGQPENNYKTTPPVLDSDGSFFLTSKLTVDKSRWQQGNVFSCSVMHEALH

NHYTQKSLSLSPGKGGGGSGGGGSGGGGSGGGGSGGGGSGDHCPLGPGRCCRLHTV

RASLEDLGWADWVLSPREVQVTMCIGACPSQFRAANMHAQIKTSLHRLKPDTVPA

PCCVPASYNPMVLIQKTDTGVSLQTYDDLLAKDCHCI
```

B2b: hIgK-hIgG1-Fc(AA)(T366Y)
(SEQ ID NO: 60)
mdmrvpaqllglllllwlrgarcDKTHTCPPCPAPALAGGPSVFLFPPKPKDTLMISRTPEV
TCVVVDVSHEDPEVKFNWYVDGVEVHNAKTKPREEQYNSTYRVVSVLTVLHQDWLN
GKEYKCKVSNKALPAPIEKTISKAKGQPREPQVYTLPPSREEMTKNQVSLYCLVKGFYP
SDIAVEWESNGQPENNYKTTPPVLDSDGSFFLYSKLTVDKSRWQQGNVFSCSVMHEAL
HNHYTQKSLSLSPGK B3a: hIgK-hIgG1-Fc(Δhinge, AA)(T366Y)-(G₄S)₅-ΔN3-GDF15(G4-I112)
(SEQ ID NO: 61)
mdmrvpaqllglllllwlrgarcAPALAGGPSVFLFPPKPKDTLMISRTPEVTCVVVDVSH
EDPEVKFNWYVDGVEVHNAKTKPREEQYNSTYRVVSVLTVLHQDWLNGKEYKCKVS
NKALPAPIEKTISKAKGQPREPQVYTLPPSREEMTKNQVSLYCLVKGFYPSDIAVEWESN
GQPENNYKTTPPVLDSDGSFFLYSKLTVDKSRWQQGNVFSCSVMHEALHNHYTQKSLS
LSPGK<u>GGGGSGGGGSGGGGSGGGGSGGGGS</u>GDHCPLGPGRCCRLHTVRASLEDLG
WADWVLSPREVQVTMCIGACPSQFRAANMHAQIKTSLHRLKPDTVPAPCCVPASY
NPMVLIQKTDTGVSLQTYDDLLAKDCHCI

B3b: hIgK-hIgG1-Fc(Δhinge, AA)(Y407T)
(SEQ ID NO: 62)
mdmrvpaqllglllllwlrgarcAPALAGGPSVFLFPPKPKDTLMISRTPEVTCVVVDVSH
EDPEVKFNWYVDGVEVHNAKTKPREEQYNSTYRVVSVLTVLHQDWLNGKEYKCKVS
NKALPAPIEKTISKAKGQPREPQVYTLPPSREEMTKNQVSLTCLVKGFYPSDIAVEWESN
GQPENNYKTTPPVLDSDGSFFLTSKLTVDKSRWQQGNVFSCSVMHEALHNHYTQKSLS
LSPGK B4a: hIgK-hIgG1-Fc(Δhinge, AA)(Y407T)-(G₄S)₅-ΔN3-GDF15(G4-I112)
(SEQ ID NO: 63)
mdmrvpaqllglllllwlrgarcAPALAGGPSVFLFPPKPKDTLMISRTPEVTCVVVDVSH
EDPEVKFNWYVDGVEVHNAKTKPREEQYNSTYRVVSVLTVLHQDWLNGKEYKCKVS
NKALPAPIEKTISKAKGQPREPQVYTLPPSREEMTKNQVSLTCLVKGFYPSDIAVEWESN
GQPENNYKTTPPVLDSDGSFFLTSKLTVDKSRWQQGNVFSCSVMHEALHNHYTQKSLS
LSPGK<u>GGGGSGGGGSGGGGSGGGGSGGGGS</u>GDHCPLGPGRCCRLHTVRASLEDLG
WADWVLSPREVQVTMCIGACPSQFRAANMHAQIKTSLHRLKPDTVPAPCCVPASY
NPMVLIQKTDTGVSLQTYDDLLAKDCHCI

B4b: hIgK-hIgG1-Fc(Δhinge, AA)(T366Y)
(SEQ ID NO: 64)
mdmrvpaqllglllllwlrgarcAPALAGGPSVFLFPPKPKDTLMISRTPEVTCVVVDVSH
EDPEVKFNWYVDGVEVHNAKTKPREEQYNSTYRVVSVLTVLHQDWLNGKEYKCKVS
NKALPAPIEKTISKAKGQPREPQVYTLPPSREEMTKNQVSLYCLVKGFYPSDIAVEWESN
GQPENNYKTTPPVLDSDGSFFLYSKLTVDKSRWQQGNVFSCSVMHEALHNHYTQKSLS
LSPGK B5a: hIgK-hIgG1-Fc(AA)(T366W)-(G₄S)₅-ΔN3-GDF15(G4-I112)
(SEQ ID NO: 65)
mdmrvpaqllglllllwlrgarcDKTHTCPPCPAPALAGGPSVFLFPPKPKDTLMISRTPEV
TCVVVDVSHEDPEVKFNWYVDGVEVHNAKTKPREEQYNSTYRVVSVLTVLHQDWLN
GKEYKCKVSNKALPAPIEKTISKAKGQPREPQVYTLPPSREEMTKNQVSLWCLVKGFYP
SDIAVEWESNGQPENNYKTTPPVLDSDGSFFLYSKLTVDKSRWQQGNVFSCSVMHEAL -continued

HNHYTQKSLSLSPGKGGGGSGGGGSGGGGSGGGGSGGGGSGGGGSGDHCPLGPGRCCRLHT

VRASLEDLGWADWVLSPREVQVTMCIGACPSQFRAANMHAQIKTSLHRLKPDTVP

APCCVPASYNPMVLIQKTDTGVSLQTYDDLLAKDCHCI

B5b: hIgK-hIgG1-Fc(AA)(T366S)(L368A)(Y407V)
(SEQ ID NO: 66)
mdmrvpaqllglllllwlrgarcDKTHTCPPCPAPALAGGPSVFLFPPKPKDTLMISRTPEV

TCVVVDVSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSLSCAVKGFYPS

DIAVEWESNGQPENNYKTTPPVLDSDGSFFLVSKLTVDKSRWQQGNVFSCSVMHEALH

NHYTQKSLSLSPGK

B6a: hIgK-hIgG1-Fc(AA)(T366S)(L368A)(Y407V)-(G4S)5-ΔN6-GDF15(C7-I112)
(SEQ ID NO: 67)
mdmrvpaqllglllllwlrgarcDKTHTCPPCPAPALAGGPSVFLFPPKPKDTLMISRTPEV

TCVVVDVSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSLSCAVKGFYPS

DIAVEWESNGQPENNYKTTPPVLDSDGSFFLVSKLTVDKSRWQQGNVFSCSVMHEALH

NHYTQKSLSLSPGKGGGGSGGGGSGGGGSGGGGSGGGGSCPLGPGRCCRLHTVRASL

EDLGWADWVLSPREVQVTMCIGACPSQFRAANMHAQIKTSLHRLKPDTVPAPCCV

PASYNPMVLIQKTDTGVSLQTYDDLLAKDCHCI

B6b: hIgK-hIgG1-Fc(AA)(T366W)
(SEQ ID NO: 68)
mdmrvpaqllglllllwlrgarcDKTHTCPPCPAPALAGGPSVFLFPPKPKDTLMISRTPEV

TCVVVDVSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSLWCLVKGFYP

SDIAVEWESNGQPENNYKTTPPVLDSDGSFFLYSKLTVDKSRWQQGNVFSCSVMHEAL

HNHYTQKSLSLSPGK

B7a: hIgK-hIgG1-Fc(Δhinge, AA)(T366W)-(G4S)5-ΔN3-GDF15(G4-I112)
(SEQ ID NO: 69)
mdmrvpaqllglllllwlrgarcAPALAGGPSVFLFPPKPKDTLMISRTPEVTCVVVDVSH

EDPEVKFNWYVDGVEVHNAKTKPREEQYNSTYRVVSVLTVLHQDWLNGKEYKCKVS

NKALPAPIEKTISKAKGQPREPQVYTLPPSREEMTKNQVSLWCLVKGFYPSDIAVEWES

NGQPENNYKTTPPVLDSDGSFFLYSKLTVDKSRWQQGNVFSCSVMHEALHNHYTQKSL

SLSPGKGGGGSGGGGSGGGGSGGGGSGGGGSGDHCPLGPGRCCRLHTVRASLEDLG

WADWVLSPREVQVTMCIGACPSQFRAANMHAQIKTSLHRLKPDTVPAPCCVPASY

NPMVLIQKTDTGVSLQTYDDLLAKDCHCI

B7b: hIgK-hIgG1-Fc(Δhinge AA)(T366S)(L368A)(Y407V)
(SEQ ID NO: 70)
mdmrvpaqllglllllwlrgarcAPALAGGPSVFLFPPKPKDTLMISRTPEVTCVVVDVSH

EDPEVKFNWYVDGVEVHNAKTKPREEQYNSTYRVVSVLTVLHQDWLNGKEYKCKVS

NKALPAPIEKTISKAKGQPREPQVYTLPPSREEMTKNQVSLSCAVKGFYPSDIAVEWESN

GQPENNYKTTPPVLDSDGSFFLVSKLTVDKSRWQQGNVFSCSVMHEALHNHYTQKSLS

LSPGK

B8a: hIgK-hIgG1-Fc(Δh, AA)(T366S)(L368A)(Y407V)-(G4S)5-ΔN6-GDF15(C7-I112)
(SEQ ID NO: 71)
mdmrvpaqllglllllwlrgarcAPALAGGPSVFLFPPKPKDTLMISRTPEVTCVVVDVSH

EDPEVKFNWYVDGVEVHNAKTKPREEQYNSTYRVVSVLTVLHQDWLNGKEYKCKVS

NKALPAPIEKTISKAKGQPREPQVYTLPPSREEMTKNQVSLSCAVKGFYPSDIAVEWESN

-continued

GQPENNYKTTPPVLDSDGSFFLVSKLTVDKSRWQQGNVFSCSVMHEALHNHYTQKSLS

LSPGK<u>GGGGSGGGGSGGGGSGGGGSGGGGS</u>CPLGPGRCCRLHTVRASLEDLGWAD

WVLSPREVQVTMCIGACPSQFRAANMHAQIKTSLHRLKPDTVPAPCCVPASYNPM

VLIQKTDTGVSLQTYDDLLAKDCHCI

B8b: hIgK-hIgG1-Fc(Δh, AA)(T366W)
(SEQ ID NO: 72)

mdmrvpaqllglllllwlrgarcAPALAGGPSVFLFPPKPKDTLMISRTPEVTCVVVDVSH

EDPEVKFNWYVDGVEVHNAKTKPREEQYNSTYRVVSVLTVLHQDWLNGKEYKCKVS

NKALPAPIEKTISKAKGQPREPQVYTLPPSREEMTKNQVSLWCLVKGFYPSDIAVEWES

NGQPENNYKTTPPVLDSDGSFFLYSKLTVDKSRWQQGNVFSCSVMHEALHNHYTQKSL

SLSPGK

B9a: hIgK-hIgG1-Fc(AA)(T366W)-(G$_4$S)$_3$-GDF15(A1-I112)(D5T)
(SEQ ID NO: 73)

mdmrvpaqllglllllwlrgarcDKTHTCPPCPAPALAGGPSVFLFPPKPKDTLMISRTPEV

TCVVVDVSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSLWCLVKGFYP

SDIAVEWESNGQPENNYKTTPPVLDSDGSFFLYSKLTVDKSRWQQGNVFSCSVMHEAL

HNHYTQKSLSLSPGK<u>GGGGSGGGGSGGGGS</u>ARNGTHCPLGPGRCCRLHTVRASLED

LGWADWVLSPREVQVTMCIGACPSQFRAANMHAQIKTSLHRLKPDTVPAPCCVPA

SYNPMVLIQKTDTGVSLQTYDDLLAKDCHCI

B9b: hIgK-hIgG1-Fc(AA)(T366S)(L368A)(Y407V)
(SEQ ID NO: 74)

mdmrvpaqllglllllwlrgarcDKTHTCPPCPAPALAGGPSVFLFPPKPKDTLMISRTPEV

TCVVVDVSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSLSCAVKGFYPS

DIAVEWESNGQPENNYKTTPPVLDSDGSFFLVSKLTVDKSRWQQGNVFSCSVMHEALH

NHYTQKSLSLSPGK

B10a: hIgK-hIgG1-Fc(AA)(T366W)-(G$_4$S)$_4$-GDF15(A1-I112)(D5T)
(SEQ ID NO: 75)

mdmrvpaqllglllllwlrgarcDKTHTCPPCPAPALAGGPSVFLFPPKPKDTLMISRTPEV

TCVVVDVSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSLWCLVKGFYP

SDIAVEWESNGQPENNYKTTPPVLDSDGSFFLYSKLTVDKSRWQQGNVFSCSVMHEAL

HNHYTQKSLSLSPGK<u>GGGGSGGGGSGGGGSGGGGS</u>ARNGTHCPLGPGRCCRLHTVR

ASLEDLGWADWVLSPREVQVTMCIGACPSQFRAANMHAQIKTSLHRLKPDTVPAP

CCVPASYNPMVLIQKTDTGVSLQTYDDLLAKDCHCI

B10b: hIgK-hIgG1-Fc(AA)(T366S)(L368A)(Y407V)
(SEQ ID NO: 76)

mdmrvpaqllglllllwlrgarcDKTHTCPPCPAPALAGGPSVFLFPPKPKDTLMISRTPEV

TCVVVDVSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSLSCAVKGFYPS

DIAVEWESNGQPENNYKTTPPVLDSDGSFFLVSKLTVDKSRWQQGNVFSCSVMHEALH

NHYTQKSLSLSPGK

-continued

B11a: hIgK-hIgG1-Fc(AA)(T366W)-(G₄S)₅-GDF15(A1-I112)(D5T)
(SEQ ID NO: 77)
mdmrvpaqllglllllwlrgarcDKTHTCPPCPAPALAGGPSVFLFPPKPKDTLMISRTPEV

TCVVVDVSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSLWCLVKGFYP

SDIAVEWESNGQPENNYKTTPPVLDSDGSFFLYSKLTVDKSRWQQGNVFSCSVMHEAL

HNHYTQKSLSLSPGK<u>GGGGSGGGGSGGGGSGGGGSGGGGS</u>ARNGTHCPLGPGRCCR

LHTVRASLEDLGWADWVLSPREVQVTMCIGACPSQFRAANMHAQIKTSLHRLKPD

TVPAPCCVPASYNPMVLIQKTDTGVSLQTYDDLLAKDCHCI

B11b: hIgK-hIgG1-Fc(AA)(T366S)(L368A)(Y407V)
(SEQ ID NO: 76)
mdmrvpaqllglllllwlrgarcDKTHTCPPCPAPALAGGPSVFLFPPKPKDTLMISRTPEV

TCVVVDVSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSLSCAVKGFYPS

DIAVEWESNGQPENNYKTTPPVLDSDGSFFLVSKLTVDKSRWQQGNVFSCSVMHEALH

NHYTQKSLSLSPGK

B12a: hIgK-hIgG1-Fc(AA)(T366W)-(G₄S)₂-ΔN2-GDF15(N3-I112)(D5T)
(SEQ ID NO: 78)
mdmrvpaqllglllllwlrgarcDKTHTCPPCPAPALAGGPSVFLFPPKPKDTLMISRTPEV

TCVVVDVSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSLWCLVKGFYP

SDIAVEWESNGQPENNYKTTPPVLDSDGSFFLYSKLTVDKSRWQQGNVFSCSVMHEAL

HNHYTQKSLSLSPGK<u>GGGGSGGGGS</u>NGTHCPLGPGRCCRLHTVRASLEDLGWADW

VLSPREVQVTMCIGACPSQFRAANMHAQIKTSLHRLKPDTVPAPCCVPASYNPMVL

IQKTDTGVSLQTYDDLLAKDCHCI

B12b: hIgK-hIgG1-Fc(AA)(T366S)(L368A)(Y407V)
(SEQ ID NO: 79)
mdmrvpaqllglllllwlrgarcDKTHTCPPCPAPALAGGPSVFLFPPKPKDTLMISRTPEV

TCVVVDVSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSLSCAVKGFYPS

DIAVEWESNGQPENNYKTTPPVLDSDGSFFLVSKLTVDKSRWQQGNVFSCSVMHEALH

NHYTQKSLSLSPGK

B13a: hIgK-hIgG1-Fc(AA)(T366W)-(G₄S)₅-ΔN2-GDF15(N3-I112)(D5T)
(SEQ ID NO: 80)
mdmrvpaqllglllllwlrgarcDKTHTCPPCPAPALAGGPSVFLFPPKPKDTLMISRTPEV

TCVVVDVSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSLWCLVKGFYP

SDIAVEWESNGQPENNYKTTPPVLDSDGSFFLYSKLTVDKSRWQQGNVFSCSVMHEAL

HNHYTQKSLSLSPGK<u>GGGGSGGGGSGGGGSGGGGSGGGGS</u>NGTHCPLGPGRCCRLH

TVRASLEDLGWADWVLSPREVQVTMCIGACPSQFRAANMHAQIKTSLHRLKPDTV

PAPCCVPASYNPMVLIQKTDTGVSLQTYDDLLAKDCHCI

B13b: hIgK-hIgG1-Fc(AA)(T366S)(L368A)(Y407V)
(SEQ ID NO: 81)
mdmrvpaqllglllllwlrgarcDKTHTCPPCPAPALAGGPSVFLFPPKPKDTLMISRTPEV

TCVVVDVSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSLSCAVKGFYPS

-continued

DIAVEWESNGQPENNYKTTPPVLDSDGSFFLVSKLTVDKSRWQQGNVFSCSVMHEALH

NHYTQKSLSLSPGK

B14a: hIgK-hIgG1-Fc(AA)(T366W)-(G4S)5-ΔN3-GDF15(G4-I112)(R21N)
(SEQ ID NO: 82)

mdmrvpaqllglllwlrgarcDKTHTCPPCPAPALAGGPSVFLFPPKPKDTLMISRTPEV

TCVVVDVSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSLWCLVKGFYP

SDIAVEWESNGQPENNYKTTPPVLDSDGSFFLYSKLTVDKSRWQQGNVFSCSVMHEAL

HNHYTQKSLSLSPGK<u>GGGGSGGGGSGGGGSGGGGSGGGGS</u>GDHCPLGPGRCCRLHT

VNASLEDLGWADWVLSPREVQVTMCIGACPSQFRAANMHAQIKTSLHRLKPDTVP

APCCVPASYNPMVLIQKTDTGVSLQTYDDLLAKDCHCI

B14b: hIgK-hIgG1-Fc(AA)(T366S)(L368A)(Y407V)
(SEQ ID NO: 83)

mdmrvpaqllglllwlrgarcDKTHTCPPCPAPALAGGPSVFLFPPKPKDTLMISRTPEV

TCVVVDVSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSLSCAVKGFYPS

DIAVEWESNGQPENNYKTTPPVLDSDGSFFLVSKLTVDKSRWQQGNVFSCSVMHEALH

NHYTQKSLSLSPGK

B15a: hIgK-hIgG1-Fc(AA)(T366W)-(G4S)5-ΔN3-GDF15(G4-I112)(S23N/E25T)
(SEQ ID NO: 84)

mdmrvpaqllglllwlrgarcDKTHTCPPCPAPALAGGPSVFLFPPKPKDTLMISRTPEV

TCVVVDVSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSLWCLVKGFYP

SDIAVEWESNGQPENNYKTTPPVLDSDGSFFLYSKLTVDKSRWQQGNVFSCSVMHEAL

HNHYTQKSLSLSPGK<u>GGGGSGGGGSGGGGSGGGGSGGGGS</u>GDHCPLGPGRCCRLHT

VRANLTDLGWADWVLSPREVQVTMCIGACPSQFRAANMHAQIKTSLHRLKPDTVP

APCCVPASYNPMVLIQKTDTGVSLQTYDDLLAKDCHCI

B15b: hIgK-hIgG1-Fc(AA)(T366S)(L368A)(Y407V)
(SEQ ID NO: 85)

mdmrvpaqllglllwlrgarcDKTHTCPPCPAPALAGGPSVFLFPPKPKDTLMISRTPEV

TCVVVDVSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSLSCAVKGFYPS

DIAVEWESNGQPENNYKTTPPVLDSDGSFFLVSKLTVDKSRWQQGNVFSCSVMHEALH

NHYTQKSLSLSPGK

B16a: hIgK-hIgG1-Fc(AA)(T366W)-(G4S)5-ΔN3-GDF15(G4-I112)(F52N/A54T)
(SEQ ID NO: 86)

mdmrvpaqllglllwlrgarcDKTHTCPPCPAPALAGGPSVFLFPPKPKDTLMISRTPEV

TCVVVDVSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSLWCLVKGFYP

SDIAVEWESNGQPENNYKTTPPVLDSDGSFFLYSKLTVDKSRWQQGNVFSCSVMHEAL

HNHYTQKSLSLSPGK<u>GGGGSGGGGSGGGGSGGGGSGGGGS</u>GDHCPLGPGRCCRLHT

VRASLEDLGWADWVLSPREVQVTMCIGACPSQNRTANMHAQIKTSLHRLKPDTVP

APCCVPASYNPMVLIQKTDTGVSLQTYDDLLAKDCHCI

B16b: hIgK-hIgG1-Fc(AA)(T366S)(L368A)(Y407V)
(SEQ ID NO: 87)

mdmrvpaqllglllwlrgarcDKTHTCPPCPAPALAGGPSVFLFPPKPKDTLMISRTPEV

TCVVVDVSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSLSCAVKGFYPS

DIAVEWESNGQPENNYKTTPPVLDSDGSFFLVSKLTVDKSRWQQGNVFSCSVMHEALH

NHYTQKSLSLSPGK

B17a: hIgK-hIgG1-Fc(AA)(T366W)-(G₄S)₅-ΔN3-GDF15(G4-I112)(R53N/A55T)
(SEQ ID NO: 88)

mdmrvpaqllglllllwlrgarcDKTHTCPPCPAPALAGGPSVFLFPPKPKDTLMISRTPEV

TCVVVDVSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSLWCLVKGFYP

SDIAVEWESNGQPENNYKTTPPVLDSDGSFFLYSKLTVDKSRWQQGNVFSCSVMHEAL

HNHYTQKSLSLSPGK<u>GGGGSGGGGSGGGGSGGGGSGGGGS</u>GDHCPLGPGRCCRLHT

VRASLEDLGWADWVLSPREVQVTMCIGACPSQFNATNMHAQIKTSLHRLKPDTVP

APCCVPASYNPMVLIQKTDTGVSLQTYDDLLAKDCHCI

B17b: hIgK-hIgG1-Fc(AA)(T366S)(L368A)(Y407V)
(SEQ ID NO: 89)

mdmrvpaqllglllllwlrgarcDKTHTCPPCPAPALAGGPSVFLFPPKPKDTLMISRTPEV

TCVVVDVSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSLSCAVKGFYPS

DIAVEWESNGQPENNYKTTPPVLDSDGSFFLVSKLTVDKSRWQQGNVFSCSVMHEALH

NHYTQKSLSLSPGK

B18a: hIgK-hIgG1-Fc(AA)(T366W)-(G₄S)₅-ΔN3-GDF15(G4-I112)(K91N/D93T)
(SEQ ID NO: 90)

mdmrvpaqllglllllwlrgarcDKTHTCPPCPAPALAGGPSVFLFPPKPKDTLMISRTPEV

TCVVVDVSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSLWCLVKGFYP

SDIAVEWESNGQPENNYKTTPPVLDSDGSFFLYSKLTVDKSRWQQGNVFSCSVMHEAL

HNHYTQKSLSLSPGK<u>GGGGSGGGGSGGGGSGGGGSGGGGS</u>GDHCPLGPGRCCRLHT

VRASLEDLGWADWVLSPREVQVTMCIGACPSQFRAANMHAQIKTSLHRLKPDTVP

APCCVPASYNPMVLIQNTTTGVSLQTYDDLLAKDCHCI

B18b: hIgK-hIgG1-Fc(AA)(T366S)(L368A)(Y407V)
(SEQ ID NO: 91)

mdmrvpaqllglllllwlrgarcDKTHTCPPCPAPALAGGPSVFLFPPKPKDTLMISRTPEV

TCVVVDVSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSLSCAVKGFYPS

DIAVEWESNGQPENNYKTTPPVLDSDGSFFLVSKLTVDKSRWQQGNVFSCSVMHEALH

NHYTQKSLSLSPGK

B19a: hIgK-hIgG1-Fc(AA)(T366W)-(G₄S)₅-ΔN3-GDF15(G4-I112)(D93N/G95T)
(SEQ ID NO: 92)

mdmrvpaqllglllllwlrgarcDKTHTCPPCPAPALAGGPSVFLFPPKPKDTLMISRTPEV

TCVVVDVSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSLWCLVKGFYP

SDIAVEWESNGQPENNYKTTPPVLDSDGSFFLYSKLTVDKSRWQQGNVFSCSVMHEAL

HNHYTQKSLSLSPGK<u>GGGGSGGGGSGGGGSGGGGSGGGGS</u>GDHCPLGPGRCCRLHT

VRASLEDLGWADWVLSPREVQVTMCIGACPSQFRAANMHAQIKTSLHRLKPDTVP

APCCVPASYNPMVLIQKTNTTVSLQTYDDLLAKDCHCI

-continued

B19b: hIgK-hIgG1-Fc(AA)(T366S)(L368A)(Y407V)
(SEQ ID NO: 93)
mdmrvpaqllglllllwlrgarcDKTHTCPPCPAPALAGGPSVFLFPPKPKDTLMISRTPEV
TCVVVDVSHEDPEVKFNWYVDGVEVHNAKTKPREEQYNSTYRVVSVLTVLHQDWLN
GKEYKCKVSNKALPAPIEKTISKAKGQPREPQVYTLPPSREEMTKNQVSLSCAVKGFYPS
DIAVEWESNGQPENNYKTTPPVLDSDGSFFLVSKLTVDKSRWQQGNVFSCSVMHEALH
NHYTQKSLSLSPGK Sequences of the wild type human mature GDF15 (SEQ ID NO: 1) and GDF15 glycomuteins listed in FIG. 2B are as follows:

IgK-Wild type human mature GDF15
(SEQ ID NO: 108)
mdmrvpaqllglllllwlrgarcARNGDHCPLGPGRCCRLHTVRASLEDLGWADWVLSP
REVQVTMCIGACPSQFRAANMHAQIKTSLHRLKPDTVPAPCCVPASYNPMVLIQKTDTG
VSLQTYDDLLAKDCHCI IgK-GDF15-glycomutein R21N
(SEQ ID NO: 109)
mdmrvpaqllglllllwlrgarcARNGDHCPLGPGRCCRLHTVNASLEDLGWADWVLSP
REVQVTMCIGACPSQFRAANMHAQIKTSLHRLKPDTVPAPCCVPASYNPMVLIQKTDTG
VSLQTYDDLLAKDCHCI IgK-GDF15-glycomutein R53N/A55T
(SEQ ID NO: 110)
mdmrvpaqllglllllwlrgarcARNGDHCPLGPGRCCRLHTVRASLEDLGWADWVLSP
REVQVTMCIGACPSQFNATNMHAQIKTSLHRLKPDTVPAPCCVPASYNPMVLIQKTDTG
VSLQTYDDLLAKDCHCI IgK-GDF15-glycomutein S64N/H66T
(SEQ ID NO: 111)
mdmrvpaqllglllllwlrgarcARNGDHCPLGPGRCCRLHTVRASLEDLGWADWVLSP
REVQVTMCIGACPSQFRAANMHAQIKTNLTRLKPDTVPAPCCVPASYNPMVLIQKTDTG
VSLQTYDDLLAKDCHCI IgK-GDF15-glycomutein P70N
(SEQ ID NO: 112)
mdmrvpaqllglllllwlrgarcARNGDHCPLGPGRCCRLHTVRASLEDLGWADWVLSP
REVQVTMCIGACPSQFRAANMHAQIKTSLHRLKNDTVPAPCCVPASYNPMVLIQKTDT
GVSLQTYDDLLAKDCHCI IgK-GDF15-glycomutein Q90N
(SEQ ID NO: 113)
mdmrvpaqllglllllwlrgarcARNGDHCPLGPGRCCRLHTVRASLEDLGWADWVLSP
REVQVTMCIGACPSQFRAANMHAQIKTSLHRLKPDTVPAPCCVPASYNPMVLINKTDTG
VSLQTYDDLLAKDCHCI IgK-GDF15-glycomutein K91N/D93T
(SEQ ID NO: 114)
mdmrvpaqllglllllwlrgarcARNGDHCPLGPGRCCRLHTVRASLEDLGWADWVLSP
REVQVTMCIGACPSQFRAANMHAQIKTSLHRLKPDTVPAPCCVPASYNPMVLIQNTTTG
VSLQTYDDLLAKDCHCI -continued IgK-GDF15-glycomutein D93N/G95T
(SEQ ID NO: 115)
mdmrvpaqllglllwlrgarcARNGDHCPLGPGRCCRLHTVRASLEDLGWADWVLSP

REVQVTMCIGACPSQFRAANMHAQIKTSLHRLKPDTVPAPCCVPASYNPMVLIQKTNTT

VSLQTYDDLLAKDCHCI

IgK-GDF15-glycomutein G95N
(SEQ ID NO: 116)
mdmrvpaqllglllwlrgarcARNGDHCPLGPGRCCRLHTVRASLEDLGWADWVLSP

REVQVTMCIGACPSQFRAANMHAQIKTSLHRLKPDTVPAPCCVPASYNPMVLIQKTDTN

VSLQTYDDLLAKDCHCI

IgK-GDF15-glycomutein S97N/Q99T
(SEQ ID NO: 117)
mdmrvpaqllglllwlrgarcARNGDHCPLGPGRCCRLHTVRASLEDLGWADWVLSP

REVQVTMCIGACPSQFRAANMHAQIKTSLHRLKPDTVPAPCCVPASYNPMVLIQKTDTG

VNLTTYDDLLAKDCHCI

IgK-GDF15-glycomutein L98N
(SEQ ID NO: 118)
mdmrvpaqllglllwlrgarcARNGDHCPLGPGRCCRLHTVRASLEDLGWADWVLSP

REVQVTMCIGACPSQFRAANMHAQIKTSLHRLKPDTVPAPCCVPASYNPMVLIQKTDTG

VSNQTYDDLLAKDCHCI

The GDF15 molecules were expressed using the IgK signal peptide, which is cleaved off from the secreted polypeptide by a signal peptidase expressed by the 293 cells. The recovery of the wild type human mature GDF15 (SEQ ID NO: 1) and GDF15 glycomuteins is listed in FIG. 2B.

Exemplary GDF15 glycomuteins that may be expressed as Fc-Fc(knob/hole)GDF15 glycomuteins are described in U.S. Ser. No. 14/811,578 filed on Jul. 28, 2015.

Example 2: Effects of (Fc/Fc)-GDF15 Fusion Molecules on Body Weight and Food Intake in DIO Mouse Model The effects of a subcutaneously administered fusion molecule having recombinant Fc-heterodimer fused to recombinant human GDF15 (i.e., a complex of two heterodimers, each heterodimer having a Fc polypeptide dimerized with a Fc-GDF15 glycomutein polypeptide) on body weight were evaluated over a 35 day period. Briefly, the fusion molecules B9a/B9b, B11a/B11b and B13a/B13b were administered weekly for 21 days at doses of 0.4 nmol/kg and 4 nmol/kg as a single subcutaneous bolus injection (10 mL/kg) to DIO mice weighing approximately 35-40 g. Following administration of vehicle control or the fusion molecules, body weight reduction was monitored at various time points over a 35 day time period which comprised 21 days of protein dosing followed by a 14 day wash out (post-dose) to monitor efficacy.

As depicted in FIGS. 3-6, administration of the Fc fusion molecules (heterodimer-heterodimer complex) at a dose of 0.4 nmol/kg and 4 nmol/kg resulted in significant body weight reduction. In each group of mice, n=6 and p-values (*, $p<0.05$; , $p<0.01$; *, $p<0.001$, ns=not significant) were determined by student's unpaired T-test comparing to vehicle control group at each specified time point. As depicted in FIG. 7, total body weight with SEM analysis is shown at each time point sampling for all groups. As depicted in FIG. 8, changes in body weight (g) with SEM analysis and p-values are shown at each time point sampling for all groups. As depicted in FIG. 9, percent changes in body weight (%) with SEM analysis and p-values are shown at each time point sampling for all groups.

As depicted in FIGS. 3 & 5, there is an observed increased efficacy in body weight reduction for B13a/B13b as compared to B9a/B9b and B11a/B11b in the 0.4 nmol/kg dose study. The increased in vivo efficacy for B13a/B13b is attributed to enhanced stability due to the truncation of the 2 N-terminal residues of GDF15 (ΔΔR).

Particular embodiments of this invention are described herein, including the best mode known to the inventors for carrying out the invention. Upon reading the foregoing description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:

1. A complex comprising a first heterodimer and a second heterodimer, each of the first heterodimer and second heterodimer comprising:
(i) a first polypeptide comprising from the N-terminus to the C-terminus:
a first human IgG1 Fc comprising a first hinge region, a first CH2 domain, and a first CH3 domain comprising at least one substitution selected from the group consisting of Q347W/Y, T366W/Y, and T394W/Y, according to EU numbering, and
(ii) a second polypeptide comprising from the N-terminus to the C-terminus:
a second human IgG1 Fc comprising a second hinge region, a second CH2 domain, and a second CH3 domain comprising at least one substitution selected from the group consisting of T366S, L368A, T394S, F405T/V/A, and Y407T/V/A, according to EU numbering;
wherein the first polypeptide dimerizes with the second polypeptide, wherein either the C-terminus of the first polypeptide or the C-terminus of the second polypeptide is conjugated to the N-terminus of a GDF15 mutein via a linker, wherein the GDF15 mutein comprises a contiguous amino acid sequence at least 98 amino acids long and at least 95% identical to a corresponding stretch of the amino acid sequence of SEQ ID NO:1, and wherein the GDF15 mutein comprises a D5T substitution relative to the amino acid sequence of SEQ ID NO:1;
wherein the GDF15 mutein in the first heterodimer dimerizes with the GDF15 mutein in the second heterodimer thereby forming the complex comprising the first heterodimer and second heterodimer; and
wherein the complex reduces food intake and/or body weight in diet-induced obese mice.

2. The complex of claim 1, wherein the first polypeptide comprises the linker and the GDF15 mutein.

3. The complex of claim 1, wherein the second polypeptide comprises the linker and the GDF15 mutein.

4. The complex of claim 1, wherein the GDF15 mutein is N-glycosylated.

5. The complex of claim 1, wherein the linker comprises n copies of the amino acid sequence Glycine-Glycine-Glycine-Glycine-Serine (SEQ ID NO: 126), wherein n=2-10.

6. The complex of claim 5, wherein the linker comprises 5 copies of the amino acid sequence of SEQ ID NO: 126.

7. The complex of claim 1, wherein the GDF15 mutein comprises the amino acid sequence of SEQ ID NO:128.

8. The complex of claim 1, wherein the GDF15 mutein does not comprise the first two amino acids present at the N-terminus of SEQ ID NO:1.

9. The complex of claim 1, wherein the GDF15 mutein comprises the amino acid sequence of SEQ ID NO:129.

10. The complex of claim 1, wherein
(i) the first polypeptide comprises:
(a) the first IgG1 Fc comprising a substitution of T366W;
(b) the linker, and
(c) the GDF15 mutein, wherein the GDF15 mutein is N-glycosylated; and
(ii) the second polypeptide comprises:
(a) the second IgG1 Fc comprising substitutions of T366S, L368A, and Y407V.

11. The complex of claim 1, wherein
(i) the first polypeptide comprises:
  (a) the first IgG1 Fc comprising a substitution of T366W; and
(ii) the second polypeptide comprises:
  (a) the second IgG1 Fc comprising substitutions of T366S, L368A, and Y407V;
  (b) the linker, and
  (c) the GDF15 mutein, wherein the GDF15 mutein is N-glycosylated.

12. A pharmaceutical composition comprising the complex of claim 1 and a pharmaceutically acceptable diluent, carrier or excipient.

13. A method of treating a body weight disorder, a glucose metabolism disorder, or a metabolic syndrome in a human subject, the method comprising administering to the human subject a therapeutically effective amount of the complex of claim 1.

14. The method of claim 13, wherein the human subject has one or more of the following traits: hypertension, hyperglycemia, hyperinsulinemia, abnormal glucose tolerance, obesity, redistribution of fat to the abdominal or upper body compartment, abnormal cholesterol levels, abnormal triglyceride levels, low high density lipoprotein (HDL)-cholesterol, or high small dense low density lipoprotein (LDL) particles.

15. The method of claim 14, wherein the human subject has diabetes mellitus.

16. The method of claim 14, wherein the human subject is obese.

17. A method of treating hyperglycemia in a human subject, the method comprising administering to the human subject a therapeutically effective amount of the complex of claim 1.

18. A method of treating obesity in a human subject, the method comprising administering to the human subject a therapeutically effective amount of the complex of claim 1.

19. The complex of claim 10, wherein the linker comprises 5 copies of the amino acid sequence of SEQ ID NO: 126.

20. The method of claim 17, wherein the administering results in reduction in blood glucose in the subject.

21. The method of claim 17, wherein the administering results in reduction in body weight in the subject.

22. The method of claim 17, wherein the subject has diabetes mellitus.

23. The method of claim 17, wherein the subject is obese.

24. The method of claim 17, wherein the parenteral injection is subcutaneous.

25. The method of claim 18, wherein the treating results in reduction in blood glucose in the subject.

26. The method of claim 18, wherein the administering is by subcutaneous injection.

27. The complex of claim 11, wherein the linker comprises 5 copies of the amino acid sequence of SEQ ID NO: 126.

28. A complex comprising a first heterodimer and a second heterodimer, each of the first heterodimer and second heterodimer comprising:
(i) a first polypeptide comprising from the N-terminus to the C-terminus:
  a first human IgG1 Fc comprising a first hinge region, a first CH2 domain, and a first CH3 domain comprising a substitution of T366W, according to EU numbering, and
(ii) a second polypeptide comprising from the N-terminus to the C-terminus:
  a second human IgG1 Fc comprising a second hinge region, a second CH2 domain, a second CH3 domain comprising substitutions of T366S, L368A, Y407V, according to EU numbering, a linker, and a GDF15 mutein,
wherein the first polypeptide dimerizes with the second polypeptide,
wherein the GDF15 mutein in the first heterodimer dimerizes with the GDF15 mutein in the second heterodimer thereby forming the complex comprising the first heterodimer and second heterodimer; and
wherein the GDF15 mutein comprises the amino acid sequence of SEQ ID NO:129.

29. A pharmaceutical composition comprising the complex of claim 10 and a pharmaceutically acceptable diluent, carrier or excipient.

30. A pharmaceutical composition comprising the complex of claim 11 and a pharmaceutically acceptable diluent, carrier or excipient.

31. A pharmaceutical composition comprising the complex of claim 28 and a pharmaceutically acceptable diluent, carrier or excipient.

32. A method of treating a body weight disorder, a glucose metabolism disorder, or a metabolic syndrome in a human subject, the method comprising administering to the human subject a therapeutically effective amount of the complex of claim 28.

33. The method of claim 32, wherein the human subject has one or more of the following traits: hypertension, hyperglycemia, hyperinsulinemia, abnormal glucose tolerance, obesity, redistribution of fat to the abdominal or upper body compartment, abnormal cholesterol levels, abnormal triglyceride levels, low high density lipoprotein (HDL)-cholesterol, or high small dense low density lipoprotein (LDL) particles.

34. The method of claim 32, wherein the human subject has diabetes mellitus.

35. The method of claim 32, wherein the human subject is obese.

36. A method of treating hyperglycemia in a human subject, the method comprising administering to the human subject a therapeutically effective amount of the complex of claim 28.

37. The method of claim 36, wherein the administering results in reduction in blood glucose in the subject.

38. The method of claim 36, wherein the administering results in reduction in body weight in the subject.

39. The method of claim 36, wherein the subject has diabetes mellitus.

40. The method of claim 36, wherein the subject is obese.

41. The method of claim 36, wherein the administering is by subcutaneous injection.

42. A method of treating obesity in a human subject, the method comprising administering to the human subject a therapeutically effective amount of the complex of claim 28.

43. The method of claim 42, wherein the treating results in reduction in blood glucose in the subject.

44. The method of claim 42, wherein the administering is by subcutaneous injection.

* * * * *

UNITED STATES PATENT AND TRADEMARK OFFICE
CERTIFICATE OF CORRECTION

PATENT NO. : 11,530,260 B2
APPLICATION NO. : 16/743712
DATED : December 20, 2022
INVENTOR(S) : Wenyan Shen et al.

It is certified that error appears in the above-identified patent and that said Letters Patent is hereby corrected as shown below:

In the Claims

Column 215, Line 27:
In Claim 15, delete "claim 14," and insert -- claim 13, --.

Column 215, Line 29:
In Claim 16, delete "claim 14," and insert -- claim 13, --.

Column 215, Line 48:
In Claim 24, delete "parenteral injection is subcutaneous." and insert -- administering is by subcutaneous injection. --.

Signed and Sealed this
Fourteenth Day of March, 2023

Katherine Kelly Vidal
*Director of the United States Patent and Trademark Office*

SEQUENCE LISTING

<160> NUMBER OF SEQ ID NOS: 136

<210> SEQ ID NO 1

```
<211> LENGTH: 112
<212> TYPE: PRT
<213> ORGANISM: Homo sapiens

<400> SEQUENCE: 1

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 2
<211> LENGTH: 232
<212> TYPE: PRT
<213> ORGANISM: Homo sapiens

<400> SEQUENCE: 2

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 3
<211> LENGTH: 347
<212> TYPE: PRT
<213> ORGANISM: Artificial sequence
<220> FEATURE:
<223> OTHER INFORMATION: synthetic polypeptide sequence

<400> SEQUENCE: 3

```
Asp Lys Thr His Thr Cys Pro Pro Cys Pro Ala Pro Ala Leu Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Ser Gly Gly Gly Ser Asn Gly Thr
225                 230                 235                 240

His Cys Pro Leu Gly Pro Gly Arg Cys Cys Arg Leu His Thr Val Arg
                245                 250                 255

Ala Ser Leu Glu Asp Leu Gly Trp Ala Asp Trp Val Leu Ser Pro Arg
            260                 265                 270

Glu Val Gln Val Thr Met Cys Ile Gly Ala Cys Pro Ser Gln Phe Arg
        275                 280                 285

Ala Ala Asn Met His Ala Gln Ile Lys Thr Ser Leu His Arg Leu Lys
    290                 295                 300

Pro Asp Thr Val Pro Ala Pro Cys Cys Val Pro Ala Ser Tyr Asn Pro
305                 310                 315                 320

Met Val Leu Ile Gln Lys Thr Asp Thr Gly Val Ser Leu Gln Thr Tyr
                325                 330                 335

Asp Asp Leu Leu Ala Lys Asp Cys His Cys Ile
            340                 345
```

<210> SEQ ID NO 4

```
<211> LENGTH: 227
<212> TYPE: PRT
<213> ORGANISM: Artificial sequence
<220> FEATURE:
<223> OTHER INFORMATION: synthetic polypeptide sequence

<400> SEQUENCE: 4
```

Asp Lys Thr His Thr Cys Pro Pro Cys Pro Ala Pro Ala Leu Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

```
<210> SEQ ID NO 5
<211> LENGTH: 362
<212> TYPE: PRT
<213> ORGANISM: Artificial sequence
<220> FEATURE:
<223> OTHER INFORMATION: synthetic polypeptide sequence

<400> SEQUENCE: 5
```

Asp Lys Thr His Thr Cys Pro Pro Cys Pro Ala Pro Ala Leu Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly

```
            85                  90                  95
Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
            130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys Gly Gly Gly Ser Gly Gly Gly Ser Gly Gly Gly Gly Gly
225                 230                 235                 240

Gly Ser Gly Gly Gly Ser Gly Gly Gly Ser Asn Gly Thr His
            245                 250                 255

Cys Pro Leu Gly Pro Gly Arg Cys Cys Arg Leu His Thr Val Arg Ala
            260                 265                 270

Ser Leu Glu Asp Leu Gly Trp Ala Asp Trp Val Leu Ser Pro Arg Glu
            275                 280                 285

Val Gln Val Thr Met Cys Ile Gly Ala Cys Pro Ser Gln Phe Arg Ala
            290                 295                 300

Ala Asn Met His Ala Gln Ile Lys Thr Ser Leu His Arg Leu Lys Pro
305                 310                 315                 320

Asp Thr Val Pro Ala Pro Cys Cys Val Pro Ala Ser Tyr Asn Pro Met
            325                 330                 335

Val Leu Ile Gln Lys Thr Asp Thr Gly Val Ser Leu Gln Thr Tyr Asp
            340                 345                 350

Asp Leu Leu Ala Lys Asp Cys His Cys Ile
            355                 360

<210> SEQ ID NO 6
<211> LENGTH: 227
<212> TYPE: PRT
<213> ORGANISM: Artificial sequence
<220> FEATURE:
<223> OTHER INFORMATION: synthetic polypeptide sequence

<400> SEQUENCE: 6

Asp Lys Thr His Thr Cys Pro Pro Cys Pro Ala Pro Ala Leu Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
            50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
```

```
            85                  90                  95
Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys
225

<210> SEQ ID NO 7
<211> LENGTH: 361
<212> TYPE: PRT
<213> ORGANISM: Artificial sequence
<220> FEATURE:
<223> OTHER INFORMATION: synthetic polypeptide sequence

<400> SEQUENCE: 7

Asp Lys Thr His Thr Cys Pro Pro Cys Pro Ala Pro Ala Leu Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
```

```
            210                 215                 220
Pro Gly Lys Gly Gly Gly Ser Gly Gly Gly Ser Gly Gly
225                 230                 235                 240

Gly Ser Gly Gly Gly Ser Gly Gly Gly Ser Gly Asp His Cys
                245                 250                 255

Pro Leu Gly Pro Gly Arg Cys Cys Arg Leu His Thr Val Asn Ala Ser
                260                 265                 270

Leu Glu Asp Leu Gly Trp Ala Asp Trp Val Leu Ser Pro Arg Glu Val
                275                 280                 285

Gln Val Thr Met Cys Ile Gly Ala Cys Pro Ser Gln Phe Arg Ala Ala
                290                 295                 300

Asn Met His Ala Gln Ile Lys Thr Ser Leu His Arg Leu Lys Pro Asp
305                 310                 315                 320

Thr Val Pro Ala Pro Cys Cys Val Pro Ala Ser Tyr Asn Pro Met Val
                325                 330                 335

Leu Ile Gln Lys Thr Asp Thr Gly Val Ser Leu Gln Thr Tyr Asp Asp
                340                 345                 350

Leu Leu Ala Lys Asp Cys His Cys Ile
                355                 360

<210> SEQ ID NO 8
<211> LENGTH: 227
<212> TYPE: PRT
<213> ORGANISM: Artificial sequence
<220> FEATURE:
<223> OTHER INFORMATION: synthetic polypeptide sequence

<400> SEQUENCE: 8

Asp Lys Thr His Thr Cys Pro Pro Cys Pro Ala Pro Ala Leu Ala Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
                35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
                115                 120                 125

Tyr Thr Leu Pro Pro Ser Arg Glu Glu Met Thr Lys Asn Gln Val Ser
                130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
```

Pro Gly Lys
225

<210> SEQ ID NO 9
<211> LENGTH: 361
<212> TYPE: PRT
<213> ORGANISM: Artificial sequence
<220> FEATURE:
<223> OTHER INFORMATION: synthetic polypeptide sequence

<400> SEQUENCE: 9

Asp Lys Thr His Thr Cys Pro Pro Cys Pro Ala Pro Ala Leu Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Ser Gly Gly Gly Ser Gly Gly Gly
225                 230                 235                 240

Gly Ser Gly Gly Gly Ser Gly Gly Gly Ser Gly Asp His Cys
            245                 250                 255

Pro Leu Gly Pro Gly Arg Cys Cys Arg Leu His Thr Val Arg Ala Asn
        260                 265                 270

Leu Thr Asp Leu Gly Trp Ala Asp Trp Val Leu Ser Pro Arg Glu Val
    275                 280                 285

Gln Val Thr Met Cys Ile Gly Ala Cys Pro Ser Gln Phe Arg Ala Ala
    290                 295                 300

Asn Met His Ala Gln Ile Lys Thr Ser Leu His Arg Leu Lys Pro Asp
305                 310                 315                 320

Thr Val Pro Ala Pro Cys Cys Val Pro Ala Ser Tyr Asn Pro Met Val
                325                 330                 335

Leu Ile Gln Lys Thr Asp Thr Gly Val Ser Leu Gln Thr Tyr Asp Asp

```
                    340                 345                 350
Leu Leu Ala Lys Asp Cys His Cys Ile
        355                 360

<210> SEQ ID NO 10
<211> LENGTH: 227
<212> TYPE: PRT
<213> ORGANISM: Artificial sequence
<220> FEATURE:
<223> OTHER INFORMATION: synthetic polypeptide sequence

<400> SEQUENCE: 10

Asp Lys Thr His Thr Cys Pro Pro Cys Pro Ala Pro Ala Leu Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 11
<211> LENGTH: 361
<212> TYPE: PRT
<213> ORGANISM: Artificial sequence
<220> FEATURE:
<223> OTHER INFORMATION: synthetic polypeptide sequence

<400> SEQUENCE: 11

Asp Lys Thr His Thr Cys Pro Pro Cys Pro Ala Pro Ala Leu Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45
```

Glu Asp Pro Glu Val Lys Phe Asn Trp Tyr Val Asp Gly Val Glu Val
 50                  55                  60

His Asn Ala Lys Thr Lys Pro Arg Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys Gly Gly Gly Ser Gly Gly Gly Ser Gly Gly Gly
225                 230                 235                 240

Gly Ser Gly Gly Gly Gly Ser Gly Gly Gly Gly Ser Gly Asp His Cys
                245                 250                 255

Pro Leu Gly Pro Gly Arg Cys Cys Arg Leu His Thr Val Arg Ala Ser
            260                 265                 270

Leu Glu Asp Leu Gly Trp Ala Asp Trp Val Leu Ser Pro Arg Glu Val
        275                 280                 285

Gln Val Thr Met Cys Ile Gly Ala Cys Pro Ser Gln Asn Arg Thr Ala
290                 295                 300

Asn Met His Ala Gln Ile Lys Thr Ser Leu His Arg Leu Lys Pro Asp
305                 310                 315                 320

Thr Val Pro Ala Pro Cys Cys Val Pro Ala Ser Tyr Asn Pro Met Val
                325                 330                 335

Leu Ile Gln Lys Thr Asp Thr Gly Val Ser Leu Gln Thr Tyr Asp Asp
            340                 345                 350

Leu Leu Ala Lys Asp Cys His Cys Ile
        355                 360

<210> SEQ ID NO 12
<211> LENGTH: 227
<212> TYPE: PRT
<213> ORGANISM: Artificial sequence
<220> FEATURE:
<223> OTHER INFORMATION: synthetic polypeptide sequence

<400> SEQUENCE: 12

Asp Lys Thr His Thr Cys Pro Pro Cys Pro Ala Pro Ala Leu Ala Gly
 1                   5                  10                  15

Gly Pro Ser Val Phe Leu Phe Pro Pro Lys Pro Lys Asp Thr Leu Met
                 20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
 50                  55                  60

His Asn Ala Lys Thr Lys Pro Arg Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
                115                 120                 125

Tyr Thr Leu Pro Pro Ser Arg Glu Glu Met Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
210                 215                 220

Pro Gly Lys
225

<210> SEQ ID NO 13
<211> LENGTH: 361
<212> TYPE: PRT
<213> ORGANISM: Artificial sequence
<220> FEATURE:
<223> OTHER INFORMATION: synthetic polypeptide sequence

<400> SEQUENCE: 13

Asp Lys Thr His Thr Cys Pro Pro Cys Pro Ala Pro Ala Leu Ala Gly
 1               5                  10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
                35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
                115                 120                 125

Tyr Thr Leu Pro Pro Ser Arg Glu Glu Met Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

```
Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys Gly Gly Gly Ser Gly Gly Gly Ser Gly Gly Gly Gly Gly
225                 230                 235                 240

Gly Ser Gly Gly Gly Ser Gly Gly Gly Ser Gly Asp His Cys
                245                 250                 255

Pro Leu Gly Pro Gly Arg Cys Cys Arg Leu His Thr Val Arg Ala Ser
            260                 265                 270

Leu Glu Asp Leu Gly Trp Ala Asp Trp Val Leu Ser Pro Arg Glu Val
        275                 280                 285

Gln Val Thr Met Cys Ile Gly Ala Cys Pro Ser Gln Phe Asn Ala Thr
            290                 295                 300

Asn Met His Ala Gln Ile Lys Thr Ser Leu His Arg Leu Lys Pro Asp
305                 310                 315                 320

Thr Val Pro Ala Pro Cys Cys Val Pro Ala Ser Tyr Asn Pro Met Val
                325                 330                 335

Leu Ile Gln Lys Thr Asp Thr Gly Val Ser Leu Gln Thr Tyr Asp Asp
            340                 345                 350

Leu Leu Ala Lys Asp Cys His Cys Ile
            355                 360

<210> SEQ ID NO 14
<211> LENGTH: 227
<212> TYPE: PRT
<213> ORGANISM: Artificial sequence
<220> FEATURE:
<223> OTHER INFORMATION: synthetic polypeptide sequence

<400> SEQUENCE: 14

Asp Lys Thr His Thr Cys Pro Pro Cys Pro Ala Pro Ala Leu Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175
```

```
Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys
225

<210> SEQ ID NO 15
<211> LENGTH: 361
<212> TYPE: PRT
<213> ORGANISM: Artificial sequence
<220> FEATURE:
<223> OTHER INFORMATION: synthetic polypeptide sequence

<400> SEQUENCE: 15

Asp Lys Thr His Thr Cys Pro Pro Cys Pro Ala Pro Ala Leu Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
            85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
            130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
            165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys Gly Gly Gly Ser Gly Gly Gly Ser Gly Gly Gly Ser Gly
225                 230                 235                 240

Gly Ser Gly Gly Gly Ser Gly Gly Gly Ser Gly Asp His Cys
            245                 250                 255

Pro Leu Gly Pro Gly Arg Cys Cys Arg Leu His Thr Val Arg Ala Ser
            260                 265                 270

Leu Glu Asp Leu Gly Trp Ala Asp Trp Val Leu Ser Pro Arg Glu Val
            275                 280                 285

Gln Val Thr Met Cys Ile Gly Ala Cys Pro Ser Gln Phe Arg Ala Ala
            290                 295                 300
```

```
Asn Met His Ala Gln Ile Lys Thr Ser Leu His Arg Leu Lys Pro Asp
305                 310                 315                 320

Thr Val Pro Ala Pro Cys Cys Val Pro Ala Ser Tyr Asn Pro Met Val
                325                 330                 335

Leu Ile Gln Asn Thr Thr Thr Gly Val Ser Leu Gln Thr Tyr Asp Asp
            340                 345                 350

Leu Leu Ala Lys Asp Cys His Cys Ile
        355                 360

<210> SEQ ID NO 16
<211> LENGTH: 227
<212> TYPE: PRT
<213> ORGANISM: Artificial sequence
<220> FEATURE:
<223> OTHER INFORMATION: synthetic polypeptide sequence

<400> SEQUENCE: 16

Asp Lys Thr His Thr Cys Pro Pro Cys Pro Ala Pro Ala Leu Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 17
<211> LENGTH: 361
<212> TYPE: PRT
<213> ORGANISM: Artificial sequence
<220> FEATURE:
<223> OTHER INFORMATION: synthetic polypeptide sequence

<400> SEQUENCE: 17

Asp Lys Thr His Thr Cys Pro Pro Cys Pro Ala Pro Ala Leu Ala Gly
1               5                   10                  15
```

```
Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys Gly Gly Gly Gly Ser Gly Gly Gly Gly Ser Gly Gly Gly
225                 230                 235                 240

Gly Ser Gly Gly Gly Gly Ser Gly Gly Gly Gly Ser Gly Asp His Cys
                245                 250                 255

Pro Leu Gly Pro Gly Arg Cys Cys Arg Leu His Thr Val Arg Ala Ser
            260                 265                 270

Leu Glu Asp Leu Gly Trp Ala Asp Trp Val Leu Ser Pro Arg Glu Val
            275                 280                 285

Gln Val Thr Met Cys Ile Gly Ala Cys Pro Ser Gln Phe Arg Ala Ala
            290                 295                 300

Asn Met His Ala Gln Ile Lys Thr Ser Leu His Arg Leu Lys Pro Asp
305                 310                 315                 320

Thr Val Pro Ala Pro Cys Cys Val Pro Ala Ser Tyr Asn Pro Met Val
            325                 330                 335

Leu Ile Gln Lys Thr Asn Thr Gly Val Ser Leu Gln Thr Tyr Asp Asp
            340                 345                 350

Leu Leu Ala Lys Asp Cys His Cys Ile
            355                 360

<210> SEQ ID NO 18
<211> LENGTH: 227
<212> TYPE: PRT
<213> ORGANISM: Artificial sequence
<220> FEATURE:
<223> OTHER INFORMATION: synthetic polypeptide sequence

<400> SEQUENCE: 18

Asp Lys Thr His Thr Cys Pro Pro Cys Pro Ala Pro Ala Leu Ala Gly
1               5                   10                  15
```

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
 210                 215                 220

Pro Gly Lys
225

<210> SEQ ID NO 19
<211> LENGTH: 4
<212> TYPE: PRT
<213> ORGANISM: Artificial sequence
<220> FEATURE:
<223> OTHER INFORMATION: synthetic polypeptide sequence

<400> SEQUENCE: 19

Gly Gly Gly Ser
1

<210> SEQ ID NO 20
<211> LENGTH: 5
<212> TYPE: PRT
<213> ORGANISM: Artificial sequence
<220> FEATURE:
<223> OTHER INFORMATION: synthetic polypeptide sequence

<400> SEQUENCE: 20

Gly Gly Gly Gly Ser
1               5

<210> SEQ ID NO 21
<211> LENGTH: 4
<212> TYPE: PRT
<213> ORGANISM: Artificial sequence
<220> FEATURE:
<223> OTHER INFORMATION: synthetic polypeptide sequence

<400> SEQUENCE: 21

Gly Gly Ser Gly
1

<210> SEQ ID NO 22
<211> LENGTH: 5
<212> TYPE: PRT
<213> ORGANISM: Artificial sequence
<220> FEATURE:
<223> OTHER INFORMATION: synthetic polypeptide sequence

<400> SEQUENCE: 22

Gly Gly Ser Gly Gly
1               5

<210> SEQ ID NO 23
<211> LENGTH: 5
<212> TYPE: PRT
<213> ORGANISM: Artificial sequence
<220> FEATURE:
<223> OTHER INFORMATION: synthetic polypeptide sequence

<400> SEQUENCE: 23

Gly Ser Gly Ser Gly
1               5

<210> SEQ ID NO 24
<211> LENGTH: 5
<212> TYPE: PRT
<213> ORGANISM: Artificial sequence
<220> FEATURE:
<223> OTHER INFORMATION: synthetic polypeptide sequence

<400> SEQUENCE: 24

Gly Ser Gly Gly Gly
1               5

<210> SEQ ID NO 25
<211> LENGTH: 5
<212> TYPE: PRT
<213> ORGANISM: Artificial sequence
<220> FEATURE:
<223> OTHER INFORMATION: synthetic polypeptide sequence

<400> SEQUENCE: 25

Gly Gly Gly Ser Gly
1               5

<210> SEQ ID NO 26
<211> LENGTH: 5
<212> TYPE: PRT
<213> ORGANISM: Artificial sequence
<220> FEATURE:
<223> OTHER INFORMATION: synthetic polypeptide sequence

<400> SEQUENCE: 26

Gly Ser Ser Ser Gly
1               5

<210> SEQ ID NO 27
<211> LENGTH: 5
<212> TYPE: PRT
<213> ORGANISM: Artificial sequence
<220> FEATURE:
<223> OTHER INFORMATION: synthetic polypeptide sequence

<400> SEQUENCE: 27

Gly Gly Gly Gly Gly

```
1               5

<210> SEQ ID NO 28
<211> LENGTH: 5
<212> TYPE: PRT
<213> ORGANISM: Artificial sequence
<220> FEATURE:
<223> OTHER INFORMATION: synthetic polypeptide sequence

<400> SEQUENCE: 28

Glu Gly Gly Gly Ser
1               5

<210> SEQ ID NO 29
<211> LENGTH: 4
<212> TYPE: PRT
<213> ORGANISM: Artificial sequence
<220> FEATURE:
<223> OTHER INFORMATION: synthetic polypeptide sequence
<220> FEATURE:
<221> NAME/KEY: MISC_FEATURE
<222> LOCATION: (2)..(3)
<223> OTHER INFORMATION: the amino acid at this position may be any
      amino acid
<220> FEATURE:
<221> NAME/KEY: MISC_FEATURE
<222> LOCATION: (4)..(4)
<223> OTHER INFORMATION: the amino acid at this position may be any
      hydrophobic amino acid

<400> SEQUENCE: 29

Pro Xaa Xaa Xaa
1

<210> SEQ ID NO 30
<211> LENGTH: 5
<212> TYPE: PRT
<213> ORGANISM: Artificial sequence
<220> FEATURE:
<223> OTHER INFORMATION: synthetic polypeptide sequence
<220> FEATURE:
<221> NAME/KEY: MISC_FEATURE
<222> LOCATION: (2)..(3)
<223> OTHER INFORMATION: the amino acid at this position may be any
      amino acid
<220> FEATURE:
<221> NAME/KEY: MISC_FEATURE
<222> LOCATION: (4)..(4)
<223> OTHER INFORMATION: the amino acid at this position may be any
      hydrophobic amino acid
<220> FEATURE:
<221> NAME/KEY: MISC_FEATURE
<222> LOCATION: (5)..(5)
<223> OTHER INFORMATION: the amino acid at this position may be any Ser
      or Thr

<400> SEQUENCE: 30

Pro Xaa Xaa Xaa Xaa
1               5

<210> SEQ ID NO 31
<211> LENGTH: 6
<212> TYPE: PRT
<213> ORGANISM: Artificial sequence
<220> FEATURE:
<223> OTHER INFORMATION: synthetic polypeptide sequence
<220> FEATURE:
<221> NAME/KEY: MISC_FEATURE
<222> LOCATION: (2)..(2)
<223> OTHER INFORMATION: the amino acid at this position may be Leu or
      Gln
```

```
<400> SEQUENCE: 31

Pro Xaa Gly Met Thr Ser
1               5

<210> SEQ ID NO 32
<211> LENGTH: 5
<212> TYPE: PRT
<213> ORGANISM: Artificial sequence
<220> FEATURE:
<223> OTHER INFORMATION: synthetic polypeptide sequence
<220> FEATURE:
<221> NAME/KEY: MISC_FEATURE
<222> LOCATION: (2)..(2)
<223> OTHER INFORMATION: the amino acid at this position may be Leu or
      Gln

<400> SEQUENCE: 32

Pro Xaa Gly Met Thr
1               5

<210> SEQ ID NO 33
<211> LENGTH: 10
<212> TYPE: PRT
<213> ORGANISM: Artificial sequence
<220> FEATURE:
<223> OTHER INFORMATION: synthetic polypeptide sequence

<400> SEQUENCE: 33

Cys Gly Leu Val Pro Ala Gly Ser Gly Pro
1               5                   10

<210> SEQ ID NO 34
<211> LENGTH: 12
<212> TYPE: PRT
<213> ORGANISM: Artificial sequence
<220> FEATURE:
<223> OTHER INFORMATION: synthetic polypeptide sequence

<400> SEQUENCE: 34

Ser Leu Leu Lys Ser Arg Met Val Pro Asn Phe Asn
1               5                   10

<210> SEQ ID NO 35
<211> LENGTH: 12
<212> TYPE: PRT
<213> ORGANISM: Artificial sequence
<220> FEATURE:
<223> OTHER INFORMATION: synthetic polypeptide sequence

<400> SEQUENCE: 35

Ser Leu Leu Ile Ala Arg Arg Met Pro Asn Phe Asn
1               5                   10

<210> SEQ ID NO 36
<211> LENGTH: 12
<212> TYPE: PRT
<213> ORGANISM: Artificial sequence
<220> FEATURE:
<223> OTHER INFORMATION: synthetic polypeptide sequence

<400> SEQUENCE: 36

Ser Lys Leu Val Gln Ala Ser Ala Ser Gly Val Asn
1               5                   10

<210> SEQ ID NO 37
<211> LENGTH: 12
<212> TYPE: PRT
```

<213> ORGANISM: Artificial sequence
<220> FEATURE:
<223> OTHER INFORMATION: synthetic polypeptide sequence

<400> SEQUENCE: 37

Ser Ser Tyr Leu Lys Ala Ser Asp Ala Pro Asp Asn
1               5                   10

<210> SEQ ID NO 38
<211> LENGTH: 12
<212> TYPE: PRT
<213> ORGANISM: Artificial sequence
<220> FEATURE:
<223> OTHER INFORMATION: synthetic polypeptide sequence

<400> SEQUENCE: 38

Arg Pro Lys Pro Gln Gln Phe Phe Gly Leu Met Asn
1               5                   10

<210> SEQ ID NO 39
<211> LENGTH: 12
<212> TYPE: PRT
<213> ORGANISM: Artificial sequence
<220> FEATURE:
<223> OTHER INFORMATION: synthetic polypeptide sequence

<400> SEQUENCE: 39

Ser Leu Arg Pro Leu Ala Leu Trp Arg Ser Phe Asn
1               5                   10

<210> SEQ ID NO 40
<211> LENGTH: 12
<212> TYPE: PRT
<213> ORGANISM: Artificial sequence
<220> FEATURE:
<223> OTHER INFORMATION: synthetic polypeptide sequence

<400> SEQUENCE: 40

Ser Pro Gln Gly Ile Ala Gly Gln Arg Asn Phe Asn
1               5                   10

<210> SEQ ID NO 41
<211> LENGTH: 14
<212> TYPE: PRT
<213> ORGANISM: Artificial sequence
<220> FEATURE:
<223> OTHER INFORMATION: synthetic polypeptide sequence

<400> SEQUENCE: 41

Asp Val Asp Glu Arg Asp Val Arg Gly Phe Ala Ser Phe Leu
1               5                   10

<210> SEQ ID NO 42
<211> LENGTH: 12
<212> TYPE: PRT
<213> ORGANISM: Artificial sequence
<220> FEATURE:
<223> OTHER INFORMATION: synthetic polypeptide sequence

<400> SEQUENCE: 42

Ser Leu Pro Leu Gly Leu Trp Ala Pro Asn Phe Asn
1               5                   10

<210> SEQ ID NO 43
<211> LENGTH: 12
<212> TYPE: PRT
<213> ORGANISM: Artificial sequence

```
<220> FEATURE:
<223> OTHER INFORMATION: synthetic polypeptide sequence

<400> SEQUENCE: 43

Ser Leu Leu Ile Phe Arg Ser Trp Ala Asn Phe Asn
1               5                   10

<210> SEQ ID NO 44
<211> LENGTH: 12
<212> TYPE: PRT
<213> ORGANISM: Artificial sequence
<220> FEATURE:
<223> OTHER INFORMATION: synthetic polypeptide sequence

<400> SEQUENCE: 44

Ser Gly Val Val Ile Ala Thr Val Ile Val Ile Thr
1               5                   10

<210> SEQ ID NO 45
<211> LENGTH: 12
<212> TYPE: PRT
<213> ORGANISM: Artificial sequence
<220> FEATURE:
<223> OTHER INFORMATION: synthetic polypeptide sequence

<400> SEQUENCE: 45

Ser Leu Gly Pro Gln Gly Ile Trp Gly Gln Phe Asn
1               5                   10

<210> SEQ ID NO 46
<211> LENGTH: 12
<212> TYPE: PRT
<213> ORGANISM: Artificial sequence
<220> FEATURE:
<223> OTHER INFORMATION: synthetic polypeptide sequence

<400> SEQUENCE: 46

Lys Lys Ser Pro Gly Arg Val Val Gly Gly Ser Val
1               5                   10

<210> SEQ ID NO 47
<211> LENGTH: 12
<212> TYPE: PRT
<213> ORGANISM: Artificial sequence
<220> FEATURE:
<223> OTHER INFORMATION: synthetic polypeptide sequence

<400> SEQUENCE: 47

Pro Gln Gly Leu Leu Gly Ala Pro Gly Ile Leu Gly
1               5                   10

<210> SEQ ID NO 48
<211> LENGTH: 12
<212> TYPE: PRT
<213> ORGANISM: Artificial sequence
<220> FEATURE:
<223> OTHER INFORMATION: synthetic polypeptide sequence

<400> SEQUENCE: 48

Gly Gly Gly Ser Gly Gly Gly Ser Ile Glu Gly Arg
1               5                   10

<210> SEQ ID NO 49
<211> LENGTH: 12
<212> TYPE: PRT
<213> ORGANISM: Artificial sequence
<220> FEATURE:
```

```
<223> OTHER INFORMATION: synthetic polypeptide sequence

<400> SEQUENCE: 49

Gly Pro Gln Gly Leu Ala Gly Gln Arg Gly Ile Val
1               5                   10

<210> SEQ ID NO 50
<211> LENGTH: 12
<212> TYPE: PRT
<213> ORGANISM: Artificial sequence
<220> FEATURE:
<223> OTHER INFORMATION: synthetic polypeptide sequence

<400> SEQUENCE: 50

Gly Gly Ser Gly Gln Arg Gly Arg Lys Ala Leu Glu
1               5                   10

<210> SEQ ID NO 51
<211> LENGTH: 12
<212> TYPE: PRT
<213> ORGANISM: Artificial sequence
<220> FEATURE:
<223> OTHER INFORMATION: synthetic polypeptide sequence

<400> SEQUENCE: 51

Ser Leu Ser Ala Leu Leu Ser Ser Asp Ile Phe Asn
1               5                   10

<210> SEQ ID NO 52
<211> LENGTH: 12
<212> TYPE: PRT
<213> ORGANISM: Artificial sequence
<220> FEATURE:
<223> OTHER INFORMATION: synthetic polypeptide sequence

<400> SEQUENCE: 52

Ser Leu Pro Arg Phe Lys Ile Ile Gly Gly Phe Asn
1               5                   10

<210> SEQ ID NO 53
<211> LENGTH: 12
<212> TYPE: PRT
<213> ORGANISM: Artificial sequence
<220> FEATURE:
<223> OTHER INFORMATION: synthetic polypeptide sequence

<400> SEQUENCE: 53

Ser Leu Leu Gly Ile Ala Val Pro Gly Asn Phe Asn
1               5                   10

<210> SEQ ID NO 54
<211> LENGTH: 12
<212> TYPE: PRT
<213> ORGANISM: Artificial sequence
<220> FEATURE:
<223> OTHER INFORMATION: synthetic polypeptide sequence

<400> SEQUENCE: 54

Phe Phe Lys Asn Ile Val Thr Pro Arg Thr Pro Pro
1               5                   10

<210> SEQ ID NO 55
<211> LENGTH: 227
<212> TYPE: PRT
<213> ORGANISM: Homo sapiens

<400> SEQUENCE: 55
```

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Lys
225

<210> SEQ ID NO 56
<211> LENGTH: 69
<212> TYPE: DNA
<213> ORGANISM: Artificial sequence
<220> FEATURE:
<223> OTHER INFORMATION: synthetic polypeptide sequence

<400> SEQUENCE: 56
accatggaca tgagggtccc cgctcagctc ctggggctcc tgctactctg gctccgaggt      60
gccagatgt                                                             69

<210> SEQ ID NO 57
<211> LENGTH: 383
<212> TYPE: PRT
<213> ORGANISM: Artificial sequence
<220> FEATURE:
<223> OTHER INFORMATION: synthetic polypeptide sequence

<400> SEQUENCE: 57

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
                20                  25                  30

Ala Pro Ala Leu Ala Gly Gly Pro Ser Val Phe Leu Phe Pro Pro Lys
            35                  40                  45

```
Pro Lys Asp Thr Leu Met Ile Ser Arg Thr Pro Glu Val Thr Cys Val
 50                  55                  60
Val Val Asp Val Ser His Glu Asp Pro Glu Val Lys Phe Asn Trp Tyr
 65                  70                  75                  80
Val Asp Gly Val Glu Val His Asn Ala Lys Thr Lys Pro Arg Glu Glu
                 85                  90                  95
Gln Tyr Asn Ser Thr Tyr Arg Val Val Ser Val Leu Thr Val Leu His
            100                 105                 110
Gln Asp Trp Leu Asn Gly Lys Glu Tyr Lys Cys Lys Val Ser Asn Lys
        115                 120                 125
Ala Leu Pro Ala Pro Ile Glu Lys Thr Ile Ser Lys Ala Lys Gly Gln
130                 135                 140
Pro Arg Glu Pro Gln Val Tyr Thr Leu Pro Pro Ser Arg Glu Glu Met
145                 150                 155                 160
Thr Lys Asn Gln Val Ser Leu Tyr Cys Leu Val Lys Gly Phe Tyr Pro
                165                 170                 175
Ser Asp Ile Ala Val Glu Trp Glu Ser Asn Gly Gln Pro Glu Asn Asn
            180                 185                 190
Tyr Lys Thr Thr Pro Pro Val Leu Asp Ser Asp Gly Ser Phe Phe Leu
        195                 200                 205
Tyr Ser Lys Leu Thr Val Asp Lys Ser Arg Trp Gln Gln Gly Asn Val
210                 215                 220
Phe Ser Cys Ser Val Met His Glu Ala Leu His Asn His Tyr Thr Gln
225                 230                 235                 240
Lys Ser Leu Ser Leu Ser Pro Gly Lys Gly Gly Gly Ser Gly Gly
                245                 250                 255
Gly Gly Ser Gly Gly Gly Ser Gly Gly Gly Ser Gly Gly Gly
            260                 265                 270
Gly Ser Gly Asp His Cys Pro Leu Gly Pro Gly Arg Cys Cys Arg Leu
        275                 280                 285
His Thr Val Arg Ala Ser Leu Glu Asp Leu Gly Trp Ala Asp Trp Val
        290                 295                 300
Leu Ser Pro Arg Glu Val Gln Val Thr Met Cys Ile Gly Ala Cys Pro
305                 310                 315                 320
Ser Gln Phe Arg Ala Ala Asn Met His Ala Gln Ile Lys Thr Ser Leu
                325                 330                 335
His Arg Leu Lys Pro Asp Thr Val Pro Ala Pro Cys Cys Val Pro Ala
            340                 345                 350
Ser Tyr Asn Pro Met Val Leu Ile Gln Lys Thr Asp Thr Gly Val Ser
        355                 360                 365
Leu Gln Thr Tyr Asp Asp Leu Leu Ala Lys Asp Cys His Cys Ile
370                 375                 380

<210> SEQ ID NO 58
<211> LENGTH: 249
<212> TYPE: PRT
<213> ORGANISM: Artificial sequence
<220> FEATURE:
<223> OTHER INFORMATION: synthetic polypeptide sequence

<400> SEQUENCE: 58

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30
```

```
Ala Pro Ala Leu Ala Gly Gly Pro Ser Val Phe Leu Phe Pro Pro Lys
            35                  40                  45

Pro Lys Asp Thr Leu Met Ile Ser Arg Thr Pro Glu Val Thr Cys Val
 50                  55                  60

Val Val Asp Val Ser His Glu Asp Pro Glu Val Lys Phe Asn Trp Tyr
 65                  70                  75                  80

Val Asp Gly Val Glu Val His Asn Ala Lys Thr Lys Pro Arg Glu Glu
                 85                  90                  95

Gln Tyr Asn Ser Thr Tyr Arg Val Val Ser Val Leu Thr Val Leu His
                100                 105                 110

Gln Asp Trp Leu Asn Gly Lys Glu Tyr Lys Cys Lys Val Ser Asn Lys
            115                 120                 125

Ala Leu Pro Ala Pro Ile Glu Lys Thr Ile Ser Lys Ala Lys Gly Gln
130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Thr Ser Lys Leu Thr Val Asp Lys Ser Arg Trp Gln Gln Gly Asn Val
210                 215                 220

Phe Ser Cys Ser Val Met His Glu Ala Leu His Asn His Tyr Thr Gln
225                 230                 235                 240

Lys Ser Leu Ser Leu Ser Pro Gly Lys
                245

<210> SEQ ID NO 59
<211> LENGTH: 383
<212> TYPE: PRT
<213> ORGANISM: Artificial sequence
<220> FEATURE:
<223> OTHER INFORMATION: synthetic polypeptide sequence

<400> SEQUENCE: 59

Met Asp Met Arg Val Pro Ala Gln Leu Leu Gly Leu Leu Leu Leu Trp
 1               5                  10                  15

Leu Arg Gly Ala Arg Cys Asp Lys Thr His Thr Cys Pro Pro Cys Pro
            20                  25                  30

Ala Pro Ala Leu Ala Gly Gly Pro Ser Val Phe Leu Phe Pro Pro Lys
            35                  40                  45

Pro Lys Asp Thr Leu Met Ile Ser Arg Thr Pro Glu Val Thr Cys Val
 50                  55                  60

Val Val Asp Val Ser His Glu Asp Pro Glu Val Lys Phe Asn Trp Tyr
 65                  70                  75                  80

Val Asp Gly Val Glu Val His Asn Ala Lys Thr Lys Pro Arg Glu Glu
                 85                  90                  95

Gln Tyr Asn Ser Thr Tyr Arg Val Val Ser Val Leu Thr Val Leu His
                100                 105                 110

Gln Asp Trp Leu Asn Gly Lys Glu Tyr Lys Cys Lys Val Ser Asn Lys
            115                 120                 125

Ala Leu Pro Ala Pro Ile Glu Lys Thr Ile Ser Lys Ala Lys Gly Gln
130                 135                 140
```

```
Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
            165                 170                 175

Ser Asp Ile Ala Val Glu Trp Glu Ser Asn Gly Gln Pro Glu Asn Asn
        180                 185                 190

Tyr Lys Thr Thr Pro Pro Val Leu Asp Ser Asp Gly Ser Phe Phe Leu
    195                 200                 205

Thr Ser Lys Leu Thr Val Asp Lys Ser Arg Trp Gln Gln Gly Asn Val
210                 215                 220

Phe Ser Cys Ser Val Met His Glu Ala Leu His Asn His Tyr Thr Gln
225                 230                 235                 240

Lys Ser Leu Ser Leu Ser Pro Gly Lys Gly Gly Gly Ser Gly Gly
                245                 250                 255

Gly Gly Ser Gly Gly Gly Ser Gly Gly Gly Ser Gly Gly
            260                 265                 270

Gly Ser Gly Asp His Cys Pro Leu Gly Pro Gly Arg Cys Cys Arg Leu
        275                 280                 285

His Thr Val Arg Ala Ser Leu Glu Asp Leu Gly Trp Ala Asp Trp Val
    290                 295                 300

Leu Ser Pro Arg Glu Val Gln Val Thr Met Cys Ile Gly Ala Cys Pro
305                 310                 315                 320

Ser Gln Phe Arg Ala Ala Asn Met His Ala Gln Ile Lys Thr Ser Leu
                325                 330                 335

His Arg Leu Lys Pro Asp Thr Val Pro Ala Pro Cys Cys Val Pro Ala
            340                 345                 350

Ser Tyr Asn Pro Met Val Leu Ile Gln Lys Thr Asp Thr Gly Val Ser
        355                 360                 365

Leu Gln Thr Tyr Asp Asp Leu Leu Ala Lys Asp Cys His Cys Ile
    370                 375                 380

<210> SEQ ID NO 60
<211> LENGTH: 249
<212> TYPE: PRT
<213> ORGANISM: Artificial sequence
<220> FEATURE:
<223> OTHER INFORMATION: synthetic polypeptide sequence

<400> SEQUENCE: 60

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Ala Leu Ala Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125
```

Ala Leu Pro Ala Pro Ile Glu Lys Thr Ile Ser Lys Ala Lys Gly Gln
130                 135                 140

Pro Arg Glu Pro Gln Val Tyr Thr Leu Pro Pro Ser Arg Glu Glu Met
145                 150                 155                 160

Thr Lys Asn Gln Val Ser Leu Tyr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
210                 215                 220

Phe Ser Cys Ser Val Met His Glu Ala Leu His Asn His Tyr Thr Gln
225                 230                 235                 240

Lys Ser Leu Ser Leu Ser Pro Gly Lys
                245

<210> SEQ ID NO 61
<211> LENGTH: 373
<212> TYPE: PRT
<213> ORGANISM: Artificial sequence
<220> FEATURE:
<223> OTHER INFORMATION: synthetic polypeptide sequence

<400> SEQUENCE: 61

Met Asp Met Arg Val Pro Ala Gln Leu Leu Gly Leu Leu Leu Leu Trp
1               5                   10                  15

Leu Arg Gly Ala Arg Cys Ala Pro Leu Ala Gly Gly Pro Ser Val
            20                  25                  30

Phe Leu Phe Pro Pro Lys Pro Lys Asp Thr Leu Met Ile Ser Arg Thr
                35                  40                  45

Pro Glu Val Thr Cys Val Val Val Asp Val Ser His Glu Asp Pro Glu
            50                  55                  60

Val Lys Phe Asn Trp Tyr Val Asp Gly Val Glu Val His Asn Ala Lys
65                  70                  75                  80

Thr Lys Pro Arg Glu Glu Gln Tyr Asn Ser Thr Tyr Arg Val Val Ser
                85                  90                  95

Val Leu Thr Val Leu His Gln Asp Trp Leu Asn Gly Lys Glu Tyr Lys
            100                 105                 110

Cys Lys Val Ser Asn Lys Ala Leu Pro Ala Pro Ile Glu Lys Thr Ile
        115                 120                 125

Ser Lys Ala Lys Gly Gln Pro Arg Glu Pro Gln Val Tyr Thr Leu Pro
130                 135                 140

Pro Ser Arg Glu Glu Met Thr Lys Asn Gln Val Ser Leu Tyr Cys Leu
145                 150                 155                 160

Val Lys Gly Phe Tyr Pro Ser Asp Ile Ala Val Glu Trp Glu Ser Asn
                165                 170                 175

Gly Gln Pro Glu Asn Asn Tyr Lys Thr Thr Pro Val Leu Asp Ser
            180                 185                 190

Asp Gly Ser Phe Phe Leu Tyr Ser Lys Leu Thr Val Asp Lys Ser Arg
        195                 200                 205

Trp Gln Gln Gly Asn Val Phe Ser Cys Ser Val Met His Glu Ala Leu
210                 215                 220

His Asn His Tyr Thr Gln Lys Ser Leu Ser Leu Ser Pro Gly Lys Gly
225                 230                 235                 240

Gly Gly Gly Ser Gly Gly Gly Ser Gly Gly Gly Ser Gly Gly
            245                 250                 255
Gly Gly Ser Gly Gly Gly Ser Gly Asp His Cys Pro Leu Gly Pro
        260                 265                 270
Gly Arg Cys Cys Arg Leu His Thr Val Arg Ala Ser Leu Glu Asp Leu
    275                 280                 285
Gly Trp Ala Asp Trp Val Leu Ser Pro Arg Glu Val Gln Val Thr Met
290                 295                 300
Cys Ile Gly Ala Cys Pro Ser Gln Phe Arg Ala Ala Asn Met His Ala
305                 310                 315                 320
Gln Ile Lys Thr Ser Leu His Arg Leu Lys Pro Asp Thr Val Pro Ala
            325                 330                 335
Pro Cys Cys Val Pro Ala Ser Tyr Asn Pro Met Val Leu Ile Gln Lys
        340                 345                 350
Thr Asp Thr Gly Val Ser Leu Gln Thr Tyr Asp Asp Leu Leu Ala Lys
    355                 360                 365
Asp Cys His Cys Ile
    370

<210> SEQ ID NO 62
<211> LENGTH: 239
<212> TYPE: PRT
<213> ORGANISM: Artificial sequence
<220> FEATURE:
<223> OTHER INFORMATION: synthetic polypeptide sequence

<400> SEQUENCE: 62

Met Asp Met Arg Val Pro Ala Gln Leu Leu Gly Leu Leu Leu Leu Trp
1               5                   10                  15
Leu Arg Gly Ala Arg Cys Ala Pro Ala Leu Ala Gly Gly Pro Ser Val
            20                  25                  30
Phe Leu Phe Pro Pro Lys Pro Lys Asp Thr Leu Met Ile Ser Arg Thr
        35                  40                  45
Pro Glu Val Thr Cys Val Val Val Asp Val Ser His Glu Asp Pro Glu
    50                  55                  60
Val Lys Phe Asn Trp Tyr Val Asp Gly Val Glu Val His Asn Ala Lys
65                  70                  75                  80
Thr Lys Pro Arg Glu Glu Gln Tyr Asn Ser Thr Tyr Arg Val Val Ser
            85                  90                  95
Val Leu Thr Val Leu His Gln Asp Trp Leu Asn Gly Lys Glu Tyr Lys
        100                 105                 110
Cys Lys Val Ser Asn Lys Ala Leu Pro Ala Pro Ile Glu Lys Thr Ile
    115                 120                 125
Ser Lys Ala Lys Gly Gln Pro Arg Glu Pro Gln Val Tyr Thr Leu Pro
    130                 135                 140
Pro Ser Arg Glu Glu Met Thr Lys Asn Gln Val Ser Leu Thr Cys Leu
145                 150                 155                 160
Val Lys Gly Phe Tyr Pro Ser Asp Ile Ala Val Glu Trp Glu Ser Asn
            165                 170                 175
Gly Gln Pro Glu Asn Asn Tyr Lys Thr Thr Pro Pro Val Leu Asp Ser
        180                 185                 190
Asp Gly Ser Phe Phe Leu Thr Ser Lys Leu Thr Val Asp Lys Ser Arg
    195                 200                 205
Trp Gln Gln Gly Asn Val Phe Ser Cys Ser Val Met His Glu Ala Leu
    210                 215                 220

His Asn His Tyr Thr Gln Lys Ser Leu Ser Leu Ser Pro Gly Lys
225                 230                 235

<210> SEQ ID NO 63
<211> LENGTH: 373
<212> TYPE: PRT
<213> ORGANISM: Artificial sequence
<220> FEATURE:
<223> OTHER INFORMATION: synthetic polypeptide sequence

<400> SEQUENCE: 63

Met Asp Met Arg Val Pro Ala Gln Leu Leu Gly Leu Leu Leu Leu Trp
1               5                   10                  15

Leu Arg Gly Ala Arg Cys Ala Pro Ala Leu Ala Gly Gly Pro Ser Val
            20                  25                  30

Phe Leu Phe Pro Pro Lys Pro Lys Asp Thr Leu Met Ile Ser Arg Thr
        35                  40                  45

Pro Glu Val Thr Cys Val Val Asp Val Ser His Glu Asp Pro Glu
    50                  55                  60

Val Lys Phe Asn Trp Tyr Val Asp Gly Val Glu Val His Asn Ala Lys
65                  70                  75                  80

Thr Lys Pro Arg Glu Glu Gln Tyr Asn Ser Thr Tyr Arg Val Val Ser
                85                  90                  95

Val Leu Thr Val Leu His Gln Asp Trp Leu Asn Gly Lys Glu Tyr Lys
            100                 105                 110

Cys Lys Val Ser Asn Lys Ala Leu Pro Ala Pro Ile Glu Lys Thr Ile
        115                 120                 125

Ser Lys Ala Lys Gly Gln Pro Arg Glu Pro Gln Val Tyr Thr Leu Pro
    130                 135                 140

Pro Ser Arg Glu Glu Met Thr Lys Asn Gln Val Ser Leu Thr Cys Leu
145                 150                 155                 160

Val Lys Gly Phe Tyr Pro Ser Asp Ile Ala Val Glu Trp Glu Ser Asn
                165                 170                 175

Gly Gln Pro Glu Asn Asn Tyr Lys Thr Thr Pro Pro Val Leu Asp Ser
            180                 185                 190

Asp Gly Ser Phe Phe Leu Thr Ser Lys Leu Thr Val Asp Lys Ser Arg
        195                 200                 205

Trp Gln Gln Gly Asn Val Phe Ser Cys Ser Val Met His Glu Ala Leu
    210                 215                 220

His Asn His Tyr Thr Gln Lys Ser Leu Ser Leu Ser Pro Gly Lys Gly
225                 230                 235                 240

Gly Gly Gly Ser Gly Gly Gly Ser Gly Gly Gly Ser Gly
                245                 250                 255

Gly Gly Ser Gly Gly Gly Ser Gly Asp His Cys Pro Leu Gly
            260                 265                 270

Gly Arg Cys Cys Arg Leu His Thr Val Arg Ala Ser Leu Glu Asp Leu
        275                 280                 285

Gly Trp Ala Asp Trp Val Leu Ser Pro Arg Glu Val Gln Val Thr Met
    290                 295                 300

Cys Ile Gly Ala Cys Pro Ser Gln Phe Arg Ala Ala Asn Met His Ala
305                 310                 315                 320

Gln Ile Lys Thr Ser Leu His Arg Leu Lys Pro Asp Thr Val Pro Ala
                325                 330                 335

Pro Cys Cys Val Pro Ala Ser Tyr Asn Pro Met Val Leu Ile Gln Lys
            340                 345                 350

Thr Asp Thr Gly Val Ser Leu Gln Thr Tyr Asp Leu Ala Lys
          355                 360                 365
Asp Cys His Cys Ile
        370

<210> SEQ ID NO 64
<211> LENGTH: 239
<212> TYPE: PRT
<213> ORGANISM: Artificial sequence
<220> FEATURE:
<223> OTHER INFORMATION: synthetic polypeptide sequence

<400> SEQUENCE: 64

Met Asp Met Arg Val Pro Ala Gln Leu Leu Gly Leu Leu Leu Leu Trp
1               5                   10                  15

Leu Arg Gly Ala Arg Cys Ala Pro Ala Leu Ala Gly Gly Pro Ser Val
            20                  25                  30

Phe Leu Phe Pro Pro Lys Pro Lys Asp Thr Leu Met Ile Ser Arg Thr
        35                  40                  45

Pro Glu Val Thr Cys Val Val Val Asp Val Ser His Glu Asp Pro Glu
    50                  55                  60

Val Lys Phe Asn Trp Tyr Val Asp Gly Val Glu Val His Asn Ala Lys
65                  70                  75                  80

Thr Lys Pro Arg Glu Glu Gln Tyr Asn Ser Thr Tyr Arg Val Val Ser
                85                  90                  95

Val Leu Thr Val Leu His Gln Asp Trp Leu Asn Gly Lys Glu Tyr Lys
            100                 105                 110

Cys Lys Val Ser Asn Lys Ala Leu Pro Ala Pro Ile Glu Lys Thr Ile
        115                 120                 125

Ser Lys Ala Lys Gly Gln Pro Arg Glu Pro Gln Val Tyr Thr Leu Pro
    130                 135                 140

Pro Ser Arg Glu Glu Met Thr Lys Asn Gln Val Ser Leu Tyr Cys Leu
145                 150                 155                 160

Val Lys Gly Phe Tyr Pro Ser Asp Ile Ala Val Glu Trp Glu Ser Asn
                165                 170                 175

Gly Gln Pro Glu Asn Asn Tyr Lys Thr Thr Pro Pro Val Leu Asp Ser
            180                 185                 190

Asp Gly Ser Phe Phe Leu Tyr Ser Lys Leu Thr Val Asp Lys Ser Arg
        195                 200                 205

Trp Gln Gln Gly Asn Val Phe Ser Cys Ser Val Met His Glu Ala Leu
    210                 215                 220

His Asn His Tyr Thr Gln Lys Ser Leu Ser Leu Ser Pro Gly Lys
225                 230                 235

<210> SEQ ID NO 65
<211> LENGTH: 383
<212> TYPE: PRT
<213> ORGANISM: Artificial sequence
<220> FEATURE:
<223> OTHER INFORMATION: synthetic polypeptide sequence

<400> SEQUENCE: 65

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Ala Leu Ala Gly Gly Pro Ser Val Phe Leu Phe Pro Pro Lys
        35                  40                  45

Pro Lys Asp Thr Leu Met Ile Ser Arg Thr Pro Glu Val Thr Cys Val
 50                  55                  60

Val Val Asp Val Ser His Glu Asp Pro Glu Val Lys Phe Asn Trp Tyr
 65                  70                  75                  80

Val Asp Gly Val Glu Val His Asn Ala Lys Thr Lys Pro Arg Glu Glu
                 85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
130                 135                 140

Pro Arg Glu Pro Gln Val Tyr Thr Leu Pro Pro Ser Arg Glu Glu Met
145                 150                 155                 160

Thr Lys Asn Gln Val Ser Leu Trp Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
210                 215                 220

Phe Ser Cys Ser Val Met His Glu Ala Leu His Asn His Tyr Thr Gln
225                 230                 235                 240

Lys Ser Leu Ser Leu Ser Pro Gly Lys Gly Gly Gly Ser Gly Gly
                245                 250                 255

Gly Gly Ser Gly Gly Gly Ser Gly Gly Gly Ser Gly Gly Gly
            260                 265                 270

Gly Ser Gly Asp His Cys Pro Leu Gly Pro Gly Arg Cys Cys Arg Leu
        275                 280                 285

His Thr Val Arg Ala Ser Leu Glu Asp Leu Gly Trp Ala Asp Trp Val
290                 295                 300

Leu Ser Pro Arg Glu Val Gln Val Thr Met Cys Ile Gly Ala Cys Pro
305                 310                 315                 320

Ser Gln Phe Arg Ala Ala Asn Met His Ala Gln Ile Lys Thr Ser Leu
                325                 330                 335

His Arg Leu Lys Pro Asp Thr Val Pro Ala Pro Cys Cys Val Pro Ala
            340                 345                 350

Ser Tyr Asn Pro Met Val Leu Ile Gln Lys Thr Asp Thr Gly Val Ser
        355                 360                 365

Leu Gln Thr Tyr Asp Asp Leu Leu Ala Lys Asp Cys His Cys Ile
370                 375                 380

<210> SEQ ID NO 66
<211> LENGTH: 249
<212> TYPE: PRT
<213> ORGANISM: Artificial sequence
<220> FEATURE:
<223> OTHER INFORMATION: synthetic polypeptide sequence

<400> SEQUENCE: 66

Met Asp Met Arg Val Pro Ala Gln Leu Leu Gly Leu Leu Leu Leu Trp
 1               5                  10                  15

Leu Arg Gly Ala Arg Cys Asp Lys Thr His Thr Cys Pro Pro Cys Pro
                 20                  25                  30

```
Ala Pro Ala Leu Ala Gly Gly Pro Ser Val Phe Leu Phe Pro Pro Lys
        35                  40                  45

Pro Lys Asp Thr Leu Met Ile Ser Arg Thr Pro Glu Val Thr Cys Val
 50                  55                  60

Val Val Asp Val Ser His Glu Asp Pro Glu Val Lys Phe Asn Trp Tyr
 65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
                100                 105                 110

Gln Asp Trp Leu Asn Gly Lys Glu Tyr Lys Cys Lys Val Ser Asn Lys
            115                 120                 125

Ala Leu Pro Ala Pro Ile Glu Lys Thr Ile Ser Lys Ala Lys Gly Gln
        130                 135                 140

Pro Arg Glu Pro Gln Val Tyr Thr Leu Pro Pro Ser Arg Glu Glu Met
145                 150                 155                 160

Thr Lys Asn Gln Val Ser Leu Ser Cys Ala Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Val Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Lys
                245

<210> SEQ ID NO 67
<211> LENGTH: 380
<212> TYPE: PRT
<213> ORGANISM: Artificial sequence
<220> FEATURE:
<223> OTHER INFORMATION: synthetic polypeptide sequence

<400> SEQUENCE: 67

Met Asp Met Arg Val Pro Ala Gln Leu Leu Gly Leu Leu Leu Leu Trp
 1               5                  10                  15

Leu Arg Gly Ala Arg Cys Asp Lys Thr His Thr Cys Pro Pro Cys Pro
            20                  25                  30

Ala Pro Ala Leu Ala Gly Gly Pro Ser Val Phe Leu Phe Pro Pro Lys
        35                  40                  45

Pro Lys Asp Thr Leu Met Ile Ser Arg Thr Pro Glu Val Thr Cys Val
 50                  55                  60

Val Val Asp Val Ser His Glu Asp Pro Glu Val Lys Phe Asn Trp Tyr
 65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
                100                 105                 110

Gln Asp Trp Leu Asn Gly Lys Glu Tyr Lys Cys Lys Val Ser Asn Lys
            115                 120                 125

Ala Leu Pro Ala Pro Ile Glu Lys Thr Ile Ser Lys Ala Lys Gly Gln
        130                 135                 140
```

```
Pro Arg Glu Pro Gln Val Tyr Thr Leu Pro Pro Ser Arg Glu Glu Met
145                 150                 155                 160

Thr Lys Asn Gln Val Ser Leu Ser Cys Ala Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Val Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Lys Gly Gly Gly Ser Gly Gly
                245                 250                 255

Gly Gly Ser Gly Gly Gly Ser Gly Gly Gly Ser Gly Gly Gly
            260                 265                 270

Gly Ser Cys Pro Leu Gly Pro Gly Arg Cys Cys Arg Leu His Thr Val
        275                 280                 285

Arg Ala Ser Leu Glu Asp Leu Gly Trp Ala Asp Trp Val Leu Ser Pro
    290                 295                 300

Arg Glu Val Gln Val Thr Met Cys Ile Gly Ala Cys Pro Ser Gln Phe
305                 310                 315                 320

Arg Ala Ala Asn Met His Ala Gln Ile Lys Thr Ser Leu His Arg Leu
                325                 330                 335

Lys Pro Asp Thr Val Pro Ala Pro Cys Cys Val Pro Ala Ser Tyr Asn
            340                 345                 350

Pro Met Val Leu Ile Gln Lys Thr Asp Thr Gly Val Ser Leu Gln Thr
        355                 360                 365

Tyr Asp Asp Leu Leu Ala Lys Asp Cys His Cys Ile
    370                 375                 380

<210> SEQ ID NO 68
<211> LENGTH: 249
<212> TYPE: PRT
<213> ORGANISM: Artificial sequence
<220> FEATURE:
<223> OTHER INFORMATION: synthetic polypeptide sequence

<400> SEQUENCE: 68

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
                20                  25                  30

Ala Pro Ala Leu Ala Gly Gly Pro Ser Val Phe Leu Phe Pro Pro Lys
            35                  40                  45

Pro Lys Asp Thr Leu Met Ile Ser Arg Thr Pro Glu Val Thr Cys Val
        50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125
```

```
Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Trp Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Lys
                245

<210> SEQ ID NO 69
<211> LENGTH: 373
<212> TYPE: PRT
<213> ORGANISM: Artificial sequence
<220> FEATURE:
<223> OTHER INFORMATION: synthetic polypeptide sequence

<400> SEQUENCE: 69

Met Asp Met Arg Val Pro Ala Gln Leu Leu Gly Leu Leu Leu Leu Trp
1               5                   10                  15

Leu Arg Gly Ala Arg Cys Ala Pro Ala Leu Ala Gly Gly Pro Ser Val
            20                  25                  30

Phe Leu Phe Pro Pro Lys Pro Lys Asp Thr Leu Met Ile Ser Arg Thr
        35                  40                  45

Pro Glu Val Thr Cys Val Val Val Asp Val Ser His Glu Asp Pro Glu
    50                  55                  60

Val Lys Phe Asn Trp Tyr Val Asp Gly Val Glu Val His Asn Ala Lys
65                  70                  75                  80

Thr Lys Pro Arg Glu Glu Gln Tyr Asn Ser Thr Tyr Arg Val Val Ser
                85                  90                  95

Val Leu Thr Val Leu His Gln Asp Trp Leu Asn Gly Lys Glu Tyr Lys
            100                 105                 110

Cys Lys Val Ser Asn Lys Ala Leu Pro Ala Pro Ile Glu Lys Thr Ile
        115                 120                 125

Ser Lys Ala Lys Gly Gln Pro Arg Glu Pro Gln Val Tyr Thr Leu Pro
    130                 135                 140

Pro Ser Arg Glu Glu Met Thr Lys Asn Gln Val Ser Leu Trp Cys Leu
145                 150                 155                 160

Val Lys Gly Phe Tyr Pro Ser Asp Ile Ala Val Glu Trp Glu Ser Asn
                165                 170                 175

Gly Gln Pro Glu Asn Asn Tyr Lys Thr Thr Pro Pro Val Leu Asp Ser
            180                 185                 190

Asp Gly Ser Phe Phe Leu Tyr Ser Lys Leu Thr Val Asp Lys Ser Arg
        195                 200                 205

Trp Gln Gln Gly Asn Val Phe Ser Cys Ser Val Met His Glu Ala Leu
    210                 215                 220

His Asn His Tyr Thr Gln Lys Ser Leu Ser Leu Ser Pro Gly Lys Gly
225                 230                 235                 240
```

```
Gly Gly Gly Ser Gly Gly Gly Ser Gly Gly Gly Ser Gly Gly
            245                 250                 255

Gly Gly Ser Gly Gly Gly Ser Gly Asp His Cys Pro Leu Gly Pro
            260                 265                 270

Gly Arg Cys Cys Arg Leu His Thr Val Arg Ala Ser Leu Glu Asp Leu
            275                 280                 285

Gly Trp Ala Asp Trp Val Leu Ser Pro Arg Glu Val Gln Val Thr Met
    290                 295                 300

Cys Ile Gly Ala Cys Pro Ser Gln Phe Arg Ala Ala Asn Met His Ala
305                 310                 315                 320

Gln Ile Lys Thr Ser Leu His Arg Leu Lys Pro Asp Thr Val Pro Ala
                325                 330                 335

Pro Cys Cys Val Pro Ala Ser Tyr Asn Pro Met Val Leu Ile Gln Lys
                340                 345                 350

Thr Asp Thr Gly Val Ser Leu Gln Thr Tyr Asp Asp Leu Leu Ala Lys
                355                 360                 365

Asp Cys His Cys Ile
            370

<210> SEQ ID NO 70
<211> LENGTH: 239
<212> TYPE: PRT
<213> ORGANISM: Artificial sequence
<220> FEATURE:
<223> OTHER INFORMATION: synthetic polypeptide sequence

<400> SEQUENCE: 70

Met Asp Met Arg Val Pro Ala Gln Leu Leu Gly Leu Leu Leu Leu Trp
1               5                   10                  15

Leu Arg Gly Ala Arg Cys Ala Pro Ala Leu Ala Gly Gly Pro Ser Val
            20                  25                  30

Phe Leu Phe Pro Pro Lys Pro Lys Asp Thr Leu Met Ile Ser Arg Thr
        35                  40                  45

Pro Glu Val Thr Cys Val Val Asp Val Ser His Glu Asp Pro Glu
    50                  55                  60

Val Lys Phe Asn Trp Tyr Val Asp Gly Val Glu Val His Asn Ala Lys
65                  70                  75                  80

Thr Lys Pro Arg Glu Glu Gln Tyr Asn Ser Thr Tyr Arg Val Val Ser
                85                  90                  95

Val Leu Thr Val Leu His Gln Asp Trp Leu Asn Gly Lys Glu Tyr Lys
            100                 105                 110

Cys Lys Val Ser Asn Lys Ala Leu Pro Ala Pro Ile Glu Lys Thr Ile
        115                 120                 125

Ser Lys Ala Lys Gly Gln Pro Arg Glu Pro Gln Val Tyr Thr Leu Pro
    130                 135                 140

Pro Ser Arg Glu Glu Met Thr Lys Asn Gln Val Ser Leu Ser Cys Ala
145                 150                 155                 160

Val Lys Gly Phe Tyr Pro Ser Asp Ile Ala Val Glu Trp Glu Ser Asn
                165                 170                 175

Gly Gln Pro Glu Asn Asn Tyr Lys Thr Thr Pro Pro Val Leu Asp Ser
            180                 185                 190

Asp Gly Ser Phe Phe Leu Val Ser Lys Leu Thr Val Asp Lys Ser Arg
        195                 200                 205

Trp Gln Gln Gly Asn Val Phe Ser Cys Ser Val Met His Glu Ala Leu
    210                 215                 220
```

```
His Asn His Tyr Thr Gln Lys Ser Leu Ser Leu Ser Pro Gly Lys
225                 230                 235

<210> SEQ ID NO 71
<211> LENGTH: 370
<212> TYPE: PRT
<213> ORGANISM: Artificial sequence
<220> FEATURE:
<223> OTHER INFORMATION: synthetic polypeptide sequence

<400> SEQUENCE: 71

Met Asp Met Arg Val Pro Ala Gln Leu Leu Gly Leu Leu Leu Leu Trp
1               5                   10                  15

Leu Arg Gly Ala Arg Cys Ala Pro Ala Leu Ala Gly Gly Pro Ser Val
                20                  25                  30

Phe Leu Phe Pro Pro Lys Pro Lys Asp Thr Leu Met Ile Ser Arg Thr
            35                  40                  45

Pro Glu Val Thr Cys Val Val Asp Val Ser His Glu Asp Pro Glu
    50                  55                  60

Val Lys Phe Asn Trp Tyr Val Asp Gly Val Glu Val His Asn Ala Lys
65              70                  75                  80

Thr Lys Pro Arg Glu Glu Gln Tyr Asn Ser Thr Tyr Arg Val Val Ser
                85                  90                  95

Val Leu Thr Val Leu His Gln Asp Trp Leu Asn Gly Lys Glu Tyr Lys
            100                 105                 110

Cys Lys Val Ser Asn Lys Ala Leu Pro Ala Pro Ile Glu Lys Thr Ile
        115                 120                 125

Ser Lys Ala Lys Gly Gln Pro Arg Glu Pro Gln Val Tyr Thr Leu Pro
130                 135                 140

Pro Ser Arg Glu Glu Met Thr Lys Asn Gln Val Ser Leu Ser Cys Ala
145                 150                 155                 160

Val Lys Gly Phe Tyr Pro Ser Asp Ile Ala Val Glu Trp Glu Ser Asn
                165                 170                 175

Gly Gln Pro Glu Asn Asn Tyr Lys Thr Thr Pro Pro Val Leu Asp Ser
            180                 185                 190

Asp Gly Ser Phe Phe Leu Val Ser Lys Leu Thr Val Asp Lys Ser Arg
        195                 200                 205

Trp Gln Gln Gly Asn Val Phe Ser Cys Ser Val Met His Glu Ala Leu
210                 215                 220

His Asn His Tyr Thr Gln Lys Ser Leu Ser Leu Ser Pro Gly Lys Gly
225                 230                 235                 240

Gly Gly Gly Ser Gly Gly Gly Ser Gly Gly Gly Ser Gly Gly
                245                 250                 255

Gly Gly Ser Gly Gly Gly Ser Cys Pro Leu Gly Pro Gly Arg Cys
            260                 265                 270

Cys Arg Leu His Thr Val Arg Ala Ser Leu Glu Asp Leu Gly Trp Ala
        275                 280                 285

Asp Trp Val Leu Ser Pro Arg Glu Val Gln Val Thr Met Cys Ile Gly
    290                 295                 300

Ala Cys Pro Ser Gln Phe Arg Ala Ala Asn Met His Ala Gln Ile Lys
305                 310                 315                 320

Thr Ser Leu His Arg Leu Lys Pro Asp Thr Val Pro Ala Pro Cys Cys
                325                 330                 335

Val Pro Ala Ser Tyr Asn Pro Met Val Leu Ile Gln Lys Thr Asp Thr
            340                 345                 350
```

```
Gly Val Ser Leu Gln Thr Tyr Asp Asp Leu Leu Ala Lys Asp Cys His
        355                 360                 365

Cys Ile
    370

<210> SEQ ID NO 72
<211> LENGTH: 239
<212> TYPE: PRT
<213> ORGANISM: Artificial sequence
<220> FEATURE:
<223> OTHER INFORMATION: synthetic polypeptide sequence

<400> SEQUENCE: 72

Met Asp Met Arg Val Pro Ala Gln Leu Leu Gly Leu Leu Leu Leu Trp
1               5                   10                  15

Leu Arg Gly Ala Arg Cys Ala Pro Ala Leu Ala Gly Gly Pro Ser Val
            20                  25                  30

Phe Leu Phe Pro Pro Lys Pro Lys Asp Thr Leu Met Ile Ser Arg Thr
        35                  40                  45

Pro Glu Val Thr Cys Val Val Asp Val Ser His Glu Asp Pro Glu
    50                  55                  60

Val Lys Phe Asn Trp Tyr Val Asp Gly Val Glu Val His Asn Ala Lys
65                  70                  75                  80

Thr Lys Pro Arg Glu Glu Gln Tyr Asn Ser Thr Tyr Arg Val Val Ser
                85                  90                  95

Val Leu Thr Val Leu His Gln Asp Trp Leu Asn Gly Lys Glu Tyr Lys
            100                 105                 110

Cys Lys Val Ser Asn Lys Ala Leu Pro Ala Pro Ile Glu Lys Thr Ile
        115                 120                 125

Ser Lys Ala Lys Gly Gln Pro Arg Glu Pro Gln Val Tyr Thr Leu Pro
    130                 135                 140

Pro Ser Arg Glu Glu Met Thr Lys Asn Gln Val Ser Leu Trp Cys Leu
145                 150                 155                 160

Val Lys Gly Phe Tyr Pro Ser Asp Ile Ala Val Glu Trp Glu Ser Asn
                165                 170                 175

Gly Gln Pro Glu Asn Asn Tyr Lys Thr Thr Pro Pro Val Leu Asp Ser
            180                 185                 190

Asp Gly Ser Phe Phe Leu Tyr Ser Lys Leu Thr Val Asp Lys Ser Arg
        195                 200                 205

Trp Gln Gln Gly Asn Val Phe Ser Cys Ser Val Met His Glu Ala Leu
    210                 215                 220

His Asn His Tyr Thr Gln Lys Ser Leu Ser Leu Ser Pro Gly Lys
225                 230                 235

<210> SEQ ID NO 73
<211> LENGTH: 376
<212> TYPE: PRT
<213> ORGANISM: Artificial sequence
<220> FEATURE:
<223> OTHER INFORMATION: synthetic polypeptide sequence

<400> SEQUENCE: 73

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Ala Leu Ala Gly Gly Pro Ser Val Phe Leu Phe Pro Pro Lys
```

```
            35                  40                  45
Pro Lys Asp Thr Leu Met Ile Ser Arg Thr Pro Glu Val Thr Cys Val
 50                  55                  60

Val Val Asp Val Ser His Glu Asp Pro Glu Val Lys Phe Asn Trp Tyr
 65                  70                  75                  80

Val Asp Gly Val Glu Val His Asn Ala Lys Thr Lys Pro Arg Glu Glu
                 85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Trp Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Lys Gly Gly Gly Ser Gly Gly
                245                 250                 255

Gly Gly Ser Gly Gly Gly Ser Ala Arg Asn Gly Thr His Cys Pro
            260                 265                 270

Leu Gly Pro Gly Arg Cys Cys Arg Leu His Thr Val Arg Ala Ser Leu
        275                 280                 285

Glu Asp Leu Gly Trp Ala Asp Trp Val Leu Ser Pro Arg Glu Val Gln
    290                 295                 300

Val Thr Met Cys Ile Gly Ala Cys Pro Ser Gln Phe Arg Ala Ala Asn
305                 310                 315                 320

Met His Ala Gln Ile Lys Thr Ser Leu His Arg Leu Lys Pro Asp Thr
                325                 330                 335

Val Pro Ala Pro Cys Cys Val Pro Ala Ser Tyr Asn Pro Met Val Leu
            340                 345                 350

Ile Gln Lys Thr Asp Thr Gly Val Ser Leu Gln Thr Tyr Asp Asp Leu
        355                 360                 365

Leu Ala Lys Asp Cys His Cys Ile
    370                 375

<210> SEQ ID NO 74
<211> LENGTH: 249
<212> TYPE: PRT
<213> ORGANISM: Artificial sequence
<220> FEATURE:
<223> OTHER INFORMATION: synthetic polypeptide sequence

<400> SEQUENCE: 74

Met Asp Met Arg Val Pro Ala Gln Leu Leu Gly Leu Leu Leu Leu Trp
  1               5                  10                  15

Leu Arg Gly Ala Arg Cys Asp Lys Thr His Thr Cys Pro Pro Cys Pro
```

```
                20                  25                  30
Ala Pro Ala Leu Ala Gly Gly Pro Ser Val Phe Leu Phe Pro Pro Lys
            35                  40                  45
Pro Lys Asp Thr Leu Met Ile Ser Arg Thr Pro Glu Val Thr Cys Val
 50                  55                  60
Val Val Asp Val Ser His Glu Asp Pro Glu Val Lys Phe Asn Trp Tyr
 65                  70                  75                  80
Val Asp Gly Val Glu Val His Asn Ala Lys Thr Lys Pro Arg Glu Glu
                85                  90                  95
Gln Tyr Asn Ser Thr Tyr Arg Val Val Ser Val Leu Thr Val Leu His
                100                 105                 110
Gln Asp Trp Leu Asn Gly Lys Glu Tyr Lys Cys Lys Val Ser Asn Lys
            115                 120                 125
Ala Leu Pro Ala Pro Ile Glu Lys Thr Ile Ser Lys Ala Lys Gly Gln
        130                 135                 140
Pro Arg Glu Pro Gln Val Tyr Thr Leu Pro Pro Ser Arg Glu Glu Met
145                 150                 155                 160
Thr Lys Asn Gln Val Ser Leu Ser Cys Ala Val Lys Gly Phe Tyr Pro
                165                 170                 175
Ser Asp Ile Ala Val Glu Trp Glu Ser Asn Gly Gln Pro Glu Asn Asn
            180                 185                 190
Tyr Lys Thr Thr Pro Pro Val Leu Asp Ser Asp Gly Ser Phe Phe Leu
        195                 200                 205
Val Ser Lys Leu Thr Val Asp Lys Ser Arg Trp Gln Gln Gly Asn Val
    210                 215                 220
Phe Ser Cys Ser Val Met His Glu Ala Leu His Asn His Tyr Thr Gln
225                 230                 235                 240
Lys Ser Leu Ser Leu Ser Pro Gly Lys
                245

<210> SEQ ID NO 75
<211> LENGTH: 381
<212> TYPE: PRT
<213> ORGANISM: Artificial sequence
<220> FEATURE:
<223> OTHER INFORMATION: synthetic polypeptide sequence

<400> SEQUENCE: 75

Met Asp Met Arg Val Pro Ala Gln Leu Leu Gly Leu Leu Leu Leu Trp
 1               5                  10                  15
Leu Arg Gly Ala Arg Cys Asp Lys Thr His Thr Cys Pro Pro Cys Pro
            20                  25                  30
Ala Pro Ala Leu Ala Gly Gly Pro Ser Val Phe Leu Phe Pro Pro Lys
            35                  40                  45
Pro Lys Asp Thr Leu Met Ile Ser Arg Thr Pro Glu Val Thr Cys Val
 50                  55                  60
Val Val Asp Val Ser His Glu Asp Pro Glu Val Lys Phe Asn Trp Tyr
 65                  70                  75                  80
Val Asp Gly Val Glu Val His Asn Ala Lys Thr Lys Pro Arg Glu Glu
                85                  90                  95
Gln Tyr Asn Ser Thr Tyr Arg Val Val Ser Val Leu Thr Val Leu His
                100                 105                 110
Gln Asp Trp Leu Asn Gly Lys Glu Tyr Lys Cys Lys Val Ser Asn Lys
            115                 120                 125
Ala Leu Pro Ala Pro Ile Glu Lys Thr Ile Ser Lys Ala Lys Gly Gln
```

```
            130                 135                 140
Pro Arg Glu Pro Gln Val Tyr Thr Leu Pro Pro Ser Arg Glu Met
145                 150                 155                 160

Thr Lys Asn Gln Val Ser Leu Trp Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Lys Gly Gly Gly Ser Gly Gly
                245                 250                 255

Gly Gly Ser Gly Gly Gly Gly Ser Gly Gly Gly Gly Ser Ala Arg Asn
            260                 265                 270

Gly Thr His Cys Pro Leu Gly Pro Gly Arg Cys Cys Arg Leu His Thr
        275                 280                 285

Val Arg Ala Ser Leu Glu Asp Leu Gly Trp Ala Asp Trp Val Leu Ser
    290                 295                 300

Pro Arg Glu Val Gln Val Thr Met Cys Ile Gly Ala Cys Pro Ser Gln
305                 310                 315                 320

Phe Arg Ala Ala Asn Met His Ala Gln Ile Lys Thr Ser Leu His Arg
                325                 330                 335

Leu Lys Pro Asp Thr Val Pro Ala Pro Cys Cys Val Pro Ala Ser Tyr
            340                 345                 350

Asn Pro Met Val Leu Ile Gln Lys Thr Asp Thr Gly Val Ser Leu Gln
        355                 360                 365

Thr Tyr Asp Asp Leu Leu Ala Lys Asp Cys His Cys Ile
    370                 375                 380

<210> SEQ ID NO 76
<211> LENGTH: 249
<212> TYPE: PRT
<213> ORGANISM: Artificial sequence
<220> FEATURE:
<223> OTHER INFORMATION: synthetic polypeptide sequence

<400> SEQUENCE: 76

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Ala Leu Ala Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
```

```
            115                 120                 125
Ala Leu Pro Ala Pro Ile Glu Lys Thr Ile Ser Lys Ala Lys Gly Gln
        130                 135                 140

Pro Arg Glu Pro Gln Val Tyr Thr Leu Pro Pro Ser Arg Glu Glu Met
145                 150                 155                 160

Thr Lys Asn Gln Val Ser Leu Ser Cys Ala Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Val Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Lys
                245

<210> SEQ ID NO 77
<211> LENGTH: 386
<212> TYPE: PRT
<213> ORGANISM: Artificial sequence
<220> FEATURE:
<223> OTHER INFORMATION: synthetic polypeptide sequence

<400> SEQUENCE: 77

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Ala Leu Ala Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Trp Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
```

```
225                 230                 235                 240
Lys Ser Leu Ser Leu Ser Pro Gly Lys Gly Gly Gly Ser Gly Gly
                245                 250                 255

Gly Gly Ser Gly Gly Gly Ser Gly Gly Gly Ser Gly Gly Gly
                260                 265                 270

Gly Ser Ala Arg Asn Gly Thr His Cys Pro Leu Gly Pro Gly Arg Cys
            275                 280                 285

Cys Arg Leu His Thr Val Arg Ala Ser Leu Glu Asp Leu Gly Trp Ala
    290                 295                 300

Asp Trp Val Leu Ser Pro Arg Glu Val Gln Val Thr Met Cys Ile Gly
305                 310                 315                 320

Ala Cys Pro Ser Gln Phe Arg Ala Ala Asn Met His Ala Gln Ile Lys
                325                 330                 335

Thr Ser Leu His Arg Leu Lys Pro Asp Thr Val Pro Ala Pro Cys Cys
                340                 345                 350

Val Pro Ala Ser Tyr Asn Pro Met Val Leu Ile Gln Lys Thr Asp Thr
                355                 360                 365

Gly Val Ser Leu Gln Thr Tyr Asp Asp Leu Leu Ala Lys Asp Cys His
    370                 375                 380

Cys Ile
385

<210> SEQ ID NO 78
<211> LENGTH: 369
<212> TYPE: PRT
<213> ORGANISM: Artificial sequence
<220> FEATURE:
<223> OTHER INFORMATION: synthetic polypeptide sequence

<400> SEQUENCE: 78

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Ala Leu Ala Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Trp Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
```

```
                195                 200                 205
Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Lys Gly Gly Gly Ser Gly Gly
                245                 250                 255

Gly Gly Ser Asn Gly Thr His Cys Pro Leu Gly Pro Gly Arg Cys Cys
            260                 265                 270

Arg Leu His Thr Val Arg Ala Ser Leu Glu Asp Leu Gly Trp Ala Asp
        275                 280                 285

Trp Val Leu Ser Pro Arg Glu Val Gln Val Thr Met Cys Ile Gly Ala
    290                 295                 300

Cys Pro Ser Gln Phe Arg Ala Ala Asn Met His Ala Gln Ile Lys Thr
305                 310                 315                 320

Ser Leu His Arg Leu Lys Pro Asp Thr Val Pro Ala Pro Cys Cys Val
                325                 330                 335

Pro Ala Ser Tyr Asn Pro Met Val Leu Ile Gln Lys Thr Asp Thr Gly
            340                 345                 350

Val Ser Leu Gln Thr Tyr Asp Asp Leu Leu Ala Lys Asp Cys His Cys
        355                 360                 365

Ile

<210> SEQ ID NO 79
<211> LENGTH: 249
<212> TYPE: PRT
<213> ORGANISM: Artificial sequence
<220> FEATURE:
<223> OTHER INFORMATION: synthetic polypeptide sequence

<400> SEQUENCE: 79

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Ala Leu Ala Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Ser Cys Ala Val Lys Gly Phe Tyr Pro
                165                 170                 175

Ser Asp Ile Ala Val Glu Trp Glu Ser Asn Gly Gln Pro Glu Asn Asn
            180                 185                 190
```

```
Tyr Lys Thr Thr Pro Pro Val Leu Asp Ser Asp Gly Ser Phe Phe Leu
        195                 200                 205

Val Ser Lys Leu Thr Val Asp Lys Ser Arg Trp Gln Gln Gly Asn Val
210                 215                 220

Phe Ser Cys Ser Val Met His Glu Ala Leu His Asn His Tyr Thr Gln
225                 230                 235                 240

Lys Ser Leu Ser Leu Ser Pro Gly Lys
                245

<210> SEQ ID NO 80
<211> LENGTH: 384
<212> TYPE: PRT
<213> ORGANISM: Artificial sequence
<220> FEATURE:
<223> OTHER INFORMATION: synthetic polypeptide sequence

<400> SEQUENCE: 80

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
                20                  25                  30

Ala Pro Ala Leu Ala Gly Gly Pro Ser Val Phe Leu Phe Pro Pro Lys
            35                  40                  45

Pro Lys Asp Thr Leu Met Ile Ser Arg Thr Pro Glu Val Thr Cys Val
 50                 55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Trp Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Lys Gly Gly Gly Ser Gly Gly
                245                 250                 255

Gly Gly Ser Gly Gly Gly Gly Ser Gly Gly Gly Gly Ser Gly Gly Gly
            260                 265                 270

Gly Ser Asn Gly Thr His Cys Pro Leu Gly Pro Gly Arg Cys Cys Arg
        275                 280                 285

Leu His Thr Val Arg Ala Ser Leu Glu Asp Leu Gly Trp Ala Asp Trp
    290                 295                 300
```

```
Val Leu Ser Pro Arg Glu Val Gln Val Thr Met Cys Ile Gly Ala Cys
305                 310                 315                 320

Pro Ser Gln Phe Arg Ala Ala Asn Met His Ala Gln Ile Lys Thr Ser
            325                 330                 335

Leu His Arg Leu Lys Pro Asp Thr Val Pro Ala Pro Cys Cys Val Pro
            340                 345                 350

Ala Ser Tyr Asn Pro Met Val Leu Ile Gln Lys Thr Asp Thr Gly Val
            355                 360                 365

Ser Leu Gln Thr Tyr Asp Asp Leu Leu Ala Lys Asp Cys His Cys Ile
370                 375                 380
```

<210> SEQ ID NO 81
<211> LENGTH: 249
<212> TYPE: PRT
<213> ORGANISM: Artificial sequence
<220> FEATURE:
<223> OTHER INFORMATION: synthetic polypeptide sequence

<400> SEQUENCE: 81

```
Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Ala Leu Ala Gly Gly Pro Ser Val Phe Leu Phe Pro Pro Lys
            35                  40                  45

Pro Lys Asp Thr Leu Met Ile Ser Arg Thr Pro Glu Val Thr Cys Val
50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
            85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
130                 135                 140

Pro Arg Glu Pro Gln Val Tyr Thr Leu Pro Pro Ser Arg Glu Glu Met
145                 150                 155                 160

Thr Lys Asn Gln Val Ser Leu Ser Cys Ala Val Lys Gly Phe Tyr Pro
            165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Val Ser Lys Leu Thr Val Asp Lys Ser Arg Trp Gln Gln Gly Asn Val
210                 215                 220

Phe Ser Cys Ser Val Met His Glu Ala Leu His Asn His Tyr Thr Gln
225                 230                 235                 240

Lys Ser Leu Ser Leu Ser Pro Gly Lys
                245
```

<210> SEQ ID NO 82
<211> LENGTH: 383
<212> TYPE: PRT
<213> ORGANISM: Artificial sequence
<220> FEATURE:
<223> OTHER INFORMATION: synthetic polypeptide sequence

<400> SEQUENCE: 82

```
Met Asp Met Arg Val Pro Ala Gln Leu Leu Gly Leu Leu Leu Trp
1               5                   10                  15

Leu Arg Gly Ala Arg Cys Asp Lys Thr His Thr Cys Pro Pro Cys
                20                  25                  30

Pro Ala Pro Ala Leu Ala Gly Gly Pro Ser Val Phe Leu Phe Pro
                35                  40                  45

Pro Lys Pro Lys Asp Thr Leu Met Ile Ser Arg Thr Pro Glu Val
                50                  55                  60

Thr Cys Val Val Val Asp Val Ser His Glu Asp Pro Glu Val Lys
65                  70                  75

Phe Asn Trp Tyr Val Asp Gly Val Glu Val His Asn Ala Lys Thr
                80                  85                  90

Lys Pro Arg Glu Glu Gln Tyr Asn Ser Thr Tyr Arg Val Val Ser
                95                  100                 105

Val Leu Thr Val Leu His Gln Asp Trp Leu Asn Gly Lys Glu Tyr
                110                 115                 120

Lys Cys Lys Val Ser Asn Lys Ala Leu Pro Ala Pro Ile Glu Lys
                125                 130                 135

Thr Ile Ser Lys Ala Lys Gly Gln Pro Arg Glu Pro Gln Val Tyr
                140                 145                 150

Thr Leu Pro Pro Ser Arg Glu Glu Met Thr Lys Asn Gln Val Ser
                155                 160                 165

Leu Trp Cys Leu Val Lys Gly Phe Tyr Pro Ser Asp Ile Ala Val
                170                 175                 180

Glu Trp Glu Ser Asn Gly Gln Pro Glu Asn Asn Tyr Lys Thr Thr
                185                 190                 195

Pro Pro Val Leu Asp Ser Asp Gly Ser Phe Phe Leu Tyr Ser Lys
                200                 205                 210

Leu Thr Val Asp Lys Ser Arg Trp Gln Gln Gly Asn Val Phe Ser
                215                 220                 225

Cys Ser Val Met His Glu Ala Leu His Asn His Tyr Thr Gln Lys
                230                 235                 240

Ser Leu Ser Leu Ser Pro Gly Lys Gly Gly Gly Ser Gly Gly Gly
                245                 250                 255

Gly Ser Gly Gly Gly Gly Ser Gly Gly Gly Ser Gly Gly Gly Gly
                260                 265                 270

Ser Gly Asp His Cys Pro Leu Gly Pro Gly Arg Cys Cys Arg Leu
                275                 280                 285

His Thr Val Asn Ala Ser Leu Glu Asp Leu Gly Trp Ala Asp Trp
                290                 295                 300

Val Leu Ser Pro Arg Glu Val Gln Val Thr Met Cys Ile Gly Ala
305                 310                 315

Cys Pro Ser Gln Phe Arg Ala Ala Asn Met His Ala Gln Ile Lys
                320                 325                 330

Thr Ser Leu His Arg Leu Lys Pro Asp Thr Val Pro Ala Pro Cys
                335                 340                 345

Cys Val Pro Ala Ser Tyr Asn Pro Met Val Leu Ile Gln Lys Thr
                350                 355                 360

Asp Thr Gly Val Ser Leu Gln Thr Tyr Asp Asp Leu Leu Ala Lys
                365                 370                 375

Asp Cys His Cys Ile
                380
```

<210> SEQ ID NO 83

<211> LENGTH: 249
<212> TYPE: PRT
<213> ORGANISM: Artificial sequence
<220> FEATURE:
<223> OTHER INFORMATION: synthetic polypeptide sequence

<400> SEQUENCE: 83

```
Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Ala Leu Ala Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Ser Cys Ala Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Val Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Lys
                245
```

<210> SEQ ID NO 84
<211> LENGTH: 383
<212> TYPE: PRT
<213> ORGANISM: Artificial sequence
<220> FEATURE:
<223> OTHER INFORMATION: synthetic polypeptide sequence

<400> SEQUENCE: 84

```
Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Ala Leu Ala Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
```

Val Asp Gly Val Glu Val His Asn Ala Lys Thr Lys Pro Arg Glu Glu
 65                  70                  75                  80

Gln Tyr Asn Ser Thr Tyr Arg Val Val Ser Val Leu Thr Val Leu His
             85                  90                  95

Gln Asp Trp Leu Asn Gly Lys Glu Tyr Lys Cys Lys Val Ser Asn Lys
        100                 105                 110

Ala Leu Pro Ala Pro Ile Glu Lys Thr Ile Ser Lys Ala Lys Gly Gln
    115                 120                 125

Pro Arg Glu Pro Gln Val Tyr Thr Leu Pro Pro Ser Arg Glu Glu Met
130                 135                 140

Thr Lys Asn Gln Val Ser Leu Trp Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
225                 230                 235                 240

Lys Ser Leu Ser Leu Ser Pro Gly Lys Gly Gly Gly Ser Gly Gly
                245                 250                 255

Gly Gly Ser Gly Gly Gly Gly Ser Gly Gly Gly Gly Ser Gly Gly Gly
            260                 265                 270

Gly Ser Gly Asp His Cys Pro Leu Gly Pro Gly Arg Cys Cys Arg Leu
        275                 280                 285

His Thr Val Arg Ala Asn Leu Thr Asp Leu Gly Trp Ala Asp Trp Val
    290                 295                 300

Leu Ser Pro Arg Glu Val Gln Val Thr Met Cys Ile Gly Ala Cys Pro
305                 310                 315                 320

Ser Gln Phe Arg Ala Ala Asn Met His Ala Gln Ile Lys Thr Ser Leu
                325                 330                 335

His Arg Leu Lys Pro Asp Thr Val Pro Ala Pro Cys Cys Val Pro Ala
            340                 345                 350

Ser Tyr Asn Pro Met Val Leu Ile Gln Lys Thr Asp Thr Gly Val Ser
        355                 360                 365

Leu Gln Thr Tyr Asp Asp Leu Leu Ala Lys Asp Cys His Cys Ile
    370                 375                 380

<210> SEQ ID NO 85
<211> LENGTH: 249
<212> TYPE: PRT
<213> ORGANISM: Artificial sequence
<220> FEATURE:
<223> OTHER INFORMATION: synthetic polypeptide sequence

<400> SEQUENCE: 85

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Ala Leu Ala Gly Gly Pro Ser Val Phe Leu Phe Pro Pro Lys
        35                  40                  45

Pro Lys Asp Thr Leu Met Ile Ser Arg Thr Pro Glu Val Thr Cys Val

```
            50                  55                  60
Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
                100                 105                 110

Gln Asp Trp Leu Asn Gly Lys Glu Tyr Lys Cys Lys Val Ser Asn Lys
                115                 120                 125

Ala Leu Pro Ala Pro Ile Glu Lys Thr Ile Ser Lys Ala Lys Gly Gln
                130                 135                 140

Pro Arg Glu Pro Gln Val Tyr Thr Leu Pro Pro Ser Arg Glu Glu Met
145                 150                 155                 160

Thr Lys Asn Gln Val Ser Leu Ser Cys Ala Val Lys Gly Phe Tyr Pro
                165                 170                 175

Ser Asp Ile Ala Val Glu Trp Glu Ser Asn Gly Gln Pro Glu Asn Asn
                180                 185                 190

Tyr Lys Thr Thr Pro Pro Val Leu Asp Ser Asp Gly Ser Phe Phe Leu
                195                 200                 205

Val Ser Lys Leu Thr Val Asp Lys Ser Arg Trp Gln Gln Gly Asn Val
                210                 215                 220

Phe Ser Cys Ser Val Met His Glu Ala Leu His Asn His Tyr Thr Gln
225                 230                 235                 240

Lys Ser Leu Ser Leu Ser Pro Gly Lys
                245

<210> SEQ ID NO 86
<211> LENGTH: 383
<212> TYPE: PRT
<213> ORGANISM: Artificial sequence
<220> FEATURE:
<223> OTHER INFORMATION: synthetic polypeptide sequence

<400> SEQUENCE: 86

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
                20                  25                  30

Ala Pro Ala Leu Ala Gly Gly Pro Ser Val Phe Leu Phe Pro Pro Lys
                35                  40                  45

Pro Lys Asp Thr Leu Met Ile Ser Arg Thr Pro Glu Val Thr Cys Val
50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
                100                 105                 110

Gln Asp Trp Leu Asn Gly Lys Glu Tyr Lys Cys Lys Val Ser Asn Lys
                115                 120                 125

Ala Leu Pro Ala Pro Ile Glu Lys Thr Ile Ser Lys Ala Lys Gly Gln
                130                 135                 140

Pro Arg Glu Pro Gln Val Tyr Thr Leu Pro Pro Ser Arg Glu Glu Met
145                 150                 155                 160

Thr Lys Asn Gln Val Ser Leu Trp Cys Leu Val Lys Gly Phe Tyr Pro
```

```
                165                 170                 175
Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
            195                 200                 205

Tyr Ser Lys Leu Thr Val Asp Lys Ser Arg Trp Gln Gln Gly Asn Val
            210                 215                 220

Phe Ser Cys Ser Val Met His Glu Ala Leu His Asn His Tyr Thr Gln
225                 230                 235                 240

Lys Ser Leu Ser Leu Ser Pro Gly Lys Gly Gly Gly Ser Gly Gly
                245                 250                 255

Gly Gly Ser Gly Gly Gly Ser Gly Gly Gly Ser Gly Gly Gly
            260                 265                 270

Gly Ser Gly Asp His Cys Pro Leu Gly Pro Gly Arg Cys Cys Arg Leu
            275                 280                 285

His Thr Val Arg Ala Ser Leu Glu Asp Leu Gly Trp Ala Asp Trp Val
            290                 295                 300

Leu Ser Pro Arg Glu Val Gln Val Thr Met Cys Ile Gly Ala Cys Pro
305                 310                 315                 320

Ser Gln Asn Arg Thr Ala Asn Met His Ala Gln Ile Lys Thr Ser Leu
                325                 330                 335

His Arg Leu Lys Pro Asp Thr Val Pro Ala Pro Cys Cys Val Pro Ala
                340                 345                 350

Ser Tyr Asn Pro Met Val Leu Ile Gln Lys Thr Asp Thr Gly Val Ser
                355                 360                 365

Leu Gln Thr Tyr Asp Asp Leu Leu Ala Lys Asp Cys His Cys Ile
            370                 375                 380

<210> SEQ ID NO 87
<211> LENGTH: 249
<212> TYPE: PRT
<213> ORGANISM: Artificial sequence
<220> FEATURE:
<223> OTHER INFORMATION: synthetic polypeptide sequence

<400> SEQUENCE: 87

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
                20                  25                  30

Ala Pro Ala Leu Ala Gly Gly Pro Ser Val Phe Leu Phe Pro Pro Lys
            35                  40                  45

Pro Lys Asp Thr Leu Met Ile Ser Arg Thr Pro Glu Val Thr Cys Val
        50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
```

```
                145                 150                 155                 160
        Thr Lys Asn Gln Val Ser Leu Ser Cys Ala Val Lys Gly Phe Tyr Pro
                        165                 170                 175

Ser Asp Ile Ala Val Glu Trp Glu Ser Asn Gly Gln Pro Glu Asn Asn
                        180                 185                 190

Tyr Lys Thr Thr Pro Pro Val Leu Asp Ser Asp Gly Ser Phe Phe Leu
                        195                 200                 205

Val Ser Lys Leu Thr Val Asp Lys Ser Arg Trp Gln Gln Gly Asn Val
                210                 215                 220

Phe Ser Cys Ser Val Met His Glu Ala Leu His Asn His Tyr Thr Gln
        225                 230                 235                 240

Lys Ser Leu Ser Leu Ser Pro Gly Lys
                        245

<210> SEQ ID NO 88
<211> LENGTH: 383
<212> TYPE: PRT
<213> ORGANISM: Artificial sequence
<220> FEATURE:
<223> OTHER INFORMATION: synthetic polypeptide sequence

<400> SEQUENCE: 88

Met Asp Met Arg Val Pro Ala Gln Leu Leu Gly Leu Leu Leu Leu Trp
        1               5                   10                  15

Leu Arg Gly Ala Arg Cys Asp Lys Thr His Thr Cys Pro Pro Cys Pro
                        20                  25                  30

Ala Pro Ala Leu Ala Gly Gly Pro Ser Val Phe Leu Phe Pro Pro Lys
                        35                  40                  45

Pro Lys Asp Thr Leu Met Ile Ser Arg Thr Pro Glu Val Thr Cys Val
                50                  55                  60

Val Val Asp Val Ser His Glu Asp Pro Glu Val Lys Phe Asn Trp Tyr
        65                  70                  75                  80

Val Asp Gly Val Glu Val His Asn Ala Lys Thr Lys Pro Arg Glu Glu
                        85                  90                  95

Gln Tyr Asn Ser Thr Tyr Arg Val Val Ser Val Leu Thr Val Leu His
                        100                 105                 110

Gln Asp Trp Leu Asn Gly Lys Glu Tyr Lys Cys Lys Val Ser Asn Lys
                        115                 120                 125

Ala Leu Pro Ala Pro Ile Glu Lys Thr Ile Ser Lys Ala Lys Gly Gln
                130                 135                 140

Pro Arg Glu Pro Gln Val Tyr Thr Leu Pro Pro Ser Arg Glu Glu Met
        145                 150                 155                 160

Thr Lys Asn Gln Val Ser Leu Trp Cys Leu Val Lys Gly Phe Tyr Pro
                        165                 170                 175

Ser Asp Ile Ala Val Glu Trp Glu Ser Asn Gly Gln Pro Glu Asn Asn
                        180                 185                 190

Tyr Lys Thr Thr Pro Pro Val Leu Asp Ser Asp Gly Ser Phe Phe Leu
                        195                 200                 205

Tyr Ser Lys Leu Thr Val Asp Lys Ser Arg Trp Gln Gln Gly Asn Val
                210                 215                 220

Phe Ser Cys Ser Val Met His Glu Ala Leu His Asn His Tyr Thr Gln
        225                 230                 235                 240

Lys Ser Leu Ser Leu Ser Pro Gly Lys Gly Gly Gly Ser Gly Gly
                        245                 250                 255

Gly Gly Ser Gly Gly Gly Gly Ser Gly Gly Gly Gly Ser Gly Gly Gly
```

```
                260                 265                 270
Gly Ser Gly Asp His Cys Pro Leu Gly Pro Gly Arg Cys Cys Arg Leu
            275                 280                 285

His Thr Val Arg Ala Ser Leu Glu Asp Leu Gly Trp Ala Asp Trp Val
        290                 295                 300

Leu Ser Pro Arg Glu Val Gln Val Thr Met Cys Ile Gly Ala Cys Pro
305                 310                 315                 320

Ser Gln Phe Asn Ala Thr Asn Met His Ala Gln Ile Lys Thr Ser Leu
                325                 330                 335

His Arg Leu Lys Pro Asp Thr Val Pro Ala Pro Cys Cys Val Pro Ala
            340                 345                 350

Ser Tyr Asn Pro Met Val Leu Ile Gln Lys Thr Asp Thr Gly Val Ser
        355                 360                 365

Leu Gln Thr Tyr Asp Asp Leu Leu Ala Lys Asp Cys His Cys Ile
    370                 375                 380

<210> SEQ ID NO 89
<211> LENGTH: 249
<212> TYPE: PRT
<213> ORGANISM: Artificial sequence
<220> FEATURE:
<223> OTHER INFORMATION: synthetic polypeptide sequence

<400> SEQUENCE: 89

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Ala Leu Ala Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Ser Cys Ala Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Val Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Lys
                245
```

245

<210> SEQ ID NO 90
<211> LENGTH: 383
<212> TYPE: PRT
<213> ORGANISM: Artificial sequence
<220> FEATURE:
<223> OTHER INFORMATION: synthetic polypeptide sequence

<400> SEQUENCE: 90

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Ala Leu Ala Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Trp Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Lys Gly Gly Gly Ser Gly Gly
                245                 250                 255

Gly Gly Ser Gly Gly Gly Gly Ser Gly Gly Gly Gly Ser Gly Gly Gly
            260                 265                 270

Gly Ser Gly Asp His Cys Pro Leu Gly Pro Gly Arg Cys Cys Arg Leu
        275                 280                 285

His Thr Val Arg Ala Ser Leu Glu Asp Leu Gly Trp Ala Asp Trp Val
    290                 295                 300

Leu Ser Pro Arg Glu Val Gln Val Thr Met Cys Ile Gly Ala Cys Pro
305                 310                 315                 320

Ser Gln Phe Arg Ala Ala Asn Met His Ala Gln Ile Lys Thr Ser Leu
                325                 330                 335

His Arg Leu Lys Pro Asp Thr Val Pro Ala Pro Cys Cys Val Pro Ala
            340                 345                 350

Ser Tyr Asn Pro Met Val Leu Ile Gln Asn Thr Thr Thr Gly Val Ser

```
                355                 360                 365
Leu Gln Thr Tyr Asp Asp Leu Leu Ala Lys Asp Cys His Cys Ile
    370                 375                 380
```

<210> SEQ ID NO 91
<211> LENGTH: 249
<212> TYPE: PRT
<213> ORGANISM: Artificial sequence
<220> FEATURE:
<223> OTHER INFORMATION: synthetic polypeptide sequence

<400> SEQUENCE: 91

```
Met Asp Met Arg Val Pro Ala Gln Leu Leu Gly Leu Leu Leu Trp
1               5                   10                  15

Leu Arg Gly Ala Arg Cys Asp Lys Thr His Thr Cys Pro Pro Cys Pro
                20                  25                  30

Ala Pro Ala Leu Ala Gly Gly Pro Ser Val Phe Leu Phe Pro Pro Lys
            35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Ser Cys Ala Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Val Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Lys
                245
```

<210> SEQ ID NO 92
<211> LENGTH: 383
<212> TYPE: PRT
<213> ORGANISM: Artificial sequence
<220> FEATURE:
<223> OTHER INFORMATION: synthetic polypeptide sequence

<400> SEQUENCE: 92

```
Met Asp Met Arg Val Pro Ala Gln Leu Leu Gly Leu Leu Leu Trp
1               5                   10                  15

Leu Arg Gly Ala Arg Cys Asp Lys Thr His Thr Cys Pro Pro Cys Pro
                20                  25                  30
```

Ala Pro Ala Leu Ala Gly Gly Pro Ser Val Phe Leu Phe Pro Pro Lys
             35                  40                  45

Pro Lys Asp Thr Leu Met Ile Ser Arg Thr Pro Glu Val Thr Cys Val
 50                  55                  60

Val Val Asp Val Ser His Glu Asp Pro Glu Val Lys Phe Asn Trp Tyr
 65                  70                  75                  80

Val Asp Gly Val Glu Val His Asn Ala Lys Thr Lys Pro Arg Glu Glu
                 85                  90                  95

Gln Tyr Asn Ser Thr Tyr Arg Val Val Ser Val Leu Thr Val Leu His
                100                 105                 110

Gln Asp Trp Leu Asn Gly Lys Glu Tyr Lys Cys Lys Val Ser Asn Lys
                115                 120                 125

Ala Leu Pro Ala Pro Ile Glu Lys Thr Ile Ser Lys Ala Lys Gly Gln
130                 135                 140

Pro Arg Glu Pro Gln Val Tyr Thr Leu Pro Pro Ser Arg Glu Glu Met
145                 150                 155                 160

Thr Lys Asn Gln Val Ser Leu Trp Cys Leu Val Lys Gly Phe Tyr Pro
                165                 170                 175

Ser Asp Ile Ala Val Glu Trp Glu Ser Asn Gly Gln Pro Glu Asn Asn
                180                 185                 190

Tyr Lys Thr Thr Pro Pro Val Leu Asp Ser Asp Gly Ser Phe Phe Leu
                195                 200                 205

Tyr Ser Lys Leu Thr Val Asp Lys Ser Arg Trp Gln Gln Gly Asn Val
                210                 215                 220

Phe Ser Cys Ser Val Met His Glu Ala Leu His Asn His Tyr Thr Gln
225                 230                 235                 240

Lys Ser Leu Ser Leu Ser Pro Gly Lys Gly Gly Gly Ser Gly Gly Gly
                245                 250                 255

Gly Gly Ser Gly Gly Gly Ser Gly Gly Gly Ser Gly Gly Gly
                260                 265                 270

Gly Ser Gly Asp His Cys Pro Leu Gly Pro Gly Arg Cys Cys Arg Leu
                275                 280                 285

His Thr Val Arg Ala Ser Leu Glu Asp Leu Gly Trp Ala Asp Trp Val
290                 295                 300

Leu Ser Pro Arg Glu Val Gln Val Thr Met Cys Ile Gly Ala Cys Pro
305                 310                 315                 320

Ser Gln Phe Arg Ala Ala Asn Met His Ala Gln Ile Lys Thr Ser Leu
                325                 330                 335

His Arg Leu Lys Pro Asp Thr Val Pro Ala Pro Cys Cys Val Pro Ala
                340                 345                 350

Ser Tyr Asn Pro Met Val Leu Ile Gln Lys Thr Asn Thr Thr Val Ser
                355                 360                 365

Leu Gln Thr Tyr Asp Asp Leu Leu Ala Lys Asp Cys His Cys Ile
                370                 375                 380

<210> SEQ ID NO 93
<211> LENGTH: 249
<212> TYPE: PRT
<213> ORGANISM: Artificial sequence
<220> FEATURE:
<223> OTHER INFORMATION: synthetic polypeptide sequence

<400> SEQUENCE: 93

Met Asp Met Arg Val Pro Ala Gln Leu Leu Gly Leu Leu Leu Leu Trp
 1               5                  10                  15

-continued

```
Leu Arg Gly Ala Arg Cys Asp Lys Thr His Thr Cys Pro Pro Cys Pro
             20                  25                  30
Ala Pro Ala Leu Ala Gly Gly Pro Ser Val Phe Leu Phe Pro Pro Lys
         35                  40                  45
Pro Lys Asp Thr Leu Met Ile Ser Arg Thr Pro Glu Val Thr Cys Val
 50                  55                  60
Val Val Asp Val Ser His Glu Asp Pro Glu Val Lys Phe Asn Trp Tyr
 65                  70                  75                  80
Val Asp Gly Val Glu Val His Asn Ala Lys Thr Lys Pro Arg Glu Glu
             85                  90                  95
Gln Tyr Asn Ser Thr Tyr Arg Val Val Ser Val Leu Thr Val Leu His
        100                 105                 110
Gln Asp Trp Leu Asn Gly Lys Glu Tyr Lys Cys Lys Val Ser Asn Lys
        115                 120                 125
Ala Leu Pro Ala Pro Ile Glu Lys Thr Ile Ser Lys Ala Lys Gly Gln
130                 135                 140
Pro Arg Glu Pro Gln Val Tyr Thr Leu Pro Pro Ser Arg Glu Glu Met
145                 150                 155                 160
Thr Lys Asn Gln Val Ser Leu Ser Cys Ala Val Lys Gly Phe Tyr Pro
                165                 170                 175
Ser Asp Ile Ala Val Glu Trp Glu Ser Asn Gly Gln Pro Glu Asn Asn
            180                 185                 190
Tyr Lys Thr Thr Pro Pro Val Leu Asp Ser Asp Gly Ser Phe Phe Leu
        195                 200                 205
Val Ser Lys Leu Thr Val Asp Lys Ser Arg Trp Gln Gln Gly Asn Val
210                 215                 220
Phe Ser Cys Ser Val Met His Glu Ala Leu His Asn His Tyr Thr Gln
225                 230                 235                 240
Lys Ser Leu Ser Leu Ser Pro Gly Lys
            245

<210> SEQ ID NO 94
<211> LENGTH: 31
<212> TYPE: PRT
<213> ORGANISM: Artificial sequence
<220> FEATURE:
<223> OTHER INFORMATION: synthetic polypeptide sequence

<400> SEQUENCE: 94

His Gly Pro Glu Gly Leu Arg Val Gly Phe Tyr Glu Ser Asp Val Met
 1               5                  10                  15
Gly Arg Gly His Ala Arg Leu Val His Val Glu Glu Pro His Thr
            20                  25                  30

<210> SEQ ID NO 95
<211> LENGTH: 6
<212> TYPE: PRT
<213> ORGANISM: Artificial sequence
<220> FEATURE:
<223> OTHER INFORMATION: synthetic polypeptide sequence

<400> SEQUENCE: 95

Ala Arg Asn Gly Asp His
 1               5

<210> SEQ ID NO 96
<211> LENGTH: 8
<212> TYPE: PRT
<213> ORGANISM: Artificial sequence
```

```
<220> FEATURE:
<223> OTHER INFORMATION: synthetic polypeptide sequence

<400> SEQUENCE: 96

Ala Pro Glu Leu Leu Gly Gly Pro
1               5

<210> SEQ ID NO 97
<211> LENGTH: 8
<212> TYPE: PRT
<213> ORGANISM: Artificial sequence
<220> FEATURE:
<223> OTHER INFORMATION: synthetic polypeptide sequence

<400> SEQUENCE: 97

Ala Pro Ala Leu Ala Gly Gly Pro
1               5

<210> SEQ ID NO 98
<211> LENGTH: 8
<212> TYPE: PRT
<213> ORGANISM: Artificial sequence
<220> FEATURE:
<223> OTHER INFORMATION: synthetic polypeptide sequence

<400> SEQUENCE: 98

Ala Pro Ala Leu Leu Gly Gly Pro
1               5

<210> SEQ ID NO 99
<211> LENGTH: 8
<212> TYPE: PRT
<213> ORGANISM: Artificial sequence
<220> FEATURE:
<223> OTHER INFORMATION: synthetic polypeptide sequence

<400> SEQUENCE: 99

Ala Pro Glu Leu Ala Gly Gly Pro
1               5

<210> SEQ ID NO 100
<211> LENGTH: 15
<212> TYPE: PRT
<213> ORGANISM: Artificial sequence
<220> FEATURE:
<223> OTHER INFORMATION: synthetic polypeptide sequence

<400> SEQUENCE: 100

Glu Pro Lys Ser Cys Asp Lys Thr His Thr Cys Pro Pro Cys Pro
1               5                   10                  15

<210> SEQ ID NO 101
<211> LENGTH: 13
<212> TYPE: PRT
<213> ORGANISM: Artificial sequence
<220> FEATURE:
<223> OTHER INFORMATION: synthetic polypeptide sequence

<400> SEQUENCE: 101

Lys Ser Cys Asp Lys Thr His Thr Cys Pro Pro Cys Pro
1               5                   10

<210> SEQ ID NO 102
<211> LENGTH: 12
<212> TYPE: PRT
<213> ORGANISM: Artificial sequence
<220> FEATURE:
```

<223> OTHER INFORMATION: synthetic polypeptide sequence

<400> SEQUENCE: 102

Ser Cys Asp Lys Thr His Thr Cys Pro Pro Cys Pro
1               5                   10

<210> SEQ ID NO 103
<211> LENGTH: 11
<212> TYPE: PRT
<213> ORGANISM: Artificial sequence
<220> FEATURE:
<223> OTHER INFORMATION: synthetic polypeptide sequence

<400> SEQUENCE: 103

Cys Asp Lys Thr His Thr Cys Pro Pro Cys Pro
1               5                   10

<210> SEQ ID NO 104
<211> LENGTH: 10
<212> TYPE: PRT
<213> ORGANISM: Artificial sequence
<220> FEATURE:
<223> OTHER INFORMATION: synthetic polypeptide sequence

<400> SEQUENCE: 104

Asp Lys Thr His Thr Cys Pro Pro Cys Pro
1               5                   10

<210> SEQ ID NO 105
<211> LENGTH: 9
<212> TYPE: PRT
<213> ORGANISM: Artificial sequence
<220> FEATURE:
<223> OTHER INFORMATION: synthetic polypeptide sequence

<400> SEQUENCE: 105

Lys Thr His Thr Cys Pro Pro Cys Pro
1               5

<210> SEQ ID NO 106
<211> LENGTH: 8
<212> TYPE: PRT
<213> ORGANISM: Artificial sequence
<220> FEATURE:
<223> OTHER INFORMATION: synthetic polypeptide sequence

<400> SEQUENCE: 106

Thr His Thr Cys Pro Pro Cys Pro
1               5

<210> SEQ ID NO 107
<211> LENGTH: 5
<212> TYPE: PRT
<213> ORGANISM: Artificial sequence
<220> FEATURE:
<223> OTHER INFORMATION: synthetic polypeptide sequence

<400> SEQUENCE: 107

Cys Pro Pro Cys Pro
1               5

<210> SEQ ID NO 108
<211> LENGTH: 134
<212> TYPE: PRT
<213> ORGANISM: Artificial sequence
<220> FEATURE:
<223> OTHER INFORMATION: synthetic polypeptide sequence

<400> SEQUENCE: 108

Met Asp Met Arg Val Pro Ala Gln Leu Leu Gly Leu Leu Leu Leu Trp
1               5                   10                  15

Leu Arg Gly Ala Arg Cys Ala Arg Asn Gly Asp His Cys Pro Leu Gly
            20                  25                  30

Pro Gly Arg Cys Cys Arg Leu His Thr Val Arg Ala Ser Leu Glu Asp
        35                  40                  45

Leu Gly Trp Ala Asp Trp Val Leu Ser Pro Arg Glu Val Gln Val Thr
    50                  55                  60

Met Cys Ile Gly Ala Cys Pro Ser Gln Phe Arg Ala Ala Asn Met His
65                  70                  75                  80

Ala Gln Ile Lys Thr Ser Leu His Arg Leu Lys Pro Asp Thr Val Pro
                85                  90                  95

Ala Pro Cys Cys Val Pro Ala Ser Tyr Asn Pro Met Val Leu Ile Gln
            100                 105                 110

Lys Thr Asp Thr Gly Val Ser Leu Gln Thr Tyr Asp Asp Leu Leu Ala
            115                 120                 125

Lys Asp Cys His Cys Ile
            130

<210> SEQ ID NO 109
<211> LENGTH: 134
<212> TYPE: PRT
<213> ORGANISM: Artificial sequence
<220> FEATURE:
<223> OTHER INFORMATION: synthetic polypeptide sequence

<400> SEQUENCE: 109

Met Asp Met Arg Val Pro Ala Gln Leu Leu Gly Leu Leu Leu Leu Trp
1               5                   10                  15

Leu Arg Gly Ala Arg Cys Ala Arg Asn Gly Asp His Cys Pro Leu Gly
            20                  25                  30

Pro Gly Arg Cys Cys Arg Leu His Thr Val Asn Ala Ser Leu Glu Asp
        35                  40                  45

Leu Gly Trp Ala Asp Trp Val Leu Ser Pro Arg Glu Val Gln Val Thr
    50                  55                  60

Met Cys Ile Gly Ala Cys Pro Ser Gln Phe Arg Ala Ala Asn Met His
65                  70                  75                  80

Ala Gln Ile Lys Thr Ser Leu His Arg Leu Lys Pro Asp Thr Val Pro
                85                  90                  95

Ala Pro Cys Cys Val Pro Ala Ser Tyr Asn Pro Met Val Leu Ile Gln
            100                 105                 110

Lys Thr Asp Thr Gly Val Ser Leu Gln Thr Tyr Asp Asp Leu Leu Ala
            115                 120                 125

Lys Asp Cys His Cys Ile
            130

<210> SEQ ID NO 110
<211> LENGTH: 134
<212> TYPE: PRT
<213> ORGANISM: Artificial sequence
<220> FEATURE:
<223> OTHER INFORMATION: synthetic polypeptide sequence

<400> SEQUENCE: 110

Met Asp Met Arg Val Pro Ala Gln Leu Leu Gly Leu Leu Leu Leu Trp
1               5                   10                  15

Leu Arg Gly Ala Arg Cys Ala Arg Asn Gly Asp His Cys Pro Leu Gly
            20                  25                  30

Pro Gly Arg Cys Cys Arg Leu His Thr Val Arg Ala Ser Leu Glu Asp
        35                  40                  45

Leu Gly Trp Ala Asp Trp Val Leu Ser Pro Arg Glu Val Gln Val Thr
    50                  55                  60

Met Cys Ile Gly Ala Cys Pro Ser Gln Phe Asn Ala Thr Asn Met His
65                  70                  75                  80

Ala Gln Ile Lys Thr Ser Leu His Arg Leu Lys Pro Asp Thr Val Pro
                85                  90                  95

Ala Pro Cys Cys Val Pro Ala Ser Tyr Asn Pro Met Val Leu Ile Gln
            100                 105                 110

Lys Thr Asp Thr Gly Val Ser Leu Gln Thr Tyr Asp Asp Leu Leu Ala
        115                 120                 125

Lys Asp Cys His Cys Ile
        130

<210> SEQ ID NO 111
<211> LENGTH: 134
<212> TYPE: PRT
<213> ORGANISM: Artificial sequence
<220> FEATURE:
<223> OTHER INFORMATION: synthetic polypeptide sequence

<400> SEQUENCE: 111

Met Asp Met Arg Val Pro Ala Gln Leu Leu Gly Leu Leu Leu Leu Trp
1               5                   10                  15

Leu Arg Gly Ala Arg Cys Ala Arg Asn Gly Asp His Cys Pro Leu Gly
            20                  25                  30

Pro Gly Arg Cys Cys Arg Leu His Thr Val Arg Ala Ser Leu Glu Asp
        35                  40                  45

Leu Gly Trp Ala Asp Trp Val Leu Ser Pro Arg Glu Val Gln Val Thr
    50                  55                  60

Met Cys Ile Gly Ala Cys Pro Ser Gln Phe Arg Ala Ala Asn Met His
65                  70                  75                  80

Ala Gln Ile Lys Thr Asn Leu Thr Arg Leu Lys Pro Asp Thr Val Pro
                85                  90                  95

Ala Pro Cys Cys Val Pro Ala Ser Tyr Asn Pro Met Val Leu Ile Gln
            100                 105                 110

Lys Thr Asp Thr Gly Val Ser Leu Gln Thr Tyr Asp Asp Leu Leu Ala
        115                 120                 125

Lys Asp Cys His Cys Ile
        130

<210> SEQ ID NO 112
<211> LENGTH: 134
<212> TYPE: PRT
<213> ORGANISM: Artificial sequence
<220> FEATURE:
<223> OTHER INFORMATION: synthetic polypeptide sequence

<400> SEQUENCE: 112

Met Asp Met Arg Val Pro Ala Gln Leu Leu Gly Leu Leu Leu Leu Trp
1               5                   10                  15

Leu Arg Gly Ala Arg Cys Ala Arg Asn Gly Asp His Cys Pro Leu Gly
            20                  25                  30

Pro Gly Arg Cys Cys Arg Leu His Thr Val Arg Ala Ser Leu Glu Asp

```
                35                  40                  45
Leu Gly Trp Ala Asp Trp Val Leu Ser Pro Arg Glu Val Gln Val Thr
 50                  55                  60

Met Cys Ile Gly Ala Cys Pro Ser Gln Phe Arg Ala Ala Asn Met His
65                  70                  75                  80

Ala Gln Ile Lys Thr Ser Leu His Arg Leu Lys Asn Asp Thr Val Pro
                85                  90                  95

Ala Pro Cys Cys Val Pro Ala Ser Tyr Asn Pro Met Val Leu Ile Gln
            100                 105                 110

Lys Thr Asp Thr Gly Val Ser Leu Gln Thr Tyr Asp Asp Leu Leu Ala
            115                 120                 125

Lys Asp Cys His Cys Ile
            130

<210> SEQ ID NO 113
<211> LENGTH: 134
<212> TYPE: PRT
<213> ORGANISM: Artificial sequence
<220> FEATURE:
<223> OTHER INFORMATION: synthetic polypeptide sequence

<400> SEQUENCE: 113

Met Asp Met Arg Val Pro Ala Gln Leu Leu Gly Leu Leu Leu Leu Trp
1               5                   10                  15

Leu Arg Gly Ala Arg Cys Ala Arg Asn Gly Asp His Cys Pro Leu Gly
                20                  25                  30

Pro Gly Arg Cys Cys Arg Leu His Thr Val Arg Ala Ser Leu Glu Asp
            35                  40                  45

Leu Gly Trp Ala Asp Trp Val Leu Ser Pro Arg Glu Val Gln Val Thr
 50                  55                  60

Met Cys Ile Gly Ala Cys Pro Ser Gln Phe Arg Ala Ala Asn Met His
65                  70                  75                  80

Ala Gln Ile Lys Thr Ser Leu His Arg Leu Lys Pro Asp Thr Val Pro
                85                  90                  95

Ala Pro Cys Cys Val Pro Ala Ser Tyr Asn Pro Met Val Leu Ile Asn
            100                 105                 110

Lys Thr Asp Thr Gly Val Ser Leu Gln Thr Tyr Asp Asp Leu Leu Ala
            115                 120                 125

Lys Asp Cys His Cys Ile
            130

<210> SEQ ID NO 114
<211> LENGTH: 134
<212> TYPE: PRT
<213> ORGANISM: Artificial sequence
<220> FEATURE:
<223> OTHER INFORMATION: synthetic polypeptide sequence

<400> SEQUENCE: 114

Met Asp Met Arg Val Pro Ala Gln Leu Leu Gly Leu Leu Leu Leu Trp
1               5                   10                  15

Leu Arg Gly Ala Arg Cys Ala Arg Asn Gly Asp His Cys Pro Leu Gly
                20                  25                  30

Pro Gly Arg Cys Cys Arg Leu His Thr Val Arg Ala Ser Leu Glu Asp
            35                  40                  45

Leu Gly Trp Ala Asp Trp Val Leu Ser Pro Arg Glu Val Gln Val Thr
 50                  55                  60
```

```
Met Cys Ile Gly Ala Cys Pro Ser Gln Phe Arg Ala Ala Asn Met His
 65                 70                  75                  80

Ala Gln Ile Lys Thr Ser Leu His Arg Leu Lys Pro Asp Thr Val Pro
                 85                  90                  95

Ala Pro Cys Cys Val Pro Ala Ser Tyr Asn Pro Met Val Leu Ile Gln
            100                 105                 110

Asn Thr Thr Thr Gly Val Ser Leu Gln Thr Tyr Asp Asp Leu Leu Ala
        115                 120                 125

Lys Asp Cys His Cys Ile
        130

<210> SEQ ID NO 115
<211> LENGTH: 134
<212> TYPE: PRT
<213> ORGANISM: Artificial sequence
<220> FEATURE:
<223> OTHER INFORMATION: synthetic polypeptide sequence

<400> SEQUENCE: 115

Met Asp Met Arg Val Pro Ala Gln Leu Leu Gly Leu Leu Leu Leu Trp
  1               5                  10                  15

Leu Arg Gly Ala Arg Cys Ala Arg Asn Gly Asp His Cys Pro Leu Gly
                 20                  25                  30

Pro Gly Arg Cys Cys Arg Leu His Thr Val Arg Ala Ser Leu Glu Asp
            35                  40                  45

Leu Gly Trp Ala Asp Trp Val Leu Ser Pro Arg Glu Val Gln Val Thr
     50                  55                  60

Met Cys Ile Gly Ala Cys Pro Ser Gln Phe Arg Ala Ala Asn Met His
 65                 70                  75                  80

Ala Gln Ile Lys Thr Ser Leu His Arg Leu Lys Pro Asp Thr Val Pro
                 85                  90                  95

Ala Pro Cys Cys Val Pro Ala Ser Tyr Asn Pro Met Val Leu Ile Gln
            100                 105                 110

Lys Thr Asn Thr Thr Val Ser Leu Gln Thr Tyr Asp Asp Leu Leu Ala
        115                 120                 125

Lys Asp Cys His Cys Ile
        130

<210> SEQ ID NO 116
<211> LENGTH: 134
<212> TYPE: PRT
<213> ORGANISM: Artificial sequence
<220> FEATURE:
<223> OTHER INFORMATION: synthetic polypeptide sequence

<400> SEQUENCE: 116

Met Asp Met Arg Val Pro Ala Gln Leu Leu Gly Leu Leu Leu Leu Trp
  1               5                  10                  15

Leu Arg Gly Ala Arg Cys Ala Arg Asn Gly Asp His Cys Pro Leu Gly
                 20                  25                  30

Pro Gly Arg Cys Cys Arg Leu His Thr Val Arg Ala Ser Leu Glu Asp
            35                  40                  45

Leu Gly Trp Ala Asp Trp Val Leu Ser Pro Arg Glu Val Gln Val Thr
     50                  55                  60

Met Cys Ile Gly Ala Cys Pro Ser Gln Phe Arg Ala Ala Asn Met His
 65                 70                  75                  80

Ala Gln Ile Lys Thr Ser Leu His Arg Leu Lys Pro Asp Thr Val Pro
                 85                  90                  95
```

Ala Pro Cys Cys Val Pro Ala Ser Tyr Asn Pro Met Val Leu Ile Gln
            100                 105                 110

Lys Thr Asp Thr Asn Val Ser Leu Gln Thr Tyr Asp Asp Leu Leu Ala
        115                 120                 125

Lys Asp Cys His Cys Ile
    130

<210> SEQ ID NO 117
<211> LENGTH: 134
<212> TYPE: PRT
<213> ORGANISM: Artificial sequence
<220> FEATURE:
<223> OTHER INFORMATION: synthetic polypeptide sequence

<400> SEQUENCE: 117

Met Asp Met Arg Val Pro Ala Gln Leu Leu Gly Leu Leu Leu Leu Trp
1               5                   10                  15

Leu Arg Gly Ala Arg Cys Ala Arg Asn Gly Asp His Cys Pro Leu Gly
            20                  25                  30

Pro Gly Arg Cys Cys Arg Leu His Thr Val Arg Ala Ser Leu Glu Asp
        35                  40                  45

Leu Gly Trp Ala Asp Trp Val Leu Ser Pro Arg Glu Val Gln Val Thr
    50                  55                  60

Met Cys Ile Gly Ala Cys Pro Ser Gln Phe Arg Ala Ala Asn Met His
65                  70                  75                  80

Ala Gln Ile Lys Thr Ser Leu His Arg Leu Lys Pro Asp Thr Val Pro
                85                  90                  95

Ala Pro Cys Cys Val Pro Ala Ser Tyr Asn Pro Met Val Leu Ile Gln
            100                 105                 110

Lys Thr Asp Thr Gly Val Asn Leu Thr Thr Tyr Asp Asp Leu Leu Ala
        115                 120                 125

Lys Asp Cys His Cys Ile
    130

<210> SEQ ID NO 118
<211> LENGTH: 134
<212> TYPE: PRT
<213> ORGANISM: Artificial sequence
<220> FEATURE:
<223> OTHER INFORMATION: synthetic polypeptide sequence

<400> SEQUENCE: 118

Met Asp Met Arg Val Pro Ala Gln Leu Leu Gly Leu Leu Leu Leu Trp
1               5                   10                  15

Leu Arg Gly Ala Arg Cys Ala Arg Asn Gly Asp His Cys Pro Leu Gly
            20                  25                  30

Pro Gly Arg Cys Cys Arg Leu His Thr Val Arg Ala Ser Leu Glu Asp
        35                  40                  45

Leu Gly Trp Ala Asp Trp Val Leu Ser Pro Arg Glu Val Gln Val Thr
    50                  55                  60

Met Cys Ile Gly Ala Cys Pro Ser Gln Phe Arg Ala Ala Asn Met His
65                  70                  75                  80

Ala Gln Ile Lys Thr Ser Leu His Arg Leu Lys Pro Asp Thr Val Pro
                85                  90                  95

Ala Pro Cys Cys Val Pro Ala Ser Tyr Asn Pro Met Val Leu Ile Gln
            100                 105                 110

Lys Thr Asp Thr Gly Val Ser Asn Gln Thr Tyr Asp Asp Leu Leu Ala

```
                    115                 120                 125
Lys Asp Cys His Cys Ile
    130

<210> SEQ ID NO 119
<211> LENGTH: 17
<212> TYPE: PRT
<213> ORGANISM: Artificial sequence
<220> FEATURE:
<223> OTHER INFORMATION: synthetic polypeptide sequence

<400> SEQUENCE: 119

Asn Gly Asp His Cys Pro Leu Gly Pro Gly Arg Cys Cys Arg Leu His
1               5                   10                  15

Thr

<210> SEQ ID NO 120
<211> LENGTH: 5
<212> TYPE: PRT
<213> ORGANISM: Artificial sequence
<220> FEATURE:
<223> OTHER INFORMATION: synthetic polypeptide sequence
<220> FEATURE:
<221> NAME/KEY: MISC_FEATURE
<222> LOCATION: (1)..(5)
<223> OTHER INFORMATION: this stretch of amino acids may be repeated up
      to 50 times

<400> SEQUENCE: 120

Gly Ser Gly Gly Ser
1               5

<210> SEQ ID NO 121
<211> LENGTH: 5
<212> TYPE: PRT
<213> ORGANISM: Artificial sequence
<220> FEATURE:
<223> OTHER INFORMATION: synthetic polypeptide sequence
<220> FEATURE:
<221> NAME/KEY: MISC_FEATURE
<222> LOCATION: (1)..(1)
<223> OTHER INFORMATION: this amino acid may be repeated up to 20 times
<220> FEATURE:
<221> NAME/KEY: MISC_FEATURE
<222> LOCATION: (1)..(5)
<223> OTHER INFORMATION: this stretch of amino acids may be repeated up
      to 20 times
<220> FEATURE:
<221> NAME/KEY: MISC_FEATURE
<222> LOCATION: (2)..(2)
<223> OTHER INFORMATION: this amino acid may be repeated up to 20 times
<220> FEATURE:
<221> NAME/KEY: MISC_FEATURE
<222> LOCATION: (3)..(3)
<223> OTHER INFORMATION: this amino acid may be repeated up to 20 times
<220> FEATURE:
<221> NAME/KEY: MISC_FEATURE
<222> LOCATION: (4)..(4)
<223> OTHER INFORMATION: this amino acid may be repeated up to 20 times
<220> FEATURE:
<221> NAME/KEY: MISC_FEATURE
<222> LOCATION: (5)..(5)
<223> OTHER INFORMATION: this amino acid may be repeated up to 20 times

<400> SEQUENCE: 121

Gly Ser Gly Ser Gly
1               5

<210> SEQ ID NO 122
<211> LENGTH: 5
```

```
<212> TYPE: PRT
<213> ORGANISM: Artificial sequence
<220> FEATURE:
<223> OTHER INFORMATION: synthetic polypeptide sequence
<220> FEATURE:
<221> NAME/KEY: MISC_FEATURE
<222> LOCATION: (1)..(5)
<223> OTHER INFORMATION: this stretch of amino acids may be repeated up
      to 20 times
<220> FEATURE:
<221> NAME/KEY: MISC_FEATURE
<222> LOCATION: (5)..(5)
<223> OTHER INFORMATION: this amino acid may be repeated up to 20 times

<400> SEQUENCE: 122

Gly Ser Gly Gly Ser
1               5

<210> SEQ ID NO 123
<211> LENGTH: 5
<212> TYPE: PRT
<213> ORGANISM: Artificial sequence
<220> FEATURE:
<223> OTHER INFORMATION: synthetic polypeptide sequence
<220> FEATURE:
<221> NAME/KEY: MISC_FEATURE
<222> LOCATION: (1)..(5)
<223> OTHER INFORMATION: this stretch of amino acids may be repeated up
      to 20 times
<220> FEATURE:
<221> NAME/KEY: MISC_FEATURE
<222> LOCATION: (2)..(2)
<223> OTHER INFORMATION: this amino acid may be repeated up to 20 times

<400> SEQUENCE: 123

Gly Ser Gly Ser Gly
1               5

<210> SEQ ID NO 124
<211> LENGTH: 4
<212> TYPE: PRT
<213> ORGANISM: Artificial sequence
<220> FEATURE:
<223> OTHER INFORMATION: synthetic polypeptide sequence
<220> FEATURE:
<221> NAME/KEY: MISC_FEATURE
<222> LOCATION: (1)..(4)
<223> OTHER INFORMATION: this stretch of amino acids may be repeated up
      to 20 times
<220> FEATURE:
<221> NAME/KEY: MISC_FEATURE
<222> LOCATION: (4)..(4)
<223> OTHER INFORMATION: this amino acid may be repeated up to 20 times

<400> SEQUENCE: 124

Gly Gly Gly Ser
1

<210> SEQ ID NO 125
<211> LENGTH: 4
<212> TYPE: PRT
<213> ORGANISM: Artificial sequence
<220> FEATURE:
<223> OTHER INFORMATION: synthetic polypeptide sequence
<220> FEATURE:
<221> NAME/KEY: MISC_FEATURE
<222> LOCATION: (1)..(4)
<223> OTHER INFORMATION: this stretch of amino acids may be repeated up
      to 50 times

<400> SEQUENCE: 125

Gly Gly Gly Ser
```

<210> SEQ ID NO 126
<211> LENGTH: 5
<212> TYPE: PRT
<213> ORGANISM: Artificial sequence
<220> FEATURE:
<223> OTHER INFORMATION: synthetic polypeptide sequence
<220> FEATURE:
<221> NAME/KEY: MISC_FEATURE
<222> LOCATION: (1)..(5)
<223> OTHER INFORMATION: this stretch of amino acids may be repeated up to 50 times

<400> SEQUENCE: 126

Gly Gly Gly Gly Ser
1               5

<210> SEQ ID NO 127
<211> LENGTH: 227
<212> TYPE: PRT
<213> ORGANISM: Artificial sequence
<220> FEATURE:
<223> OTHER INFORMATION: synthetic polypeptide sequence

<400> SEQUENCE: 127

Asp Lys Thr His Thr Cys Pro Pro Cys Pro Ala Pro Ala Leu Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 128
<211> LENGTH: 112
<212> TYPE: PRT

<213> ORGANISM: Artificial sequence
<220> FEATURE:
<223> OTHER INFORMATION: synthetic polypeptide sequence

<400> SEQUENCE: 128

Ala Arg Asn Gly Thr His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 129
<211> LENGTH: 110
<212> TYPE: PRT
<213> ORGANISM: Artificial sequence
<220> FEATURE:
<223> OTHER INFORMATION: synthetic polypeptide sequence

<400> SEQUENCE: 129

Asn Gly Thr His Cys Pro Leu Gly Pro Gly Arg Cys Cys Arg Leu His
1               5                   10                  15

Thr Val Arg Ala Ser Leu Glu Asp Leu Gly Trp Ala Asp Trp Val Leu
            20                  25                  30

Ser Pro Arg Glu Val Gln Val Thr Met Cys Ile Gly Ala Cys Pro Ser
        35                  40                  45

Gln Phe Arg Ala Ala Asn Met His Ala Gln Ile Lys Thr Ser Leu His
    50                  55                  60

Arg Leu Lys Pro Asp Thr Val Pro Ala Pro Cys Cys Val Pro Ala Ser
65                  70                  75                  80

Tyr Asn Pro Met Val Leu Ile Gln Lys Thr Asp Thr Gly Val Ser Leu
                85                  90                  95

Gln Thr Tyr Asp Asp Leu Leu Ala Lys Asp Cys His Cys Ile
            100                 105                 110

<210> SEQ ID NO 130
<211> LENGTH: 109
<212> TYPE: PRT
<213> ORGANISM: Artificial sequence
<220> FEATURE:
<223> OTHER INFORMATION: synthetic polypeptide sequence

<400> SEQUENCE: 130

Gly Thr His Cys Pro Leu Gly Pro Gly Arg Cys Cys Arg Leu His Thr
1               5                   10                  15

Val Arg Ala Ser Leu Glu Asp Leu Gly Trp Ala Asp Trp Val Leu Ser
            20                  25                  30

Pro Arg Glu Val Gln Val Thr Met Cys Ile Gly Ala Cys Pro Ser Gln
        35                  40                  45

Phe Arg Ala Ala Asn Met His Ala Gln Ile Lys Thr Ser Leu His Arg
    50                  55                  60

Leu Lys Pro Asp Thr Val Pro Ala Pro Cys Cys Val Pro Ala Ser Tyr
65                  70                  75                  80

Asn Pro Met Val Leu Ile Gln Lys Thr Asp Thr Gly Val Ser Leu Gln
                85                  90                  95

Thr Tyr Asp Asp Leu Leu Ala Lys Asp Cys His Cys Ile
            100                 105

<210> SEQ ID NO 131
<211> LENGTH: 109
<212> TYPE: PRT
<213> ORGANISM: Artificial sequence
<220> FEATURE:
<223> OTHER INFORMATION: synthetic polypeptide sequence

<400> SEQUENCE: 131

Gly Asp His Cys Pro Leu Gly Pro Gly Arg Cys Cys Arg Leu His Thr
1               5                   10                  15

Val Asn Ala Ser Leu Glu Asp Leu Gly Trp Ala Asp Trp Val Leu Ser
                20                  25                  30

Pro Arg Glu Val Gln Val Thr Met Cys Ile Gly Ala Cys Pro Ser Gln
            35                  40                  45

Phe Arg Ala Ala Asn Met His Ala Gln Ile Lys Thr Ser Leu His Arg
    50                  55                  60

Leu Lys Pro Asp Thr Val Pro Ala Pro Cys Cys Val Pro Ala Ser Tyr
65                  70                  75                  80

Asn Pro Met Val Leu Ile Gln Lys Thr Asp Thr Gly Val Ser Leu Gln
                85                  90                  95

Thr Tyr Asp Asp Leu Leu Ala Lys Asp Cys His Cys Ile
            100                 105

<210> SEQ ID NO 132
<211> LENGTH: 109
<212> TYPE: PRT
<213> ORGANISM: Artificial sequence
<220> FEATURE:
<223> OTHER INFORMATION: synthetic polypeptide sequence

<400> SEQUENCE: 132

Gly Asp His Cys Pro Leu Gly Pro Gly Arg Cys Cys Arg Leu His Thr
1               5                   10                  15

Val Arg Ala Asn Leu Thr Asp Leu Gly Trp Ala Asp Trp Val Leu Ser
                20                  25                  30

Pro Arg Glu Val Gln Val Thr Met Cys Ile Gly Ala Cys Pro Ser Gln
            35                  40                  45

Phe Arg Ala Ala Asn Met His Ala Gln Ile Lys Thr Ser Leu His Arg
    50                  55                  60

Leu Lys Pro Asp Thr Val Pro Ala Pro Cys Cys Val Pro Ala Ser Tyr
65                  70                  75                  80

Asn Pro Met Val Leu Ile Gln Lys Thr Asp Thr Gly Val Ser Leu Gln
                85                  90                  95

Thr Tyr Asp Asp Leu Leu Ala Lys Asp Cys His Cys Ile
            100                 105

<210> SEQ ID NO 133
<211> LENGTH: 109
<212> TYPE: PRT
<213> ORGANISM: Artificial sequence
<220> FEATURE:
<223> OTHER INFORMATION: synthetic polypeptide sequence

<400> SEQUENCE: 133

Gly Asp His Cys Pro Leu Gly Pro Gly Arg Cys Cys Arg Leu His Thr
1               5                   10                  15

Val Arg Ala Ser Leu Glu Asp Leu Gly Trp Ala Asp Trp Val Leu Ser
            20                  25                  30

Pro Arg Glu Val Gln Val Thr Met Cys Ile Gly Ala Cys Pro Ser Gln
        35                  40                  45

Asn Arg Thr Ala Asn Met His Ala Gln Ile Lys Thr Ser Leu His Arg
    50                  55                  60

Leu Lys Pro Asp Thr Val Pro Ala Pro Cys Cys Val Pro Ala Ser Tyr
65                  70                  75                  80

Asn Pro Met Val Leu Ile Gln Lys Thr Asp Thr Gly Val Ser Leu Gln
                85                  90                  95

Thr Tyr Asp Asp Leu Leu Ala Lys Asp Cys His Cys Ile
            100                 105

<210> SEQ ID NO 134
<211> LENGTH: 109
<212> TYPE: PRT
<213> ORGANISM: Artificial sequence
<220> FEATURE:
<223> OTHER INFORMATION: synthetic polypeptide sequence

<400> SEQUENCE: 134

Gly Asp His Cys Pro Leu Gly Pro Gly Arg Cys Cys Arg Leu His Thr
1               5                   10                  15

Val Arg Ala Ser Leu Glu Asp Leu Gly Trp Ala Asp Trp Val Leu Ser
            20                  25                  30

Pro Arg Glu Val Gln Val Thr Met Cys Ile Gly Ala Cys Pro Ser Gln
        35                  40                  45

Phe Asn Ala Thr Asn Met His Ala Gln Ile Lys Thr Ser Leu His Arg
    50                  55                  60

Leu Lys Pro Asp Thr Val Pro Ala Pro Cys Cys Val Pro Ala Ser Tyr
65                  70                  75                  80

Asn Pro Met Val Leu Ile Gln Lys Thr Asp Thr Gly Val Ser Leu Gln
                85                  90                  95

Thr Tyr Asp Asp Leu Leu Ala Lys Asp Cys His Cys Ile
            100                 105

<210> SEQ ID NO 135
<211> LENGTH: 109
<212> TYPE: PRT
<213> ORGANISM: Artificial sequence
<220> FEATURE:
<223> OTHER INFORMATION: synthetic polypeptide sequence

<400> SEQUENCE: 135

Gly Asp His Cys Pro Leu Gly Pro Gly Arg Cys Cys Arg Leu His Thr
1               5                   10                  15

Val Arg Ala Ser Leu Glu Asp Leu Gly Trp Ala Asp Trp Val Leu Ser
            20                  25                  30

Pro Arg Glu Val Gln Val Thr Met Cys Ile Gly Ala Cys Pro Ser Gln
        35                  40                  45

Phe Arg Ala Ala Asn Met His Ala Gln Ile Lys Thr Ser Leu His Arg
    50                  55                  60

Leu Lys Pro Asp Thr Val Pro Ala Pro Cys Cys Val Pro Ala Ser Tyr
65                  70                  75                  80

```
Asn Pro Met Val Leu Ile Gln Asn Thr Thr Thr Gly Val Ser Leu Gln
                85                  90                  95

Thr Tyr Asp Asp Leu Leu Ala Lys Asp Cys His Cys Ile
            100                 105

<210> SEQ ID NO 136
<211> LENGTH: 109
<212> TYPE: PRT
<213> ORGANISM: Artificial sequence
<220> FEATURE:
<223> OTHER INFORMATION: synthetic polypeptide sequence

<400> SEQUENCE: 136

Gly Asp His Cys Pro Leu Gly Pro Gly Arg Cys Cys Arg Leu His Thr
1               5                   10                  15

Val Arg Ala Ser Leu Glu Asp Leu Gly Trp Ala Asp Trp Val Leu Ser
                20                  25                  30

Pro Arg Glu Val Gln Val Thr Met Cys Ile Gly Ala Cys Pro Ser Gln
            35                  40                  45

Phe Arg Ala Ala Asn Met His Ala Gln Ile Lys Thr Ser Leu His Arg
    50                  55                  60

Leu Lys Pro Asp Thr Val Pro Ala Pro Cys Cys Val Pro Ala Ser Tyr
65                  70                  75                  80

Asn Pro Met Val Leu Ile Gln Lys Thr Asn Thr Thr Val Ser Leu Gln
                85                  90                  95

Thr Tyr Asp Asp Leu Leu Ala Lys Asp Cys His Cys Ile
            100                 105
```